US007169760B2

(12) United States Patent
Saksena et al.

(10) Patent No.: US 7,169,760 B2
(45) Date of Patent: Jan. 30, 2007

(54) PEPTIDES AS NS3-SERINE PROTEASE INHIBITORS OF HEPATITIS C VIRUS

(75) Inventors: Anil K. Saksena, Upper Montclair, NJ (US); Viyyoor Moopil Girijavallabhan, Parsippany, NJ (US); Stephane L. Bogen, Somerset, NJ (US); Raymond G. Lovey, West Caldwell, NJ (US); Edwin Jao, Warren, NJ (US); Frank Bennett, Piscataway, NJ (US); Jinping L. Mc Cormick, Edison, NJ (US); Haiyan Wang, Cranbury, NJ (US); Russell E. Pike, Stanhope, NJ (US); Yi-Tsung Liu, Morris Township, NJ (US); Tin-Yau Chan, Edison, NJ (US); Zhaoning Zhu, East Windsor, NJ (US); Ashok Arasappan, Bridgewater, NJ (US); Kevin X. Chen, Iselin, NJ (US); Srinkanth Venkatraman, Fords, NJ (US); Tejal Parekh, Mountain View, CA (US); Patrick A. Pinto, Morris Plains, NJ (US); Bama Santhanam, Bridgewater, NJ (US); F. George Njoroge, Warren, NJ (US); Ashit K. Ganguly, Upper Montclair, NJ (US); Henry A. Vaccaro, South Plainfield, NJ (US); Scott Jeffrey Kemp, San Diego, CA (US); Odile Esther Levy, San Diego, CA (US); Marguerita Lim-Wilby, La Jolla, CA (US); Susan Y. Tamura, Santa Fe, NM (US)

(73) Assignees: Schering Corporation, Kenilworth, NJ (US); Dendreon Corporation, Seattle, WA (US)

( * ) Notice: Subject to any disclaimer, the term of this patent is extended or adjusted under 35 U.S.C. 154(b) by 475 days.

(21) Appl. No.: 09/909,012

(22) Filed: Jul. 19, 2001

(65) Prior Publication Data
US 2002/0160962 A1 Oct. 31, 2002

Related U.S. Application Data
(60) Provisional application No. 60/220,107, filed on Jul. 21, 2000.

(51) Int. Cl.
*A61K 38/05* (2006.01)
A61K 31/44; A61K 31/16; A61K 31/227

(52) U.S. Cl. .................. 514/19; 514/616; 564/154; 564/152; 564/155

(58) Field of Classification Search .............. 514/19, 514/616, 307, 471, 314, 255, 357; 564/154, 564/414, 152, 155; 548/530; 546/336, 140; 558/414
See application file for complete search history.

(56) References Cited

U.S. PATENT DOCUMENTS

| 5,162,500 A | 11/1992 | Takeuchi et al. |
| 5,359,138 A | 10/1994 | Takeuchi et al. |
| 5,488,067 A | 1/1996 | Hanson |
| 5,496,927 A | 3/1996 | Kolb et al. |
| 5,514,694 A | 5/1996 | Powers et al. |
| 5,633,388 A | 5/1997 | Diana et al. |
| 5,739,002 A | 4/1998 | De Francesco et al. |
| 5,763,576 A | 6/1998 | Powers |
| 5,843,450 A | 12/1998 | Dawson et al. |
| 5,843,752 A | 12/1998 | Dasmahapatra et al. |
| 5,849,866 A | 12/1998 | Kolb et al. |
| 5,854,001 A | 12/1998 | Casey et al. |
| 6,265,380 B1 | 7/2001 | Tung et al. |

FOREIGN PATENT DOCUMENTS

| CA | 2362911 A1 | 9/2000 |
| EP | 0 195 212 A | 9/1986 |
| EP | 0 363 284 A | 4/1990 |
| EP | 0 423 358 A1 | 4/1991 |
| EP | 0 672 648 B1 | 9/1995 |
| EP | 0 672 648 A1 | 9/1995 |
| FR | 2778406 A1 | 11/1999 |
| GB | 2 338 482 A | 4/1998 |
| JP | 4-001140 A | 1/1992 |
| JP | 04 149166 A | 5/1992 |
| WO | WO-92/11850 | 7/1992 |
| WO | WO-94/00095 | 1/1994 |
| WO | WO-95/33764 | 12/1995 |
| WO | WO-96/40743 A | 12/1996 |
| WO | WO-97/06804 | 2/1997 |
| WO | WO-97/31937 A | 9/1997 |
| WO | WO-98/12308 | 3/1998 |
| WO | WO98/13462 | * 4/1998 |
| WO | WO-98/14181 | 4/1998 |
| WO | WO98/22496 | 5/1998 |
| WO | WO-98/29435 | 7/1998 |
| WO | WO-98/37180 | 8/1998 |
| WO | WO-99/07733 | 2/1999 |
| WO | WO-99/64422 | 12/1999 |
| WO | WO-00/05245 | 2/2000 |
| WO | WO-01/40262 A1 | 6/2001 |
| WO | WO-01/74768 A2 | 10/2001 |
| WO | WO-02/18369 A2 | 3/2002 |

OTHER PUBLICATIONS

Patel et al. Activated Ketone Based Inhibitors of Human Renin, Journal of Medicinal Chemistry, 1993, vol. 36, No. 17, Aug. 20, 1993, pp. 2431–2447.

(Continued)

*Primary Examiner*—Jon Weber
*Assistant Examiner*—Robert B. Mondesi
(74) *Attorney, Agent, or Firm*—Palaiyur S. Kalyanaraman; Larner, David, Littenberg, Krumbolz & Mentlik, LLP

(57) ABSTRACT

The present invention discloses novel peptide compounds which have HCV protease inhibitory activity as well as methods for preparing such compounds. In another embodiment, the invention discloses pharmaceutical compositions comprising such compounds as well as methods of using them to treat disorders associated with the HCV protease.

30 Claims, No Drawings

OTHER PUBLICATIONS

Asano et al., Novel Retrovirus Protease Inhibitors, RPI–856 A, B, C and D, The Journal of Antibiotics, vol. 47, No. 5, pp. 557–565 (1994).

Suto et al., Peptide Inhibitors of IKB Protease: Modification of the C–Terminal of Z–LLF–CHO, Bioorganic & Medicinal Chemistry Letters, vol. 6, No. 24, pp. 2925–2930 (1996).

Internatioal Search Report, PCT/US01/22813, Jul. 19, 2001.

Bartenschlager et al., Substrate Determinants for Cleavage in cis and in trans by the Hepatitis C Virus NS3 Proteinase, Journal of Virology, Jan. 1995, vol. 69, No. 1, pp. 198–205.

Bianchi et al., Synthetic Depsipeptide Substrates for the Assay of Human Hepatitis C Virus Protease, Analytical Biochemistry 237, 239–244 (1996).

Bouffard et al., An in Vitro Assay for Hepatitis C Virus NS3 Serine Proteinase, Virology 209, 52–59 (1995).

Cho et al., Construction of hepatitis C–SIN virus recombinants with replicative dependency on hepatitis C virus serine protease activity, Journal of Virological Methods 65 (1997), 201–207.

D'Souza et al., In vitro cleavage of hepatitis C virus polyprotein substrates by purified recombinant NS3 protease, Journal of General Virology (1995), 76, 1729–1736.

Filocamo et al., Chimeric Sindbis Viruses Dependent on the NS3 Protease of Hepatitis C Virus, Journal of Virology, Feb. 1997, p. 1417–1427.

Hahm et al., Generation of a Novel Poliovirus with a Requirement of Hepatitis C Virus Protease NS3 Activity, Virology 226, 318–326 (1996).

Hamatake et al., Establishment of an in vitro Assay to Characterize Hepatitis C Virus NS3–4A Protease Trans–Processing Activity, Intervirology 1996;39:249–258.

Harbeson et al., Stereospecific Synthesis of Peptidyl a–Keto Amides as Inhibitors of Calpain, J. Med. Chem. 1994, 37, 2918–2929.

Ito et al., Cultivation of hepatitis C virus in primary hepatocyte culture from patients with chronic hepatitis C results in release of high titre infectious virus, J. Gen. Virol May 1996; 77 (Pt 5):1043–54.

Lu et al., Poliovirus chimeras replicating under the translational control of genetic elements of hepatitis C virus reveal unusual properties of the internal ribosomal entry site of hepatitis C virus, Proc. Natl. Acad. Sci. USA, vol. 93, pp. 1412–1417, pp. 1412–1417, Feb. 1996.

Mizutani et al., Characterization of Hepatitis C Virus Replication in Cloned Cells Obtained from a Human T–Cell Leukemia Virus Type 1–Infected Cell line, MT–2, Journal of Virology, Oct. 1996, p. 7219–7223.

Mizutani et al., Inhibition of Hepatitis C Virus Replication by Antisense Oligonucleotide in Culture Cells, Biochemical and Biophysical Research Communications, vol. 212, No. 3, 1995, pp. 906–911.

Mizutani et al., Long–Term Human T–Cell Culture System Supporting Hepatitis C Virus Replication, Biochemical and Biophysical Research Communications 227, 822–826 (1996).

Ogilvie et al., Peptidomimetic Inhibitors of the Human Cytomegalovirus Protease, J. Med. Chem. 1997, 40, 4113–4135.

Scarselli et al., GB Virus B and Hepatitis C Virus NS3 Serine Proteases Share Substrate Specificity, Journal of Virology, Jul. 1997, p. 4985–4989.

Schechter et al., On the Size of the Active Site in Proteases, Biochemical and Biophysical Research Communications, vol. 27, No. 2, 1967.

Shimizu et al., Multicycle Infection of Hepatitis C Virus in Cell Culture and Inhibition by Alpha and Beta Interferons, Journal of Virology, Dec. 1994, p. 8406–8408.

Steinkuhler et al., Product Inhibition of the Hepatitis C Virus NS3 Protease, Biochemistry 1998, vol. 37, pp. 8899–8905.

Sudo et al., Establishment of an in vitro assay system for screening hepatitis C virus protease inhibitors using high performance liquid chromatography, Antiviral Research 32 (1996), pp. 9–18.

Takeshita et al., An Enzyme–Linked Immunosorbent Assay for Detecting Proteolytic Activity of Hepatitis C Virus Proteinase, Analytical Biochemistry (1997), 274, pp. 242–246.

Taliani et al., A Continuous Assay of Hepatitis C Virus Protease Based on Resonance Energy Transfer Depsipeptide Substrates, Analytical Biochemistry 240 (1996), pp. 60–67.

Taremi et al., Construction, expression, and characterization of a novel fully activated recombinant single–chain hepatitis C virus protease, Protein Science (1998), 7:2143–2149.

Tong et al., Conserved mode of peptidomimetic inhibition and substrate recognition of human cytomegalovirus protease, Nature Structural Biology (1998), vol. 5., No. 9, pp. 819–826.

Tsuda et al., Poststatin, a New Inhibitor of Prolyl Endopeptidase, The Journal of Antibiotics (1996). vol. 49, No. 3, pp. 287–291.

Tsuda et al., Poststatin, a New Inhibitor of Prolyl Endopeptidase, The Journal of Antibiotics (1996), vol. 49, No. 9, pp. 890–899.

Urbani et al., Substrate Specificity of the Hepatitis C Virus Serine Protease NS3, Journal of Biological Chemistry (1997), Apr. 4 Issue, pp. 9204–9209.

Wang et al., Expression of HCV NS3 Protease and Detection of its Activity in Mammalian Cells, 4th International Meeting on Hepatitis C Virus and Related Viruses, Molecular Virology and Pathogenesis, Mar. 6–10, 1997.

Wasserman et al., (Cyanomethylene) phosphoranes as Novel Carbonyl 1,1–Dipole Synthons: An Efficient Synthesis of a–Keto, Acids, Esters, and Amides, J. Org. Chem. (1994), vol. 59, pp. 4364–4366.

Zhang et al., Probing the Substrate Specificity of Hepatitis C Virus NS3 Serine Protease by Using Synthetic Peptides, Journal of Virology, Aug. 1997, pp. 6208–6213.

Bennett et al., The Identification of a–Ketoamides as Potent Inhibitors of Hepatitis C Virus NS3–4A Proteinase, Biorganic & Medicinal Chemistry Letters 11 (2001), pp. 355–357.

Llinas–Brunet et al., Studies on the C–Terminal of Hexapeptide Inhibitors of the Hepatitis C Virus Serine Protease, Bioorganic & Medicinal Chemistry Letters 8 (1998), pp. 2719–2724.

Narjes et al., a–Ketoacids are Potent Slow Binding Inhibitors of the Hepatitis C Virus NS3 Protease, Biochemistry (2000), vol. 39, pp. 1849–1861.

* cited by examiner

PEPTIDES AS NS3-SERINE PROTEASE INHIBITORS OF HEPATITIS C VIRUS

This application claims the benefit of Provisional Application No. 60/220,107, filed July 21, 2000.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptide compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, eg., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) Proc. Natl. Acad. Sci (USA) 91:888–892, Failla et al. (1996) Folding & Design 1:35–42. The NS3/NS4a cleavage site is also more tolerant of mutagenesis than the other sites. See, e.g., Kollykhalov et al. (1994) J. Virol. 68:7525–7533. It has also been found that acidic residues in the region upstream of the cleavage site are required for efficient cleavage. See, e.g., Komoda et al. (1994) J. Virol. 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) Biochem. 36:9340–9348, Ingallinella et al. (1998) Biochem. 37:8906–8914, Llinàs-Brunet et al. (1998) Bioorg. Med. Chem. Lett. 8:1713–1718), inhibitors based on the 70-amino acid polypeptide eglin c (Martin et al. (1998) Biochem. 37:11459–11468, inhibitors affinity selected from human pancreatic secretory trypsin inhibitor (hPSTI-C3) and mini-body repertoires (MBip) (Dimasi et al. (1997) J. Virol. 71:7461–7469), cV$_H$E2 (a "camelized" variable domain antibody fragment) (Martin et al. (1997) Protein Eng. 10:607–614), and α1-antichymotrypsin (ACT) (Elzouki et al.) (1997) J. Hepat. 27:42–28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, Synlett, S1, 1000–1002 (1999) describing the synthesis of bicylic analogs of an inhibitor of HCV NS3 protease. A compound disclosed therein has the formula:

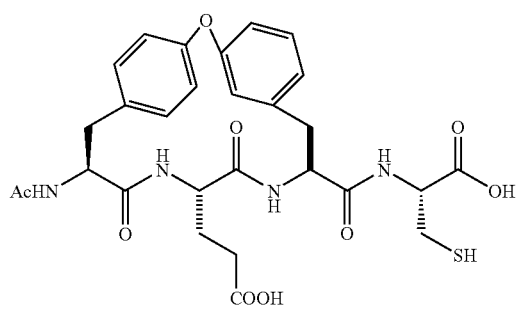

Reference is also made to W. Han et al, Bioorganic & Medicinal Chem. Lett, (2000) 10, 711–713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

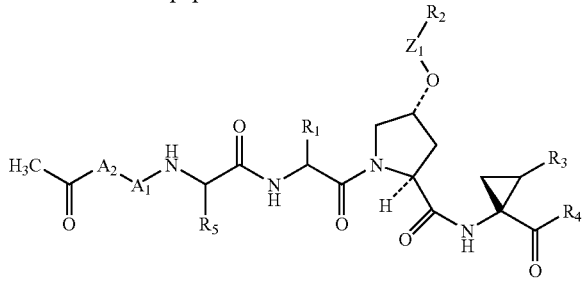

where the various elements are defined therein. An illustrative compound of that series is:

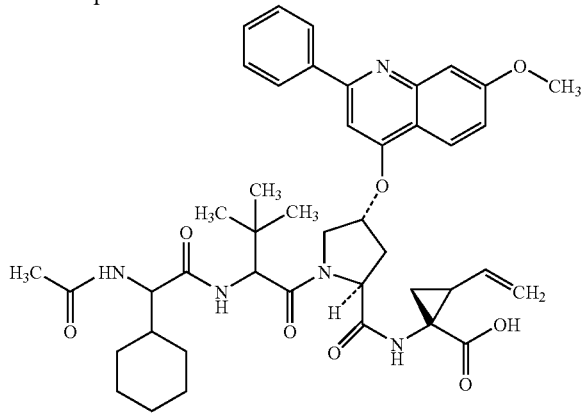

Reference is also made to WO 00/09543 (Assignee: Boehringer Ingelheim Limited; Published Feb. 24, 2000) which discloses peptide derivatives of the formula:

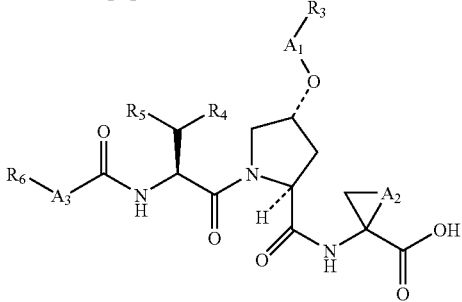

where the various elements are defined therein. An illustrative compound of that series is:

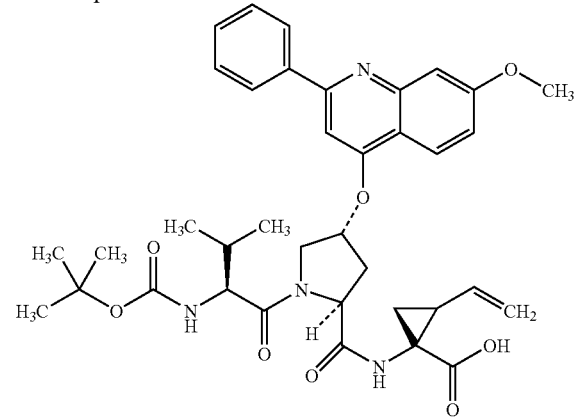

Current therapies for hepatitis C include interferon-α (INF$_\alpha$) and combination therapy with ribavirin and interferon. See, e.g., Beremguer et al. (1998) *Proc. Assoc. Am. Physicians* 110(2):98–112. These therapies suffer from a low sustained response rate and frequent side effects. See, e.g., Hoofnagle et al. (1997) *N. Engl. J. Med.* 336:347. Currently, no vaccine is available for HCV infection.

Pending and copending U.S. patent applications, Ser. No. 09/825,399, filed Apr. 3, 2001, and Ser. No. 09/836,636, filed Apr. 17, 2001, Ser. No. 09/909,077, filed Jul. 19, 2001, Ser. No. 09/909,062, filed Jul. 19, 2001, Ser. No. 09/908, 955, filed Jul. 19, 2001, and Ser. No. 09/909,164, filed Jul. 19, 2001, disclose various types of peptides as NS-3 serine protease inhibitors of hepatitis C virus.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The present application discloses peptide compounds containing an amino acid arrangement from P3 up to P2'.

In its first embodiment, the present invention provides a compound of Formula I:

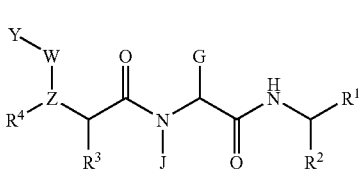

Formula I wherein:

G, J and Y are independently selected from the moieties: H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino or heterocycloalkylamino with the proviso that Y maybe optionally substituted with $X^{11}$ or $X^{12}$;

$X^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that the alkyl, alkoxy, and aryl may be additionally optionally substituted with moieties selected from $X^{12}$;

$R^1$ is $COR^5$ or $B(OR)_2$, wherein $R^5$ is H, OH, $OR^8$, $NR^9R^{10}$, $CF_3$, $C_2F_5$, $C_3F_7$, $CF_2R^6$, $R^6$, or $COR^7$ wherein $R^7$ is H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COO$ $R^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO$ $R^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COO$ $R^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COO\text{-}R^{11}$, and $CH(R^{1'})CONHCH(R^{2'})CONHCH(R^{3'})CONHCH(R^{4'})CONHCH(R^{5'})CONR^{12}R^{13}$, wherein $R^{1'}$, $R^{2'}$, $R^{3'}$, $R^{4'}$, $R^{5'}$, $R^{11}$, $R^{12}$, $R^{13}$, and R' are independently selected from the group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W maybe present or absent, and if W is present, W is selected from C=O, C=S, or $SO_2$; and R, $R^2$, $R^3$ and $R^4$ are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, and phosphorus atoms (with said oxygen, nitrogen, sulfur, or phosphorus atoms numbering zero to six); (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl; wherein said alkyl, heteroalkyl, alkenyl, heteroalkenyl, aryl, heteroaryl, cycloalkyl and heterocycloalkyl moieties may be optionally substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonylurea, hydrazide, and hydroxamate.

Among the above-stated definitions for the various moieties of Formula I, the preferred groups for the various moieties are as follows:

Preferred definition for $R^1$ is $COR^5$ with $R^5$ being H, OH, $COOR^8$ or $CONR^9R^{10}$, where $R^8$, $R^9$ and $R^{10}$ are defined above. Preferred moiety for $R^1$ is $COCONR^9R^{10}$, where $R^9$ is H and $R^{10}$ is H, $CH(R^{1'})COOR^{11}$, $CH(R^{1'})CONR^{12}R^{13}$, $CH(R^{1'})CONHCH(R^{2'})COOR^{11}$, $CH(R^{1'})CONHCH(R^{2'})CONR^{12}R^{13}$ or $CH(R^{1'})CONHCH(R^{2'})(R')$. Among these, preferred moieties for $R^{10}$ are: $CH(R^{1'})CONHCH(R^{2'})COOR^{11}$, $CH(R^{1'})CONHCH(R^{2'})CONR^{12}R^{13}$, $CH(R^{1'})CONHCH(R^{2'})(R')$, wherein $R^{1'}$ is H or alkyl, heteroalkyl and $R^{2'}$ is phenyl, substituted phenyl, hetero atom-substituted phenyl, thiophenyl, cycloalkyl, hetero atom-substituted cycloalkyl, piperidyl and pyridyl. More preferred moieties are: for $R^{1'}$ is H, and $R^{11}$ is H or tert-butyl; R' is hydroxymethyl; and $R^{2'}$ is selected from the group consisting of:

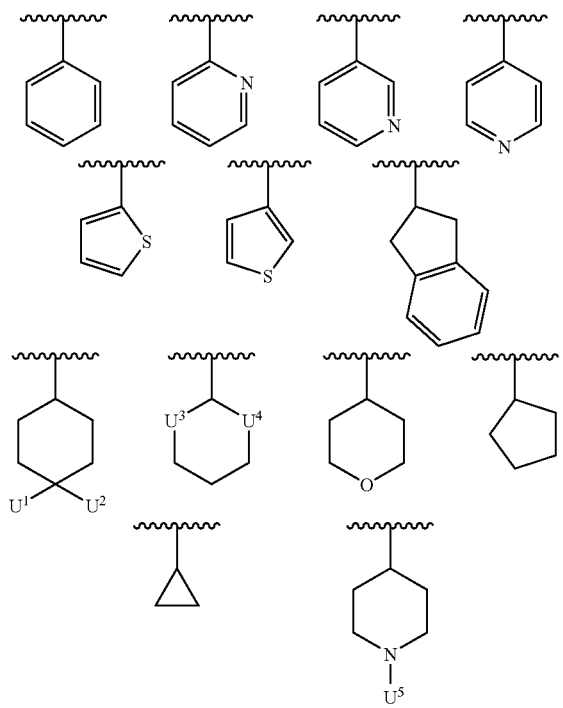

wherein:

$U^1$ and $U^2$ maybe same or different and are selected from the group consisting of H, F, $CH_2COOH$, $CH_2COOMe$, $CH_2CONH_2$, $CH_2CONHMe$, $CH_2CONMe_2$, azido, amino, hydroxyl, substituted amino, substituted hydroxyl;

$U^3$ and $U^4$ maybe same or different and are O or S;

$U^5$ is selected from the moieties consisting of alkylsulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof; and $NR^{12}R^{13}$ is selected from the group consisting of:

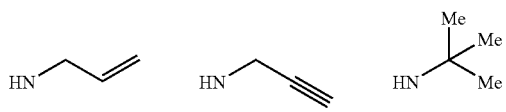

-continued
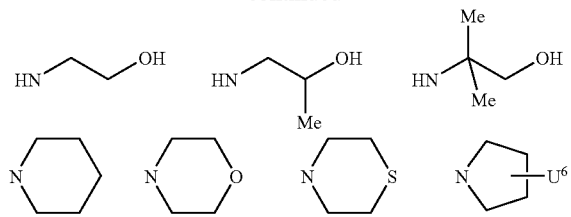
wherein U⁶ is H, OH, or CH₂OH.
Preferred moieties for R² are:
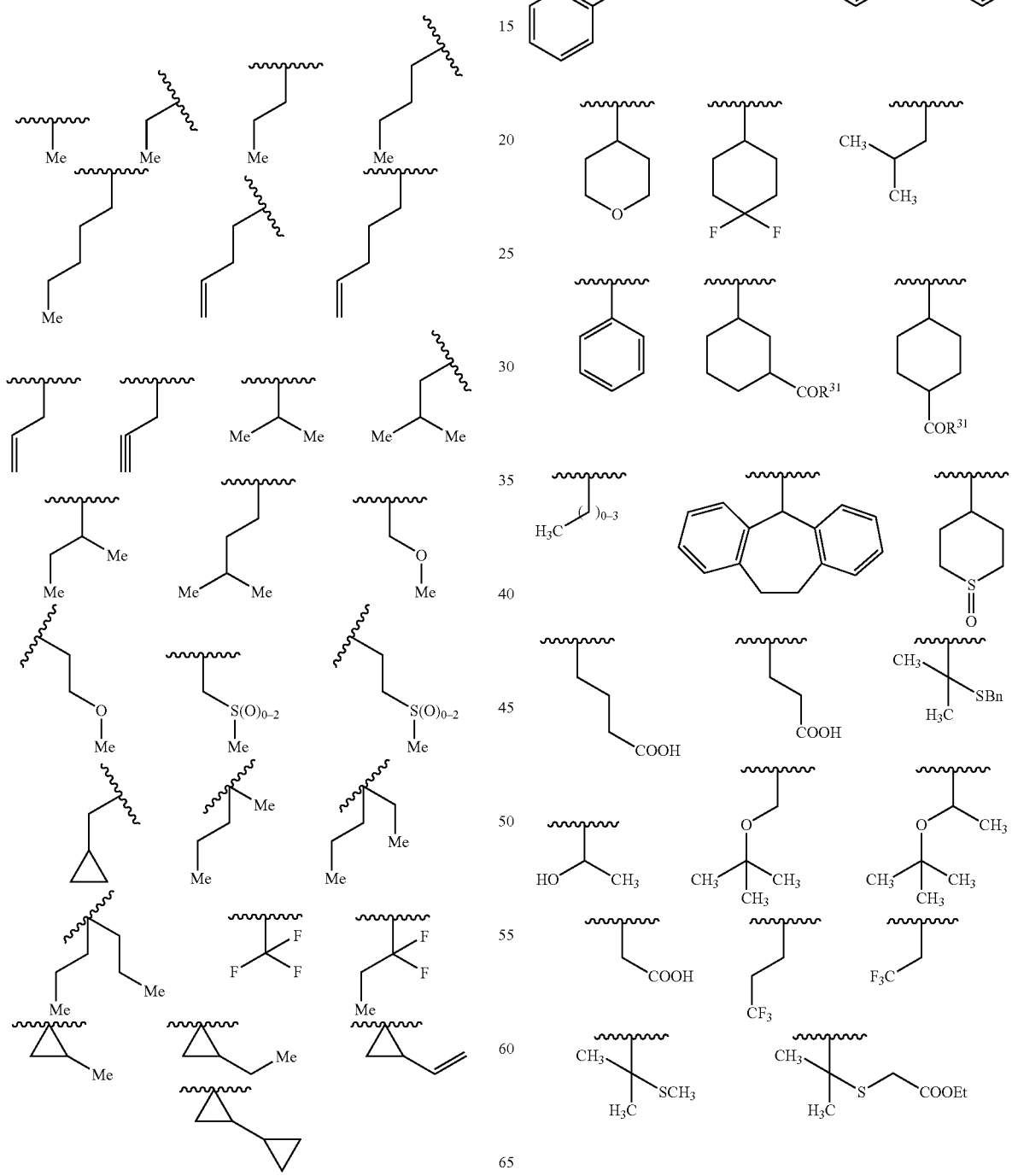
Preferred moieties for R³ are:
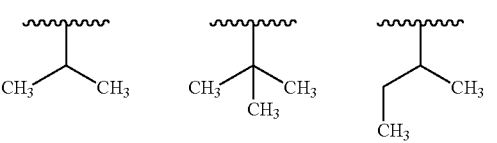
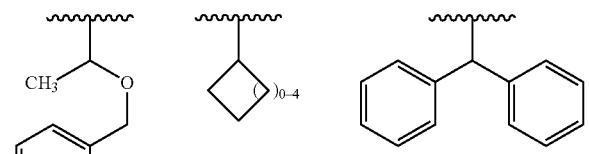
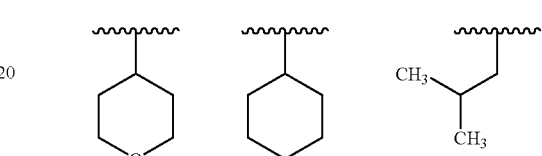
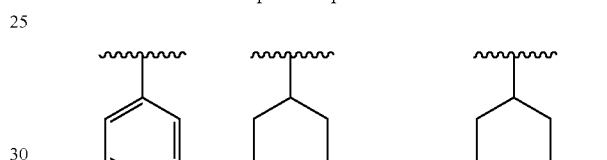
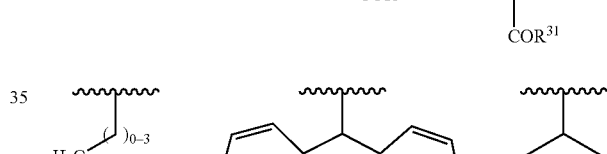
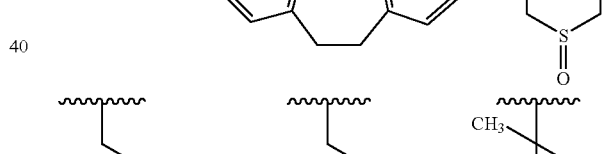

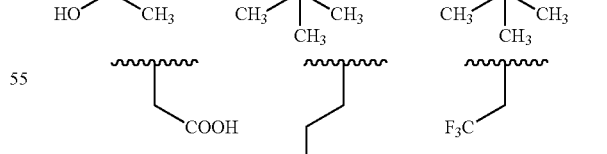

wherein R³¹=OH, or O-alkyl.

Additionally, $R^3$ can also be represented by:

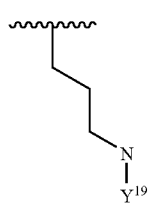

wherein $Y^{19}$ is selected from the following moieties:

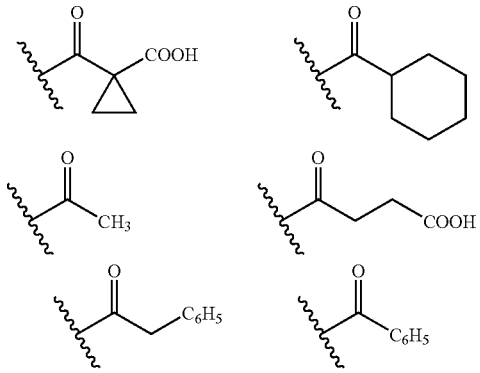

Still, additionally, $R^3$ can be represented by:

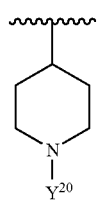

wherein $Y^{20}$ is selected from the following moieties:

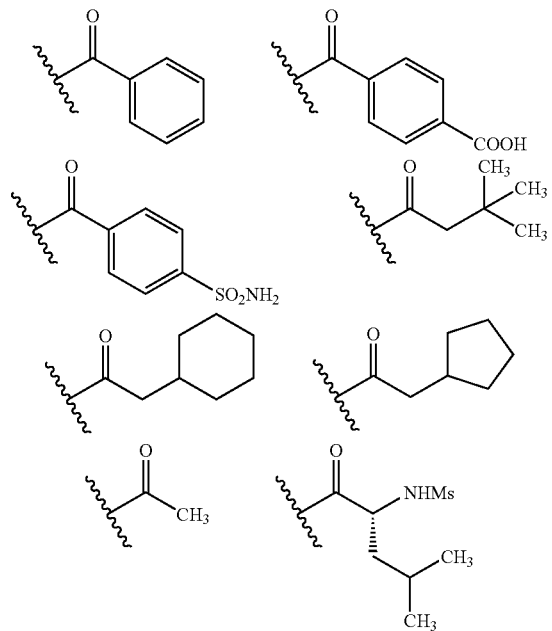

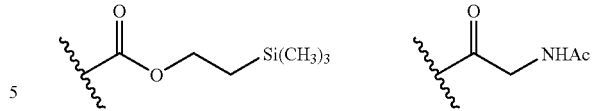

Most preferred moieties for $R^3$ are:

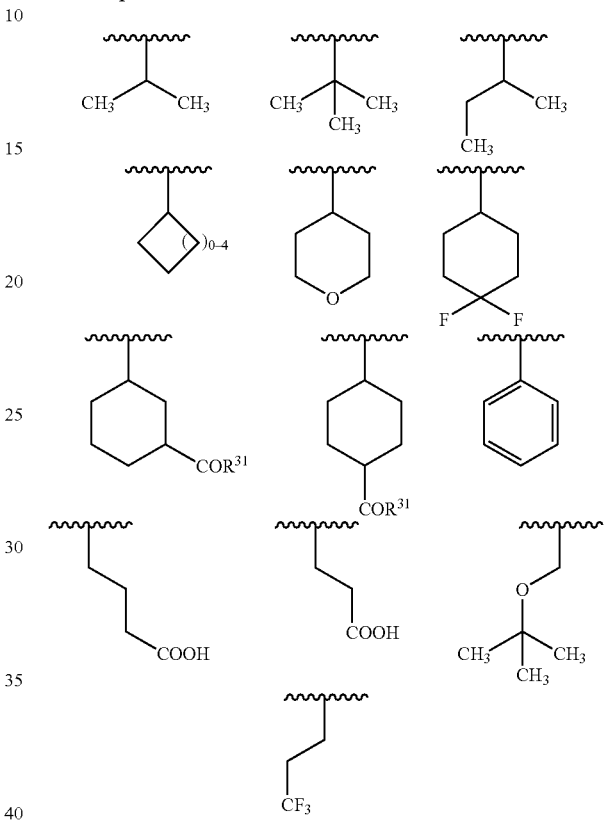

Additionally, the moiety Z-C-$R^3$ in Formula I, with $R^4$ being absent, may be represented by the following structures:

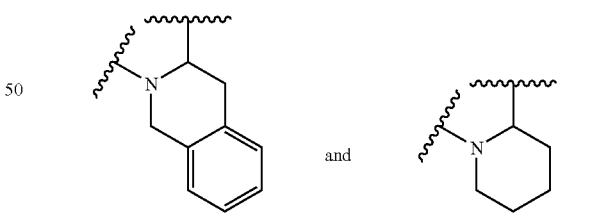

and

Some other preferred moieties are: for Z it is N, for $R^4$ it is H, and for W it is C=O, or $SO_2$. preferred moieties for Y are:

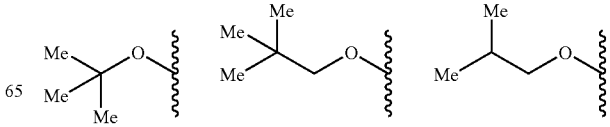

-continued
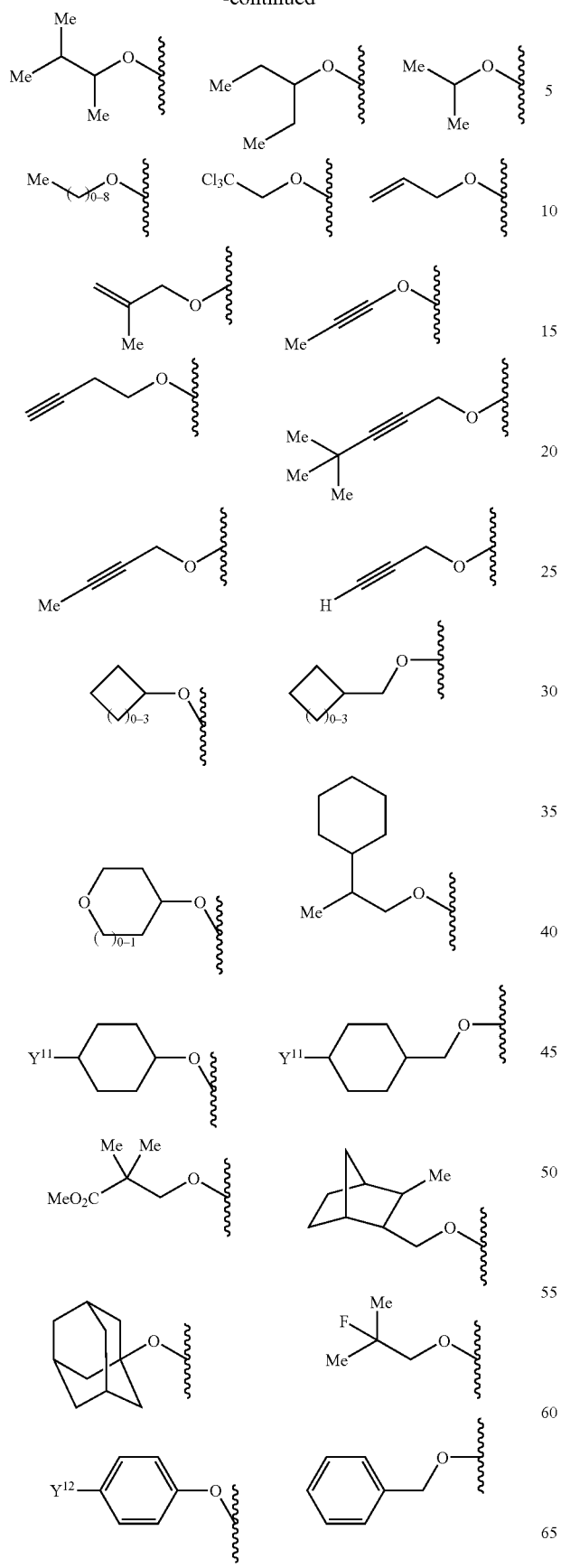
-continued
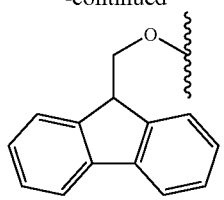
wherein:
$Y^{11}$ is selected from H, COOH, COOEt, OMe, Ph, OPh, NHMe, NHAc, NHPh, CH(Me)$_2$, 1-triazolyl, 1-imidazolyl, and NHCH$_2$COOH;
$Y^{12}$ is selected from H, COOH, COOMe, OMe, F, Cl, or Br. Y may also be represented by:
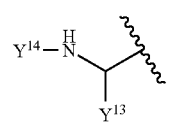
wherein:
$Y^{13}$ is selected from the following moieties:
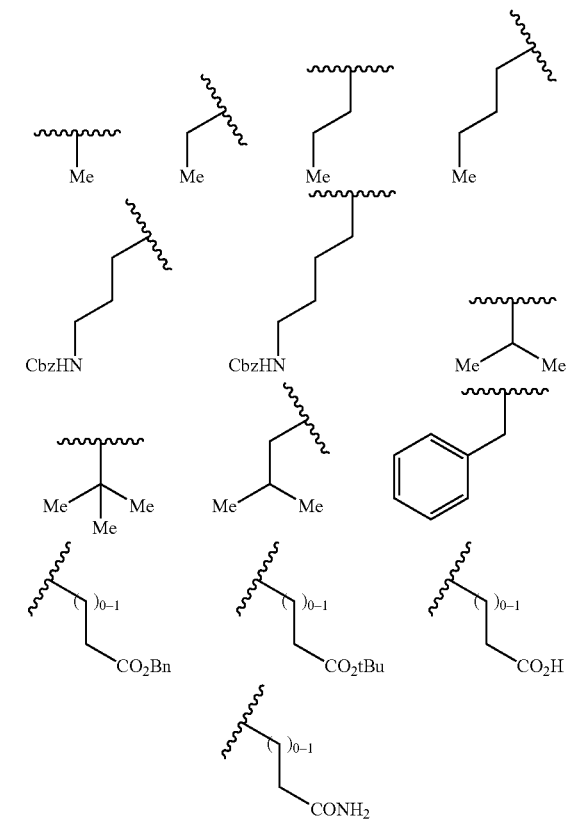
and $Y^{14}$ is selected from MeSO$_2$, Ac, Boc, $^t$Boc, Cbz, or Alloc.

Additional preferred structures for Y are:
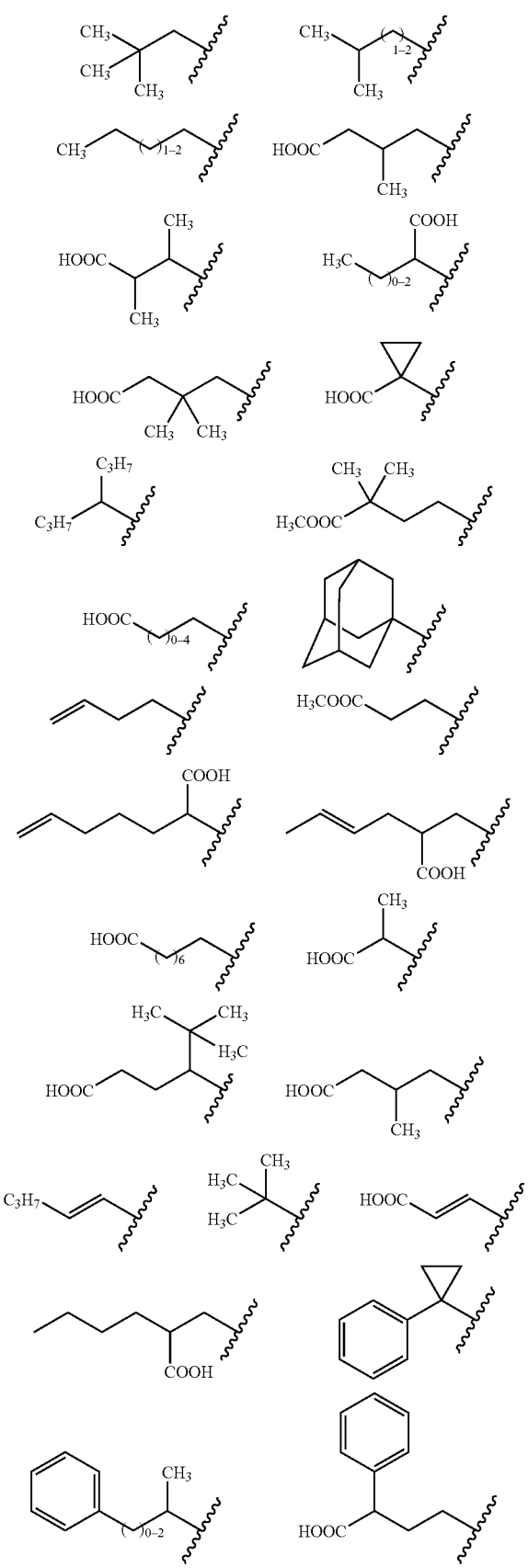
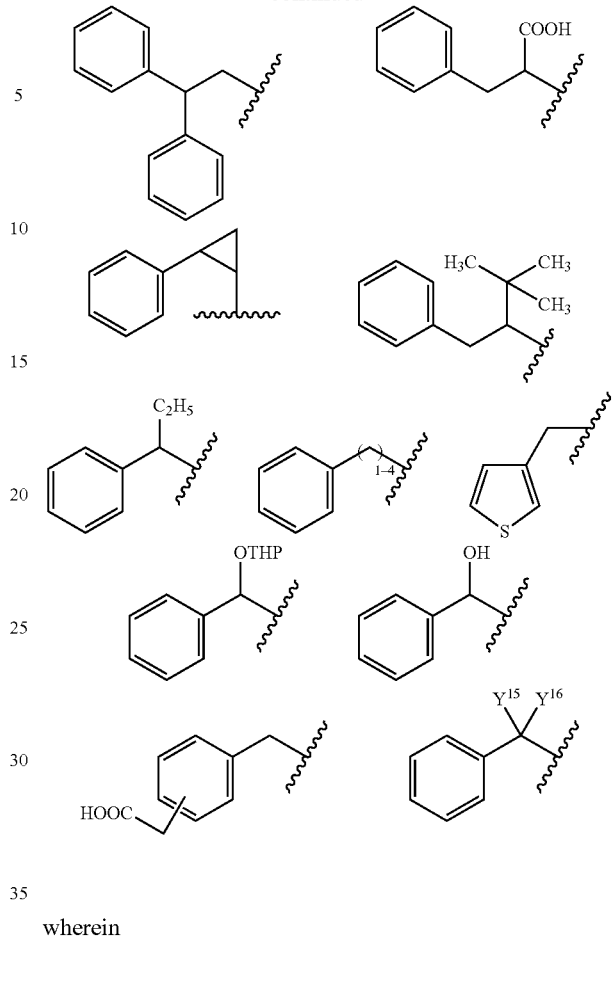
wherein
$Y^{15}$ and $Y^{16}$ may be the same or different and are independently selected from alkyl, aryl or herereoalkyl, or heteroaryl.
Still additional representations for Y are:
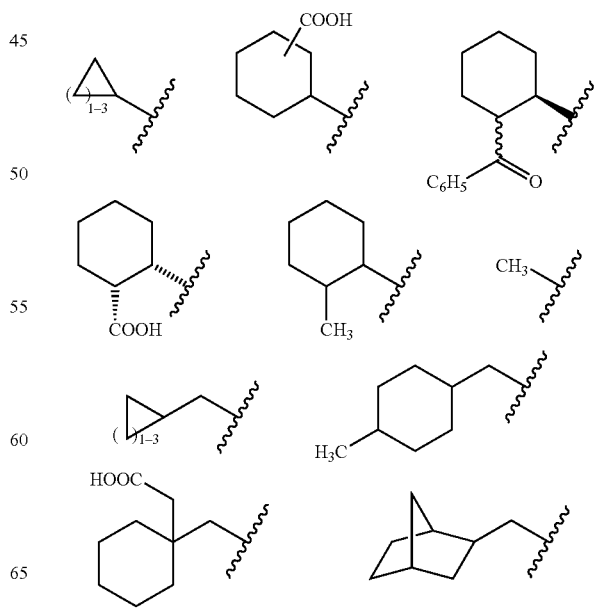

-continued
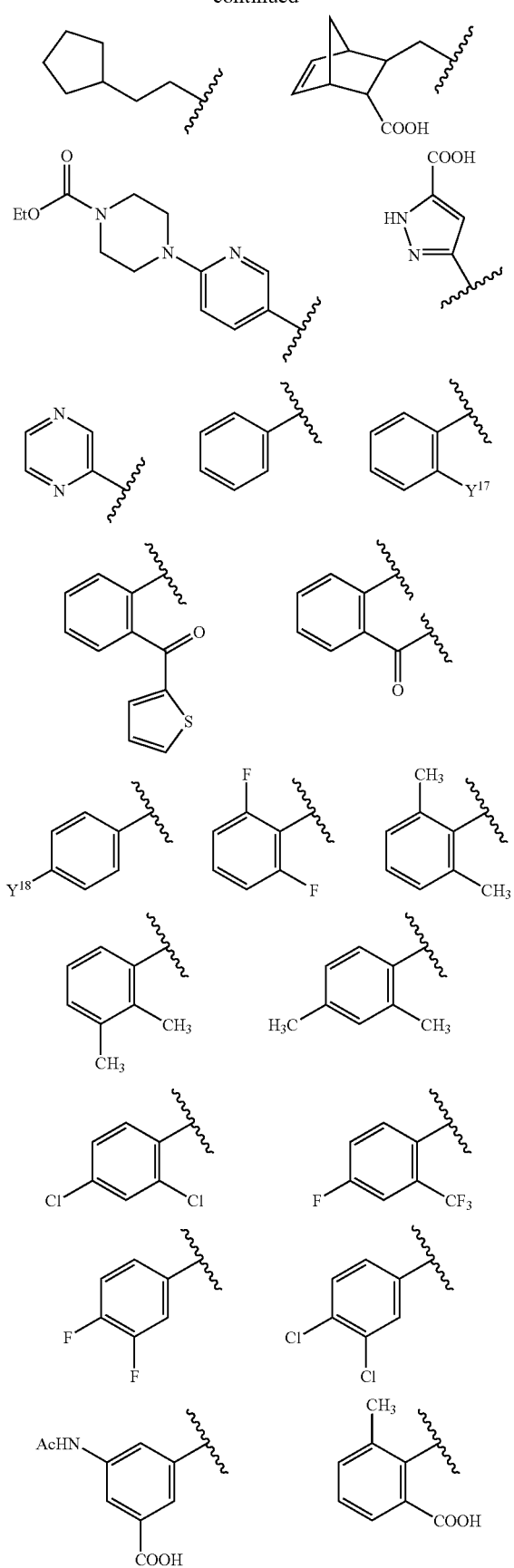
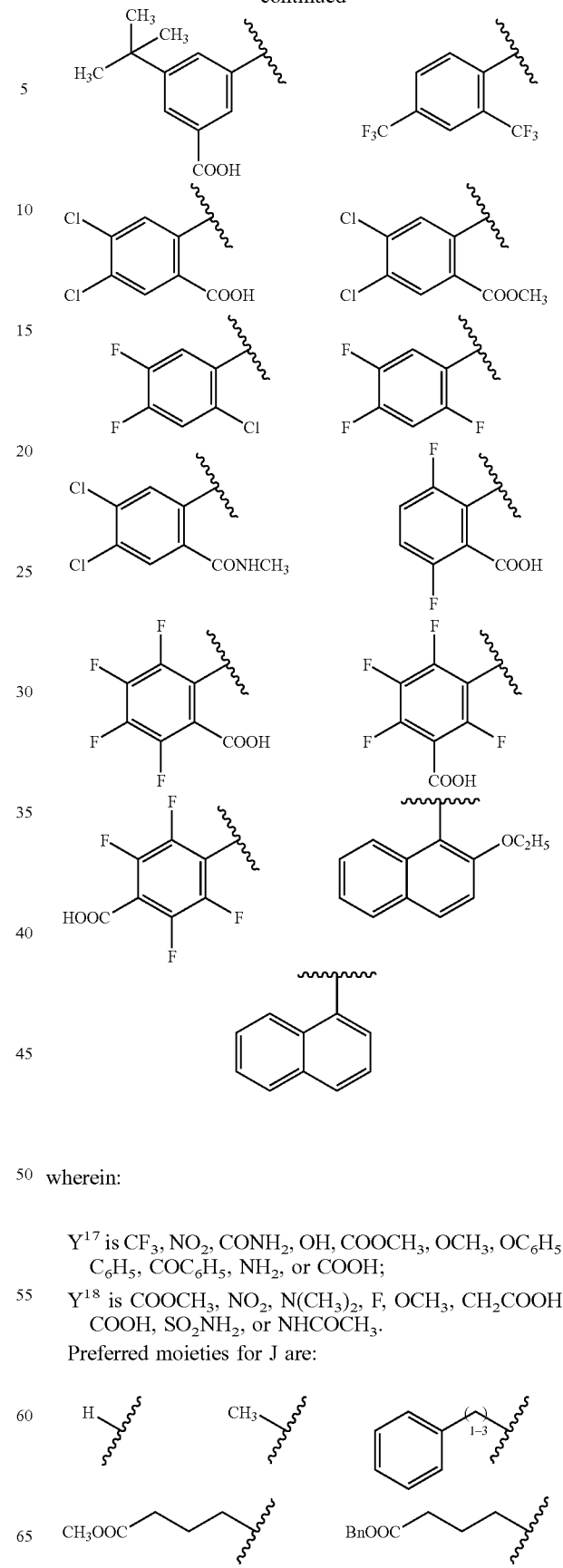
wherein:
$Y^{17}$ is $CF_3$, $NO_2$, $CONH_2$, OH, $COOCH_3$, $OCH_3$, $OC_6H_5$, $C_6H_5$, $COC_6H_5$, $NH_2$, or COOH;
$Y^{18}$ is $COOCH_3$, $NO_2$, $N(CH_3)_2$, F, $OCH_3$, $CH_2COOH$, COOH, $SO_2NH_2$, or $NHCOCH_3$.
Preferred moieties for J are:
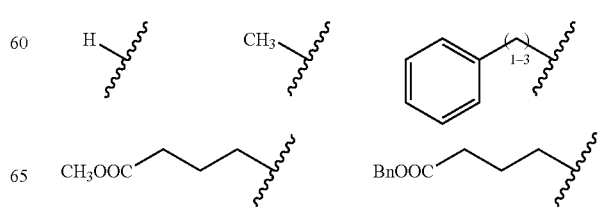

-continued
Preferred moieties for G are:
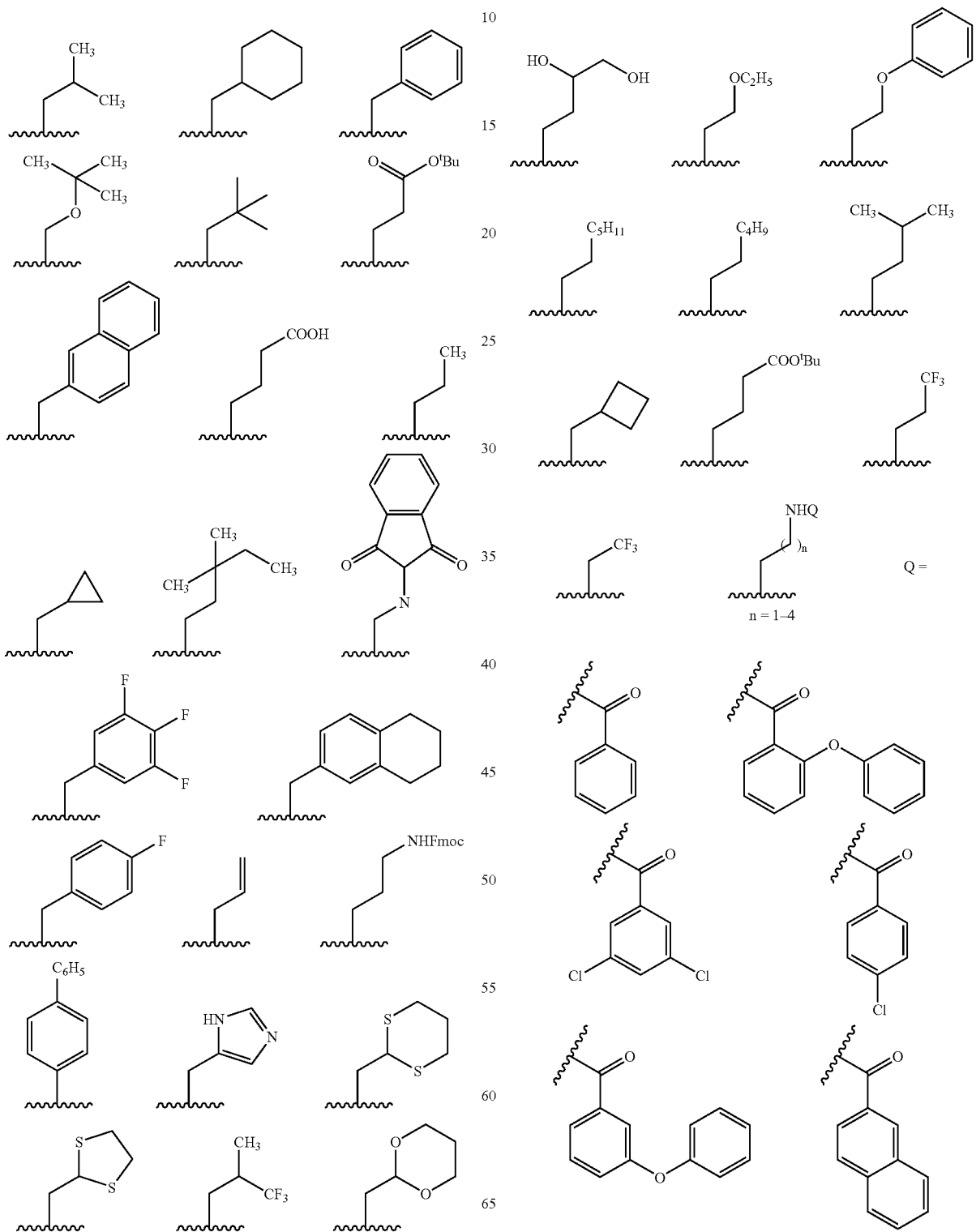

-continued

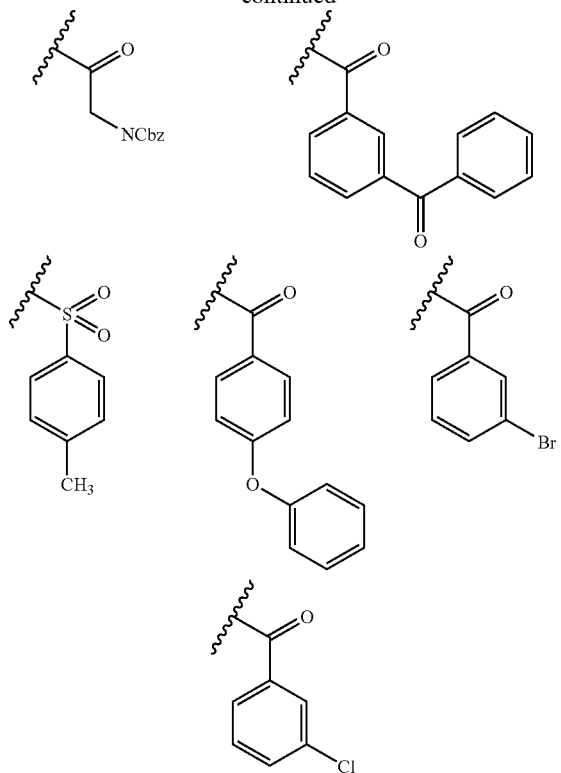

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclyl group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted. Additionally, unless otherwise specifically defined, the term "substituted or unsubstituted" or "optionally substituted" refers to the subject moiety being optionally and chemically suitably substituted with a moiety belonging to $R^{12}$ or $R^{13}$.

Also included in the invention are tautomers, rotamers, enantiomers and other optical isomers of compounds of Formula I, as well as pharmaceutically acceptable salts, solvates and derivatives thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, HCV and related disorders. The methods for treating comprise administering to a patient suffering from said disease or diseases a therapeutically effective amount of a compound of Formula I, or pharmaceutical compositions comprising a compound of Formula I.

Also disclosed is the use of a compound of Formula I for the manufacture of a medicament for treating HCV and related disorders.

DETAILED DESCRIPTION OF PREFERRED EMBODIMENTS

In one embodiment, the present invention discloses compounds of Formula I as inhibitors of HCV protease, especially the HCV NS3/NS4a serine protease, or a pharmaceutically acceptable derivative thereof, where the various definitions are given above.

Representative compounds of the invention which exhibit excellent HCV protease inhibitory activity are listed below in Table 1 along with their activity (ranges of $K_i^*$ values in nanomolar, nM).

TABLE 1

Compounds and HCV protease continuous assay results

| Compound from Example No. | Ki* Range |
|---|---|
| 1 | C |
| 2 | B |
| 3 | C |
| 4 | C |
| 5 | B |
| 6 | C |
| 7 | C |
| 8 | C |
| 9 | C |
| 10 | C |
| 11 | A |
| 12 | C |
| 13 | B |
| 14 | C |
| 15 | B |
| 16 | A |
| 17 | B |
| 18 | A |
| 19 | not available |

TABLE 1-continued

Compounds and HCV protease continuous assay results

| Compound from Example No. | Ki* Range |
|---|---|
| 20 | C |
| 21 | B |
| 22 | C |
| 23 | C |
| 24 | B |
| 25 | A |
| 26 | C |
| 27 | C |
| 28 | B |
| 29 | C |
| 30 | B |
| 31 | C |
| 32 | B |
| 33 | C |
| 34 | B |
| 35 | C |
| 36 | C |
| 37 | C |
| 38 | B |
| 39 | C |
| 40 | C |
| 41 | B |
| 42 | C |
| 43 | A |
| 44 | C |
| 45 | C |
| 47 | C |
| 48 | B |
| 49 | A |
| 50 | C |
| 51 | B |
| 52 | B |
| 53 | B |
| 54 | B |
| 55 | C |
| 56 | B |
| 57 | B |
| 58 | C |
| 59 | B |
| 60 | C |
| 61 | C |
| 62 | A |
| 63 | C |
| 64 | B |
| 65 | C |
| 66 | B |
| 67 | C |
| 68 | B |
| 69 | B |
| 70 | B |
| 71 | B |
| 72 | B |
| 73 | A |
| 74 | B |
| 75 | B |
| 76 | B |
| 77 | C |
| 78 | B |
| 79 | C |
| 80 | B |
| 81 | B |
| 82 | C |
| 83 | C |
| 84 | C |
| 85 | C |
| 86 | C |
| 87 | B |
| 88 | B |
| 89 | C |
| 90 | B |
| 91 | B |
| 92 | C |
| 93 | C |
| 94 | B |

TABLE 1-continued

Compounds and HCV protease continuous assay results

| Compound from Example No. | Ki* Range |
|---|---|
| 95 | B |
| 96 | A |
| 97 | A |
| 98 | A |
| 99 | B |
| 100 | B |
| 101 | B |
| 102 | B |
| 103 | C |
| 104 | C |
| 105 | B |
| 106 | A |
| 107 | C |
| 108 | B |
| 109 | B |
| 110 | A |
| 111 | B |
| 112 | B |
| 113 | A |
| 114 | A |
| 115 | C |
| 116 | B |
| 117 | B |
| 118 | B |
| 119 | B |
| 120 | A |
| 121 | B |
| 122 | A |
| 123 | C |
| 124 | B |
| 125 | A |
| 126 | A |
| 127 | A |
| 128 | B |
| 129 | C |
| 130 | A |
| 131 | C |
| 132 | B |
| 133 | B |

HCV continuous assay Ki* range:

Category A=0–100; B=101–1000; C=>1000 nM.

Some of the types of the inventive compounds and methods of synthesizing the various types of the inventive compounds of Formula I are listed below, then schematically described, followed by the illustrative Examples.

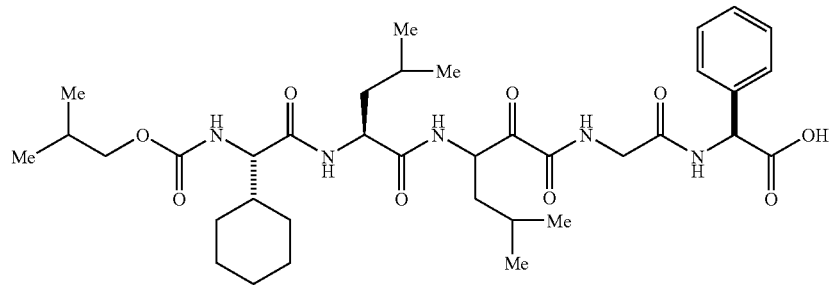
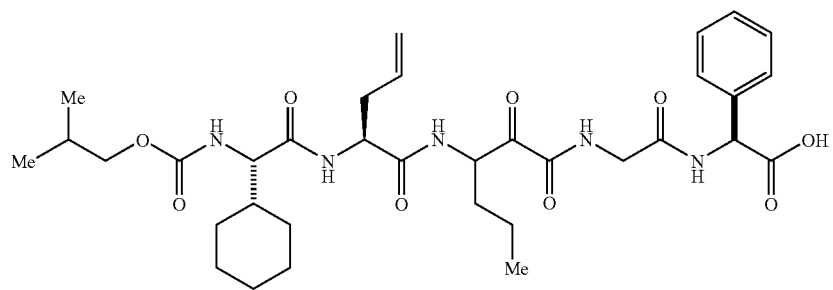
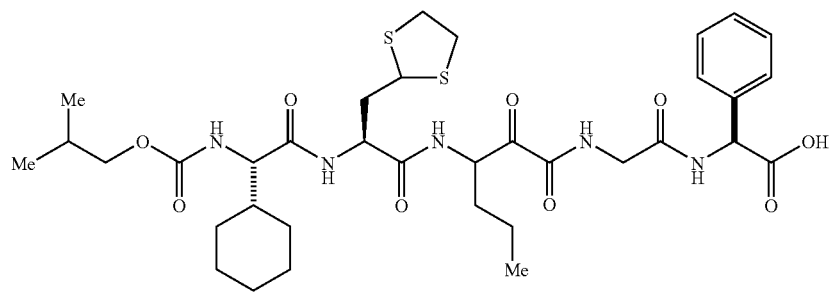
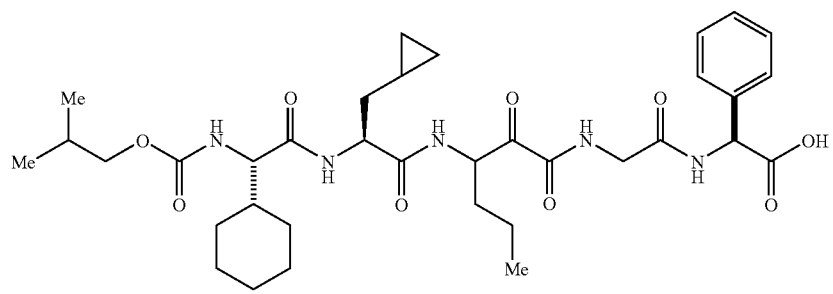

-continued

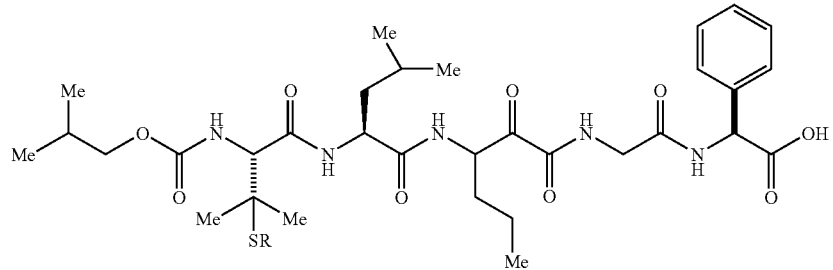
R = Me
R = Benzyl
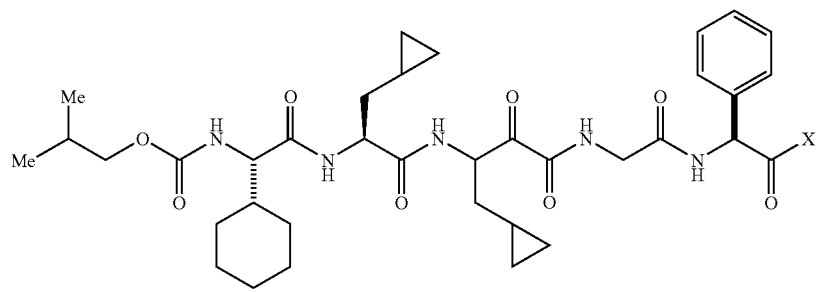
X = O$^t$Bu
X = OH
X = NH$_2$
X = NMeOMe
X = NMe$_2$
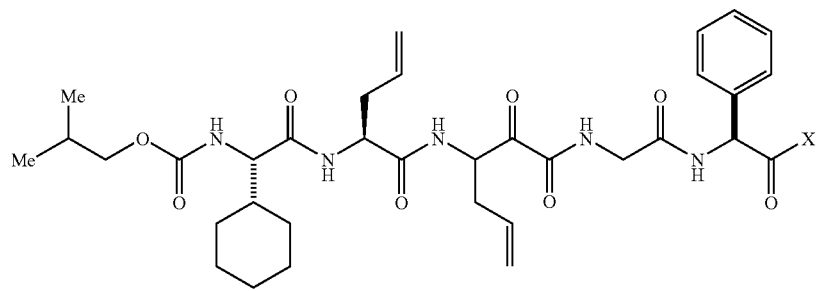
X = O$^t$Bu
X = OH
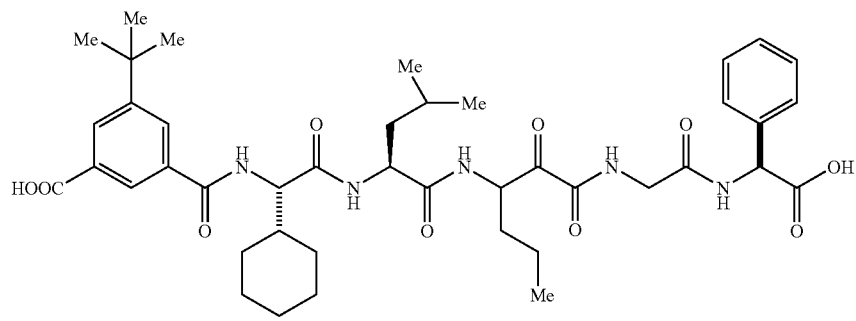

-continued
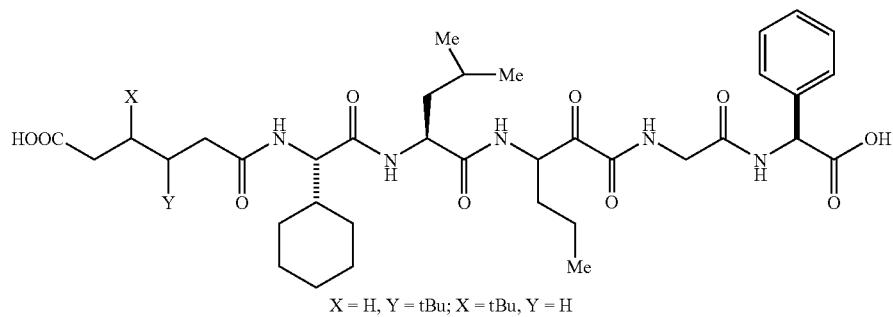
X = H, Y = tBu; X = tBu, Y = H
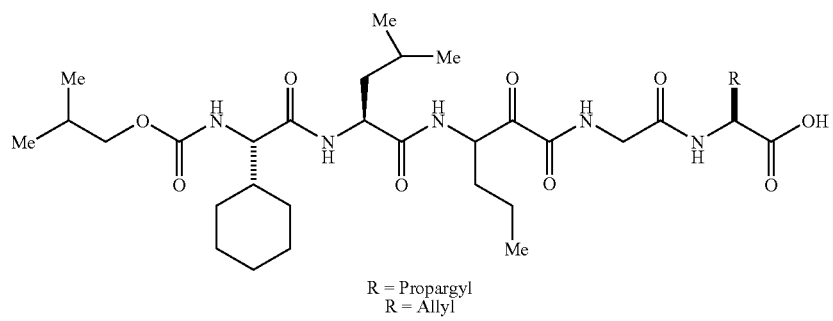
R = Propargyl
R = Allyl
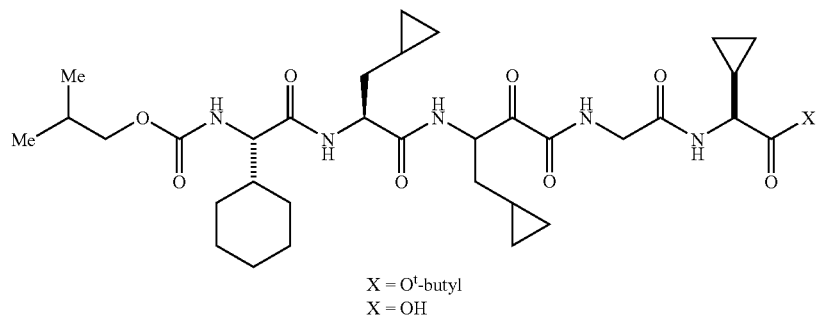
X = O$^t$-butyl
X = OH
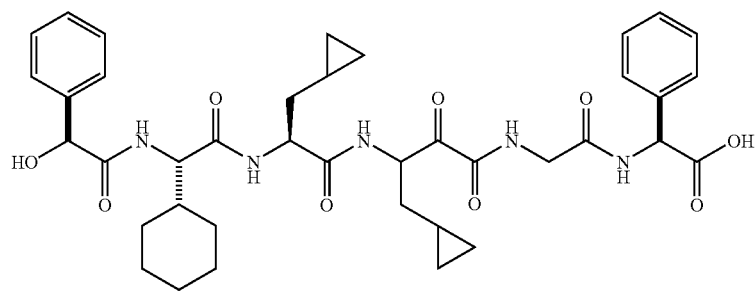
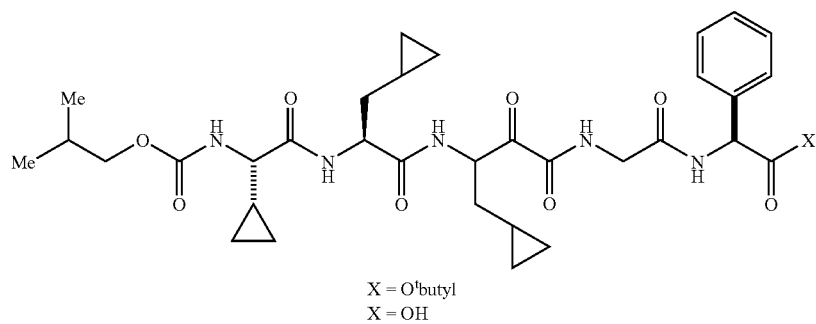
X = O$^t$butyl
X = OH

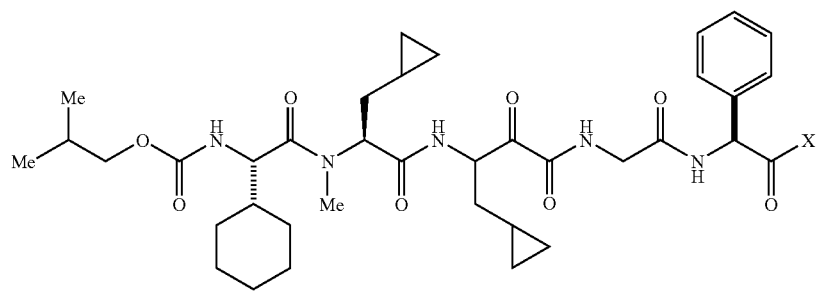
X = O^tbutyl
X = OH
X = NMe₂
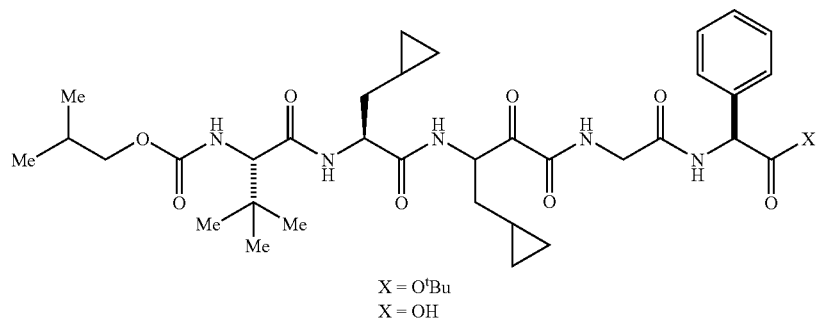
X = O^tBu
X = OH
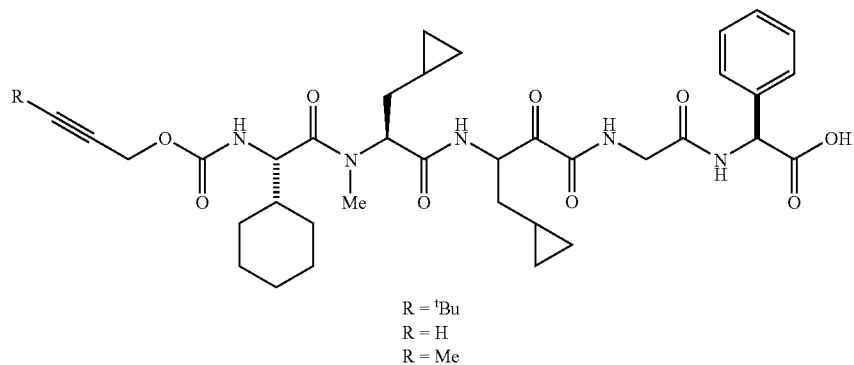
R = ^tBu
R = H
R = Me
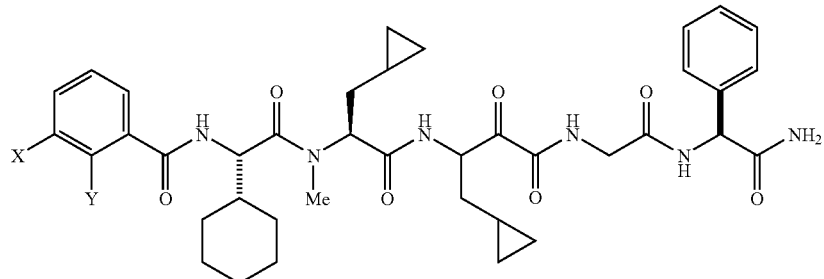
X = H, Y = COOH
X = COOH, Y = H
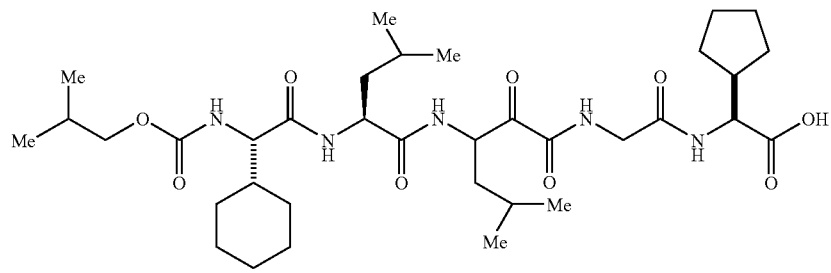

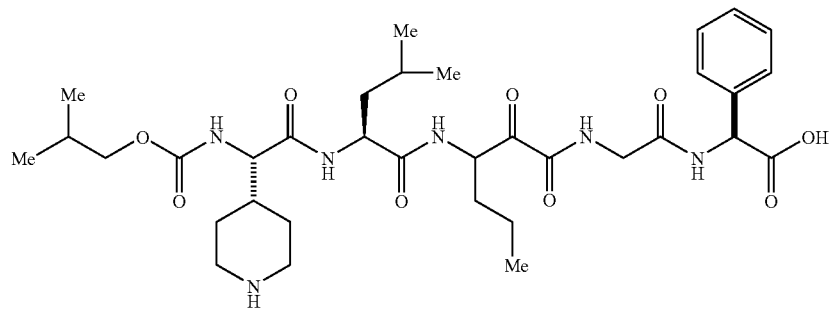
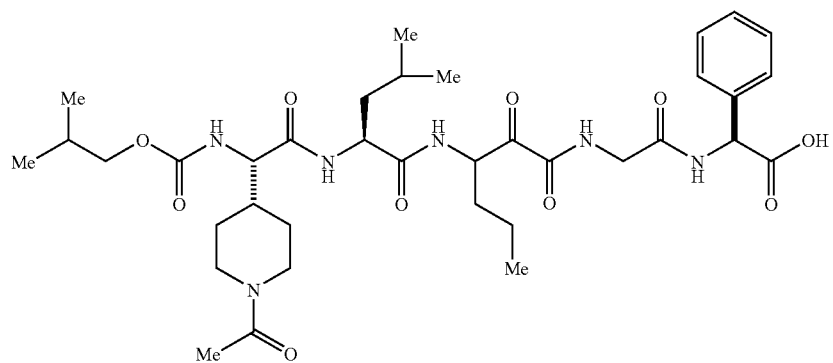
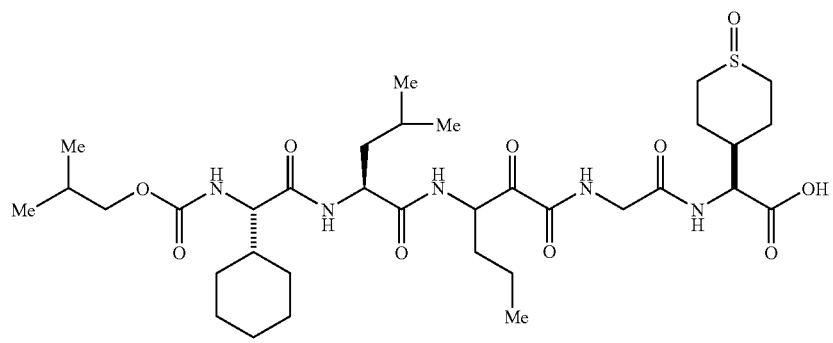
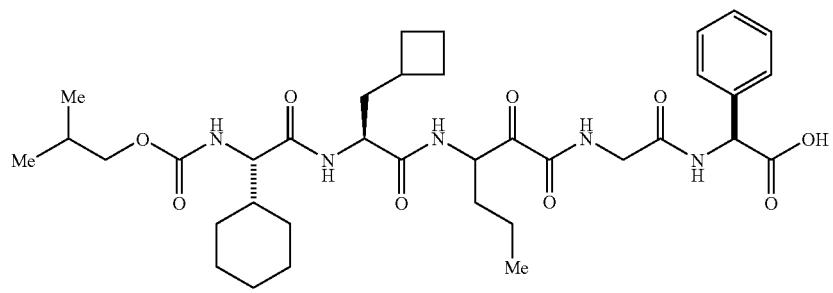
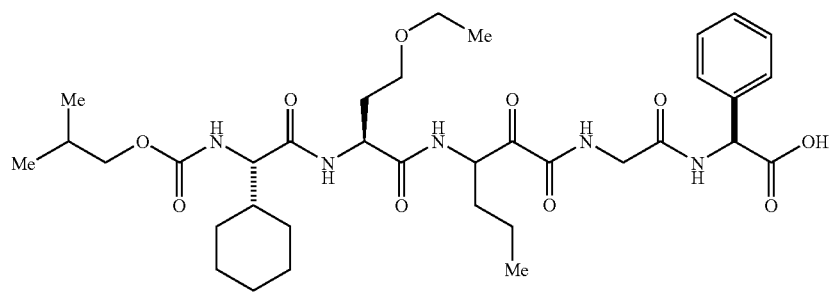

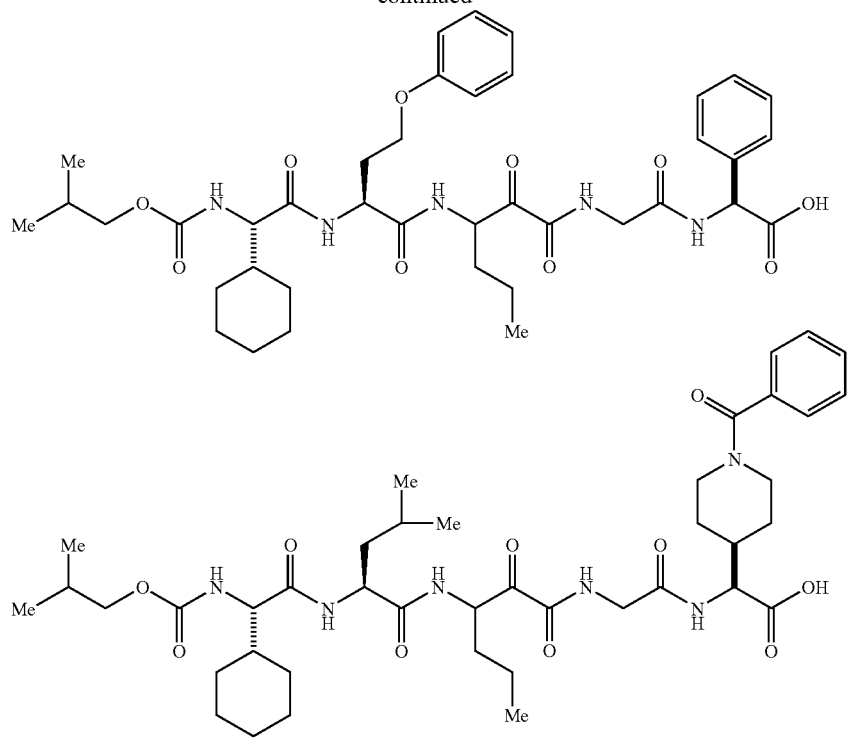

Depending upon their structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, NH$_4$OH, tetraalkylammonium hydroxide, and the like.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy mode such as, for example, in combination with antiviral agents such as, for example, ribavirin and/or interferon such as, for example, α-interferon and the like.

As stated earlier, the invention includes tautomers, rotamers, enantiomers and other stereoisomers of the compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
DEC: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
$Et_2O$: Diethyl ether
DMSO: Dimethylsulfoxide
HOBt: N-Hydroxybenzotriazole
PyBrOP: Bromo-tris-pyrrolidinophosphonium hexafluorophosphate
Bn: Benzyl
Bzl: Benzyl
Et: Ethyl
Ph: Phenyl
iBoc: isobutoxycarbonyl
iPr: isopropyl
$^tBu$ or $Bu^t$: tert-Butyl
Boc: tert-Butyloxycarbonyl
Cbz: Benzyloxycarbonyl
Cp: Cylcopentyidienyl
Ts: p-toluenesulfonyl
Me: Methyl
THP: Tetrahydropyranyl
iBoc: isobutyloxycarbonyl
Chg: cyclohexylglycine General Preparative Schemes The following schemes describe the methods of synthesis of intermediate building blocks:

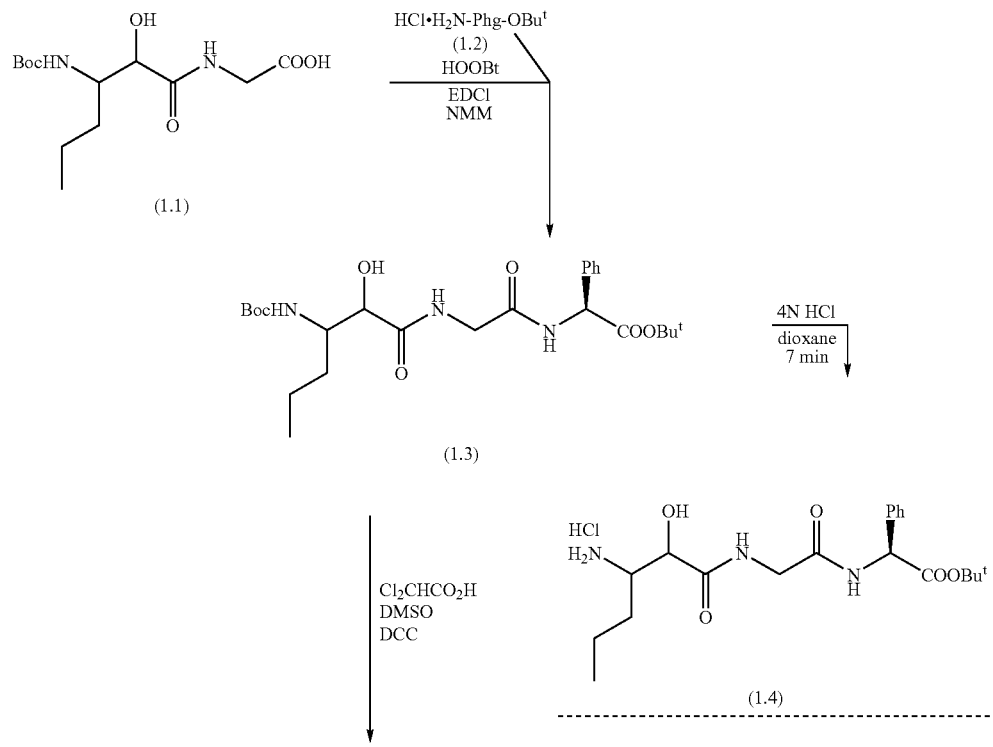

SCHEME 1

-continued
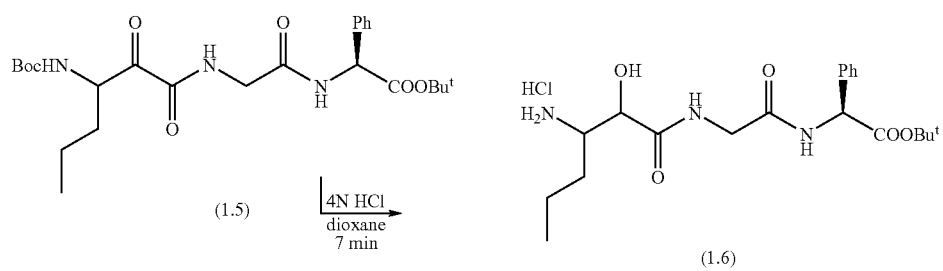
SCHEME 2
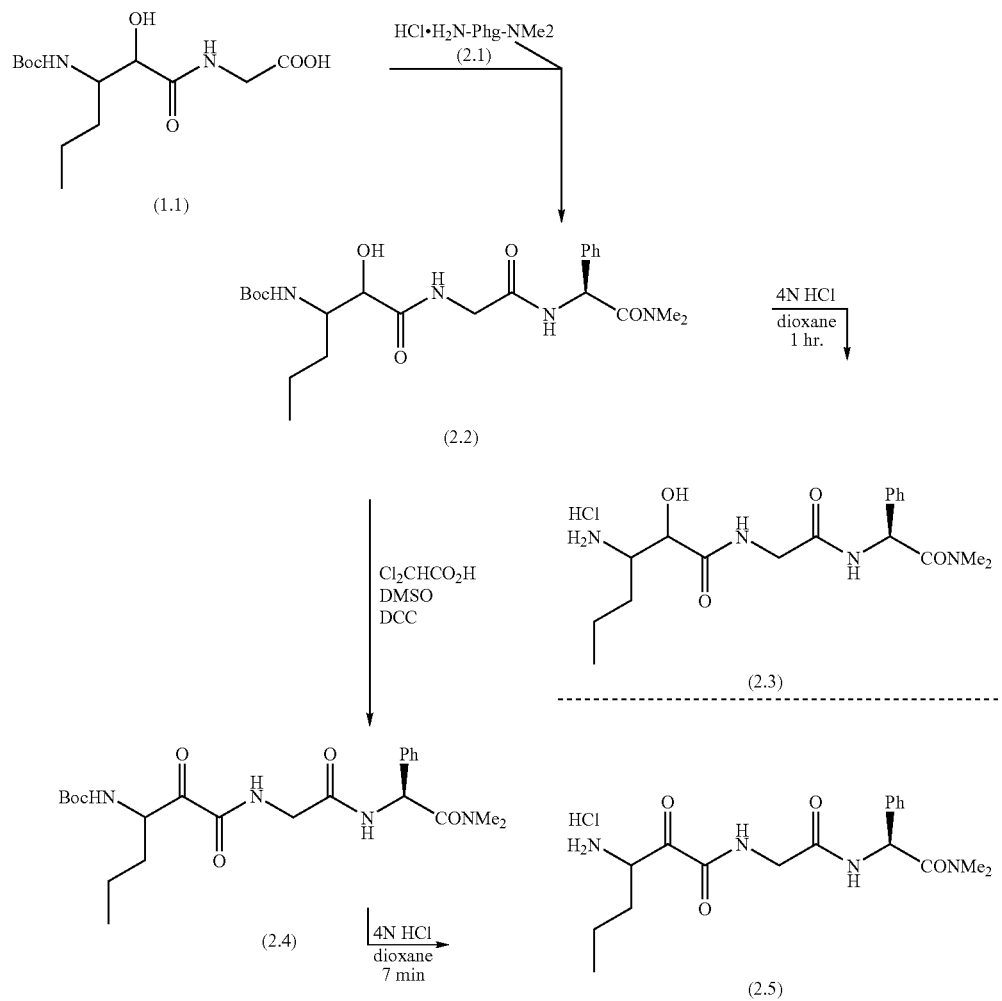
SCHEME 3
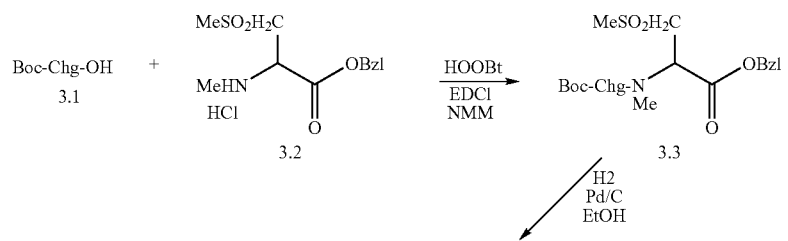

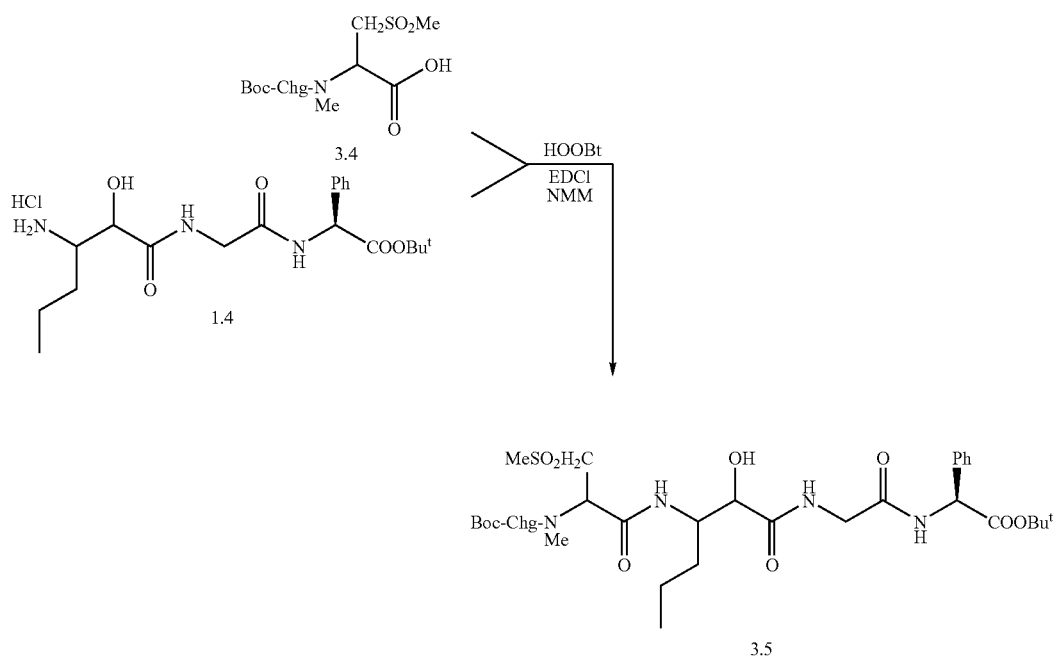
SCHEME 4
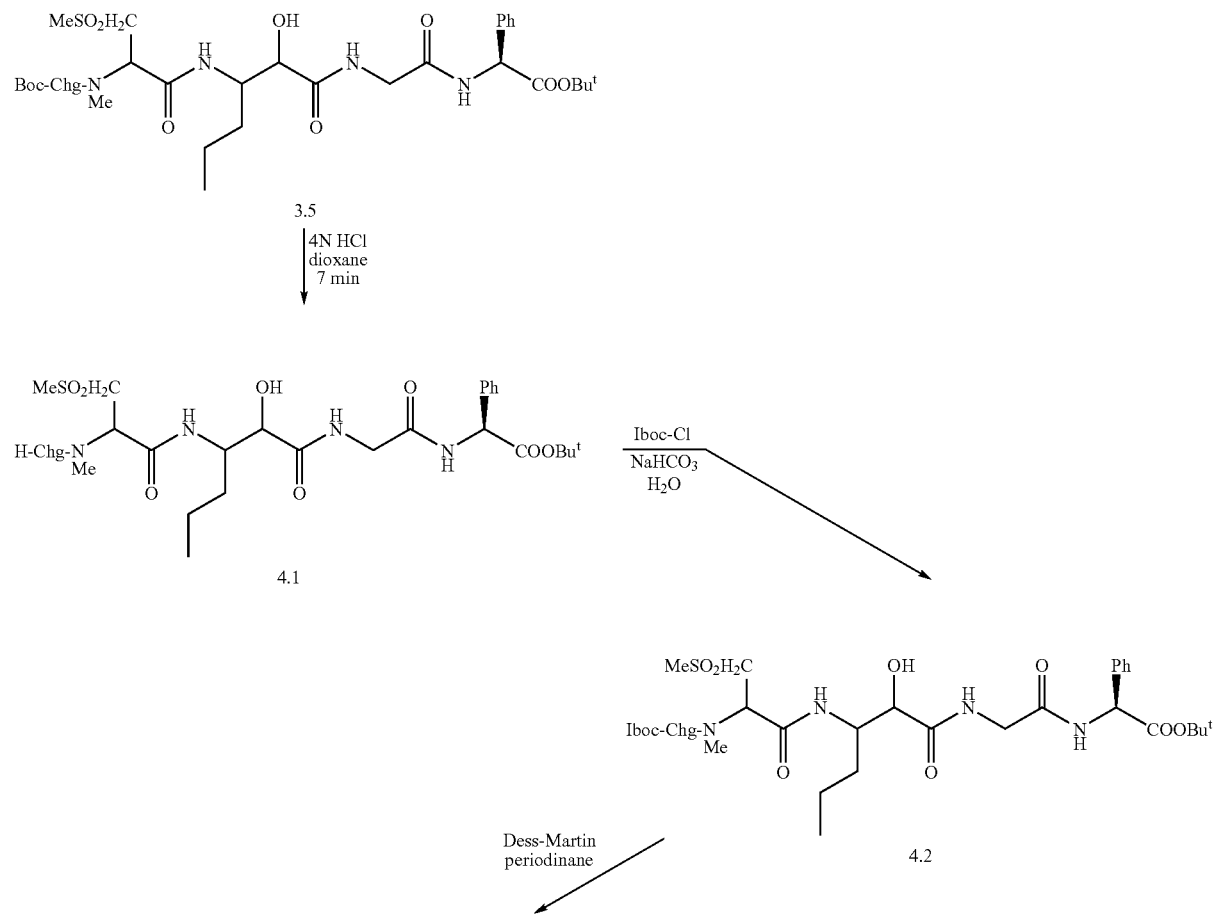

-continued

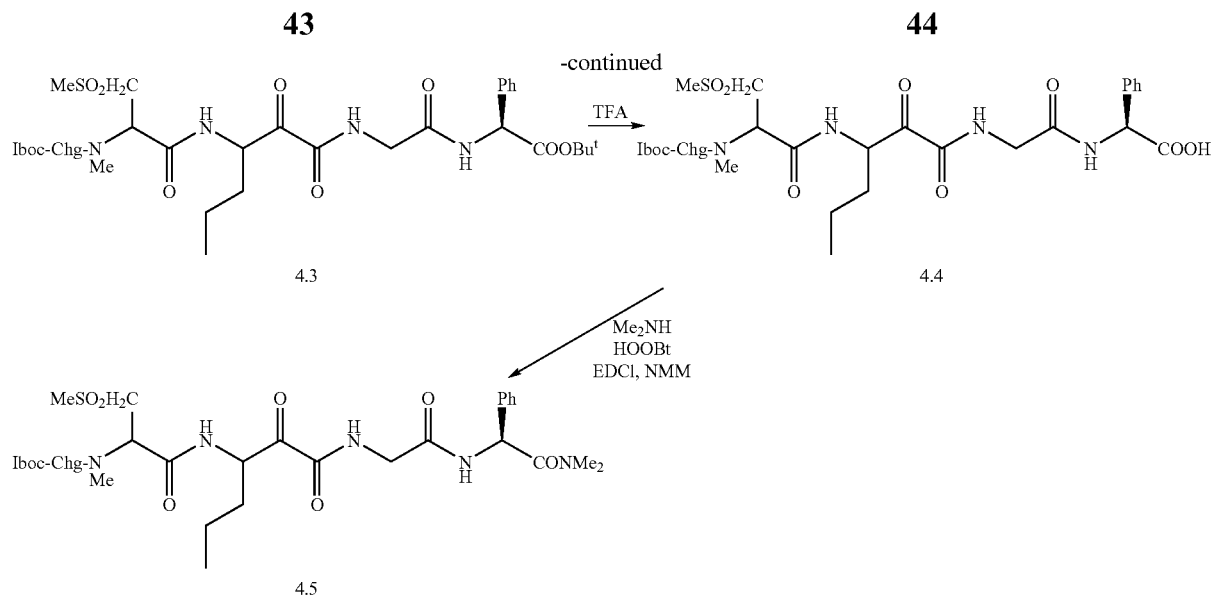

PREPARATION OF INTERMEDIATES

PREPARATIVE EXAMPLE 1

Step A:

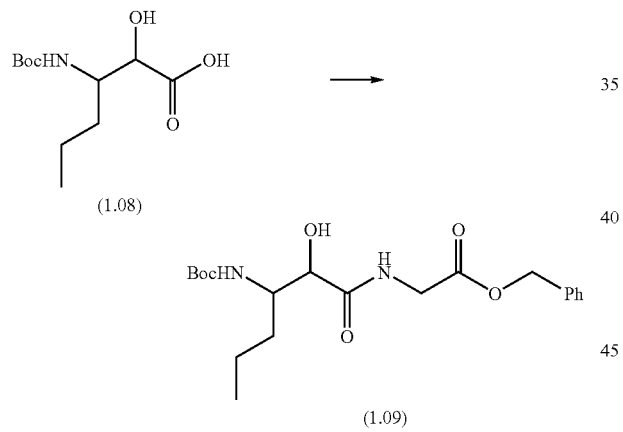

To a stirred solution of compound (1.08)(3.00 g, 12.0 mmol; Harbeson, S. L.; Abelleira, S. M.; Akiyama, A.; Barrett, R.; Carroll, R. M.; et al.; *J.Med.Chem.;* 37 (18) 1994; 2918–2929;) in DMF (15 mL) and CH$_2$Cl$_2$ (15 mL) at −20° C. was added HOOBt (1.97 g, 12.0 mmol), N-methyl morpholine (4.0 mL, 36.0 mmol) and EDCl (2.79 g, 14.5 mmol) and stirred for 10 minutes, followed by addition of HCl.H$_2$N-Gly-OBn (2.56 g, 13.0 mmol). The resulting solution was stirred at −20° C. for 2 hrs, kept refrigerated overnight and then concentrated to dryness, followed by dilution with EtOAc (150 mL). The EtOAc solution was then washed twice with saturated NaHCO3, H2O, 5% H$_3$PO$_4$, brine, dried over Na$_2$SO$_4$, filtered and concentrated to dryness to give the Compound (1.09) (4.5 g, 94%). LRMS m/z MH$^+$=395.1.

Step B:

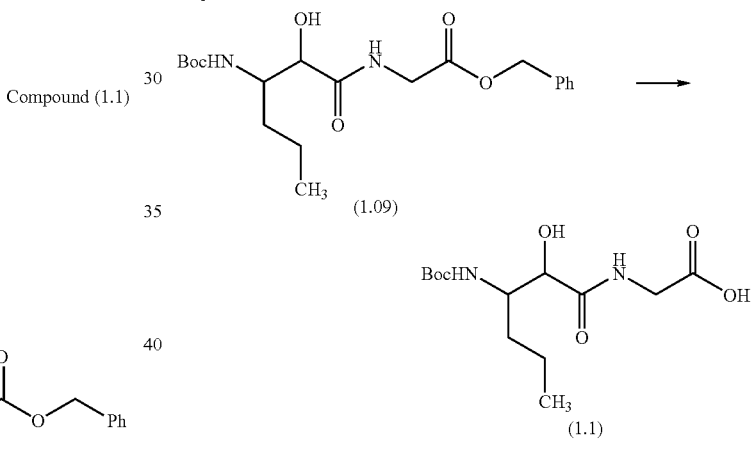

A solution of compound (1.09) (7.00 g, 17.8 mmol) in absolute ethanol (300 mL) was stirred at room temperature under a hydrogen atmosphere in the presence of Pd-C (300 mg, 10%). The reaction progress was monitored by tlc. After 2 h, the mixture was filtered through a celite pad and the resulting solution was concentrated in vacuo to give Compound (1.1) (5.40 g, quantitative). LRMS m/z MH$^+$=305.1.

PREPARATIVE EXAMPLE 2

Step A

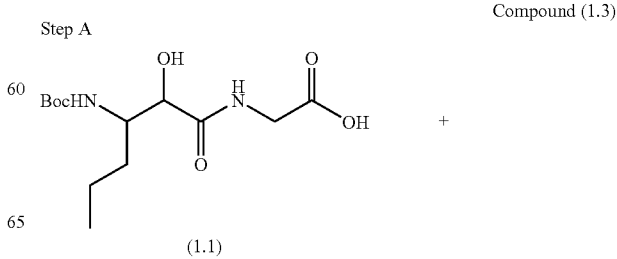

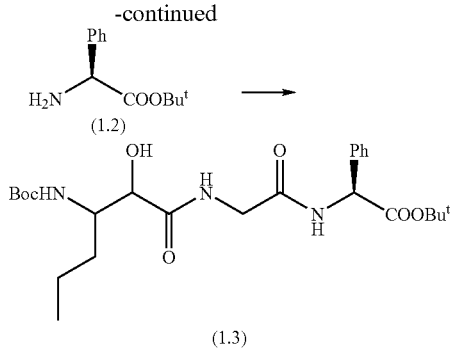

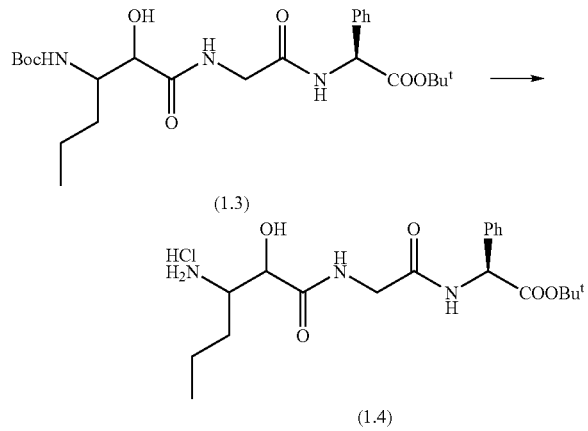

A mixture of Compound (1.1) from Preparative Example 1, Step B (1 eq.), Compound (1.2) (Novabiochem, No. 04-12-5147) (1.03 eq.), HOOBt (1.03 eq.), N-methylmorpholine (2.2 eq.), and dimethylformamide (70 mL/g) was stirred at −20° C. EDCl (1.04 eq.) was added and the reaction stirred for 48 hr. The reaction mixture was poured into 5% aqueous KH$_2$PO$_4$ and extracted with ethyl acetate (2 x). The combined organics were washed with cold 5% aqueous K$_2$CO$_3$, then 5% aqueous KH$_2$PO$_4$, then brine, and the organic layer was dried over anhydrous MgSO$_4$. The mixture was filtered, then evaporated and the filtrate dried under vacuum, the residue was triturated with Et$_2$O-hexane, and filtered to obtain the title compound (1.3)(86% yield), C$_{25}$H$_{39}$N$_3$O$_7$ (493.60), mass spec. (FAB) M+1=494.3.

Compound (1.4)

Step B

Compound (1.3) from Preparative Example 2, Step A (3.0 g) was treated with 4 N HCl/dioxane (36 mL) and stirred at room temperature for 7 min. The mixture was poured into 1.5 L cold (5° C.) hexane and stirred, then allowed to stand at 0° C. for 0.5 hr. The mixture was suction-filtered in a dry atmosphere, and the collected solid was further dried to afford the title compound (1.4) (2.3 g, 88% yield), C$_{20}$H$_{31}$N$_3$O$_5$.HCl, H$^1$ NMR (DMSO-d$_6$/NaOD) δ 7.38 (m, 5H), 5.25 (m, 1H), 4.3–4.1 (m, 1H), 3.8 (m, 2H), 3.4–3.3 (m, obscured by HDO), 1.7–1.1 (m, 4H), 1.35 (s, 9H), 0.83 (m, 3H).

PREPARATIVE EXAMPLE 3

Compound (1.5)

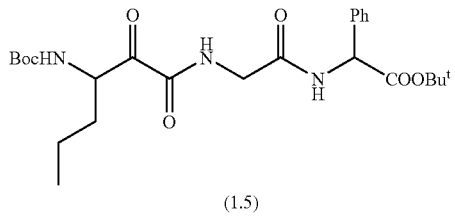

Compound (1.3) from Preparative Example 2, Step A, was treated in essentially the same manner as in Preparative Example 7, Step A below to afford Compound (1.5).

PREPARATIVE EXAMPLE 4

Compound (1.6)

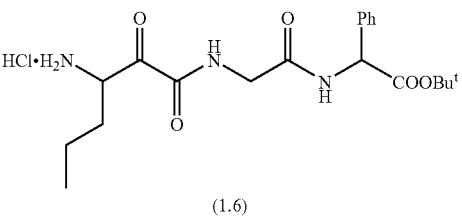

Compound (1.5) from Preparative Example 3, was treated in essentially the same manner as in Preparative Example 2, Step B, to afford Compound (1.6).

PREPARATIVE EXAMPLE 5

Compound (2.09)

Step A

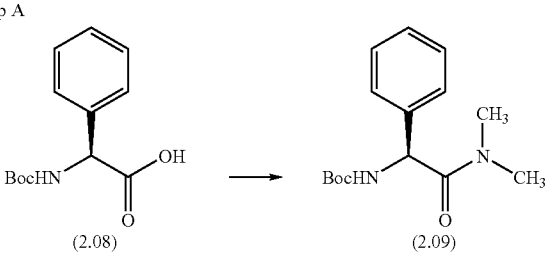

To a solution of dimethylamine hydrochloride (1.61 g, 19.7 mmol), N-Boc-phenylglycine, compound 2.08 (4.50 g, 17.9 mmol, Bachem Co. # A-2225), HOOBt (3.07 g, 18.8 mmol) and EDCl (4.12 g, 21.5 mmol) in anhydrous DMF (200 mL) and CH$_2$Cl$_2$ (150 mL) at −20° C. was added NMM (5.90 mL, 53.7 mmol). After being stirred at this temperature for 30 min, the reaction mixture was kept in a freezer overnight (18 h). It was then allowed to warm to rt, and EtOAc (450 mL), brine (100 mL) and 5% H$_3$PO$_4$ (100 mL) were added. After the layers were separated, the organic layer was washed with 5% H$_3$PO$_4$ (100 mL), saturated aqueous sodium bicarbonate solution (2×150 mL), water (150 mL), and brine (150 mL), dried (MgSO$_4$), filtered and concentrated in vacuo to afford Compound (2.09) (4.86 g) as a white solid, which was used without further purification.

Step B

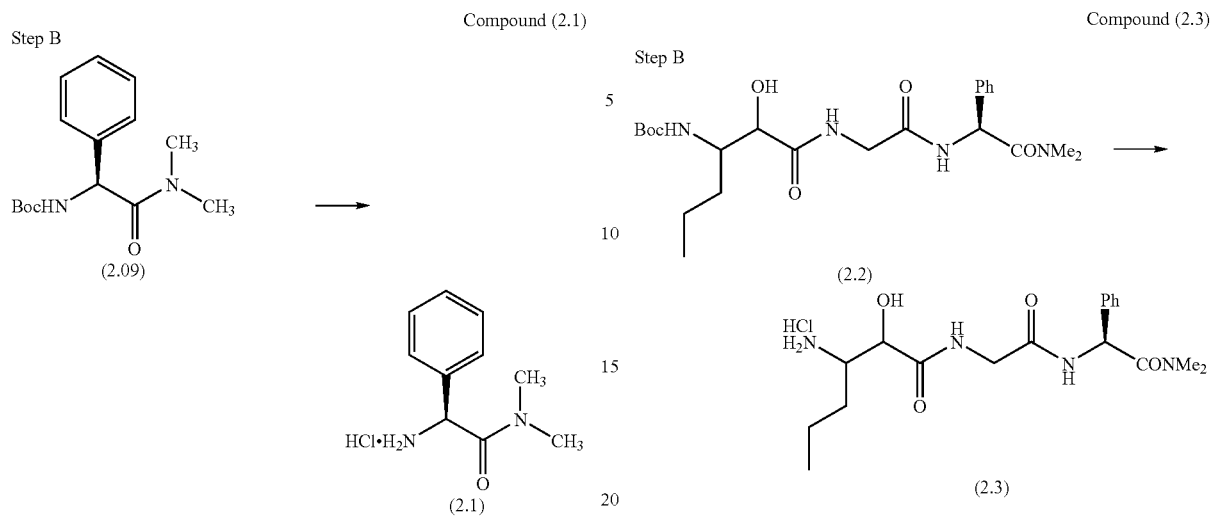

Compound (2.09) from Preparative Example 5, Step A (4.70 g, crude) was dissolved in 4 N HCl (60 mL, 240 mmol) and the resulting solution was stirred at room temperature. The progress of the reaction was monitored by TLC. After 4 h, the solution was concentrated in vacuo to yield Compound (2.1) as a white solid which was used in the next reaction without further purification. LRMS m/z MH$^+$= 179.0.

PREPARATIVE EXAMPLE 6

Step A

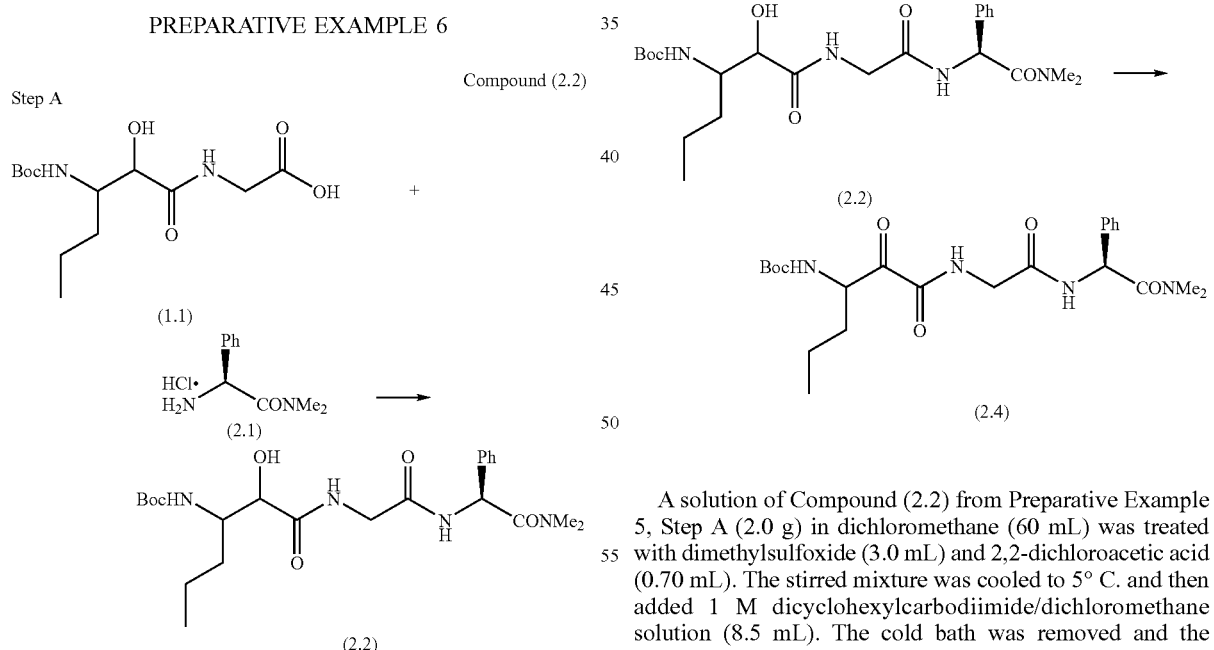

In essentially the same manner as Preparative Example 2, Step A. substituting phenylglycine N,N-dimethylamide hydrochloride in place of phenylglycine t-butyl ester hydrochloride, Compound (2.2) was prepared mass spec. (FAB) M+1=465.3.

Step B

Compound (2.2) from Step A (1.85 g) was reacted with 4 N HCl/dioxane (50 mL) at room temperature for 1 hr. The mixture was evaporated under vacuum in a 20° C. water bath, triturated under isopropyl ether, filtered, and dried to afford Compound (2.3) (1.57 g, 98% yield), $C_{18}H_{28}N_4O_4 \cdot HCl$, mass spec. (FAB) M+1=365.3

PREPARATIVE EXAMPLE 7

Step A

A solution of Compound (2.2) from Preparative Example 5, Step A (2.0 g) in dichloromethane (60 mL) was treated with dimethylsulfoxide (3.0 mL) and 2,2-dichloroacetic acid (0.70 mL). The stirred mixture was cooled to 5° C. and then added 1 M dicyclohexylcarbodiimide/dichloromethane solution (8.5 mL). The cold bath was removed and the mixture stirred for 22 hr. Then added 2-propanol (0.5 mL), and stirred for an additional 1 hr. The mixture was filtered then washed with ice-cold 0.1 N NaOH (50 mL), then ice-cold 0.1 N HCl (50 mL), then 5% aqueous $KH_2PO_4$, then saturated brine. The organic solution was dried over anydrous magnesium sulfate, then filtered. The filtrate was evaporated, and chromatographed on silica gel, eluting with ethyl acetate to afford Compound (2.3) (1.87 g, 94% yield), $C_{23}H_{34}N_4O_6$, mass spec. (FAB) M+1=463.3.

Compound (2.5)

Step B

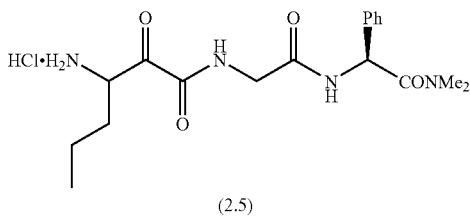

(2.5)

In essentially the same manner as Preparative Example 2, Step B Compound (2.5) was prepared.

PREPARATIVE EXAMPLE 8

Compound (3.3)

Step A

Step A-1. Compound 3.02

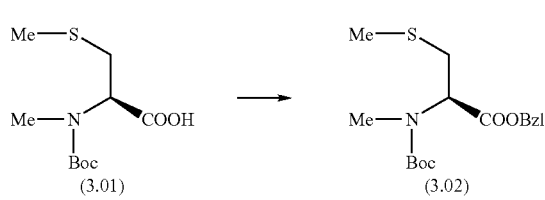

A solution of Compound 3.01 (4.6 g, prepared from N-Boc-S-methylcysteine, Bachem Biosciences Inc., according to the procedure of Boger, *J. Org. Chem.*, 1988, 53(3), 487.) in DMF (150 mL) was treated with $Cs_2CO_3$ (6.1 g) followed by benzyl bromide (2.3 mL), and the mixture was stirred at room temperature for 4 hr. The mixture was concentrated in vacuo, and the residue suspended in EtOAc (200 mL). Then mixture was washed with aqueous 5% $KH_2PO_4$, then with brine, and the organic extract was dried over anhydrous $MgSO_4$. The mixture was filtered, and the filtrate evaporated to leave the product 3.02 (6.2 g); $[\alpha]_D$-33.7 (c 1.3, $CHCl_3$).

Compound 3.03

Step A-2.

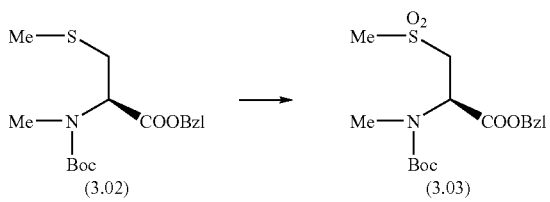

Following the procedure of U. Larsson, et al., *Acta Chem. Scan.*, 1994, 48(6), 517–525, a solution of oxone® (16.4 g, Aldrich Chemical Co.) in water (90 mL) was added slowly to a 0° C. solution of Compound 3.02 (6.1 g) in MeOH (150 mL), The mixture was stirred at room temperature for 4 hr., then concentrated to ½ volume on a rotary evaporator, cold water (100 mL) was added, and the mixture extracted with EtOAc. The extract was washed with brine, and dried over anhydrous $MgSO_4$. The mixture was filtered, and the filtrate evaporated to leave the product 3.03 (5.9 g); $[\alpha]_D$-26.3 (c 0.9, $CHCl_3$).

Compound 3.2

Step A-3.

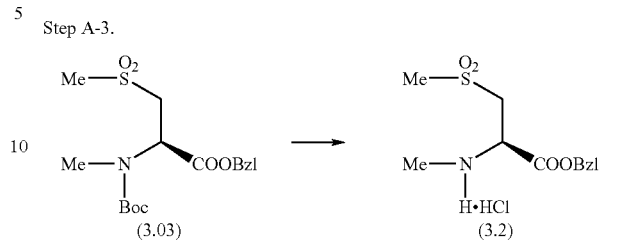

The product 3.03 of the preceding step was treated with 4N Hcl/dioxane for 0.5 hr. to afford the product 3.2, $C_{12}H_{17}NO_4S \cdot HCl$ (307.79); mass spec. (FAB) M+1=272.0.

Preparation of Compound 3.3

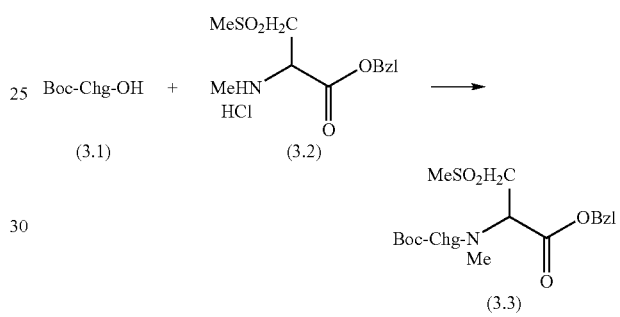

Compound (3.2) (S-methyl cysteine suffone benzyl ester hydrochloride) and Compound (3.1) (N-Boc-cyclohexylglycine) were reacted in essentially the same manner as Preparative Example 2, Step A, to afford Compound (3.3) $C_{25}H_{38}N_2O_7S$ (510.64).

Compound (3.4)

Step B

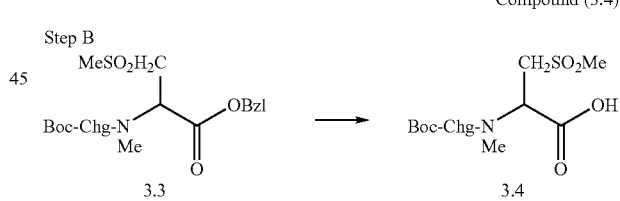

A mixture of Compound (3.3) from Step A above (0.7 g), 10% Pd/C (0.05 g), and EtOH-dioxane (100 mL) was stirred under 3 atm. $H_2$ for 5 hr. The mixture was filtered and evaporated to dryness under vacuum to afford compound (3.4) (0.56 g, 97% yield), $C_{18}H_{32}N_2O_7S$ (420.52) mass spec. (FAB) M+1=421.2.

Compound (3.5)

Step C

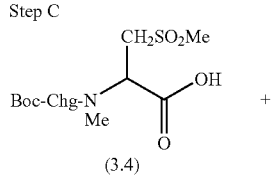

(3.4)

+

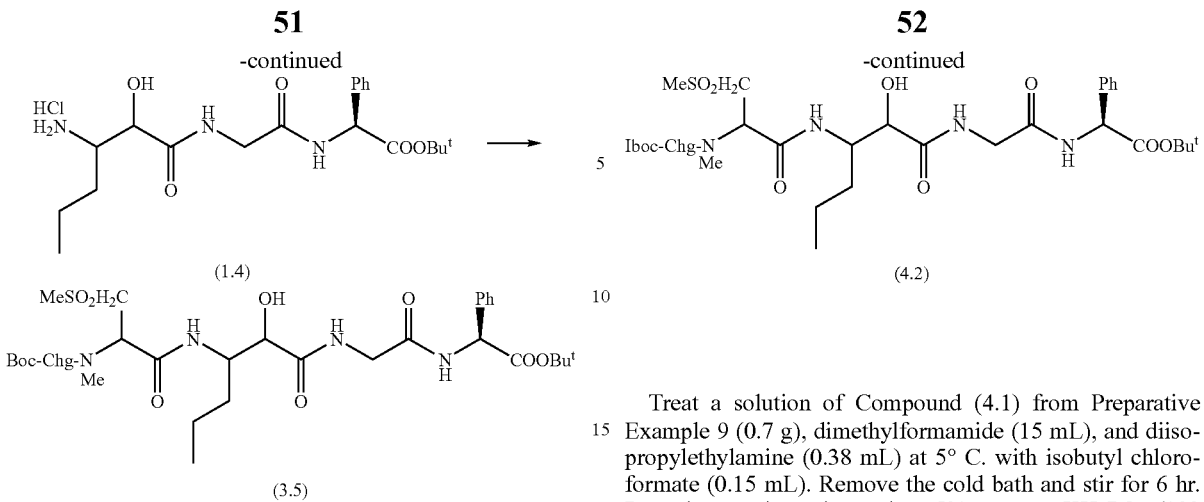

Compound (3.4) from Step B, above, was reacted with Compound (1.4) from Preparative Example 2, Step B in essentially the same manner as Preparative Example 2, Step A to afford Compound (3.5), $C_{38}H_{61}N_5O_{11}S$ (795.98), mass spec. (FAB) M+1=796.3.

PREPARATIVE EXAMPLE 9

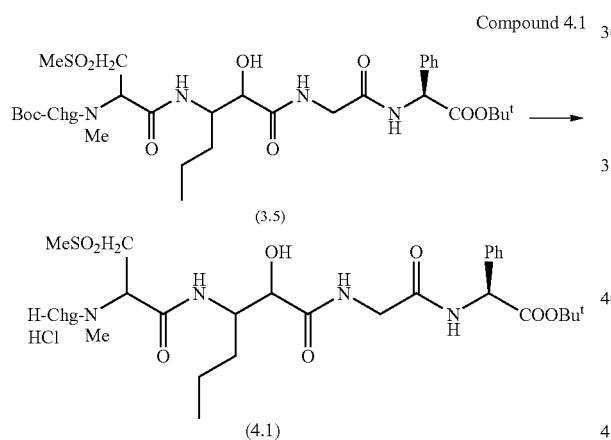

Compound (3.5) from Preparative Example 8, Step C, is reacted in essentially the same manner as Preparative Example 2, Step B, to obtain Compound (4.1) $C_{33}H_{53}N_5O_9S \cdot HCl$ (732.33).

PREPARATIVE EXAMPLE 10

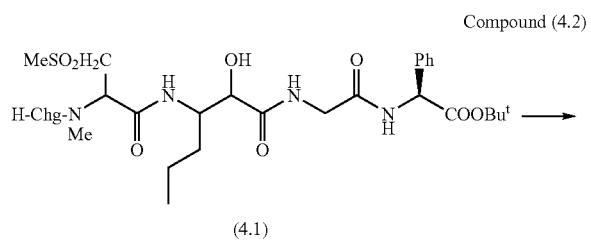

Treat a solution of Compound (4.1) from Preparative Example 9 (0.7 g), dimethylformamide (15 mL), and diisopropylethylamine (0.38 mL) at 5° C. with isobutyl chloroformate (0.15 mL). Remove the cold bath and stir for 6 hr. Pour the reaction mixture into 5% aqueous $KH_2PO_4$ (100 mL) and extract with ethyl acetate (2×100 mL). Wash the combined organics with cold 5% aqueous $K_2CO_3$, then 5% aqueous $KH_2PO_4$, then brine, and dry the organic over anhydrous $MgSO_4$. Filter the mixture, evaporate the filtrate under vacuum, triturate the residue with $Et_2O$-hexane, and filter to leave Compound (4.2).

PREPARATIVE EXAMPLE 11

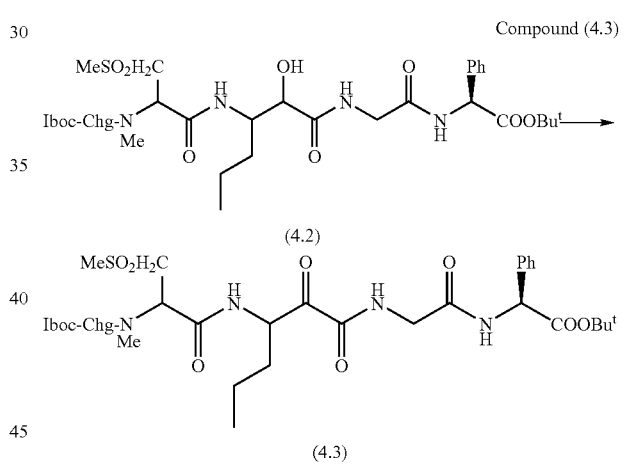

Compound (4.2) is reacted in essentially the same manner as Preparative Example 14, Step H below to obtain Compound (4.3).

PREPARATIVE EXAMPLE 12

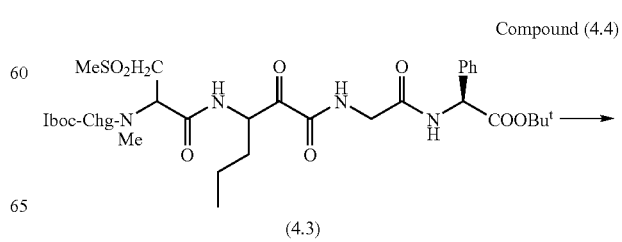

-continued

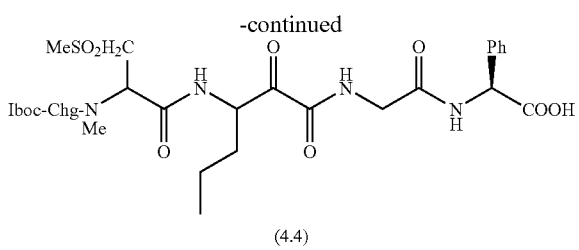

(4.4)

Compound (4.3) from Preparative Example 11 (about 0.10 g) is treated with a solution of anhydrous trifluoroacetic acid-dichloromethane (1:1, about 10 mL) for about 2 hr. The solution is diluted with xylene (about 50 mL) and evaporated under vacuum. The residue is triturated with $Et_2O$, and filtered to leave Compound (4.4).

PREPARATIVE EXAMPLE 13

Compound (4.5)

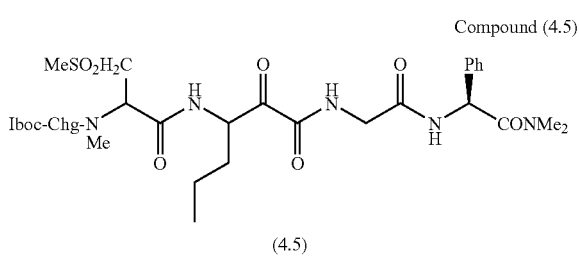

(4.5)

Compound (4.4) from Preparative Example 12 is reacted with dimethyl amine, in essentially the same manner as Preparative Example 2, Step A, to afford Compound (4.5).

PREPARATIVE EXAMPLE 14

Compound (5.2)

Step A

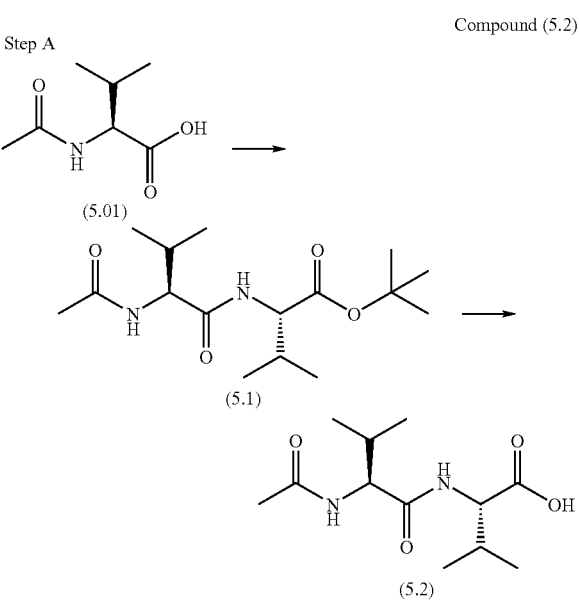

To a stirred cooling solution of Compound (5.01) (1.11 g, 7.0 mmol) in anhydrous DMF (10 mL) and anhydrous $CH_2Cl_2$ (10 mL) at 0° C., was added HOBT (1.19 g, 7.25 mmol), N-methyl morpholine (2.3 mL, 21.0 mmol) and DEC (1.6 g, 8.4 mmol). The resulting solution was stirred at 0° C. for 15 minutes, followed by the addition of H-Val-O-

$^tBu$ (1.54 g, 7.35 mmol). The solution was kept in the freezer overnight. A lot of precipitates were observed and the solution was concentrated to dryness, followed by extraction with EtOAc-saturated $NaHCO_3$. The combined organic layer was then washed with $5\%H_3PO_4$ solution, $H_2O$, brine, dried over $Na_2SO_4$, filtered to give a crude product 5.1 (2.4 g, 98% yield).

The solution of the crude product (as obtained above) in 4N HCl/Dioxane was stirred at room temperature for 7 hrs and concentrated to dryness to afford Compound (5.2).

Compound (5.4)

Step B

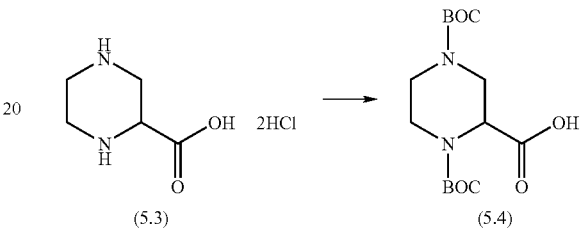

To a stirred solution of Compound (5.3) (F. L. Bach, Jr. et al, *J. Amer. Chem. Soc.,* (1955) 77, 6049) (17.5 g, 0.086 mmol) in $50\%MeOH/50\%H_2O$ (300 mL) was added Boc anhydride (47.0 g, 0.215 mol). The solution was then adjusted to pH=9.5 by dropwise addition of 50% concentrated NaOH solution. The resulting solution was stirred overnight at room temperature and then neutralized with concentrated HCl to pH=8 and acidified with citric acid to pH=2.94, followed by extraction with $CH_2Cl_2$. The combined organic layer was dried over $MgSO_4$ to give Compound (5.4) (27.16 g, 95% yield)

Compound (5.5)

Step C

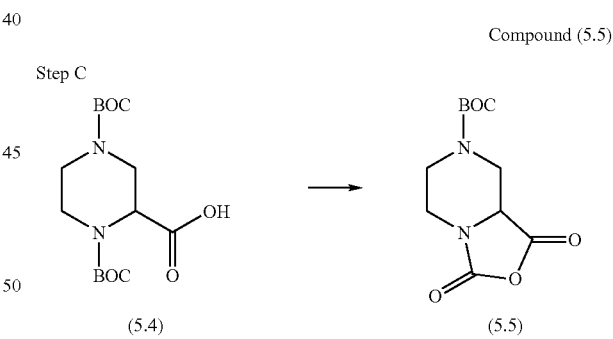

A solution of thionyl chloride (3.37 mL, 0.046 mmol) in DMF (3.59 mL, 0.046 mol) at 0° C. was warmed to room temperature and stirred for 35 minutes. The solution was then cooled to 0° C., followed by addition of Compound (5.4) from Step B above (15.0 g, 0.045 mol) in $CH_3CN$ (150 mL) and pyridine (3.73 mL, 0.046 mol). The resulting solution was warmed to room temperature and stirred overnight. The solution was then poured into ice water (700 mL) and extracted three times with EtOAc (150 mL). The combined organic layer was washed with brine, dried over $Na_2SO_4$, filtered and concentrated to dryness to give Compound (5.5) (10.8 g).

Step D

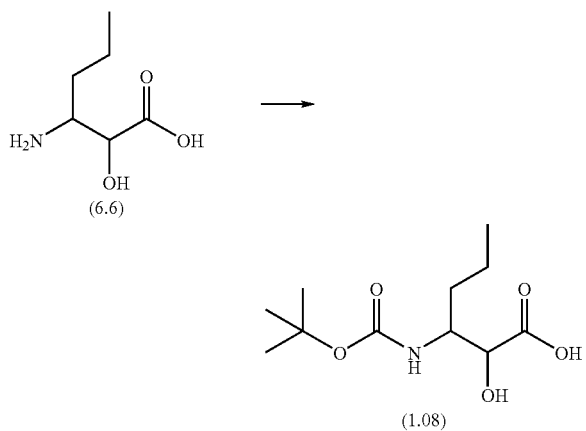

Compound (1.08)

To a stirred solution of Compound (6.6) from Preparative Example 14, Step D below (6.5 g, 0.044 mol) in CH$_2$Cl$_2$ (130 mL) was added Boc anhydride (9.65 g, 0.044 mol) and DMF (50 mL). The resulting solution was stirred at room temperature over the weekend and concentrated to dryness, followed by addition of H$_2$O (120 mL) and 50% NaOH to adjust to pH=10–11. The solution was then stirred for 2 hrs and more Boc anhydride (1.93 g, 8.8 mmol) was added and stirred overnight at room temperature. The solution was then extracted with CH$_2$Cl$_2$ and the aqueous layer was acidified to pH=4 at 0° C. with 1N HCl and then extracted 3 times with CH$_2$Cl$_2$. The combined organic layer was then washed with brine, dried over Na$_2$SO$_4$, filtered and concentrated to dryness to give Compound (1.08) (4.50 g, 41% yield, M-t-Butyl+2=192).

Step E

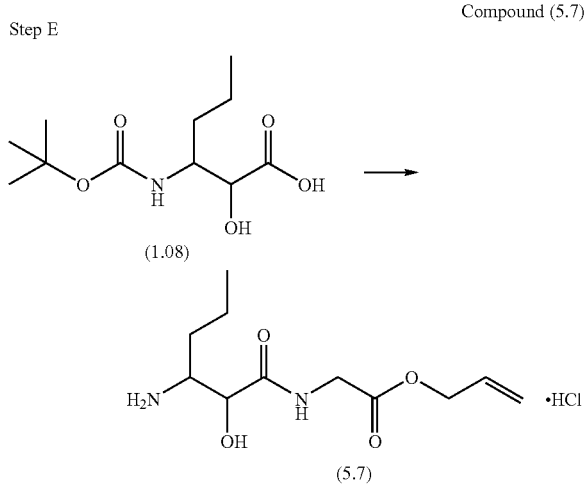

Compound (5.7)

To a stirred solution of Compound (1.08) from above (4.5 g, 0.018 mol) in DMF (22 mL) and CH$_2$Cl$_2$ (22 mL) was added HOBT (2.7 g, 0.02 mol), N-methyl morpholine (6 mL, 0.054 mol), DEC (4.17 g, 0.022 mol) and allyl glycine. TsOH (6.1 g, 0.02 mol). The resulting solution was stirred at room temperature over the weekend and then concentrated to dryness, followed by extraction with EtOAc-saturated NaHCO$_3$. The combined organic layer was washed with 10% H$_3$PO$_4$, brine, dried over Na$_2$SO$_4$, and filtered to give a crude product (5.7 g). The solution of this crude product in 4N HCl/Dioxane (50 mL) was stirred at room temperature 50 minutes and concentrated to dryness to give Compound (5.7) (4.79 g, 94% yield, MH$^+$=245.1).

Step F

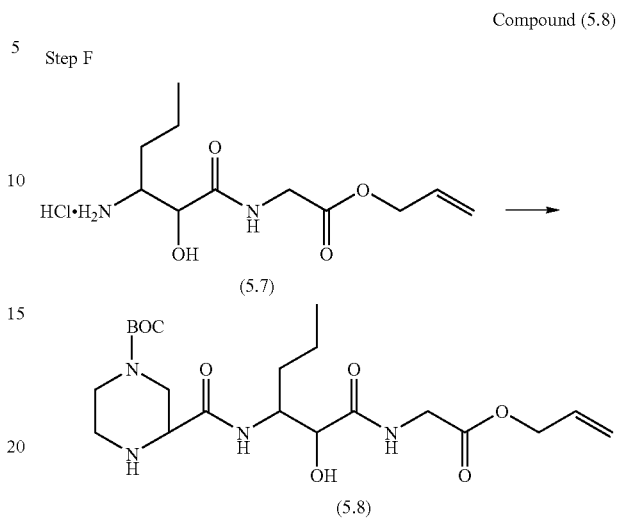

Compound (5.8)

To a stirred solution of Compound (5.7) from Step E above (3.1 g, 0.011 mol) in anhydrous CH$_2$Cl$_2$ (55 mL) was added dropwise TEA (1.69 mL, 0.012 mol) over 13 minutes and Compound (5.5) from Step C (2.83 g, 0.011 mol) in anhydrous CH$_2$Cl$_2$ (55 mL). The resulting solution was stirred at room temperature for 1.5 hrs. The organic layer was then washed with saturated NaHCO$_3$, brine, dried over Na$_2$SO$_4$, and filtered to give Compound (5.8) (4.67 g, MH$^+$=457.2)

Step G

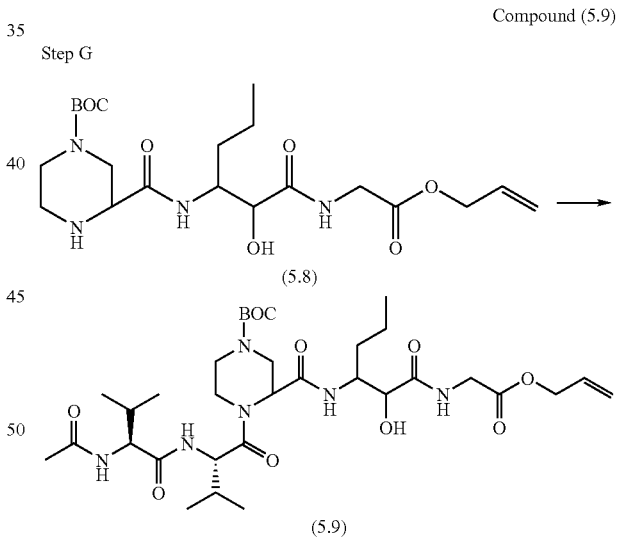

Compound (5.9)

To a stirred solution of Compound (5.2) from step A (0.34 g, 1.31 mmol) in CH$_2$Cl$_2$ (5 mL) and DMF (5 mL) at 0° C. was added HOBT (0.214 g, 1.31 mmol), N-methyl morpholine (0.43 mL, 3.9 mmol) and DEC (0.5 g, 1.09 mmol). The mixture stirred at room temperature for 15 minutes, followed by the addition of Compound (5.8) from Step F (0.5 g, 1.09 mmol). The resulting solution was kept in the freezer overnight then concentrated to dryness, followed by extraction with EtOAc-H$_2$O. The combined organic layer was washed twice with saturated NaHCO$_3$, 5%H$_3$PO$_4$, and brine, dried over Na$_2$SO$_4$, then filtered and concentrated to dryness to give Compound (5.9) (0.65 g, MH$^+$=697.4)

Step H

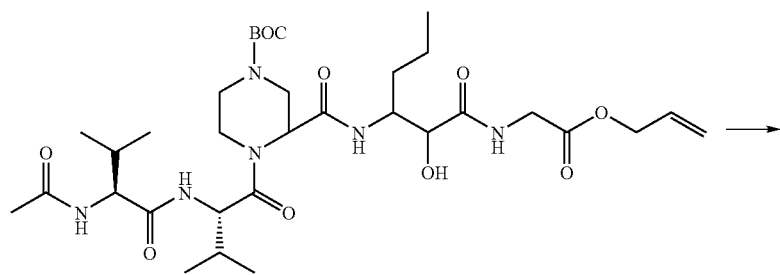

Compound (5.10)

To a stirred solution of Compound (5.9) from Step G (0.6 g, 0.8 mmol) in anhydrous CH$_2$Cl$_2$ (8 mL) was added Dess-Martin reagent (0.732 g, 1.72 mmol) and stirred at room temperature for 1 hour, followed by dropwise addition of H$_2$O (0.031 mL) and Dess-Martin reagent (0.373 g, 0.86 mmol) in CH$_2$CL$_2$ (12 mL). The resulting solution was stirred at room temperature for 2.5 hrs, followed by the addition of a solution of 50% saturated NaHCO$_3$/50% saturated Na$_2$S$_2$O$_3$ (20 mL) and stirred rapidly for 1.5 hrs at room temperature. The solution was then washed with H$_2$O, and brine, dried over Na$_2$SO$_4$ and concentrated to dryness to give Compound (5.10) (0.588 g, 100% yield, MH$^+$=695.2).

PREPARATIVE EXAMPLE 15

Compound (6.2)

Step A

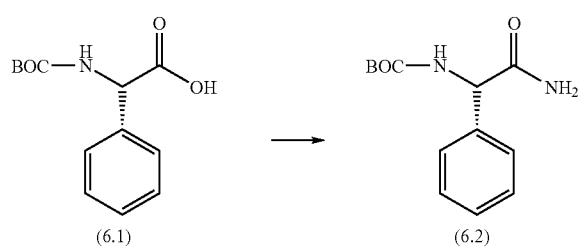

To a stirred solution of Compound (6.1) (5.0 g, 19.89 mmol) in CH$_2$Cl$_2$ (20 mL) and DMF (10 mL) at −20° C., was added HOBT (3.25 g, 19.89 mmol), EDCl (4.58 g, 23.87 mmol), and N-methyl morpholine (6.56 mL, 59.69 mmol). The resulting solution was stirred at room temperature for 10 minutes, followed by the addition of NH$_4$Cl (1.38 g) and kept at 0° C. overnight. The solution was then concentrated, and extracted with EtOAc-H2O. The combined organic layer was washed twice with NaHCO$_3$, H$_3$PO$_4$, and brine, dried over Na$_2$SO$_4$, filtered and concentrated to dryness. Crude product was purified by column chromatography, eluting with 2.5%MeOH/97.5%CH$_2$Cl$_2$ to give Compound (6.2) (1.95 g, MH$^+$=251.1).

Compound (6.3)

Step B

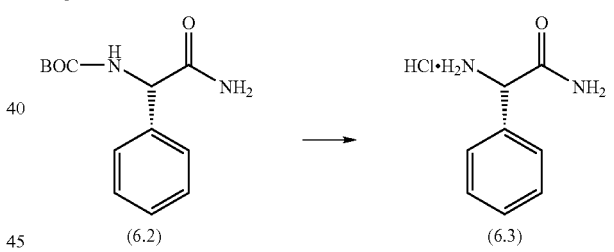

A solution of Compound (6.2) from Step A (12.32 g, 49.28 mmol) in 4N HCl/Dioxane (270 mL, 43.08 mmol) was stirred at room temperature for 2 hrs then concentrated to dryness to give Compound (6.3) (8.40 g, 100% yield).

Compound (1.08) (alternate synthesis)

Step C

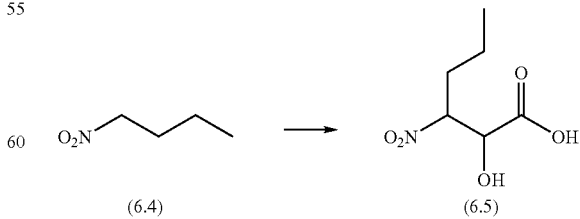

To a stirred solution of 1-nitrobutane (16.5 g, 0.16 mol) and glyoxylic acid. H$_2$O (28.1 g, 0.305 mol) in MeOH (122 mL) at 0° C.–5° C., was added dropwise triethyl amine (93 mL, 0.667 mol) over 2 hrs. The solution was warmed to room temperature, stirred overnight then concentrated to dryness to give an oil. The oil was then mixed with H₂O and acidified to pH-1 with 10% HCl, followed by extraction with EtOAc. The combined organic layer was washed with brine, dried over Na₂SO₄, filtered and concentrated to dryness to give Compound (6.5) (28.1 g, 99% yield).

Step D

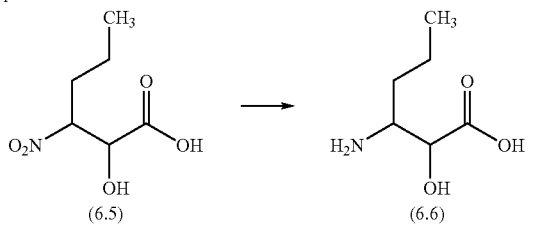

Compound (6.6)

To a stirred solution of Compound (6.5) from Step C (240 g, 1.35 mmol) in acetic acid (1.25 L) was added 10% Pd/C (37 g). The resulting solution was hydrogenated at 59 psi for 3 hrs and then at 60 psi for overnight. The acetic acid was then evaporated and the residue was azeotroped 3 times with toluene, then triturated with MeOH and ether. The solution was then filtered and azeotroped twice with toluene to give Compound (6.6) (131 g, 66% yield).

Step E

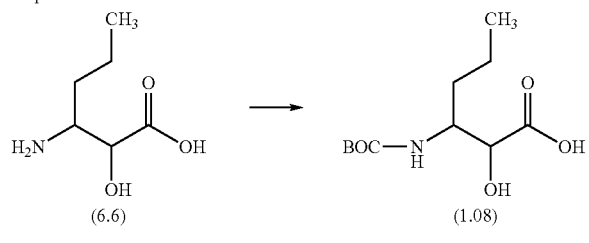

Compound (1.08)

To a stirred solution of Compound (6.6) from Step D (2.0 g, 0.0136 mol) in dioxane (10 mL) and H₂O (5 mL) at 0° C., was added 1N NaOH (aqueous) solution (4.3 mL, 0.014 mol). The resulting solution was stirred for 10 minutes, followed by the addition of Boc anhydride (0.11 g, 0.014 mol) and then stirred at 0° C. for 15 minutes. The solution was warmed to room temperature, stirred for 45 minutes, kept in the refrigerator overnight and then concentrated to dryness to give a crude material. To the solution of this crude material in EtOAc and ice, was added KHSO₄ (3.36 g) and H₂O (32 mL) and stirred for 4–6 minutes. The organic layer was then separated and the aqueous layer was extracted twice with EtOAc. The combined organic layer was washed with H₂O, brine, dried over Na₂SO₄, filtered and concentrated to dryness to give Compound (1.08) (3.0 g, 89.2% yield).

Step F

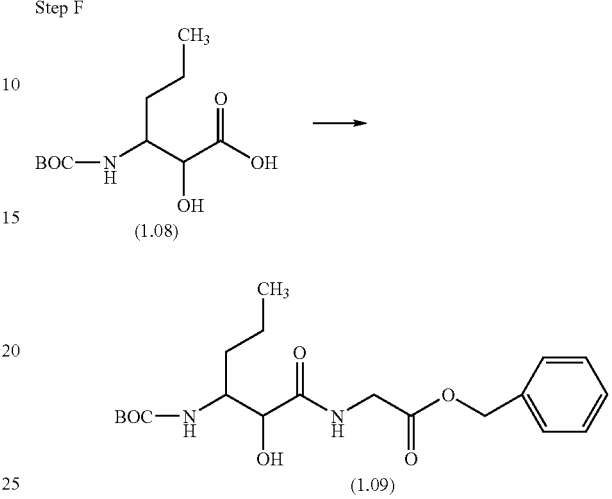

Compound (1.09)

To a stirred solution of Compound (1.08) from Step E (3.0 g, 0.012 mol) in DMF (15 mL) and CH₂Cl₂ (15 mL) at −20° C., was added HOBT (1.97 g, 0.012 mol), N-methyl morpholine (4.0 mL, 0.036 mol) and EDCl (2.79 g, 0.0145 mol). The reaction stirred for 10 minutes, followed by the addition of H-Gly-OBZ.HCl (2.56 g, 0.013 mol). The resulting solution was stirred at −20° C. for 2 hrs, kept in the refrigerator overnight, then concentrated to dryness, followed by dilution with EtOAc. The EtOAc solution was then washed twice with saturated NaHCO₃, H₂O, 5% H₃PO₄, brine, dried over Na₂SO₄, filtered and concentrated to dryness to give Compound (1.09) (4.5 g, 94% yield, MH⁺= 395.1).

Step G

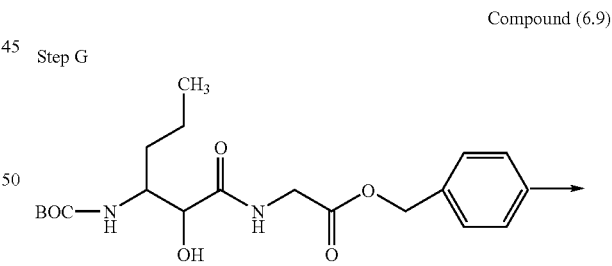

Compound (6.9)

A solution of Compound (1.09) from Step F (4.5 g, 0.0114 mol) in 4N HCl/Dioxane (45 mL) was stirred at room temperature for 45 minutes then concentrated to dryness to give Compound (6.9) (4.5 g, MH⁺=295.1).

Step H

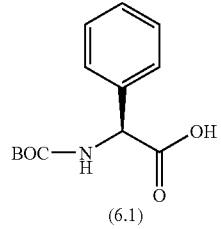

(6.1)

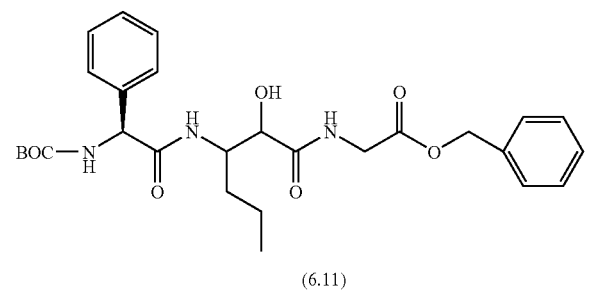

(6.11)

To a stirred solution of Boc-phenyl-glycine Compound (6.1) (0.398 g, 1.58 mmol) in CH$_2$Cl$_2$ (5 mL) and DMF (5 mL) in 100 mL round bottom flask at −20° C., was added HOBT (0.258 g, 1.58 mmol), EDCl (0.364 g, 1.903 mmol), and N-methyl morpholine (0.523 mL, 4.759 mmol). The mixture stirred for 5 minutes, followed by the addition of Compound (6.9) from step G (0.5 g, 1.51 mmol) and CH$_2$Cl$_2$ (5 mL). The resulting solution was stirred at −20° C. for 10 minutes and then kept in the freezer overnight. The reaction was concentrated to dryness, followed by extraction with EtOAc-saturated NaHCO$_3$. The combined organic layer was then washed twice with 5%H$_3$PO$_4$, and brine, dried over Na$_2$SO$_4$, filtered and concentrated to dryness to give Compound (6.11) (0.75 g, 94% yield, MH⁺=528.1).

Compound (6.12)

Step J

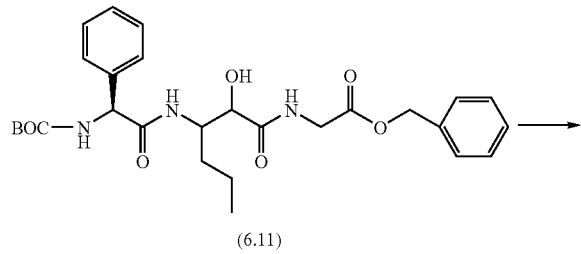

(6.11)

Compound (6.11)

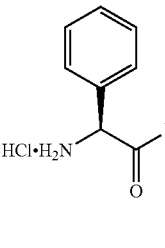

(6.12)

A solution of Compound (6.11) from Step H (0.75 g, 1.423 mmol) in 4N HCl/Dioxane (21 mL) was stirred at room temperature for 3 hrs then concentrated to dryness to give Compound (6.12) (0.68 g, 100% yield).

Compound (6.14)

Step K

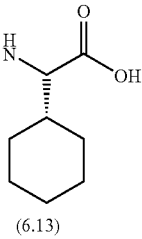

(6.13)

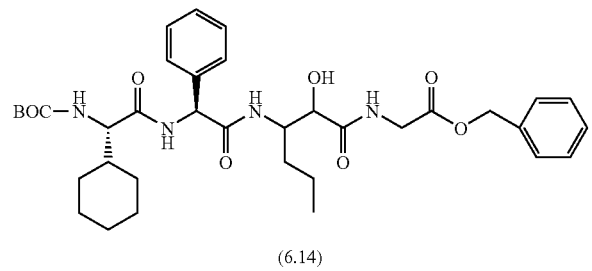

(6.14)

To a stirred solution of Compound (6.13) (0.44 g, 1.725 mmol) in CH$_2$Cl$_2$ (5 mL) and DMF (5 mL) at −20° C. was added EDCl (0.39 g, 2.07 mmol), HOBT (0.18 g, 1.725 mmol), and N-methyl morpholine (0.523 mL, 4.76 mmol). The reaction stirred for 5 minutes, followed by the addition of Compound (6.12) from Step J (0.68 g, 1.64 mmol) in CH$_2$Cl$_2$ (7 mL). The resulting solution was stirred at −20° C. for 10 minutes and kept in the freezer overnight then concentrated to dryness, followed by extraction with EtOAc-sat. NaHCO$_3$. The combined organic layer was washed twice with 5% H$_3$PO$_4$, then brine, dried over Na$_2$SO$_4$, filtered and concentrated to dryness to give Compound (6.14) (0.59 g, 54% yield, MH⁺=667.3).

Step L

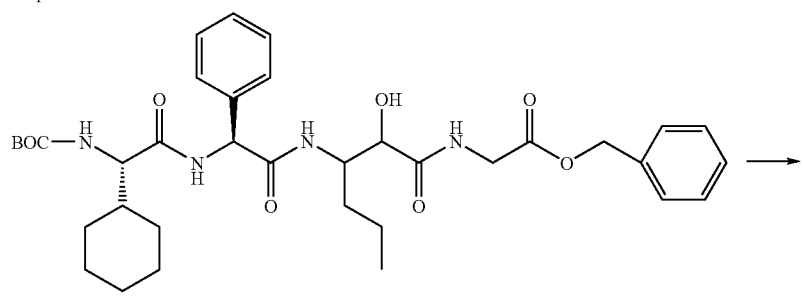

(6.14)

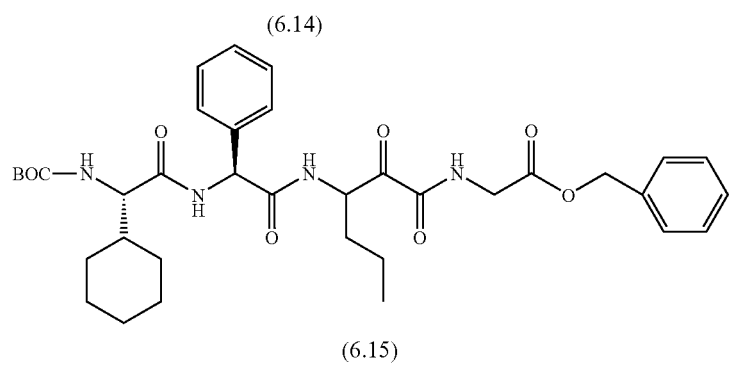

(6.15)

To a stirring solution of Compound (6.14) from Step K (0.593 g, 0.89 mmol) in CH₂Cl₂ (20 mL) was added Dess-Martin periodinane (0.76 g, 1.784 mmol). The resulting solution was stirred at room temperature for 2 hrs, followed by the addition of a mixture of H₂O/CH₂Cl₂. The mixture stirred for 45 minutes then added 50% saturated NaHCO₃/50%Na₂S₂O₃ (10 mL) and stirred for an additional 1.5 hrs. Additional CH₂Cl₂ was added to the solution and the organic layer was washed with brine, dried over Na₂SO₄, filtered, concentrated to dryness, and purified by column chromatography, eluting with 2.5% MeOH/97.5% CH₂Cl₂ to give Compound (6.15) (0.48 g, 82% yield).

Step M

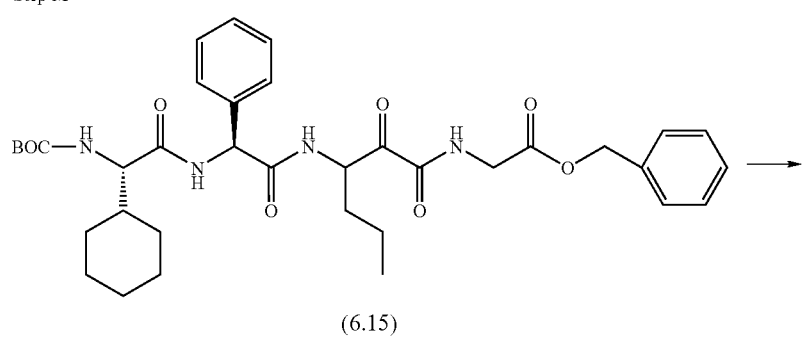

(6.15)

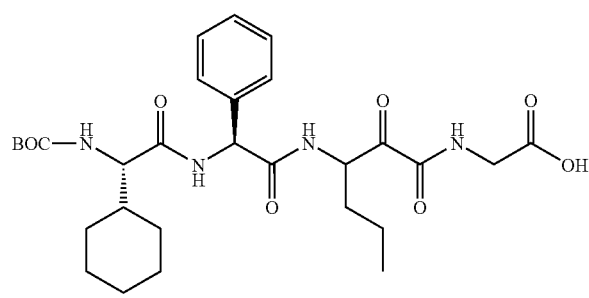

(6.16)

To a stirred solution of Compound (6.15) from Step L (0.16 g, 0.24 mmol) in absolute EtOH (10 mL) was added Pd/C (40.8 mg). The resulting solution was stirred vigorously, followed by the addition of 1 drop of AcOH. The solution was then stirred under H₂ gas for 2 hrs, and then filtered through celite to give Compound (6.16) (0.133 g, 95% yield, MH⁺=575.3).

Step N

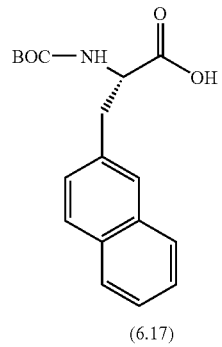

(6.17)

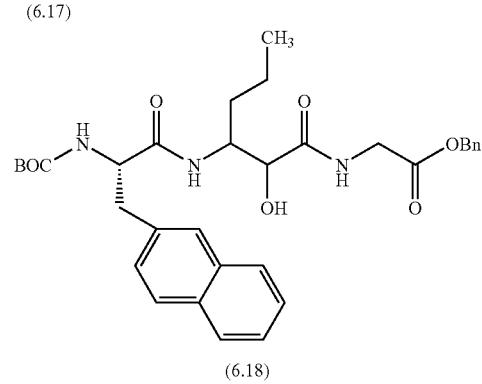

(6.18)

To a stirred solution of Compound (6.17) (0.5 g, 1.59 mmol) in CH₂Cl₂ (5 mL) and DMF (5 mL) at −20° C. was added HOBT (0.259 g, 1.59 mmol), NMM (0.48 g, 4.77 mmol), and EDCl (0.366 g, 1.91 mmol). The mixture stirred for 5 minutes, followed by the addition of Compound (6.9) from Step G (0.5 g, 1.51 mmol) and CH₂Cl₂ (5 mL). The resulting solution was stirred at −20° C. for 10 minutes, kept in the freezer overnight then concentrated to dryness, followed by extraction with EtOAc-sat.NaHCO₃. The combined organic layer was then washed twice with 5%H₃PO₄, and brine, dried over Na₂SO₄, filtered and concentrated to dryness to give Compound (6.18) (0.95 g, MH⁺=592.1).

Step O

Compound (6.19)

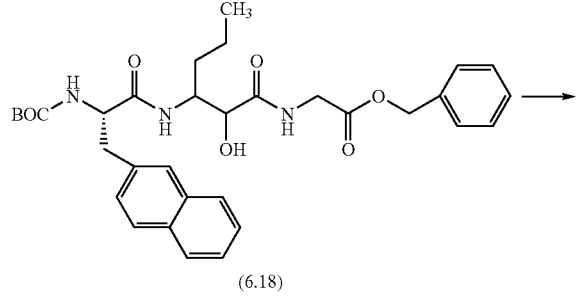

(6.18)

Compound (6.18)

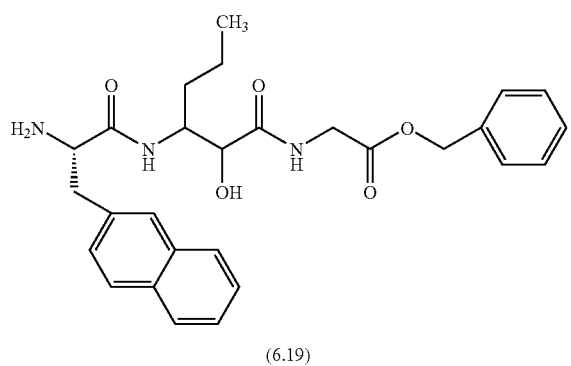

(6.19)

The solution of Compound (6.18) from Step N (0.93 g, 1.58 mmol) in 4N HCl/Dioxane (26 mL) was stirred at room temperature for 2 hr. then concentrated to dryness to give Compound (6.19) (0.96 g, 100% yield, MH⁺=492.1).

Step P

Compound (6.20)

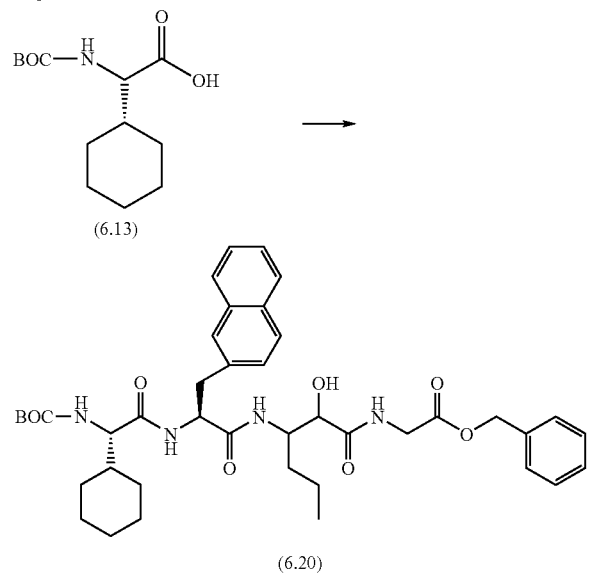

(6.13)

(6.20)

To a stirred cooling solution of Compound (6.13) (0.51 g, 2.02 mmol) in CH₂Cl₂ (5 mL) and DMF (5 mL) at −20° C., was added HOBT (0.33 g, 2.02 mmol), N-methyl morpholine (0.61 g, 6.06 mmol), and EDCl (0,46 g, 2.42 mmol). The reaction stirred for 5 minutes, followed by the addition of Compound (6.19) from Step O (0.94 g, 1.92 mmol). The resulting solution was stirred at −20° C. for 10 minutes, then refrigerated overnight, concentrated to dryness, followed by extraction with EtOAc-sat. NaHCO₃. The combined organic layer was washed with 5% H₃PO₄, and brine, dried over Na₂SO₄, filtered and concentrated to dryness to give Compound (6.20) (1.29 g, 87% yield).

Step Q

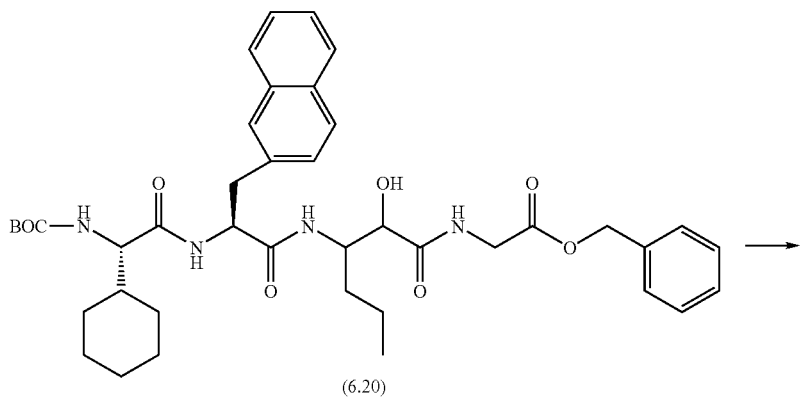

(6.20)

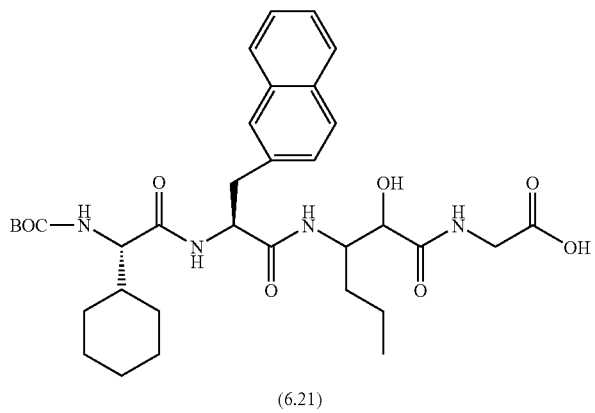

(6.21)

To a stirred solution of Compound (6.20) from Step P (1.27 g, 1.74 mmol) in absolute EtOH (50 mL), was added Pd/C (100 mg). The resulting solution was stirred vigorously, followed by addition of 2 drops of AcOH. The solution was then hydrogenated for 2 hrs and filtered through celite to give Compound (6.21) (1.07 g, 96% yield, MH+=641.1).

Step R

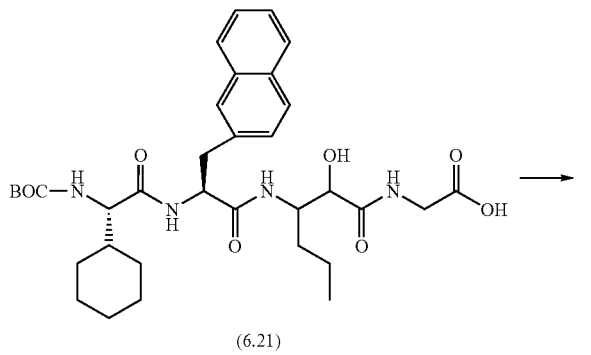

(6.21)

Compound (6.22)

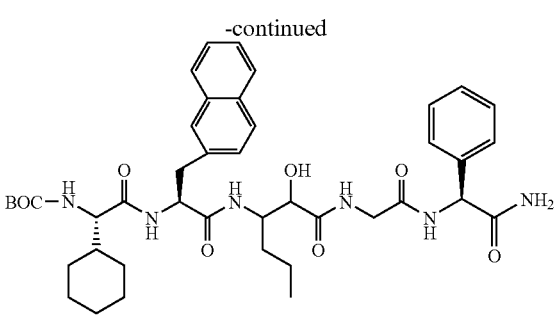

(6.22)

To a stirred solution of Compound (6.21) from Step Q (0.25 g, 0.39 mmol) in $CH_2Cl_2$ (5 mL) and DMF (5 mL) at −25° C., was added HOBT (0.06 g, 0.39 mmol), N-methyl morpholine ((0.12 g, 1.17 mmol), EDCl (0.089 g, 0.469 mmol) and stirred for 10 minutes, followed by the addition of Compound (6.3) from Step B (0.069 g, 0.37 mmol). The resulting solution was stirred at −25° C. for 15 minutes, refrigerated over night then concentrated to dryness, followed by extraction with EtOAc-sat.$NaHCO_3$. The combined organic layer was washed with 5% $H_3PO_4$, then brine, dried over $Na_2SO_4$, filtered and concentrated to dryness to give Compound (6.22).

Step S

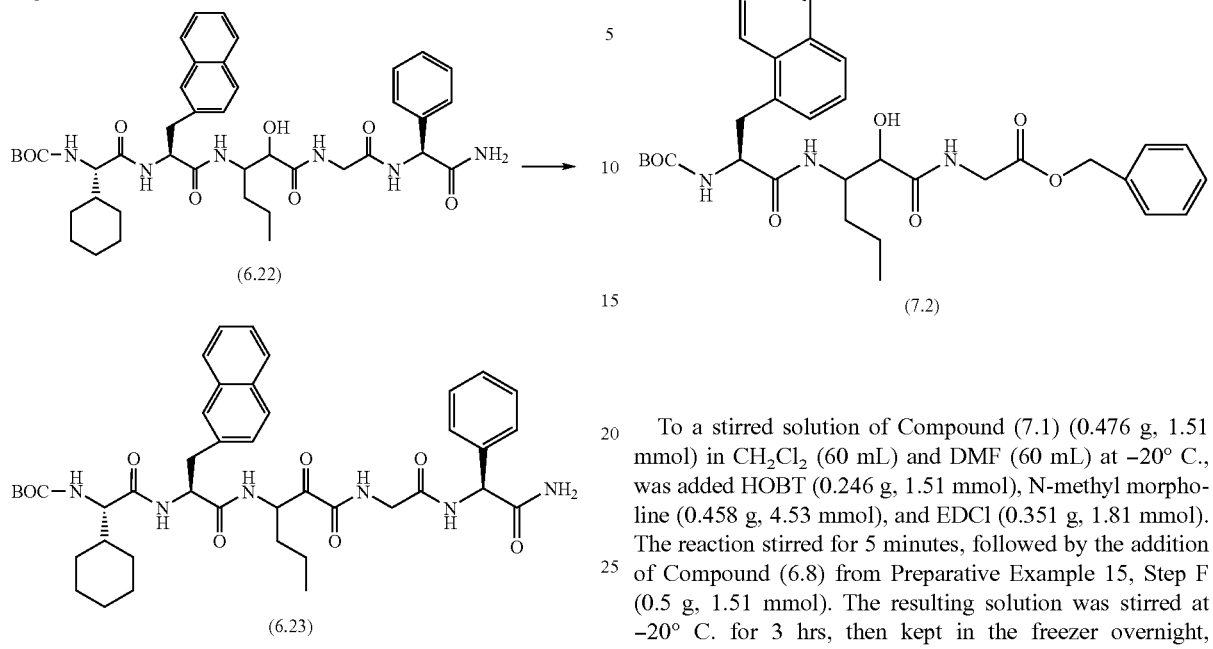

To a stirred solution of Compound (6.22) from Step R (0.23 g, 0.302 mmol) in $CH_2Cl_2$ (10 mL) was added Dess-Martin periodinane (0.256 g, 0.60 mmol). The resulting solution was stirred at room temperature for 2 hrs, followed by the addition of a mixture of $H_2O/CH_2Cl_2$ and stirred for an additional 45 minutes. To the reaction was then added 50% sat. $NaHCO_3$/50% $Na_2S_2O_3$ (10 mL) and it was stirred for 1.5 hrs. Additional $CH_2Cl_2$ was added to the solution and the organic layer was then washed with brine, dried over $Na_2SO_4$, filtered, concentrated to dryness and purified by column chromatography on silica gel, eluting with 1%–3% $MeOH$/99%–97%$CH_2Cl_2$ to give Compound (6.23) (0.08 g, 34% yield, $MH^+$=771.2)

PREPARATIVE EXAMPLE 16

Step A

Compound (7.2)

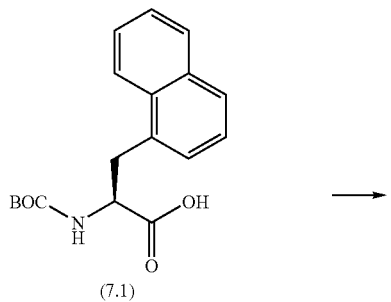

To a stirred solution of Compound (7.1) (0.476 g, 1.51 mmol) in $CH_2Cl_2$ (60 mL) and DMF (60 mL) at $-20°$ C., was added HOBT (0.246 g, 1.51 mmol), N-methyl morpholine (0.458 g, 4.53 mmol), and EDCl (0.351 g, 1.81 mmol). The reaction stirred for 5 minutes, followed by the addition of Compound (6.8) from Preparative Example 15, Step F (0.5 g, 1.51 mmol). The resulting solution was stirred at $-20°$ C. for 3 hrs, then kept in the freezer overnight, concentrated to dryness, followed by extraction with EtOAc-sat. $NaHCO_3$. The combined organic layer was washed twice with 5%$H_3PO_4$, $H_2O$, then brine, dried over $Na_2SO_4$ and concentrated to dryness to give Compound (7.2) (0.82 g, 94% yield, $MH^+$=592.1)

Step B

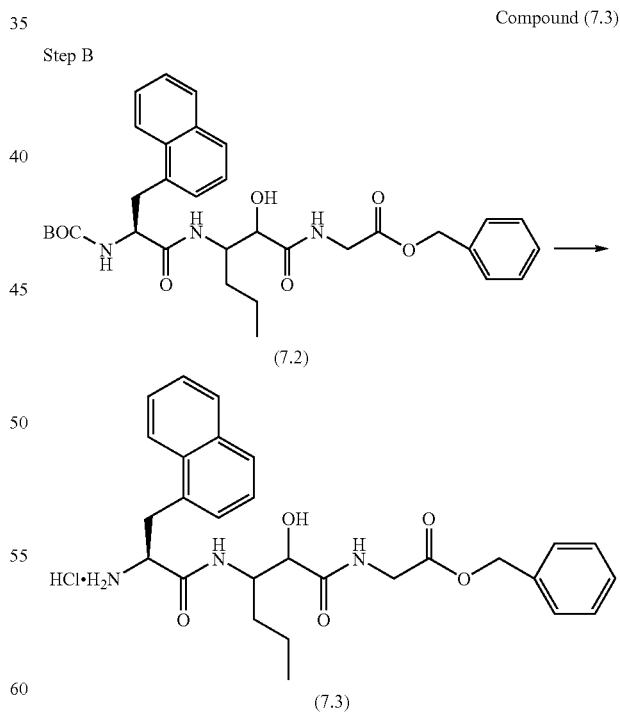

A solution of Compound (7.2) from Step A (0.82 g, 1.39 mmol) in 4N HCl/Dioxane (20 mL) was stirred at room temperature for 2 hrs and then concentrated to dryness to give Compound (7.3) (0.84 g, 100% yield, $MH^+$=492.3)

Step C

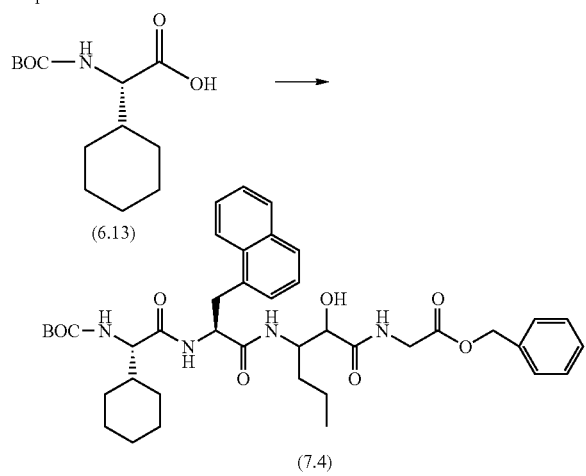

To a stirred solution of Compound (6.13) (0.36 g, 1.40 mmol) in CH$_2$Cl$_2$ (60 mL) and DMF (60 mL) at −20° C. was added HOBT (0.228 g, 1.40 mmol), NMM (0.425 g, 4.20 mmol), and EDCl (0.322 g, 1.68 mmol). The reaction stirred for 5 minutes, followed by the addition of Compound (7.3) from Step B (0.84 g, 1.40 mmol). The resulting solution was stirred at −20° C. for 3 hrs and then kept in the freezer overnight, concentrated to dryness, followed by extraction with EtOAc-sat. NaHCO$_3$. The combined organic layer was washed with 5% H$_3$PO$_4$, H$_2$O, brine, dried over Na$_2$SO$_4$, filtered and concentrated to dryness to give Compound (7.4) (0.57 g, 57% yield, MH$^+$=731.3).

Step D

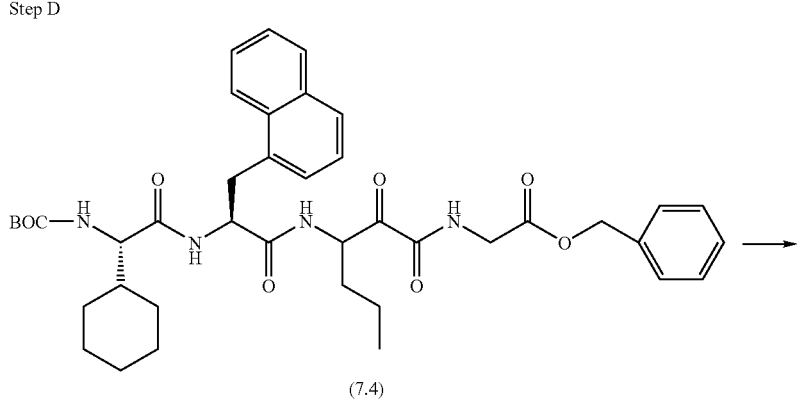

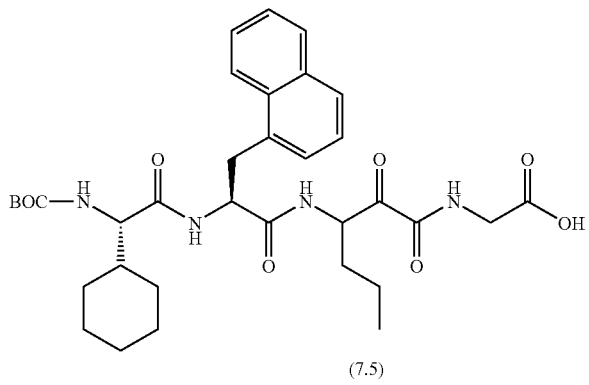

To a stirred solution of Compound (7.4) from Step C (0.55 g, 0.75 mmol) in CH$_2$Cl$_2$ (5 mL) was added Dess-Martin periodinane (0.64 g, 1.50 mmol). The resulting solution was stirred at room temperature for 2 hrs, followed by the addition of a mixture of H$_2$O/CH$_2$Cl$_2$. The mixture stirred for 45 minutes then added 50% sat. NaHCO$_3$/50% Na$_2$S$_2$O$_3$ and stirred for an additional 1.5 hrs. Addional CH$_2$Cl$_2$ was added to the solution and the organic layer was then washed with brine, dried over Na$_2$SO$_4$ and concentrated to dryness to give Compound (7.5) (0.24 g, 44% yield, MH$^+$=729.5).

Step E (7.5)

(7.6)

To a stirred solution of Compound (7.5) from Step D (0.10 g, 0.14 mmol) in absolute EtOH (20 mL), was added Pd/C (20 mg). The resulting solution was stirred vigorously in 100 ml round bottom flask, purged with H$_2$ and stirred under H$_2$ atmosphere over night. The solution was then filtered through celite, washed with EtOH and concentrated to dryness to give Compound (7.6) (93 mg, 100% yield, MH$^+$=639.1).

PREPARATIVE EXAMPLE 17

(8.1)

R = Benzyl (8.2)
R = H (8.3)

Compound (7.6)

In essentially the same manner as Preparative Example 16 Steps A–E, substituting Compound (8.1) for Compound (7.1) in Step A, Compounds (8.2) and (8.3) were prepared.

PREPARATIVE EXAMPLE 18

Compound (9.2)

Step A (9.1)

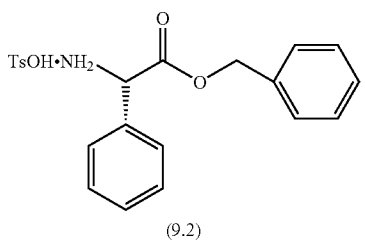

(9.2)

To a stirred solution of (S) (+)-2-phenyl glycine (9.1) (15.0 g, 0.099 mol) in benzene (350 mL) was added p-toluene sulfonic acid. H₂O (20.76 g, 0.116 mol) and benzyl alcohol (30 mL, 0.29 mol). The resulting solution was heated to reflux overnight and the solution became a slurry. The solution was then cooled to room temperature, followed by the addition of ether. The solid was filtered thruough a scintered funnel and washed twice with Et₂O, then dried under a nitrogen atmosphere to give a solid (35.4 g). The solid was then dissolved in CH₂Cl₂ and washed with sat. NaHCO₃. The combined organic layer was dried over Na₂SO₄ and concentrated to dryness to give a free amine (18.1 g, 75.7% yield). The free amine was then dissolved in ether and 1N HCl was bubbled in to form a white precipitate. The precipitate was filtered, washed with ether and dried under vacuum to give Compound (9.2) (15.2 g).

Step B

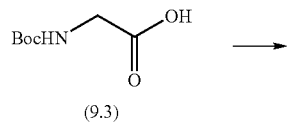

(9.3)

To a stirred solution of Boc-gly-OH (9.3) (11.35 g, 0.0648 mol) in anhydrous DMF (100 mL) and anhydrous CH₂Cl₂ (100 mL) at −20° C., was added HOBT (10.5 g, 0.065 mol), EDCl (13.6 g, 0.0712 mol) and N-methyl morpholine (21.3 mL, 0.194 mol). The resulting solution was stirred at −20° C. for 10 minutes, followed by the addition of Compound (9.2) from Step A (18.0 g, 0.065 mol). The reaction stirred for 45 minutes at −20° C. and was then kept in the freezer over night. The solution was then concentrated to dryness, followed by extraction with EtOAc-sat. NaHCO₃. The combined organic layer was washed with H₂O, then brine, dried over Na₂SO₄ and concentrated to dryness to give Compound (9.4) (26.48 g, 100% yield, MH⁺=399.2).

Compound (9.5)

Step C

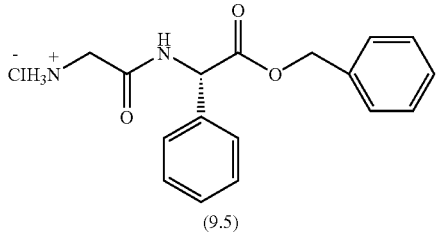

(9.4)

Compound (9.4)

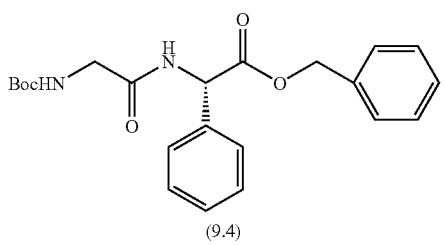

(9.4)

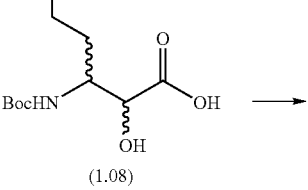

(9.5)

A solution of Compound (9.4) from Step B (26.4 g, 0.065 mol) in 4N HCl/Dioxane (100 mL) was stirred at room temperature for 1 hr and then concentrated to dryness to give Compound (9.5) (22.69 g, 100% yield, MH⁺=299.1).

Compound (9.6)

Step D

BocHN—CH(OH)—CH—C(O)—OH (1.08)

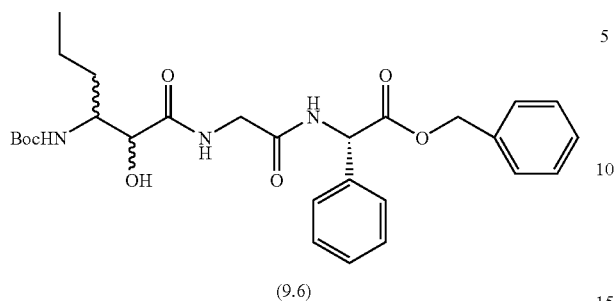

(9.6)

To a stirred solution of Compound (1.08) from Preparative Example 15, Step E (15.5 g, 0.0627 mol) in DMF (150 mL) and CH$_2$Cl$_2$ (150 mL) at –20° C., was added HOBT (10.22 g, 0.0626 mol), EDCl (13.2 g, 0.069 mol) and NMM (20.67 g, 0.188 mol). The resulting solution was stirred at –20° C. for 10 minutes, followed by the addition of Compound (9.5) from Step C (21.0 g, 0.063 mol). The reaction stirred at –20° C. for 1 hr and then was kept in the freezer overnight. The solution was then concentrated to dryness, followed by extraction with EtOAc-sat. NaHCO$_3$. The combined organic layer was washed with H$_2$O, 5%H$_3$PO$_4$, and brine, dried over Na$_2$SO$_4$, filtered and concentrated to dryness to give Compound (9.6) (30.3 g, 92% yield, MH$^+$=528.1).

Compound (9.7)

Step E

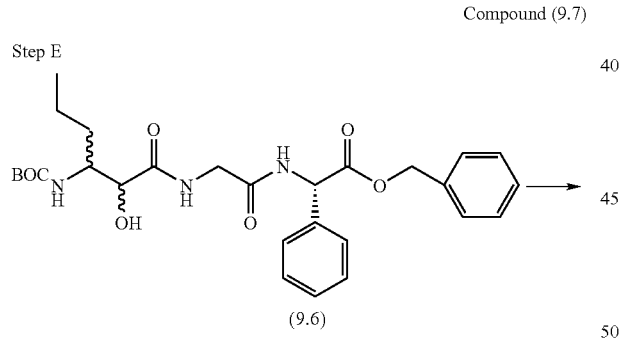

(9.6)

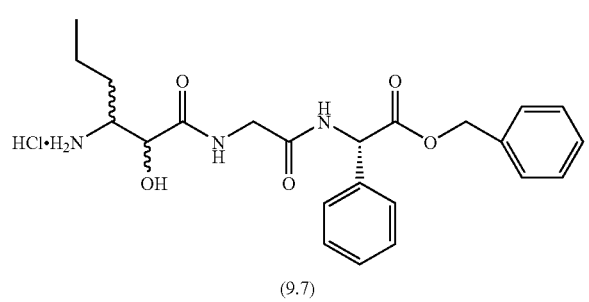

(9.7)

In essentially the same manner as Preparative Example 18, Step C above, Compound (9.7) was prepared (30.0 g, 100% yield, MH$^+$=428.1).

Compound (9.9)

Step F

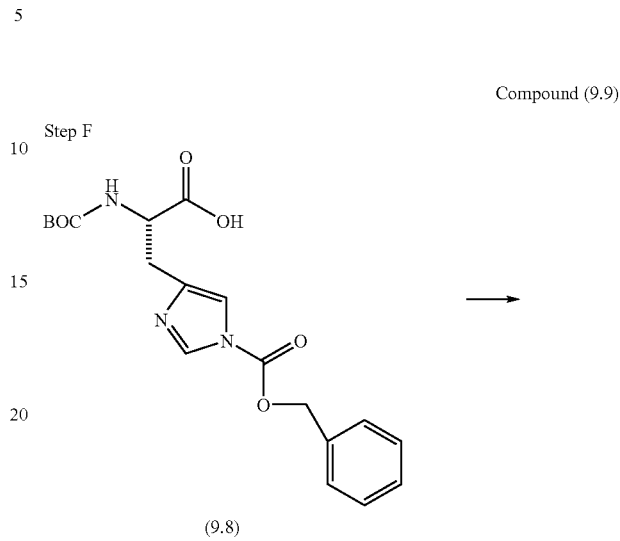

(9.8)

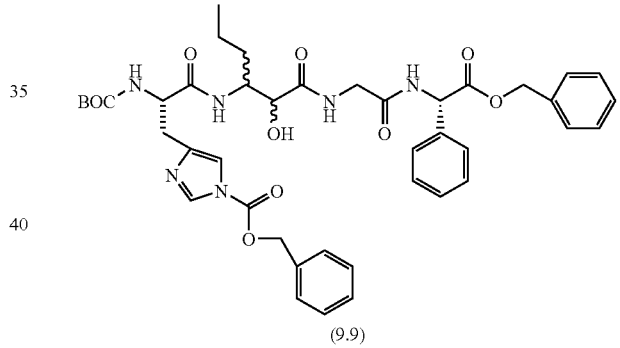

(9.9)

To a stirred solution of Boc-His(Z)-OH (9.8) (0.5 g, 1.28 mmol) in DMF (5 mL) and CH$_2$Cl$_2$ (5 mL) at –20° C., was added HOBT (0.209 g, 1.28 mmol), EDCl (0.27 g, 1.41 mmol), and NMM (0.42 mL, 3.85 mmol). The resulting solution was stirred at –20° for 10 minutes, followed by the addition of Compound (9.7) from Step E (0.673 g, 1.28 mmol) and stirred at –20° C. for 2 hr and then kept in the freezer over night. The solution was then concentrated to dryness, followed by extraction with EtOAc-sat.NaHCO$_3$. The combined organic layer was washed with H$_2$O, 5%H$_3$PO$_4$, and brine, dried over Na$_2$SO$_4$, filtered and concentrated to give Compound (9.9) (0.858 g, 84% yield, MH$^+$=799).

Step G
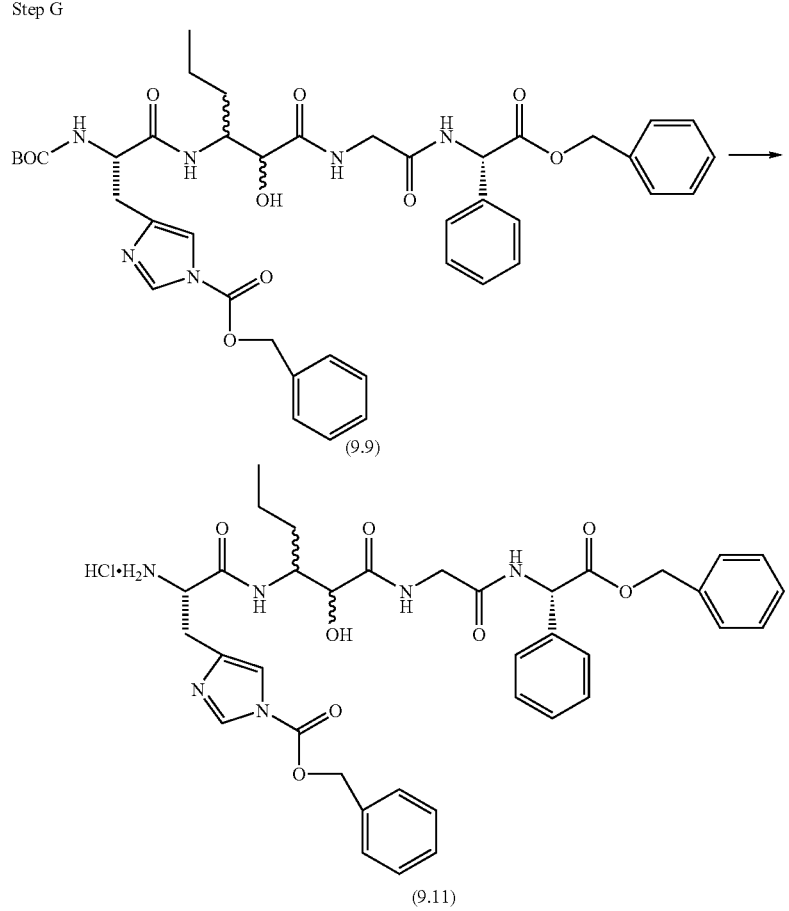
Compound (9.11)
In essentially the same manner as in Preparative Example 18, Step C, Compound (9.11) was prepared (0.76 g, 100% yield, MH$^+$=699.2).
Step H
Compound (9.12)
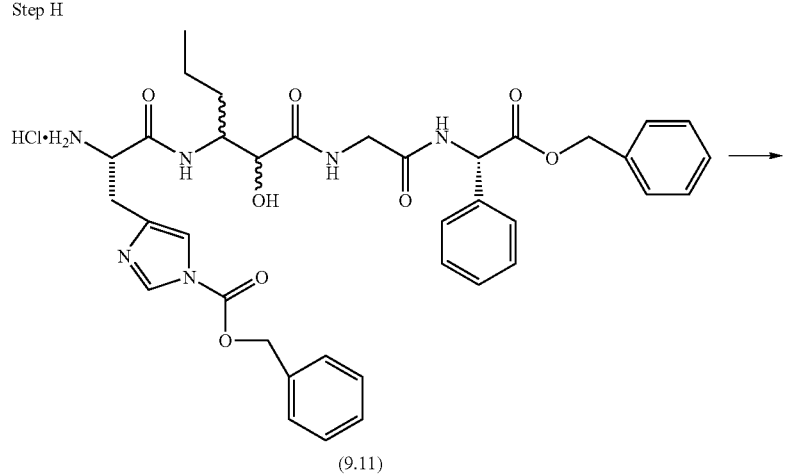

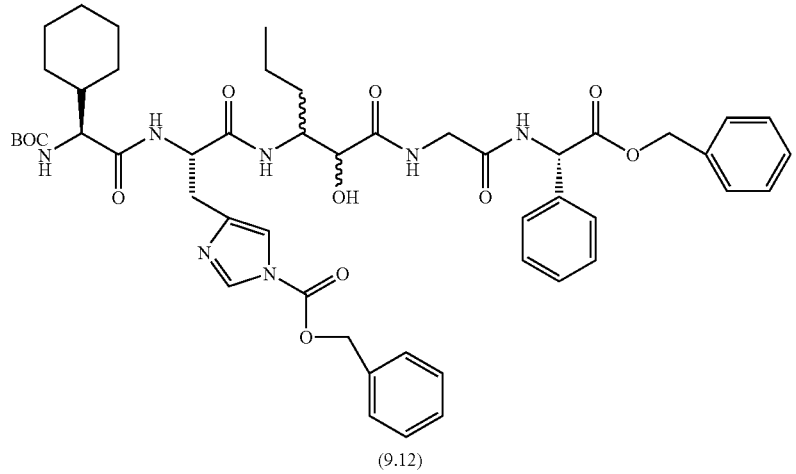

(9.12)

To a stirred solution of N-Boc-cyclohexylglycine (0.263 g, 1.026 mmol) in DMF (5 mL) and $CH_2Cl_2$ (5 mL) at $-20°$ C., was added HOBT (0.167 g, 1.026 mmol), EDCl (0.216 g, 1.13 mmol) and NMM (0.338 g, 3.078 mmol). The resulting solution was stirred at $-20°$ C. for 10 minutes, followed by the addition of Compound (9.11) from Step G (0.754 g, 1.03 mmol). The reaction stirred at $-20°$ C. for 1 hr and then was kept in the freezer over night. The solution was then concentrated to dryness, followed by extraction with EtOAc-sat.$NaHCO_3$. The combined organic layer was then washed with $H_2O$, 5%$H_3PO_4$, and brine, dried over $Na_2SO_4$, filtered and concentrated to dryness to give Compound (9.12) (0.735 g, $MH^+$=938.4).

Step I

Compound (9.13)

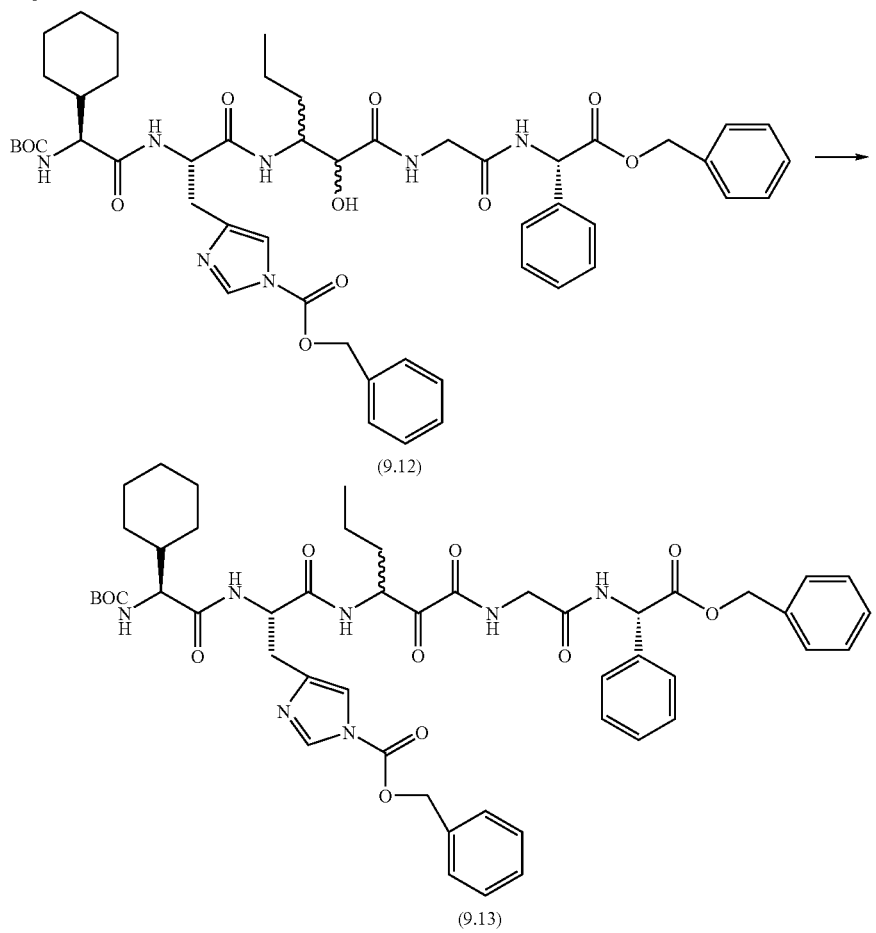

(9.12)

(9.13)

To a stirred solution of the Compound (9.12) from Step H (0.367 g, 0.377 mmol) in anhydrous $CH_2Cl_2$ (10 mL), was added Dess-Martin periodinane (0.32 g, 0.75 mmol). The resulting solution was stirred at room temperature for 2 hrs. $CH_2Cl_2$, sat. $Na_2S2O_4$ and sat.$NaHCO_3$ were added to the solution and the solution was allowed to stir at room temperature for 1 hr. The organic layer was then separated and washed with $H_2O$, and brine, dried over $Na_2SO_4$, filtered and concentrated to dryness to give a crude product (340 mg). The crude product was then purified by column chromatography on silica gel, eluting with $CH_2Cl_2$ and then 4%MeOH/$CH_2Cl_2$ to give Compound (9.13) (150 mg, $MH^+=936.3$).

Step J

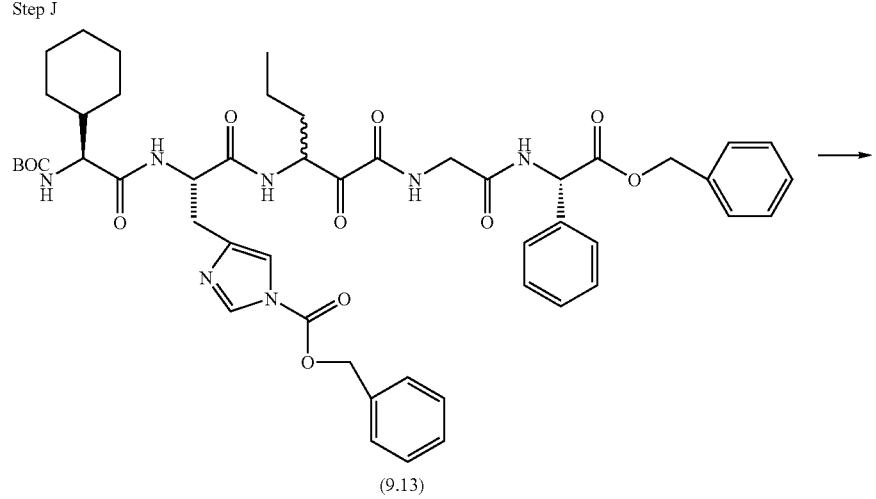

(9.13)

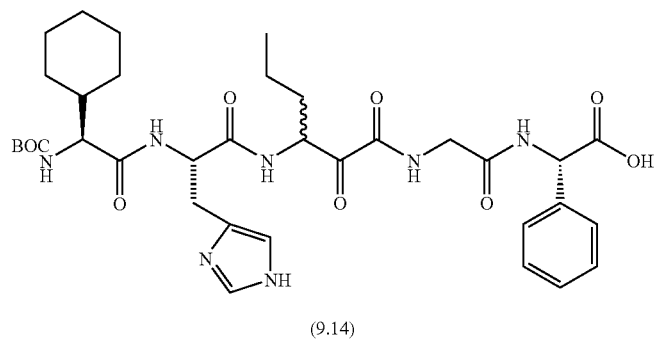

(9.14)

To a stirred solution of Compound (9.13) from Step I (0.15 g, 1.6 mmol) in absolute EtOH (40 mL) was added 10% Pd/C in 50% $H_2O$ (w/w). The solution was purged with $N_2$ and stirred under $H_2$ balloon for 45 minutes. The catalyst was then filtered through celite, washed with EtOH/$CH_2Cl_2$ and then concentrated to dryness to give Compound (9.14) (0.116 g, $MH^+=712.2$).

PREPARATIVE EXAMPLE 19

Step A

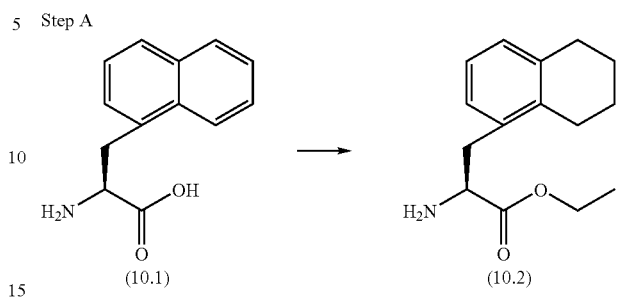

Compound (9.14)

A suspension of L-3-(1-Napthyl) Alanine (2.0 g, 9.34 mmol) in anhydrous EtOH (200 mL) was charged to a 500 ml flask. To the solution was then bubbled in, anhydrous concentrated HCl (2 mL) to dissolve all the solids. The solution was allowed to cool down to room temperature over 45 minutes and then it was concentrated to dryness, followed by the addition of EtOH (50 mL), 10% Pd/C (300 mg) and 5% Rh/C (300 mg). The resulting solution was placed in a parr shaker and hydrogenated at 60 psi. The reaction was then filtered through celite, washed with EtOH and concentrated to dryness to give a crude material (2.4 g, MH+= 254.2). The crude product was dissolved in $CH_2Cl_2$ and then washed with sat. $NaHCO_3$. The combined organic layer was concentrated to dryness and purified by column chromatography on silica gel, eluting with 5%–20%EtOAc/$CH_2Cl_2$ to give Compound (10.2) (0.65 g).

filtered and concentrated to dryness to give Compound (10.3) (1.12 g, 92% yield).

Compound (10.4)

Step C

Compound (10.3)

Step B

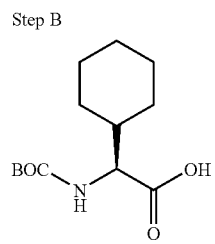

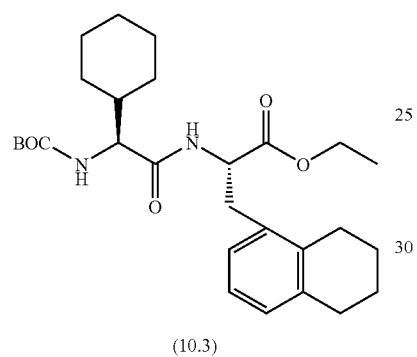

(10.3)

(10.3)

To a stirred solution of N-Boc-cyclohexylglycine (0.643 g, 2.5 mmol) in DMF (5 mL) and $CH_2Cl_2$ (5 mL) at −20° C., was added HOBT (0.407 g, 2.5 mmol), EDCl (0.527 g, 2.75 mmol) and NMM (0.825 mL, 7.5 mmol). The resulting solution was stirred for 10 minutes at −20° C., followed by the addition of Compound (10.2) from Step A and $CH_2Cl_2$ (3 mL), and then kept in the freezer over night. The solution was then concentrated to dryness, followed by extraction with EtOAc-sat. $NaHCO_3$. The combined organic layer was washed with $H_2O$, 5%$H_3PO_4$, and brine, dried over $Na_2SO_4$, To a stirred solution of Compound (10.3) from Step B (1.1 g, 2.25 mmol) in MeOH (30 mL) and $H_2O$ (7.5 mL) was added LiOH (0.283 g, 6.75 mmol). The resulting solution was stirred at room temperature over night, followed by the addition of 5%$H_3PO_4$. A precipitate formed and the solution was evaporated to remove most MeOH. Additional $CH_2Cl_2$ was added and the $CH_2Cl_2$ layer was then separated, dried over $Na_2SO_4$, filtered and concentrated to dryness to give Compound (10.4) (1.068 g, 100% yield, MH+=459.1).

Compound (10.5)

Step D

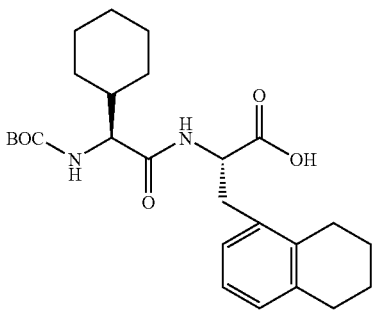

(10.4)

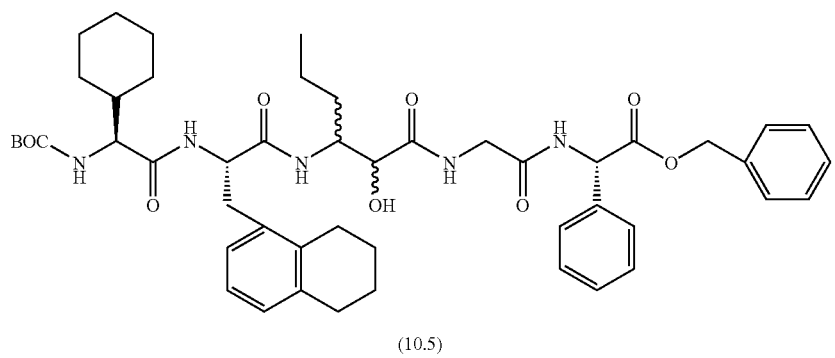

(10.5)

To a stirred solution of Compound (10.4) from Step C (1.0 g, 2.17 mmol) in DMF (10 mL) and CH$_2$Cl$_2$ (10 mL), was added HOBT (0.353 g, 2.17 mmol), EDCl (0.457 g, 2.38 mmol) and NMM (0.715 mL, 6.51 mmol). The resulting solution was stirred at −20° C. for 10 minutes, followed by the addition of Compound (9.7) from Preparative Example 18, Step E (1.13 g, 2.17 mmol). The reaction stirred for 0.5 hr. at −20° C. and then was kept in the freezer over night. The solution was then concentrated to dryness, followed by extraction with EtOAc-sat. NaHCO$_3$. The combined organic layer was washed with H$_2$O, 5%H$_3$PO$_4$, and brine, dried over Na$_2$SO$_4$, filtered and concentrated to dryness to give Compound (10.5) (1.8 g, M+Na=890.4).

To a stirred solution of Compound (10.5) from Step D (1.8 g, 2.07 mmol) in anhydrous CH$_2$Cl$_2$ (40 mL) was added Dess-Martin periodinane(1.76 g, 4.15 mmol). The resulting solution was stirred at room temperature for 1 hr, followed by adding dropwise over 1.5 hrs anhydrous CH$_2$Cl$_2$ (40 mL) and H$_2$O (0.074 mL) and stirred an addditional 2 hrs. To this solution was then added 40 mL of 50% sat. NaHCO$_3$/ 50%sat.Na$_2$S$_2$O$_4$ and the resulting solution was stirred vigorously for half an hour. The organic layer was then separated and washed with H$_2$O. The combined organic layer was concentrated to dryness and purified by column chromatography on silica gel, eluting with 2%–3%MeOH/ CH$_2$Cl$_2$ to give Compound (10.6) (0.95 g, MH$^+$=866.2).

Step E

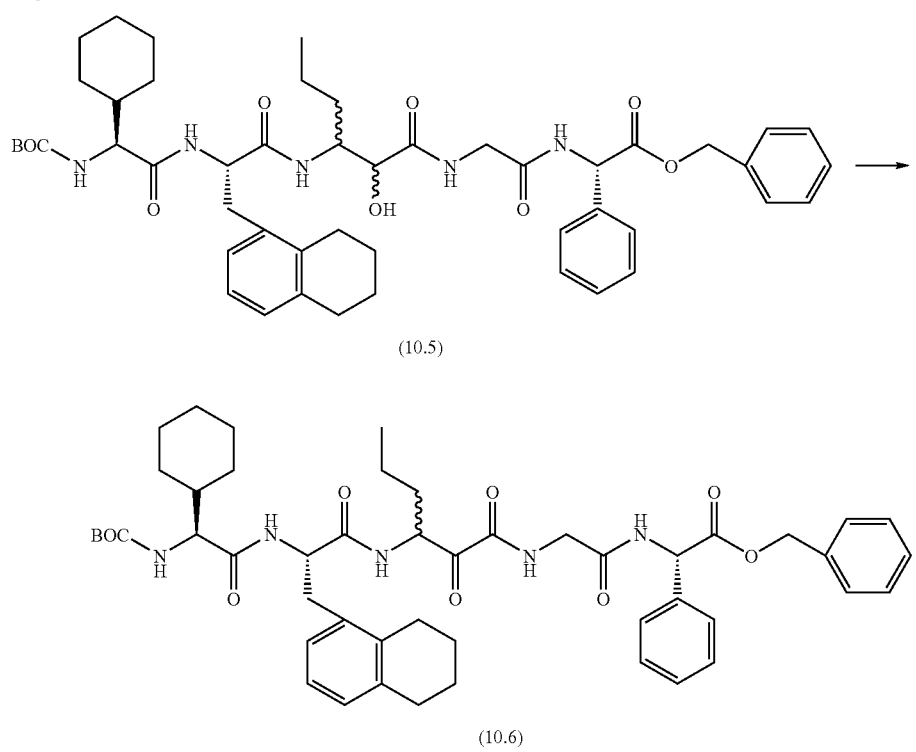

Compound (10.6)

Step F

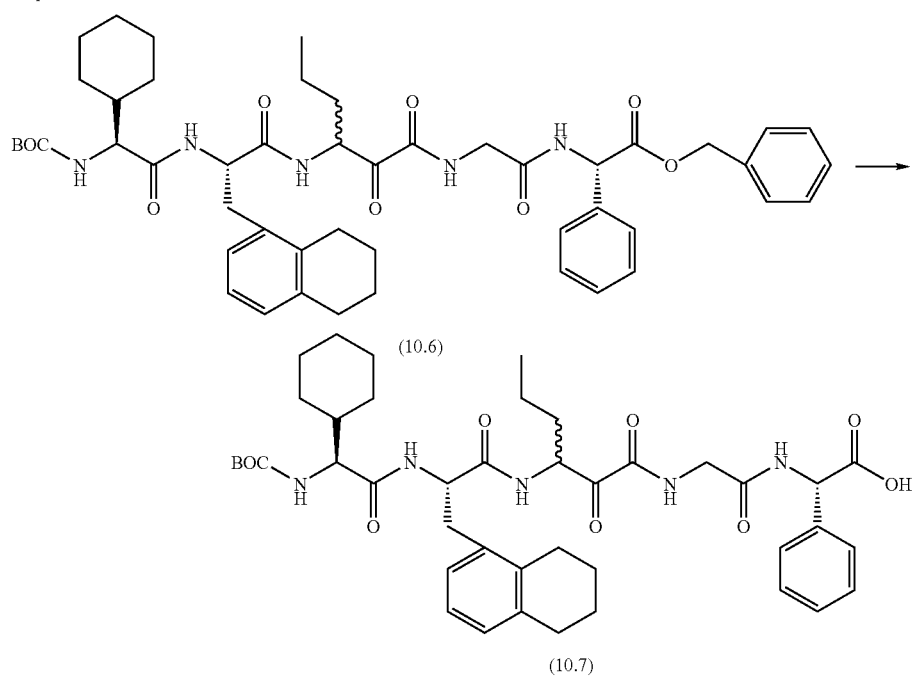

Compound (10.7)

In essentially the same manner as in Preparative Example 18, Step K, Compound (10.7) was prepared.

EXAMPLES

Using the procedures of Preparative Example 1, Step A, and Preparative Example 2, Step F, for couplings; Preparative Example 1, Step B, Preparative Example 1, Step F, Preparative Example 2, Step D, and Preparative Example 4, Step J for ester deprotection; Preparative Example 2, Step E, and Preparative Example 4, Step J, for amine deprotection; and Preparative Example 4, Step H, for oxidation of hydroxyamides to ketoamides—together with the α-amino acids of the above examples or those commercially available or those described in the literature, in the necessary various combinations, the compounds listed in the attached Table 2 were prepared.

Solid Phase Synthesis

General Procedure for Solid-Phase Coupling Reactions

The synthesis was done in a reaction vessel which was constructed from a polypropylene syringe cartridge fitted with a polypropylene frit at the bottom. The Fmoc-protected amino acids were coupled under standard solid-phase techniques. Each reaction vessel was loaded with 100 mg of the starting Fmoc-Sieber resin (approximately 0.035 mmol). The resin was washed with 2 mL portions of DMF (2 times). The Fmoc protecting group was removed by treatment with 2 mL of a 20% v/v solution of piperidine in DMF for 20 min. The resin was washed with 2 mL portions of DMF (4 times). The coupling was done in DMF (2 mL), using 0.12 mmol of Fmoc-amino acid, 0.12 mmol of HATU [O-(7-azabenzotriazol-1-yl)-1,1,3,3-tetramethyluronium hexafluorophosphate] and 0.24 mmol of DIPEA (N,N-diisopropylethylamine). After shaking for 2 h, the reaction vessel was drained and the resin was washed with 2 mL portions of DMF (4 times). The coupling cycle was repeated with the next Fmoc-amino acid or capping group.

General Procedure for Solid-Phase Dess-Martin Oxidation

The synthesis was conducted in a reaction vessel which was constructed from a polypropylene syringe cartridge fitted with a polypropylene frit at the bottom. Resin-bound hydroxy compound (approximately 0.035 mmol) was treated with a solution of 0.14 mmol of Dess-Martin periodinane and 0.14 mmol of t-BuOH in 2 mL of DCM for 4 h. The resin was washed with 2 mL portions of a 20% v/v solution of iPrOH in DCM, THF, a 50% v/v solution of THF in water (4 times), THF (4 times) and DCM (4 times).

PREPARATIVE EXAMPLE 20

N-Fmoc-2',3'-dimethoxyphenylglycine

Compound (901)

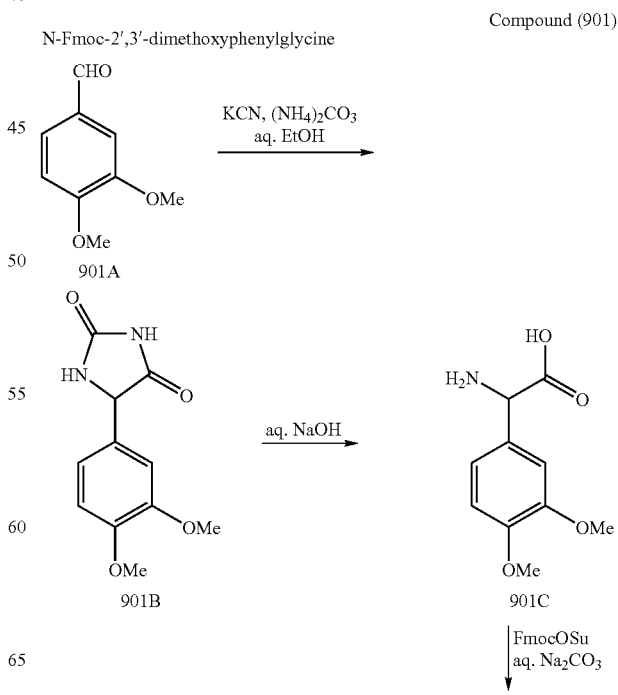

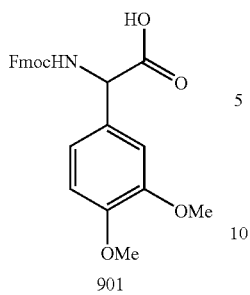

901

To a solution of potassium cyanide (1.465 g, 22.5 mmol) and ammonium carbonate (5.045 g, 52.5 mmol) in water (15 mL) was added a solution of 2,3-dimethoxybenzaldehye 901A (2.5 g, 15 mmol) in ethanol (15 mL). The reaction mixture was heated at 40° C. for 24 h. The volume of the solution was reduced to 10 mL by evaporatiog under reduced pressure. Concentrated hydrochloric acid (15 mL) was added and compound 901B was obtained as a white precipitate. Compound 901B was isolated by filtration (2.2 g, 9.3 mmol). Compound 901B was dissolved in 10% w/w aqueous sodium hydroxide solution (15 mL) and the resulting solution was heated under reflux for 24 h. Concentrated hydrochloric acid was added and the pH was adjusted to neutral (pH 7). The resulting solution containing compound 901C was evaporated under reduced pressure. The residue was dissolved in 5% w/w aqueous sodium bicarbonate solution (150 mL). The solution was cooled to 0° C. in an ice bath and 1,4-dioxane (30 mL) and a solution of 9-fluorenylmethyl succinimidyl carbonate (2.7 g, 8 mmol) in 1,4-dioxane (30 mL) was added at 0° C. The reaction mixture was allowed to warm to room temperature and was stirred at room temperature for 24 h. 1,4-dioxane was evaporated under reduced pressure. The aqueous solution was washed with diethyl ether. Concentrated hydrochloric acid was added and the pH was adjusted to acidic (pH 1). Ethyl acetate was added the organic layer was washed with water and brine. The organic layer was dried over anhydrous sodium sulfate. The solvent was evaporated under reduced pressure to afford the desired compound 901 as a white foamy solid (3.44 g, 7.9 mmol). MS (LCMS-Electrospray) 434.1 MH$^+$.

PREPARATIVE EXAMPLE 21

Compound (801)

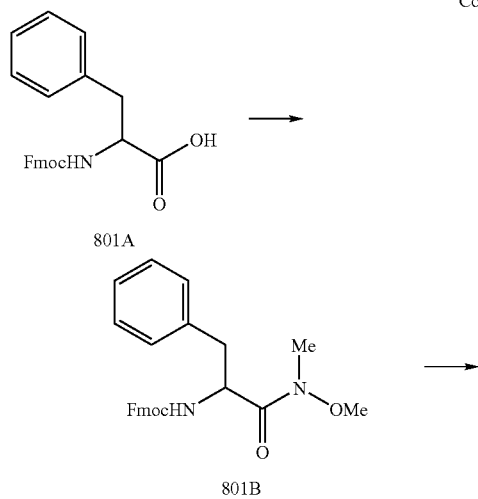

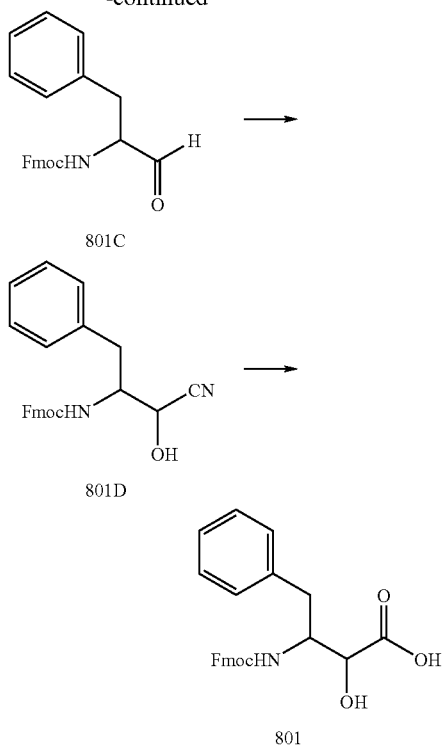

To a solution of N-Fmoc-phenylalanine 801A (5 g, 12.9 mmol) in anhydrous DCM (22 mL) cooled to −30° C. in a dry ice-acetone bath was added N-methylpyrrolidine (1.96 mL, 16.1 mmol) and methyl chloroformate (1.2 mL, 15.5 mmol) sequentially. The reaction mixture was stirred at −30° C. for 1 h and a solution of N,O-dimethylhydroxylamine hydrochloride (1.51 g, 15.5 mol) and N-methylpyrrolidine (1.96 mL, 16.1 mmol) in anhydrous DCM (8 mL) was added. The reaction mixture was allowed to warm to room temperature and was stirred at room temperature overnight. Toluene was added and the organic layer was washed with dilute hydrochloric acid, aqueous sodium bicarbonate solution and brine. The organic layer was dried over anhydrous sodium sulfate. The solvent was evaporated under reduced pressure to afforded compound 801B (4 g, 9.29 mmol).

To a solution of Red-Al (6.28 mL, 21.4 mmol) in anhydrous toluene (8 mL) cooled to −20° C. in a dry ice-acetone bath was added a solution of compound 801B (4 g, 9.29 mmol) in anhydrous toluene (12 mL). The reaction mixture was stirred at −20° C. for 1.5 h. The organic layer was washed with dilute hydrochloric acid, aqueous sodium bicarbonate solution and brine. The organic layer was dried over anhydrous sodium sulfate. The solvent was evaporated under reduced pressure and the crude product 801C was used in the next reaction without further purification.

To a solution of compound 801C (approx. 9.29 mmol) in hexane (15 mL) was added a solution of potassuim cyanide (24 mg, 0.37 mmol) and tetrabutylammonium iodide (34 mg, 0.092 mmol) in water (4 mL) and acetone cyanohydrin (1.27 mL, 13.9 mmol) sequentially. The reaction mixture was stirred at room temperature for 24 h. Ethyl acetate was added and the organic layer was washed with water and brine. The organic layer was dried over anhydrous sodium sulfate. The solvent was evaporated under reduced pressure to afford compound 801D (2.4 g, 6.03 mmol).

To a solution of compound 801D (2.4 g, 6.03 mmol) in 1,4-dioxane (11 mL) was added concentrated hydrochloric acid (11 mL). The reaction mixture was heated at 80° C. for 3 h. Ethyl acetate (25 mL) and water (25 mL) was added. The organic layer was washed with brine and dried over anhydrous sodium sulfate. The solvent was evaporated under reduced pressure to afford the desired compound 801 as a white foamy solid (2 g, 4.8 mmol). MS (LCMS-Electrospray) 418.1 MH+.
EXAMPLE 101J COMPOUND (101J)
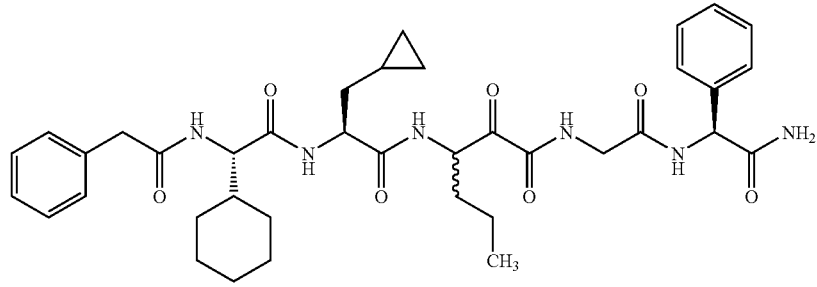
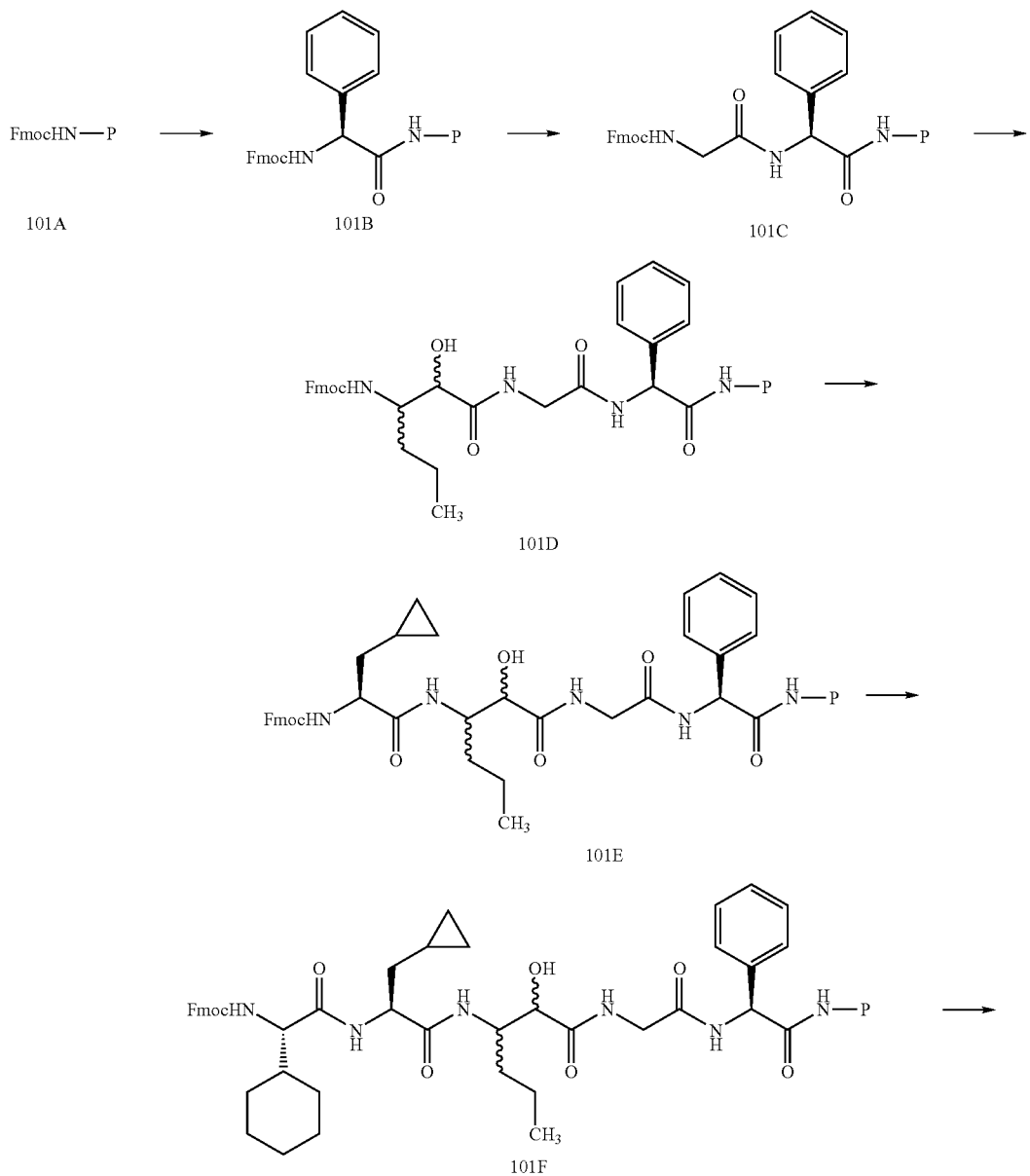

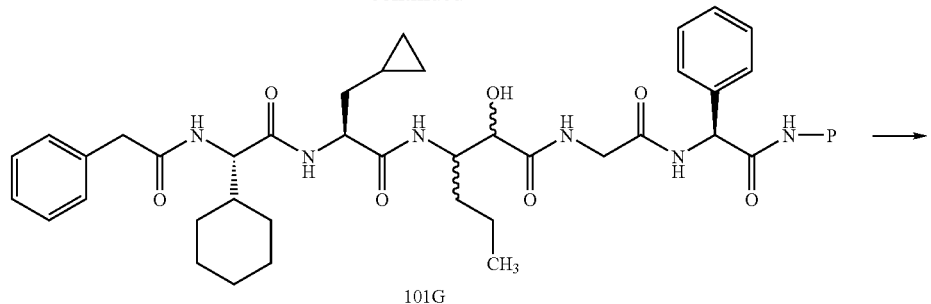

101G

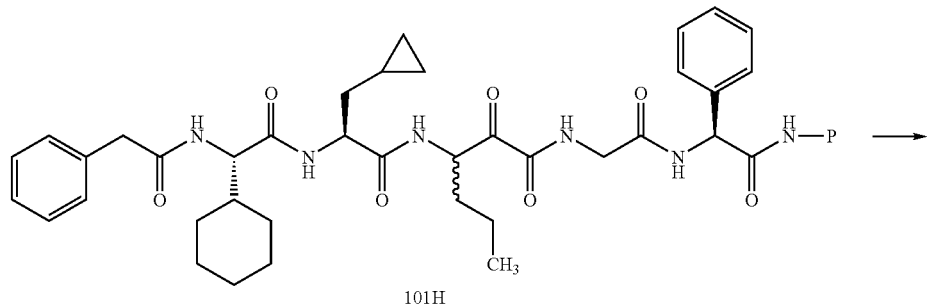

101H

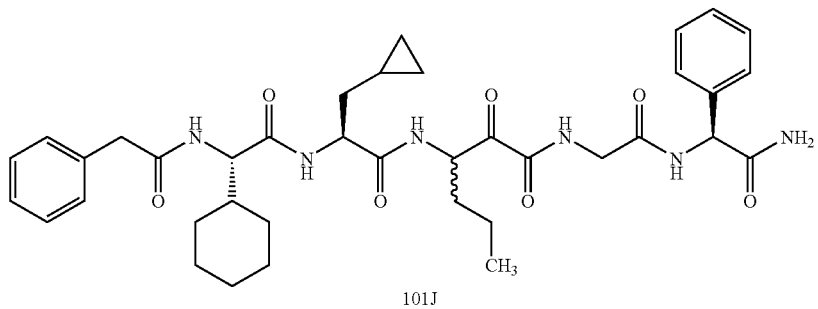

101J

Resin-bound compounds 101B, 101C, 101D, 101E, 101F and 101G were prepared according to the general procedure for solid-phase coupling reactions started with 100 mg of Fmoc-Sieber resin (0.035 mmol). Resin-bound compound 101G was oxidized to resin-bound compound 101H according to the general procedure for solid-phase Dess-Martin oxidation. The resin-bound compound 101H was treated with 4 mL of a 2% v/v solution of TFA in DCM for 5 min. The filtrate was added to 1 mL of AcOH and the solution was concentrated by vacuum centrifugation to provide compound 101J (0.011 g, 45% yield). MS (LCMS-Electrospray) 703.2 MH+.

Using the solid phase synthesis techniques defined herein above, the following moieties were prepared and used in accordance with the following Formula:

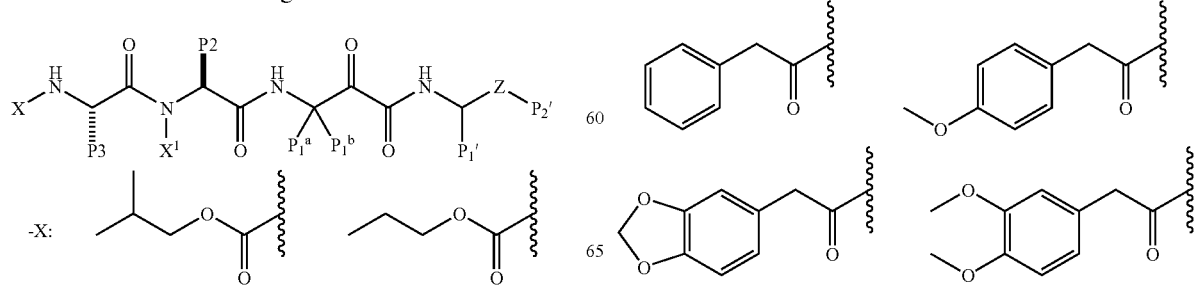

-continued
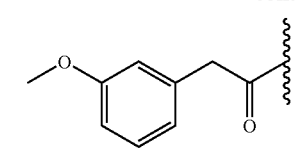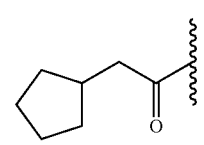
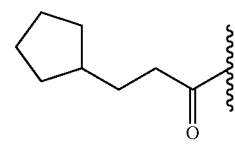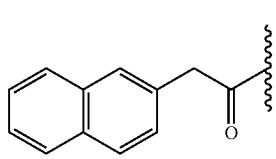
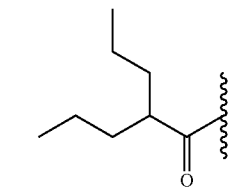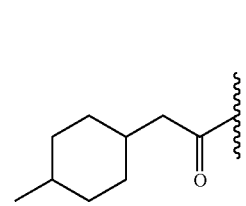
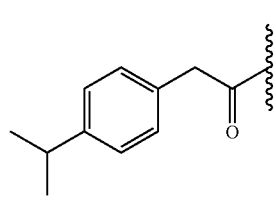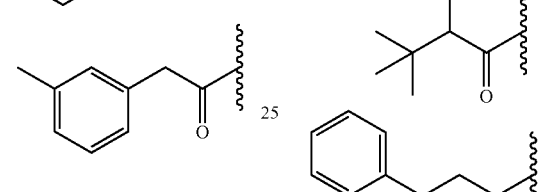
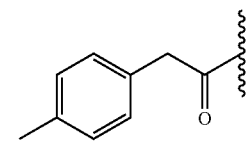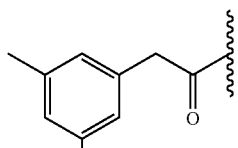
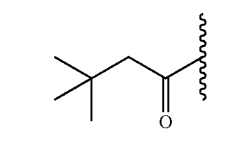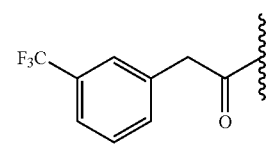
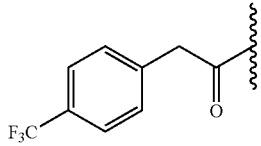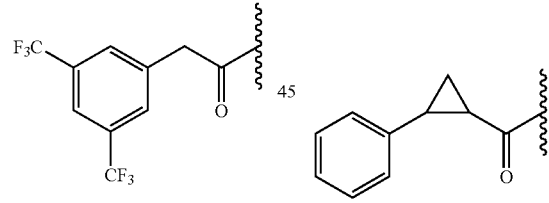
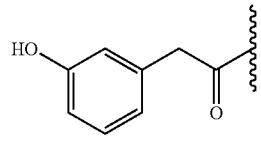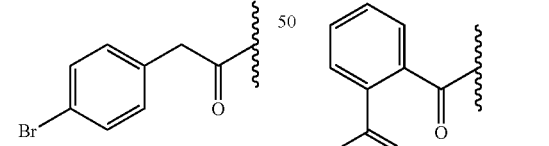
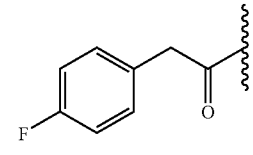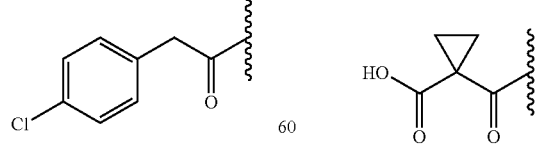
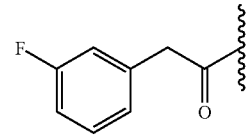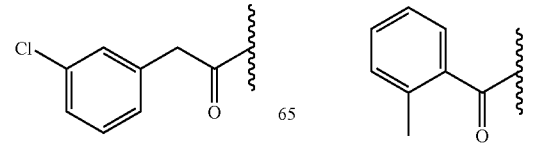
-continued
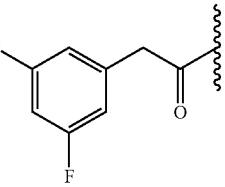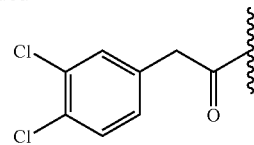
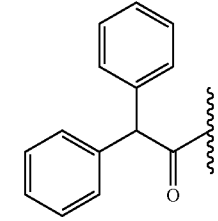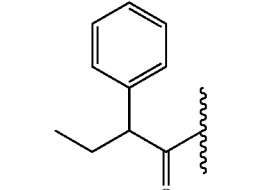
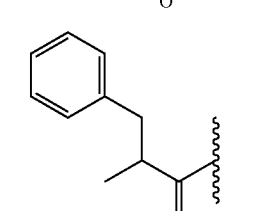
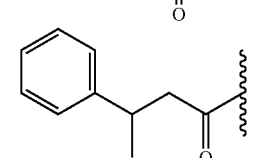
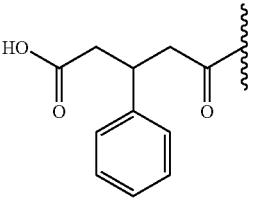
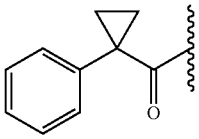
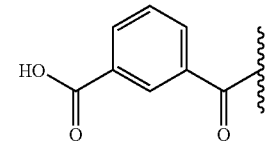
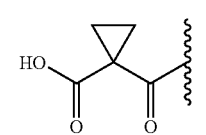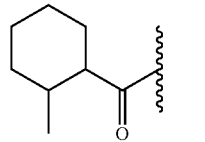
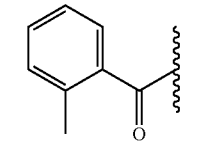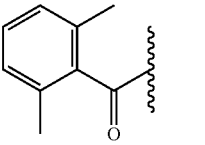

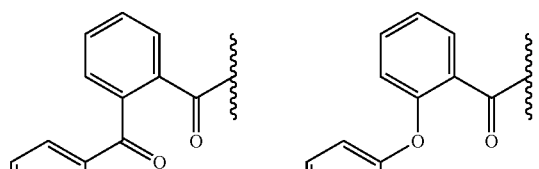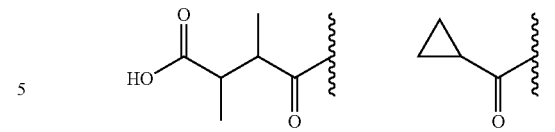

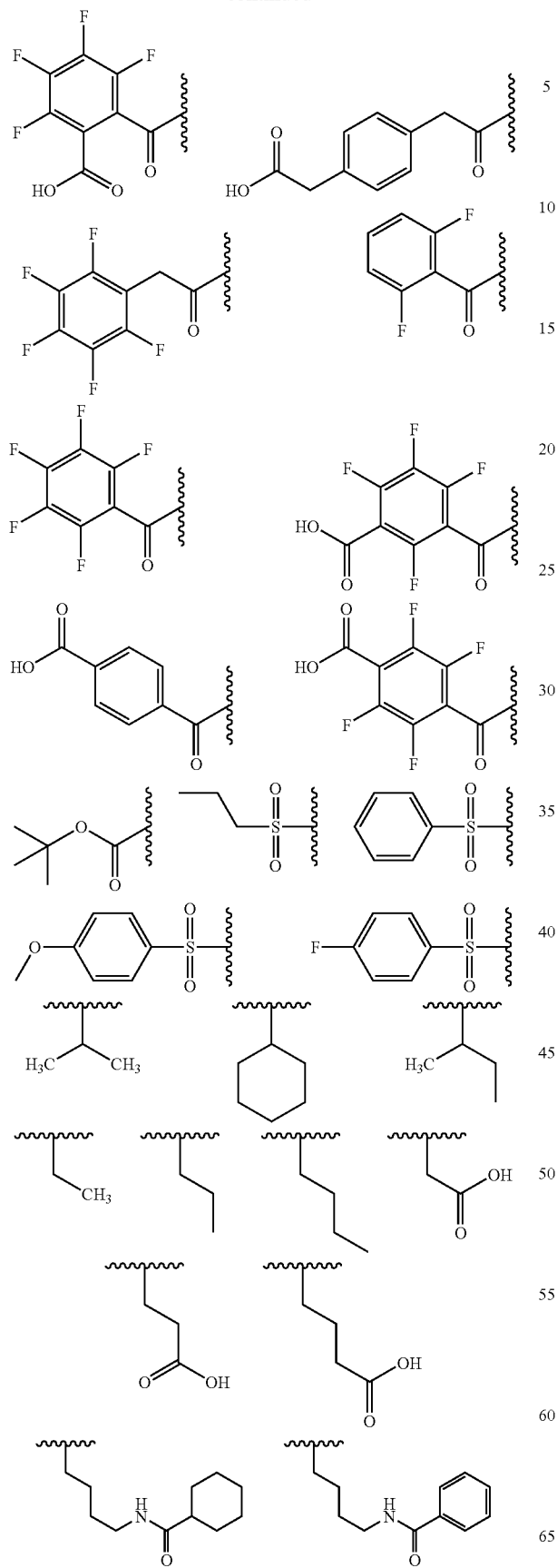
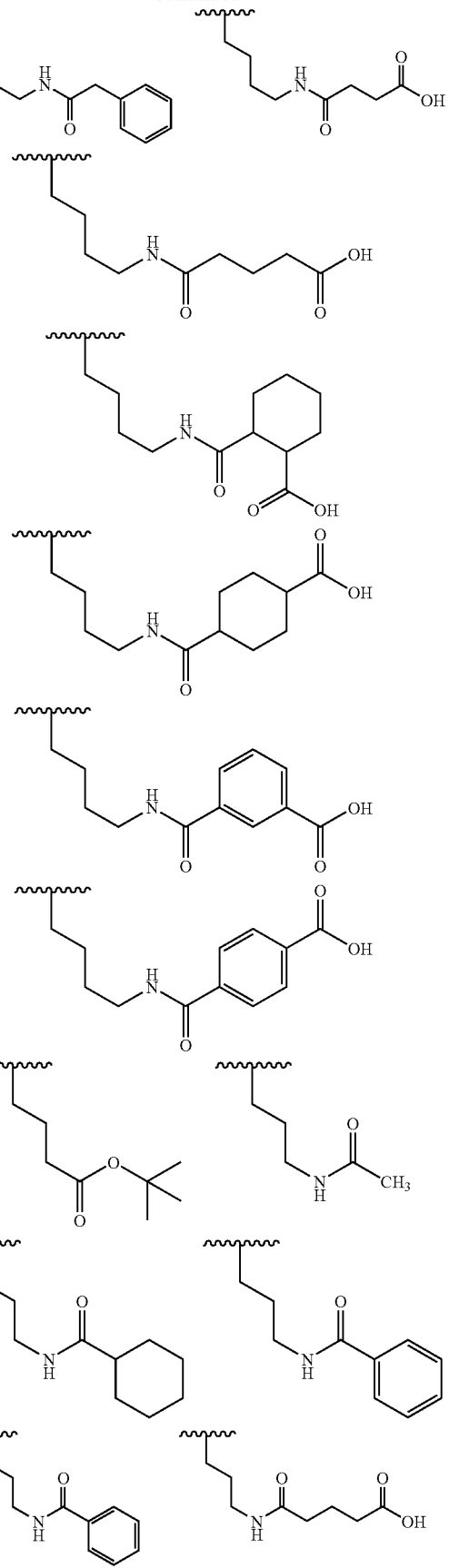

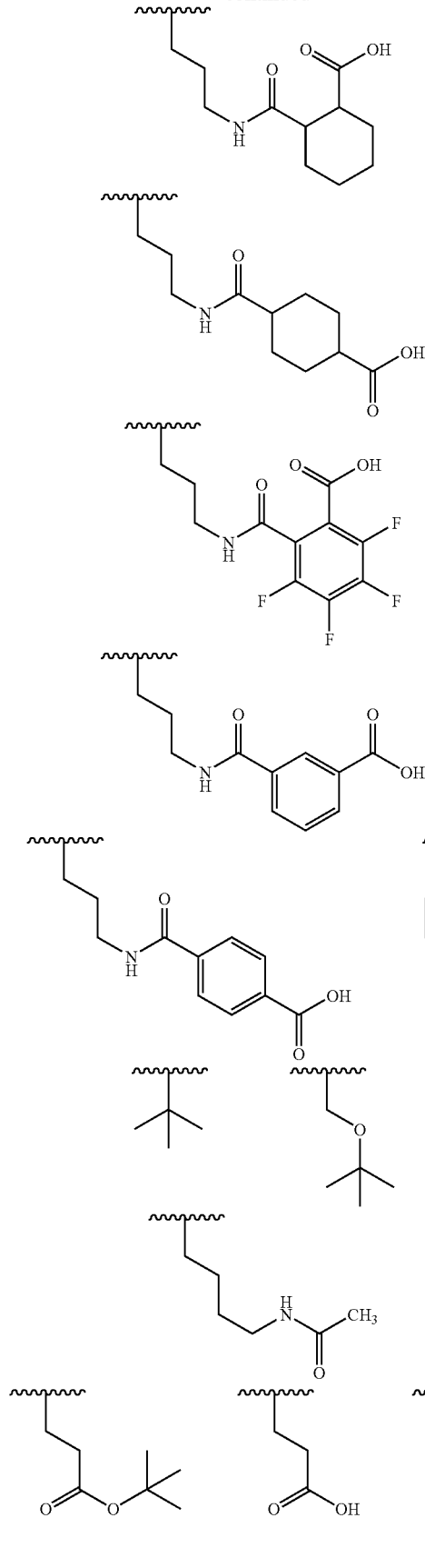
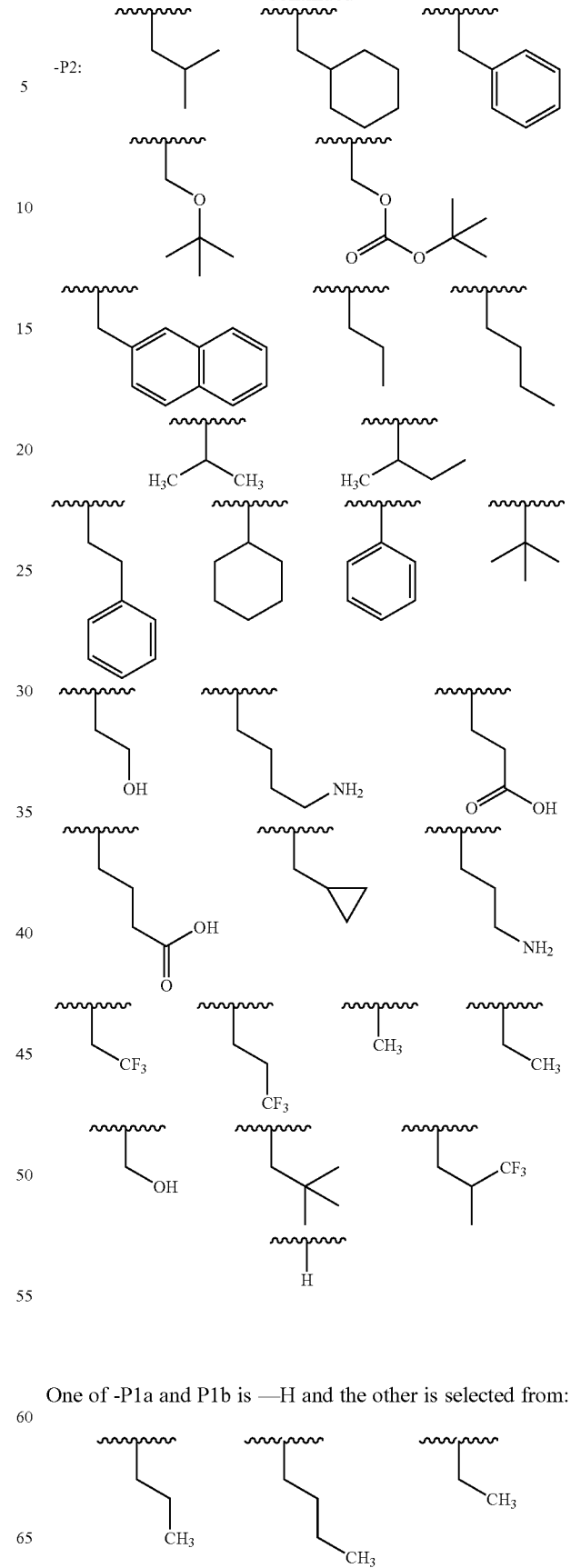
-P2:
One of -P1a and P1b is —H and the other is selected from:

-continued
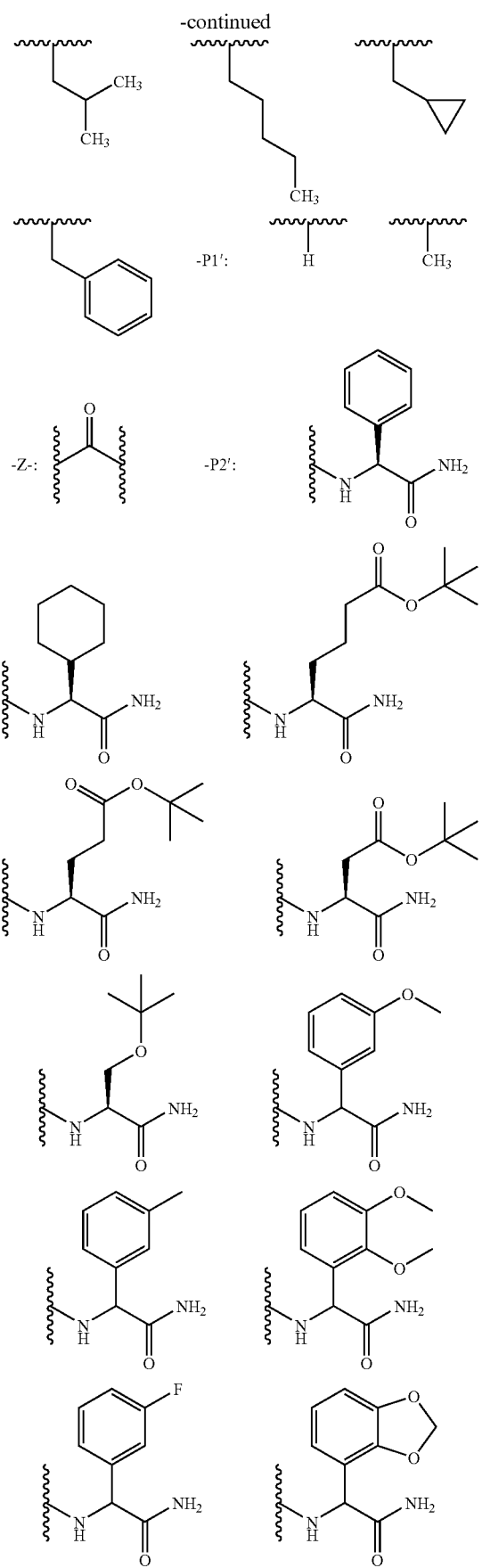
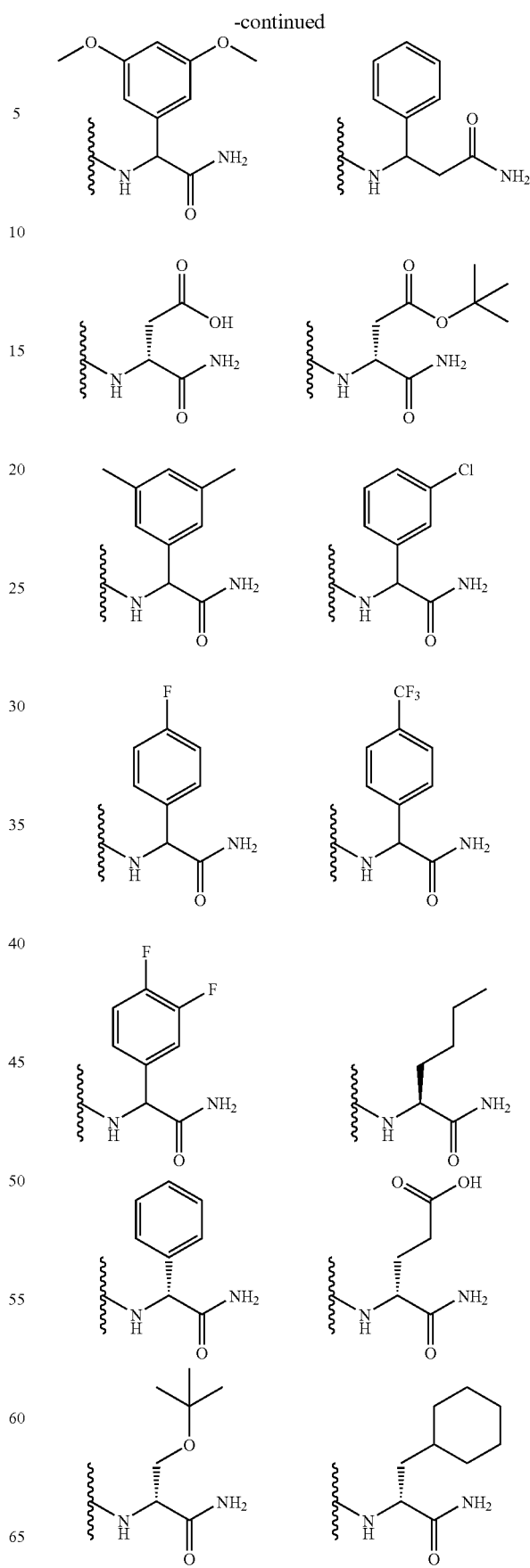

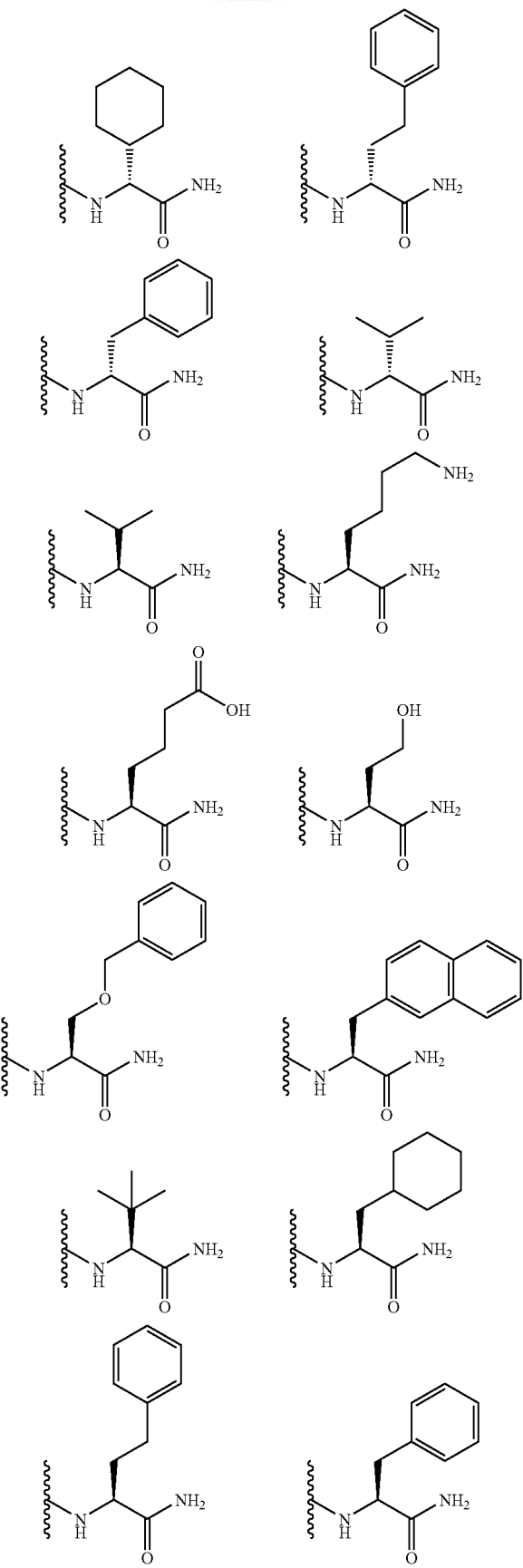

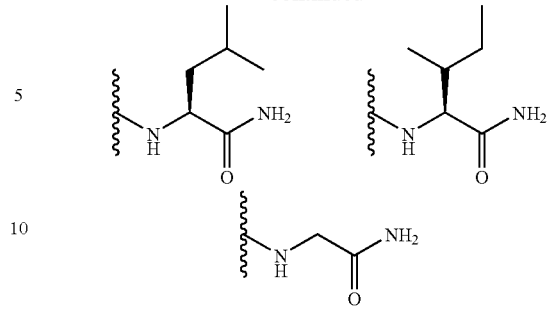

Using the above-described procedures, the compounds with their activity data listed in the attached Table 3 were prepared.

Additionally prepared were compounds as well as their activity data listed in the attached Table 4. Their preparation is described below.

General Procedures for Preparation of Compounds in Table 4 on Solid Support

Solid-phase synthesis is useful for the production of small amounts of certain compounds of the present invention. As with the conventional solid-phase synthesis of peptides, reactors for the solid-phase synthesis of peptidyl ketoamides are comprised of a reactor vessel with at least one surface permeable to solvent and dissolved reagents, but not permeable to synthesis resin of the selected mesh size. Such reactors include glass solid phase reaction vessels with a sintered glass frit, polypropylene tubes or columns with frits, or reactor Kans™ made by Irori Inc., San Diego Calif. The type of reactor chosen depends on volume of solid-phase resin needed, and different reactor types might be used at different stages of a synthesis. The following procedures will be referenced in the subsequent examples:

Procedure A: Coupling reaction: To the resin suspended in N-methylpyrrolidine (NMP) (10–15 mL/gram resin) was added N-Fmoc or N-Boc-amino acid (2 eq), HOAt (2 eq), HATU (2 eq) and diisopropylethylamine (4 eq). The mixture was let to react for 4–48 hours. The reactants were drained and the resin was washed successively with dimethylformamide, dichloromethane, methanol, dichloromethane and diethylether (use 10–15 mL solvent/gram resin). The resin was then dried in vacuo.

Procedure B: Fmoc deprotection: The Fmoc-protected resin was treated with 20% piperidine in dimethylformamide (10 mL reagent/g resin) for 30 minutes. The reagents were drained and the resin was washed successively with dimethylformamide, dichloromethane, methanol, dichloromethane and diethyl ether (10 mL solvent/gram resin).

Procedure C: Boc deprotection: The Boc-protected resin was treated with a 1:1 mixture of dichloromethane and trifluoroacetic acid for 20–60 minutes (10 mL solvent/ gram resin). The reagents were drained and the resin was washed successively with dichloromethane, dimethylformamide, 5% diisopropylethylamine in dimethylformamide, dimethylformamide, dichloromethane and dimethylformamide (10 mL solvent/ gram resin).

Procedure D: Semicarbazone hydrolysis. The resin was suspended in the cleavage cocktail (10 mL/g resin) consisting of trifluoroacetic acid: pyruvic acid: dichloromethane: water 9:2:2:1 for 2 hours. The reactants were drained and the procedure was repeated three more times. The resin was washed successively with dichloromethane, water and dichloromethane and dried under vacuum.

Procedure E: HF cleavage: The dried peptide-nVal(CO)-G-O-PAM resin (50 mg) was placed in an HF vessel containing a small stir bar. Anisole (10% of total volume) was added as a scavenger. In the presence of glutamic acid and cysteine amino acids, thioanisole (10%) and 1,2-ethanedithiol (0.2%) were also added. The HF vessel was then hooked up to the HF apparatus (Immuno Dynamics) and the system was flushed with nitrogen for five minutes. It was then cooled down to −78° C. with a dry ice/isopropanol bath. After 20 minutes, HF was distilled to the desired volume (10 mL HF/g resin). The reaction was let to proceed for 1.5 hours at 0° C. Work up consisted of removing all the HF using nitrogen. Dichloromethane was then added to the resin and the mixture was stirred for five minutes. This was followed by the addition of 20% acetic acid in water (4 mL). After stirring for 20 minutes, the resin was filtered using a fritted funnel and the dichloromethane was removed under reduced pressure. The remaining solution was washed with hexanes (3 x) to remove scavengers. Meanwhile, the resin was soaked in 1 mL methanol. The aqueous layer (20% HOAc) was added back to the resin and the mixture was agitated for five minutes and then filtered. The methanol was removed under reduced pressure and the aqueous layer was lyophilized. The peptide was then dissolved in 10–25% methanol (containing 0.1% trifluoroacetic acid) and purified by reverse phase HPLC.

II) SYNTHESIS OF INTERMEDIATES

EXAMPLE I

Synthesis of Boc-3-alkylsulfinylalanine

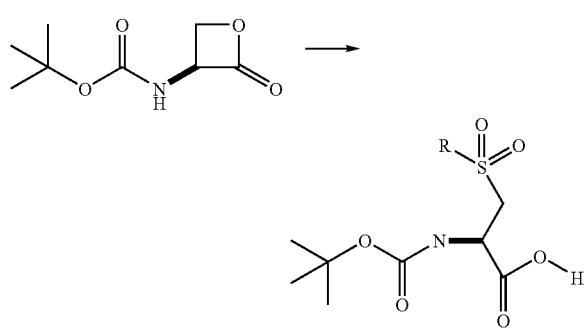

To a mixture of sodium hydride (20 mmol, 800 mg of 60% in oil, washed with hexanes) in tetrahydrofuran (30 mL) at 0° C., was added alkylthiol (20 mmol, R=Ph, R=1-Napthyl, R=2-Napthyl, R=PhCH2CH2 or R=Et) over 10 min. The cooling bath was removed and stirring was continued for 10 min, at which time Boc-2S-aminopropionyl lactone (reference: *Synthetic Communications*, (1995) 25(16), 2475–2482) (3.74 g, 20 mmol) was added. An ice bath was used to keep the temperature from exceeding 30° C. The reaction mixture was stirred at room temperature for 16 h, concentrated and then dissolved in 1 M aqueous potassium bisulfate (200 mL) and 1 M HCl (40 mL). The mixture was extracted with dichloromethane (2×200 mL). The combined organic layers were dried (sodium sulfate), filtered and concentrated. The residue was dissolved in water (200 mL), methanol (30 mL) and potassium carbonate (40 mmol, 5.5 g). Oxone (21 mmol, 13.0 g) was added in portions with cooling to maintain room temperature. The mixture was stirred for 18 hours and then concentrated in vacuo to remove the methanol. The solution was acidified with 2 M potassium bisulfate (pH=1) then extracted with ethyl acetate (2×100 mL). The combined organic layers were dried (sodium sulfate), filtered and concentrated. Purification was performed using reverse-phase HPLC. After purification the product was further purified by acid base extraction to remove de-bocylated material and then stored as the dilsopropylethyl ammonium salt to prevent further decomposition (loss of Boc group).

EXAMPLE II

Synthesis of 2-(1-methylethyl)-7-methyl-oct-4-enolc acid

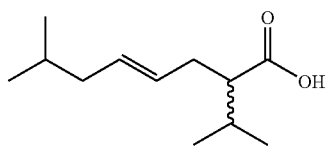

The above intermediate was synthesized according to the published procedure (Wuts, P. G. M.; Ritter, A. R.; Pruitt, L. E. *J. Org. Chem.* (1992) 57, 6696–6700).

EXAMPLE III

Synthesis of Fmoc-nV-(dpsc)-Gly-OH (Steps 1–7 below)

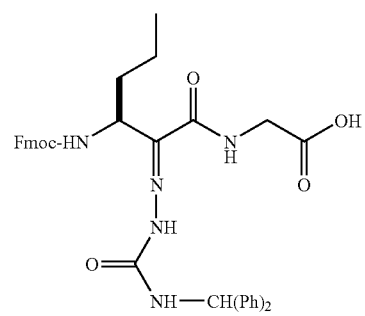

Step 1. Synthesis of Allyl Isocyanoacetate (Steps a–b Below)

a) Synthesis of isocyanoacetic acid potassium salt:

Ethyl isocyanoacetate (96.6 ml, 0.88 mol) was added dropwise to a chilled solution of ethanol (1.5 L) and potassium hydroxide (59.52 g, 1.0 mol). The reaction was slowly warmed to room temperature. After two hours the precipitated product was collected by filtration and washed with several portions of chilled ethanol. The potassium salt of isocyanoacetic acid thus obtained was dried in vacuo to a golden-brown solid (99.92 g, 91.8%).

b) Synthesis of allyl isocyanoacetate:

To the product of part a (99.92 g, 0.81 mol) dissolved in acetonitrile (810 ml) was added allyl bromide (92 ml, 1.05 mol). After heating at reflux for four hours a dark brown solution was obtained. The reaction mixture was concentrated and the remaining residue was dissolved in ether (1.5 L) and washed with water (3×500 ml). The organic layer was dried, filtered and concentrated to a dark brown syrup. The crude was purified by vacuum distillation at 7 mm Hg (98° C.) to a clear oil (78.92 g, 78%). NMR * ppm (CDCl$_3$): 5.9 (m, 1H), 5.3 (m, 2H), 4.7 (d, 2H), 4.25 (s, 2H).

Step 2. Synthesis of 9-fluorenylmethoxycarbonyl-norvalinal (Steps a–c Below)

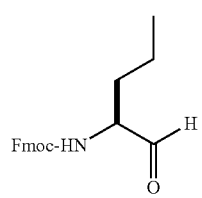

a) Synthesis of 9-fluorenylmethoxycarbonyl-L-norvaline methyl ester (Fmoc-nVal-OMe):

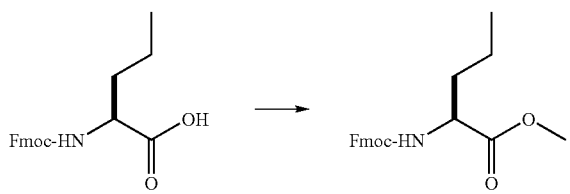

To a chilled solution of the commercially available Fmoc-L-norvaline (25 g, 73.75 mmol) in anhydrous methanol (469 ml) was added thionyl chloride (53.76 ml, 737.5 mmol) over one hour. TLC in ethylacetate taken an hour later confirmed the completion of the reaction (Rf=0.85). The reaction mixture was concentrated and the remaining residue was dissolved in ethylacetate. The organic layer was washed with saturated sodium bicarbonate (3×200 ml) followed by brine (200 ml). The organic layer was dried, filtered and concentrated to afford Fmoc-norVal-OMe as a white solid (26.03 g) in quantitative yield. NMR * ppm (CD$_3$OD): 7.7 (m, 2H), 7.6 (m, 2H), 7.4 (m, 2H), 7.3 (m, 2H), 4.3 (m, 2H), 4.1 (m, 2H), 3.7 (s, 3H), 1.7 (m,1H), 1.6 (m, 1H), 1.4 (m, 2H), 0.95 (t, 3H).

b) Synthesis of 9-fluorenylmethoxycarbonyl-norvalinol (Fmoc-nValinol):

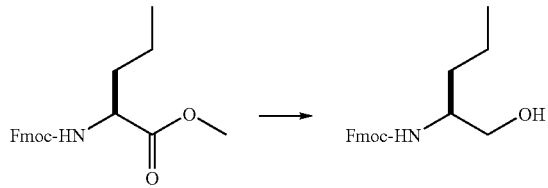

To Fmoc-nVal-OMe (26.03 g, 73.75 mmol) in tetrahydrofuran (123 ml) and methanol (246 ml) was added calcium chloride (16.37 g, 147.49 mmol). The reaction mixture was cooled to 0° C. and sodium borohydride (11.16 g, 294.98 mmol) was added in several batches. To the thick paste obtained 500 ml methanol was added and the reaction was let to stir at room temperature for 90 minutes. TLC in 2:3 ethylacetate:hexane confirmed the completion of the reaction (Rf=0.25). The reaction was quenched with the slow addition of 100 ml water at 0° C. The methanol was removed under reduced pressure and the remaining aqueous phase was diluted with ethylacetate. The organic layer was washed with water (3×500 ml), saturated sodium bicarbonate (3×500 ml) and brine (500 ml). The organic layer was dried over sodium sulfate and concentrated to a white solid (21.70 g, 90.5%). NMR * ppm (CD3OD): 7.8 (m, 2H), 7.7 (m, 2H), 7.4 (m, 2H), 7.3 (m, 2H), 4.3–4.5 (m, 2H), 4.2 (m, 1H), 3.6 (s, 1H), 3.5 (s, 2H), 1.5 (m, 1H), 1.3–1.4 (m, 3H), 0.99 (m, 3H).

c) Synthesis of 9-fluorenylmethoxycarbonyl-norvalinal (Fmoc-nVal-CHO):

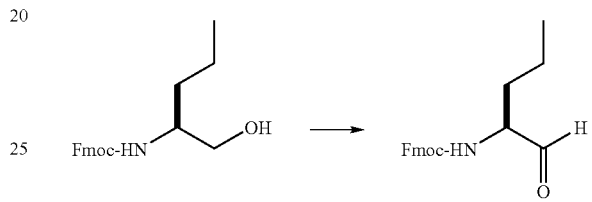

To a solution of Fmoc-norValinol (21.70 g, 66.77 mmol) in dichloromethane (668 ml) was added triethylamine (37.23 ml, 267 mmol) and the solution was cooled to 0° C. A suspension of pyridine sulfur trioxide complex (42.51 g, 267 mmol) in dimethylsulfoxide (96 ml) was added to the chilled solution. After one hour, TLC in 2:3 ethylacetate:hexanes confirmed the completion of the reaction. The dichloromethane was removed under reduced pressure and the remaining residue was dissolved in ethylacetate and washed with water (2×50 ml), 1N saturated sodium bisulfate (2×50 ml), saturated sodium bicarbonate (2×50 ml) and brine (50 ml). The organic layer was concentrated to yield a white solid. Theoretical yield (21.57 g) was assumed and the reaction was taken to the next step without further purification.

Step 3. Synthesis of Diphenylmethyl Semicarbazide (dpsc) Trifluoroacetate Salt (Steps a–b Below)

a) Synthesis of Boc-semicarbazid-4-yl diphenylmethane

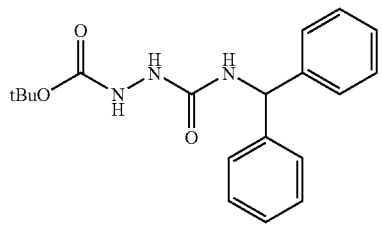

To a solution of carbonyldiimidazole (16.2 g, 0.10 mole) in dimethylformamide (225 ml) was added a solution of tert-butyl carbazate (13.2 g, 0.100 mol) in dimethylformamide (225 ml) dropwise over 30 minutes. Diphenylmethylamine (18.3 g, 0.10 mol) was added next over 30 minutes. The reaction was allowed to stir at room temperature for one hour. Water (10 mL) was added and the mixture was concentrated to about 150 mL under reduced pressure. This solution was poured into water (500 mL) and extracted with ethyl acetate (400 mL). The ethylacetate phase was washed with 1N HCl (2×75 mL), H2O (2×75 mL), saturated sodium bicarbonate solution (2×75 mL) and sodium chloride (2×75 mL), and dried with magnesium sulfate. The mixture was filtered and the solution was concentrated to give 29.5 g (85% yield) of a white foam. This material could be purified by recrystallization from ethyl acetate/hexane, but was pure enough to use directly in the next step: mp 142–143° C. 1H NMR (CDCl3) d 1.45 (s, 9H), 6.10 (dd, 2H), 6.42 (s, 1H), 6.67 (bs, 1H), 7.21–7.31 (m, 10H). Analytical calculated for C19H23N3O3: C, 66.84; H, 6.79; N, 12.31. Found: C, 66.46; H, 6.75; N; 12.90.

b) Synthesis of diphenylmethyl semicarbazide (dpsc) trifluoroacetate salt

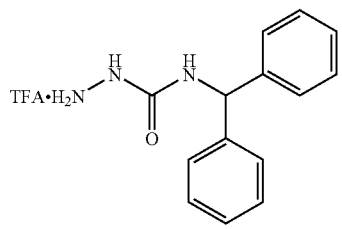

A solution of Boc-semicarbazid-4-yl diphenylmethane (3.43 g, 10 mmol) in dichloromethane (12.5 ml) was treated with trifluoroacetic acid (12.5 ml) at room temperature and allowed to stir for 30 min. The solution was added dropwise to 75 mL of ether and the resulting solid (2.7 g, 80%) was collected by filtration. mp 182–184° C. $^1$H NMR (CD$_3$OD) d 6.05 (s, 1H), 7.21–7.35 (m, 10H). $^{13}$C NMR (CD$_3$OD) d 57.6, 118.3 (q, CF$_3$), 126.7, 127.9, 141.6, 156.9, 160.9 (q, CF$_3$CO$_2$H).

Step 4. Synthesis of Fmoc-nVal-(CHOH)-Gly-Oallyl

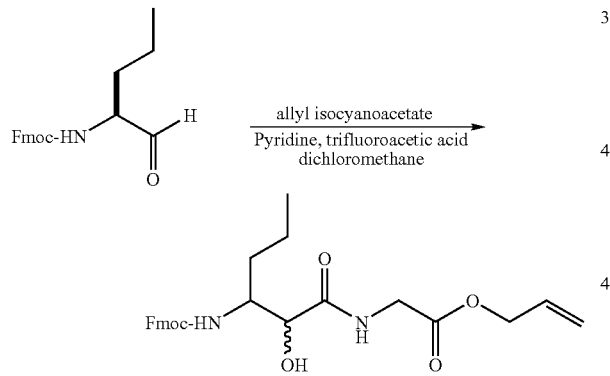

To a solution of Fmoc-nVal-CHO (Example III, Step 2c) (5.47 g, 16.90 mmol) in dichloromethane (170 ml) was added allyl isocyanoacetate (Example III, Step 1b) (2.46 ml, 20.28 mmol) and pyridine (5.47 ml, 67.61 mmol). The reaction mixture was cooled to 0° C. and trifluoroacetic acid (3.38 ml, 33.80 mmol) was added dropwise. The reaction was stirred at 0° C. for 1 h, and then at room temperature for 48 hours. TLC taken in ethylacetate confirmed the completion of the reaction. The reaction mixture was concentrated and subjected to flash chromatography using 20% to 70% ethylacetate in is hexanes. Fractions containing the desired product were pooled and concentrated to a white foam (6.88 g, 87.3%). TLC in 1:1 ethylacetate/hexanes showed one spot (Rf=0.37). NMR **ppm (CD$_3$OD): 7.8 (m, 2H), 7.65 (m, 2H), 7.4 (m, 2H), 7.3 (m, 2H), 5.9 (m, 1H), 5.1–5.4 (m, 2H), 4.55–4.65 (m, 2H), 4.3–4.4 (m, 2H), 4.15–4.25 (m, 1H), 4.01 (s, 1H), 3.9–4.0 (m, 3H), 1.5–1.6 (m, 2H), 1.35–1.45 (m, 3H), 0.9 (m, 3H).

Step 5. Synthesis of Fmoc-nVal-(CO)-Gly-Oallyl

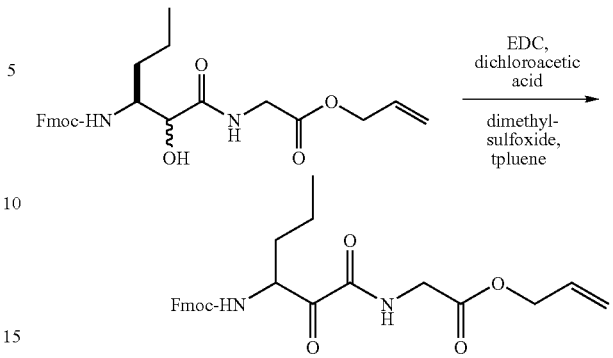

To a solution of Fmoc-nVal-(CHOH)-Gly-Oallyl (Step 4) (5.01 g, 10.77 mmol) in dimethylsulfoxide (100 ml) and toluene (100 ml) was added EDC (20.6 g, 107.7 mmol). The reaction mixture was cooled to 0° C. and dichloroacetic acid (4.44 ml, 53.83 mmol) was added dropwise. The reaction was stirred for 15 minutes at 0° C. and 1 h at room temperature. Water (70 ml) was added at 0° C. and the toluene was removed under reduced pressure. The remaining residue was diluted with ethylacetate and washed several times with a saturated sodium bicarbonate solution followed by 1N sodium bisulfate and brine. The organic layer was dried over sodium sulfate, filtered and concentrated. The theoretical yield of 4.99 g was assumed and the reaction was taken to the next step without further purification. TLC in 1:1 ethylacetate/hexanes shows one spot (Rf=0.73).

Step 6. Synthesis of Fmoc-nVal-(dpsc)-Gly-Oallyl

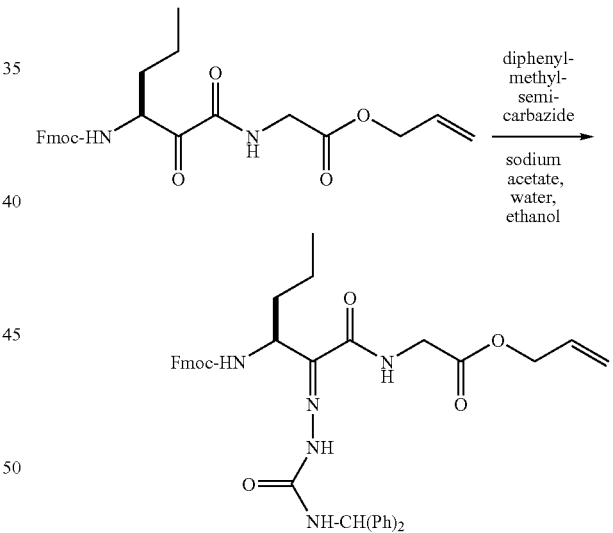

To a solution of Fmoc-nVal-(CO)-Gly-Oallyl (step 5) (4.99 g, 10.75 mmol) in ethanol (130 ml) and water (42 ml) were added diphenylmethyl semicarbazide (dpsc) trifluoroacetate salt (Example III, Step 3b) (7.6 g, 21.5 mmol) and sodium acetate *3H2O (1.76 g, 12.9 mmol). The reaction mixture was heated at reflux for 90 minutes. The completion of reaction was confirmed by thin layer chromatography taken in 1:1 ethylacetate:hexane. Ethanol was removed under reduced pressure and the remaining residue was dissloved in ethylacetate and washed with 1N sodium bisulfate (2×10 mL), saturated sodium bicarbonate (2×10 mL) and brine (2×10 mL). The organic layer was dried, filtered and concentrated. The resulting residue was purified by flash chromatography in 20% to 50% ethylacetate in hexanes to give a white solid (5.76 g, 78%). TLC in 1:1 ethylacetate/

Step 7. Synthesis of Fmoc-nVal-(dpsc)-Gly-OH

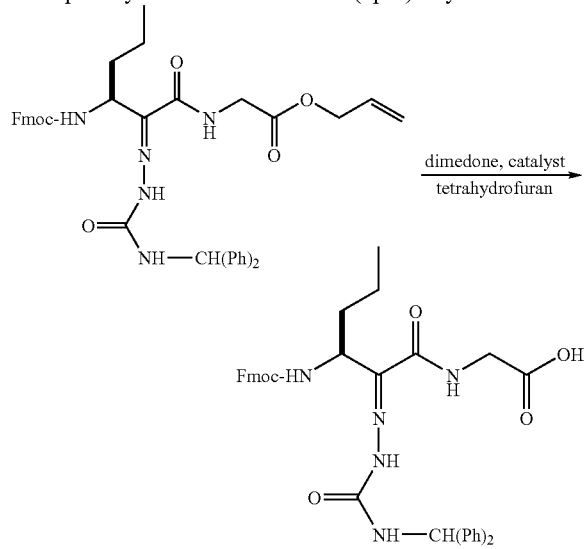

To a solution of Fmoc-nVal-(dpsc)-Gly-Oallyl (example III, Step 6) (4.53 g, 6.59 mmol) in tetrahydrofuran (300 ml) was added dimedone (4.62 g, 32.97 mmol) followed by tetrakis(triphenylphosphine) palladium(0) catalyst (0.76 g, 0.66 mmol). After 90 minutes the completion of the reaction was confirmed by TLC (9:1 dichloromethane:methanol). The reaction mixture was concentrated and the remaining residue was dissolved in ethylacetate and washed with 0.1 M potassium biphosphate (3×50 mL). The organic layer was then treated with 50 ml sodium bisulfite and the two phase system was stirred for 15 minutes. The phases were separated and the procedure was repeated twice more. The organic layer was dried, filtered and concentrated and subjected to flash column chromatography (20% to 100% ethylacetate in hexanes, then 9:1 dichloromethane:methanol) to obtain a white solid (3.99 g, 94%). TLC in 9:1 dichloromethane:methanol shows two spots (cis and trans isomers). NMR δ ppm (CD3OD): 7.75 (m, 2H), 7.6 (m, 3H), 7.2–7.4 (m, 14H), 6.1–6.2 (m, 1H), 4.25–4.4 (m, 2H), 4.1–4.2 (m, 2H), 3.85 (s, 2H), 1.6–1.8 (m, 2H), 1.3–1.5 (m, 2H), 0.95 (t, 3H).

EXAMPLE IV

Synthesis of H-nVal(dpsc)-Gly-Phg-MBHA resin (Steps 1–2 below)

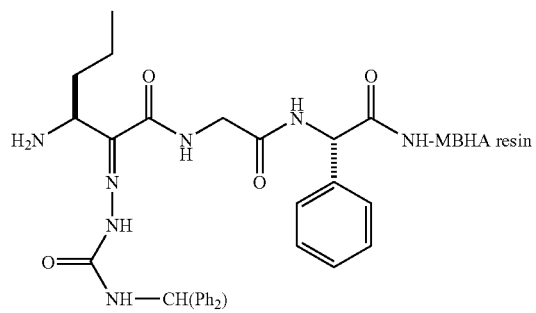

Step 1. Synthesis H-Phg-MBHA Resin

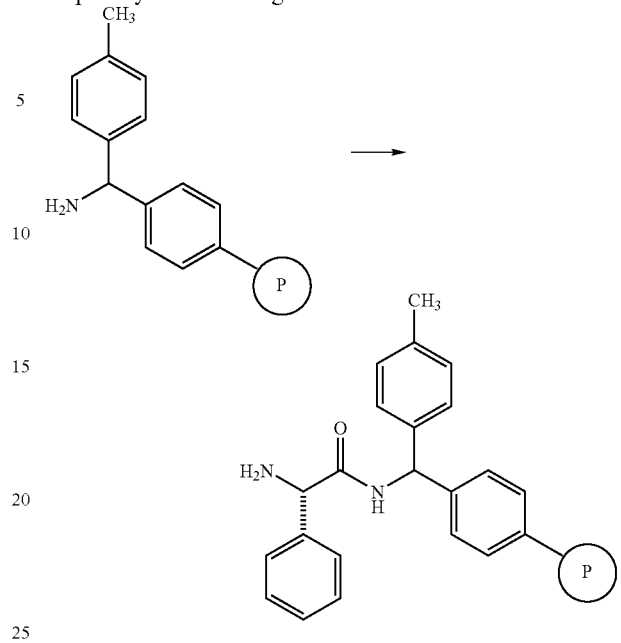

Commercially available MBHA resin (2.6 g, 1.12 mmol/g, 2.91 mmol) was transferred to a 250 mL frifted solid phase reaction vessel equipped with a nitrogen inlet. It was then washed thoroughly with 30 ml portions of dichloromethane, methanol, dimethylformamide and dichloromethane and coupled over 18 hours to the commercially available Fmoc-Phg-OH (2.17 g, 5.82 mmol) according Procedure A with 99.82% efficiency. The resin was then subjected to Fmoc deprotection according to procedure B. A qualitative ninhydrin assay on a small aliquot gave dark blue resin and solution, indicating a successful reaction.

Step 2. Synthesis of H-nVal(dpsc)-Gly-Phg-MBHA Resin

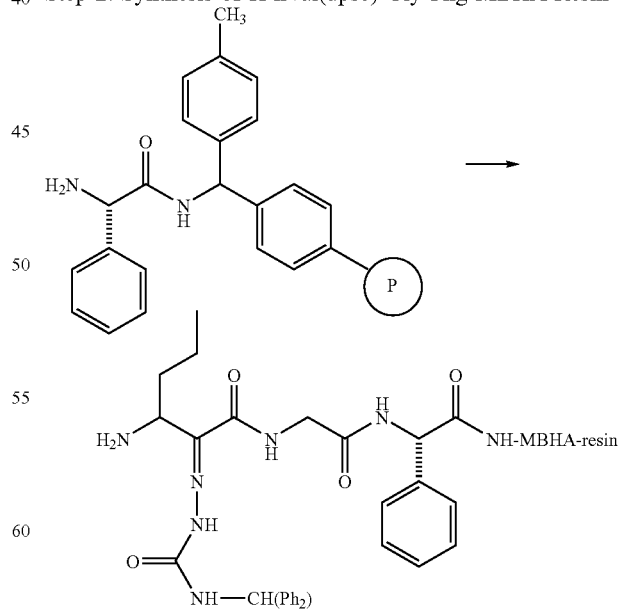

The resin obtained in step 1 above (2.6 g, 0.8 mmol/g, 2.91 mmol) was reacted with Fmoc-nVal-(dpsc)-Gly-OH Example III, Step 7) (5.82 mmol, 3.77 g) according to Procedure A. After 18 hours, quatitative ninhydrin analysis indicated 99.91% coupling efficiency. The resin was subjected to Fmoc deprotection according to procedure B. A qualitative ninhydrin assay on a small aliquot gave dark blue resin and solution, indicating a successful reaction.

III) SOLID PHASE ASSEMBLY OF REPRESENTATIVE HEPATITIS C TARGETS

EXAMPLE V

Solid Phase Synthesis of 2,5-difluoro-6-hydroxycarbonylphenylcarbonyl-G(Chx)-Leu-nVal-(CO)-Gly-Phg-NH2 (Steps 1–5 below)

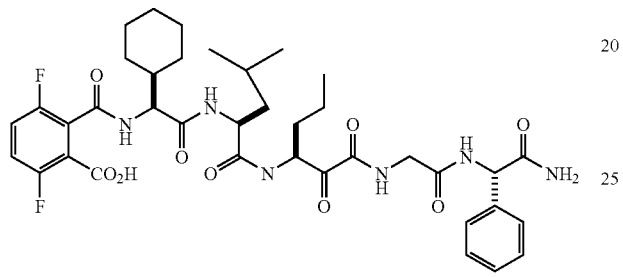

Step 1. Synthesis of Fmoc-Leu-nVal(dpsc)-Gly-Phg-MBHA Resin

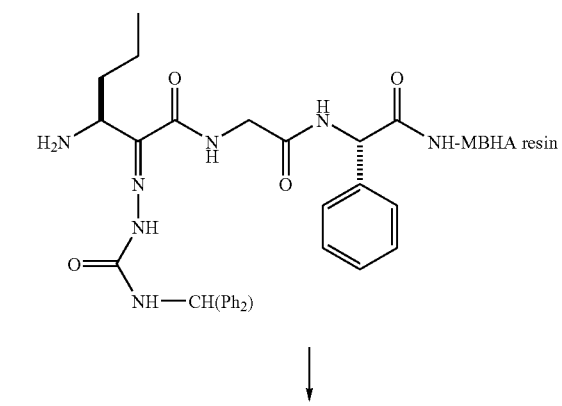

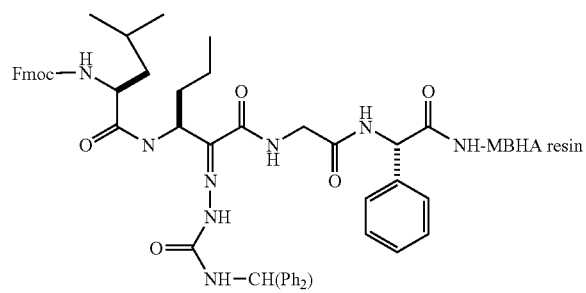

The compound H-nVal(dpsc)-Gly-Phg-MBHA resin (Example IV, Step 2) (1.5 g, 1.12 mmol/g, 1.68 mmol) was transferred to a fritted polypropylene tube and was coupled to N-Fmoc-Leu-OH (890 mg, 2.52 mmol) according to procedure A. After 18 hours, qualitative ninhydrin analysis showed colorless beads and solution.

Step 2. Synthesis of Fmoc-G(Chx)-Leu-nVal(dpsc)-Gly-Phg-MBHA Resin

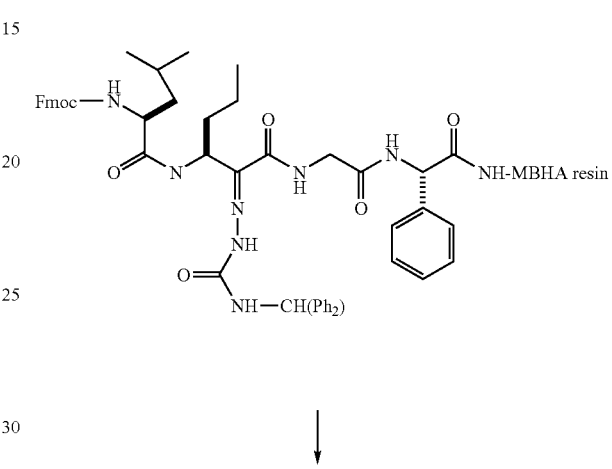

The resin obtained in Example V, Step 1 (Fmoc-Leu-nVal (dpsc)-Gly-Phg-MBHA resin, 1.68 mmol) was subjected to the Fmoc deprotection procedure according to Procedure B. Commercially available Fmoc-G(Chx)-OH (0.956 g, 0.2.52 mmol) was then coupled according to procedure A. After 18 hours quantitative ninhydrin analysis indicated 98% coupling efficiency.

Step 3. Synthesis of 2,5-difluoro-6-hydroxycarbonylphenylcarbonyl-G(Chx)-Leu-nVal(dpsc)-Gly-Phg-MBHA Resin

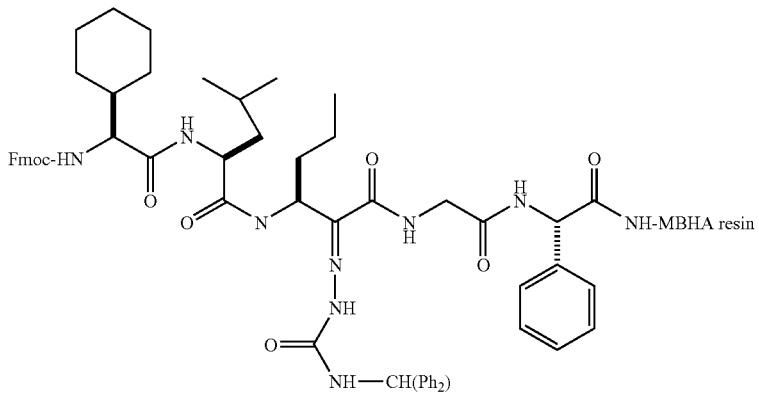

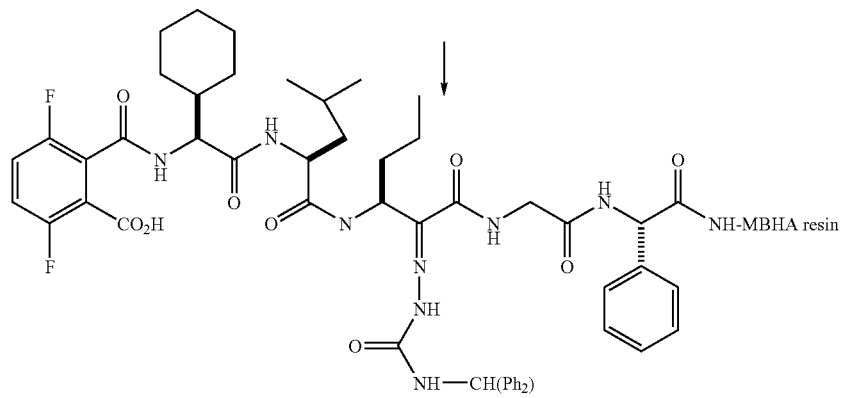

The resin obtained in Example V, Step 2 (Fmoc-G(Chx)-Leu-nVal(dpsc)-Gly-Phg-MBHA resin) was subjected to Fmoc deprotection according to procedure B. A ninhydrin assay on a small aliquot gave dark blue resin and solution, indicating a successful reaction. To the resin (150 mg, 0.168 mmol) suspended in 1 ml NMP was added 3,6-difluorophthalic anhydride (91 mg, 0.42 mmol) followed by diisopropylethylamine (0.146 ml, 84 mmol), and the reaction mixture was shaken for 18 hours at room temperature. Quantitative ninhydrin analysis indicated 97.8% coupling efficiency.

Step 4. Synthesis of 2,5-difluoro-6-hydroxycarbonylphenylcarbonyl-G(Chx)-Leu-nVal(CO)-Gly-Phg-MBHA Resin

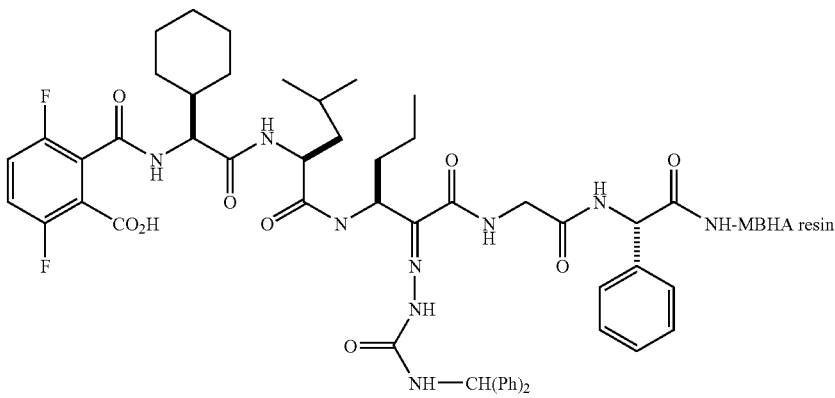

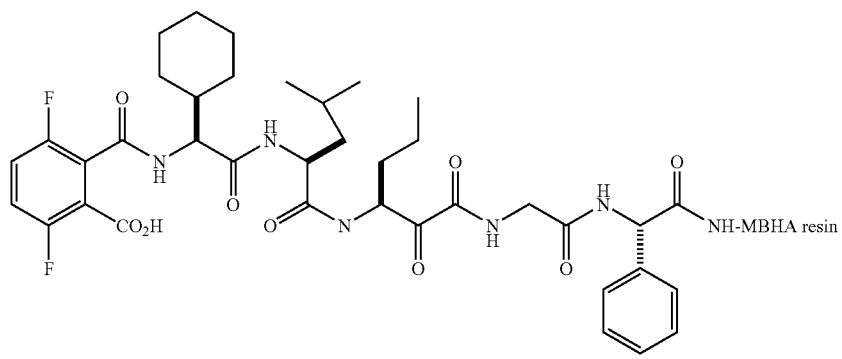

The compound of step Example V, Step 3 (2,5-difluoro-6-hydroxycarbonylphenylcarbonyl-G(Chx)-Leu-nVal(dpsc)-Gly-Phg-MBHA Resin) (200 mg) was subjected to semicarbazone hydrolysis Procedure D.

Step 5. Synthesis of 2,5-difluoro-6-hydroxycarbonylphenylcarbonyl-G(Chx)-Leu-nVal(CO)-Gly-Phg-NH$_2$

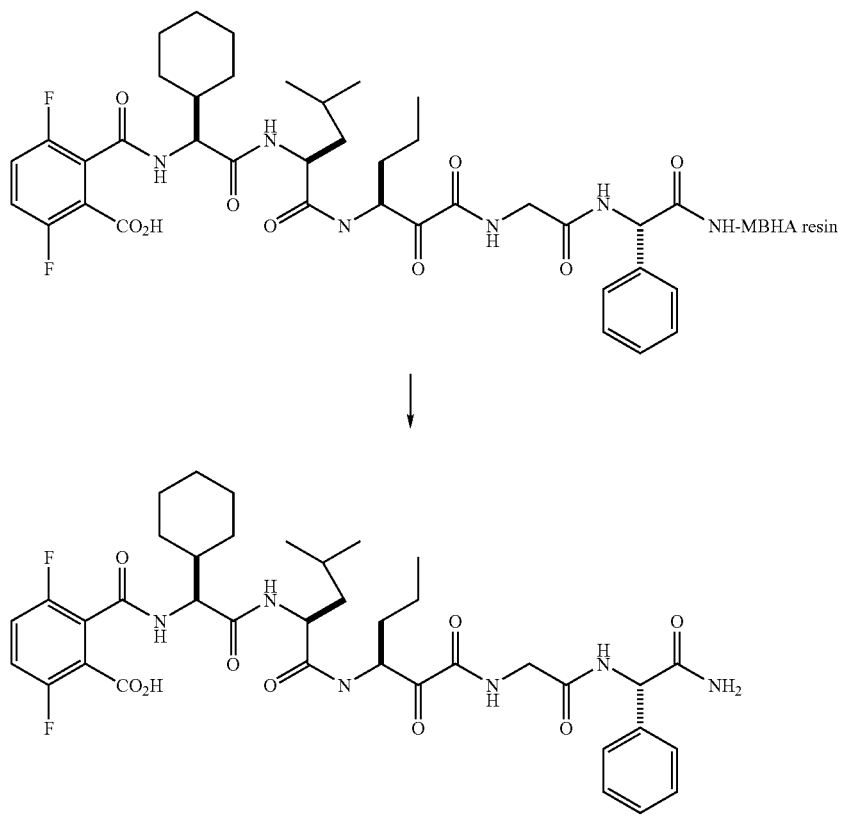

The resin of Example V, Step 4 (2,5-difluoro-6-hydroxycarbonylphenylcarbonyl-G(Chx)-Leu-nVal(CO)-Gly-Phg-MBHA resin) (100 mg) was subjected to HF cleavage condition (Procedure E) to yield the desired crude product. The material was purified by HPLC using a 2.2×25 cm reverse phase column, containing a C-18 resin comprised of 10 micron size gel particles with a 300 angstrom pore size, eluting with a gradient using 20–50% acetonitrile in water. Analytical HPLC using a 4.6×250 mm reverse phase column, containing a C-18 resin comprised of 5 micron size gel particles with a 300 angstrom pore size, eluting with 10–60% acetonitrile in water (containing 0.1% trifluoroacetic acid) showed one peak at 17.2 minutes. Low resolution mass spectrum confirmed the desired mass (MH$^+$ 771.5).

EXAMPLE VI

Solid Phase Synthesis of iBoc-G(Chx)-Cys((O2)Et)-nVal-(CO)-Gly-Phg-NH2 (Steps 1–5 Below)

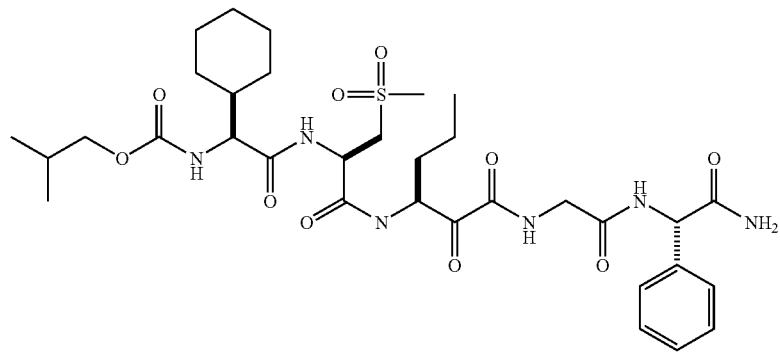

Step 1. Synthesis of Fmoc-Cys((O2)Et)-nVal(dpsc)-Gly-Phg-MBHA Resin

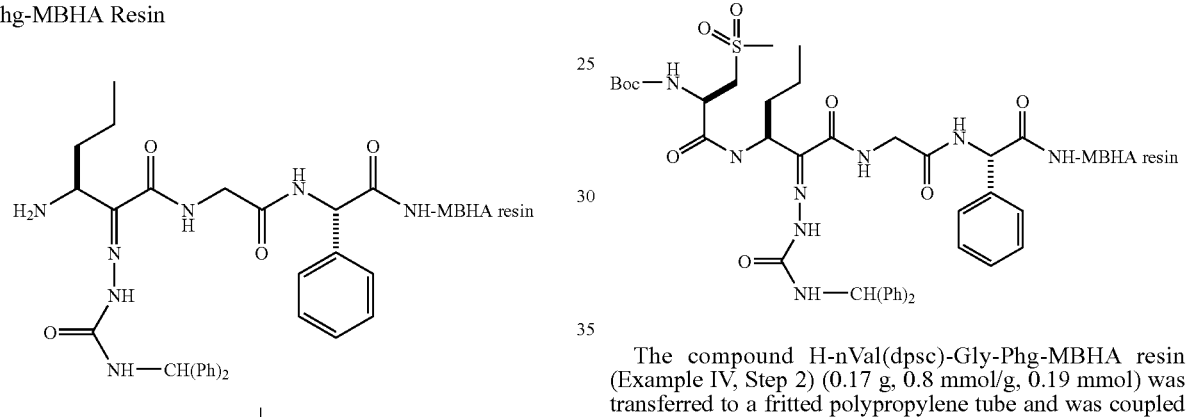

The compound H-nVal(dpsc)-Gly-Phg-MBHA resin (Example IV, Step 2) (0.17 g, 0.8 mmol/g, 0.19 mmol) was transferred to a fritted polypropylene tube and was coupled to Boc-Cys((O2)Et)-OH (Example I) (160 mg, 0.38 mmol) according to procedure A. After 18 hours, quantitative ninhydrin analysis showed the coupling was 99.98% complete.

Step 2. Synthesis of Fmoc-G(Chx)-Cys((O2)Et)-nVal(dpsc)-Gly-Phg-MBHA Resin

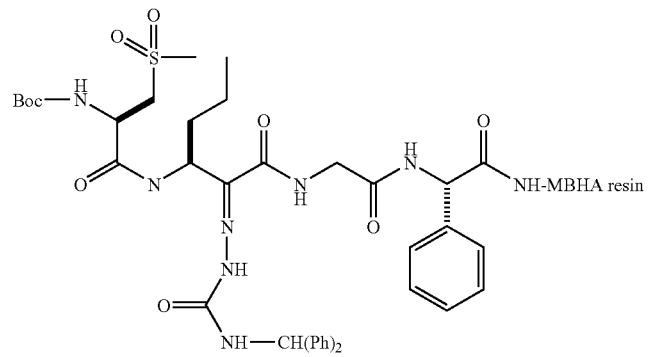

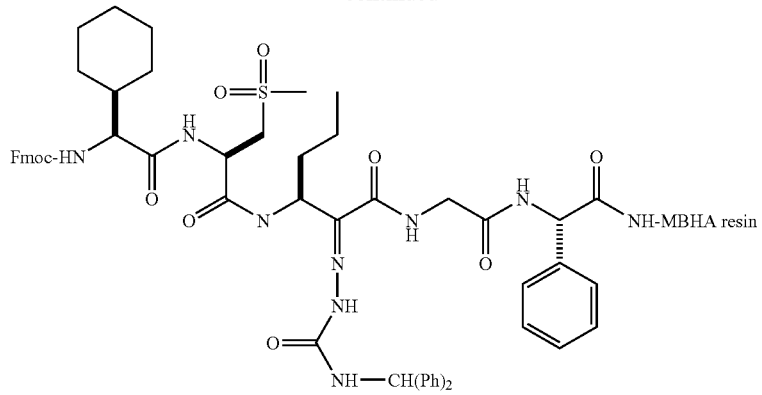

The resin obtained in the previous step (Example VI, Step 1) (Boc-Cys((O2)Et)-nVal(dpsc)-Gly-Phg-MBHA resin, 0.19 mmol) was subjected to the Boc deprotection procedure according to Procedure C. Fmoc-G(Chx)-OH (0.170 g, 0.45 mmol) was then coupled according to procedure A. After 18 hours quantitative ninhydrin analysis indicated 99.92% coupling efficiency.

Step 3. Synthesis of iBoc-G(Chx)-Cys(O2)Et)-nVal(dpsc)-Gly-Phg-MBHA Resin

The resin obtained in the previous step (Example VI, Step 2) (Fmoc-G(Chx)-Cys((O2)Et)-nVal(dpsc)-Gly-Phg-MBHA resin) was subjected to Fmoc deprotection according to procedure B. A ninhydrin assay on a small aliquot gave dark blue resin and solution, indicating a successful reaction. To the resin (170 mg, 0.19 mmol) suspended in 1 ml NMP was added isobutyl chloroformate (0.06 mL mg, 0.45 mmol) followed by diisopropylethylamine (0.16 ml, 0.90 mmol), and the reaction mixture was shaken for 18 hours at room temperature. Quantitative ninhydrin analysis indicated 99.35% coupling efficiency.

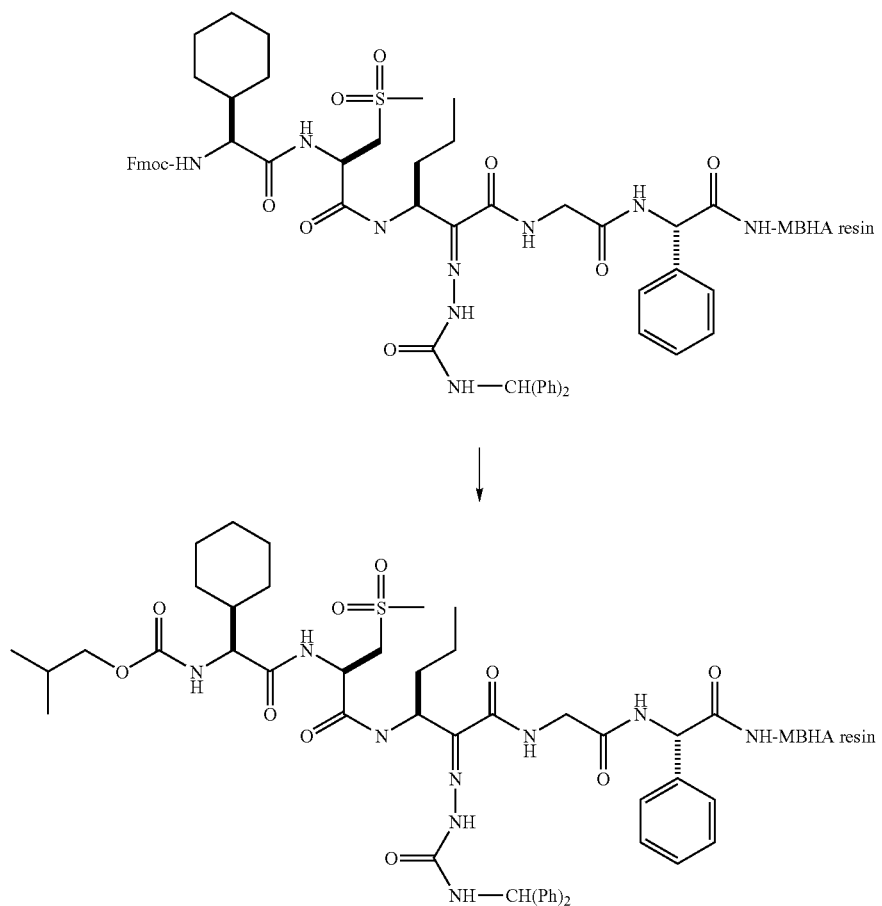

Step 4. Synthesis of iBoc-G(Chx)-Cys((O2)Et)-nVal(CO)-Gly-Phg-MBHA Resin
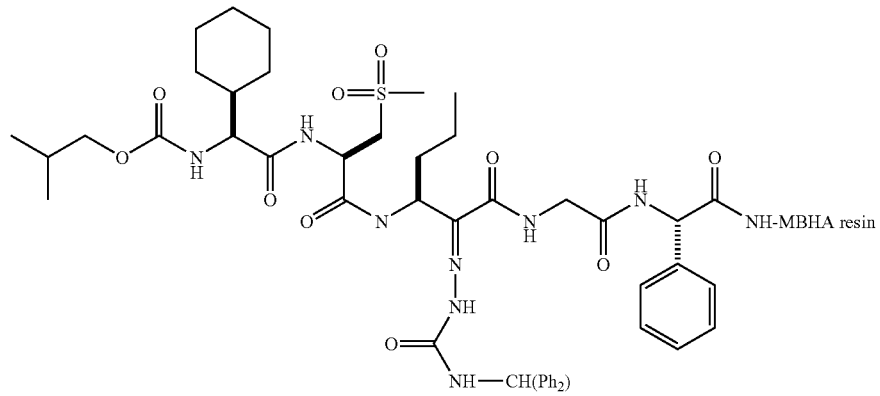
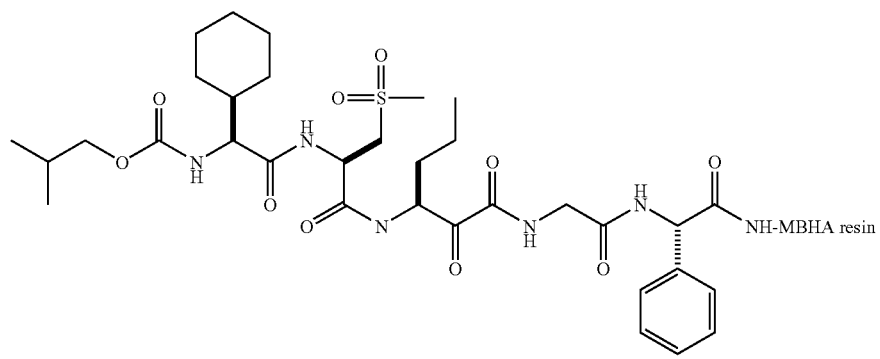
The compound of the previous step step (Example VI, Step 3) iBoc-G(Chx)-Cys(O2)Et)-nVal(dpsc)-Gly-Phg-MBHA resin (170 mg) was subjected to semicarbazone hydrolysis Procedure D.
Step 5. Synthesis of iBoc-G(Chx)-Cys((O2)Et)-nVal(CO)-Gly-Phg-NH$_2$
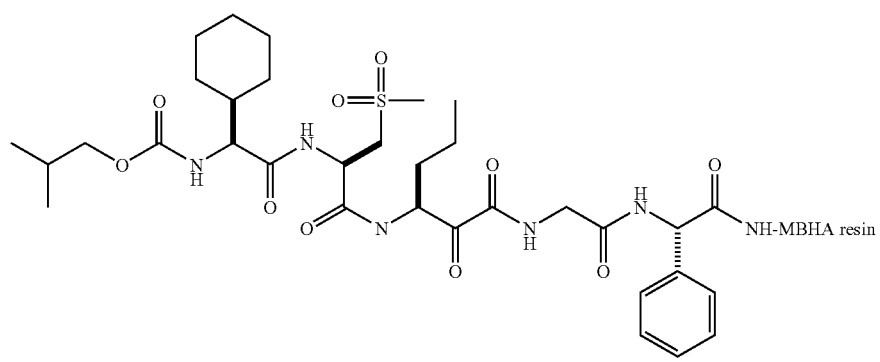

-continued

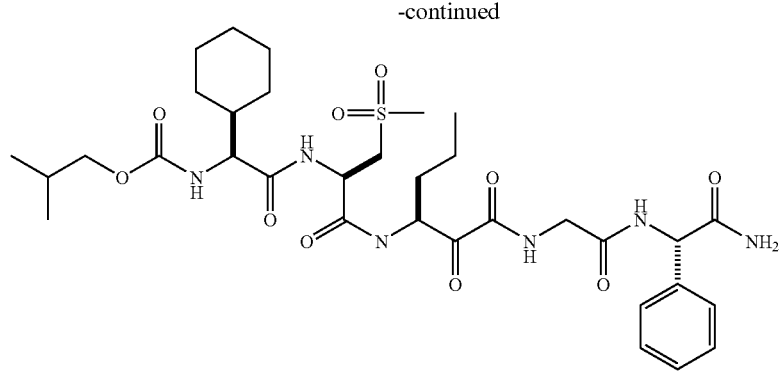

The resin of the previous step (Example VI, Step 4) (iBoc-G(Chx)-Cys((O2)Et)-nVal(CO)-Gly-Phg-MBHA resin) (170 mg) was subjected to HF cleavage condition (Procedure E) to yield the desired crude product. The material was purified by HPLC using a 2.2×25 cm reverse phase column, containing a C-18 resin comprised of 10 micron size gel particles with a 300 angstrom pore size, eluting with a gradient using 20–50% acetonitrile in water. Analytical HPLC using a 4.6×250 mm reverse phase column, containing a C-18 resin comprised of 5 micron size gel particles with a 300 angstrom pore size, eluting with 10–60% acetonitrile in water (containing 0.1% trifluoroacetic acid) showed one peak at 16.94 minutes. Low resolution mass spectrum confirmed the desired mass (MH+ 737.5).

Assay for HCV Protease Inhibitory Activity

Spectrophotometric Assay: Spectrophotometric assay for the HCV serine protease was performed on the inventive compounds by following the procedure described by R. Zhang et al, *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDVVX(Nva), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, *Int. J. Pept. Protein Res.*, 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, *Acta Chem. Scand.*, B33 (1979) 410–412). Peptide fragments were dissolved in anhydrous pyridine (30–60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD-substrate OD)/substrate OD).

Protease Assay: HCV protease assays were performed at 30° C. using a 200 μl reaction mix in a 96-well microtiter plate. Assay buffer conditions (25 mM MOPS pH 6.5, 300 mM NaCl, 10% glycerol, 0.05% lauryl maltoside, 5 μM EDTA and 5 μM DTT) were optimized for the NS3/NS4A heterodimer (D. L. Sali et al, ibid.)). Typically, 150 μl mixtures of buffer, substrate and inhibitor were placed in wells (final concentration of DMSO *4% v/v) and allowed to preincubate at 30° C. for approximately 3 minutes. Fifty μls of prewarmed protease (12 nM, 30° C.) in assay buffer, was then used to initiate the reaction (final volume 200 μl). The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 μM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants ($K_1$) for the competitive inhibitors Ac-D-(D-Gla)-L-I-(Cha)-C-OH (27), Ac-DTEDVVA(Nva)-OH and Ac-DTEDVVP(Nva)-OH were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_1(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i^*$ value.

The obtained $K_i^*$ values for the various compounds of the present invention are given in the afore-mentioned Table wherein the compounds have been arranged in the order of ranges of $K_i^*$ values. From these test results, it would be apparent to the skilled artisan that the compounds of the invention have excellent utility as NS3-serine protease inhibitors.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE 2

| Compound From Example # | STRUCTURE | FORMULA | LRMS (FAB) M + H |
|---|---|---|---|
| 1 | 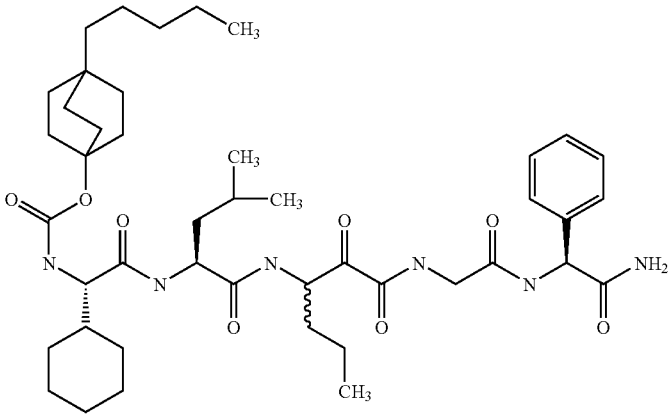 | C44 H68 N6 O8 | 809.5 |
| 2 | 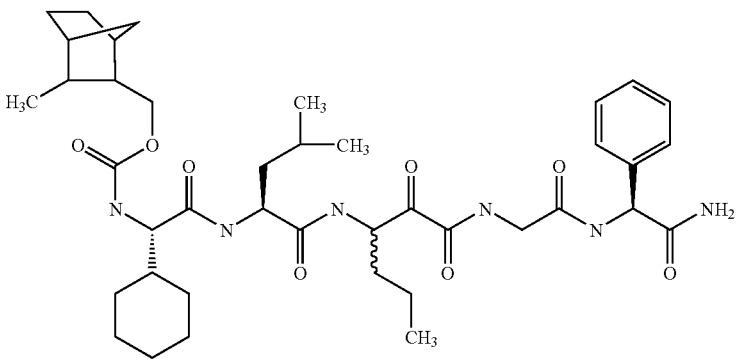 | C40 H60 N6 O8 | 753.5 |

TABLE 2-continued
| Compound From Example # | STRUCTURE | FORMULA | LRMS (FAB) M + H |
|---|---|---|---|
| 3 | 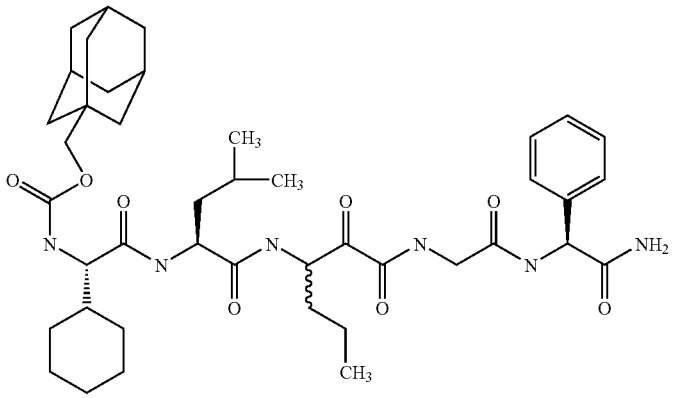 | C42 H62 N6 O8 | 779.5 |
| 4 | 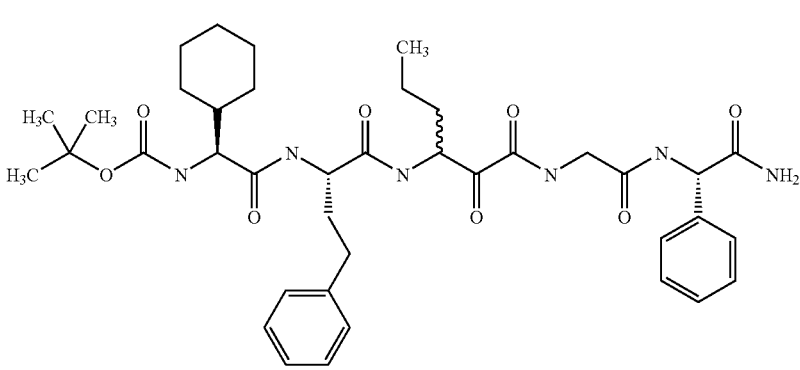 | C39 H54 N6 O8 | 735.4 |
| 5 | 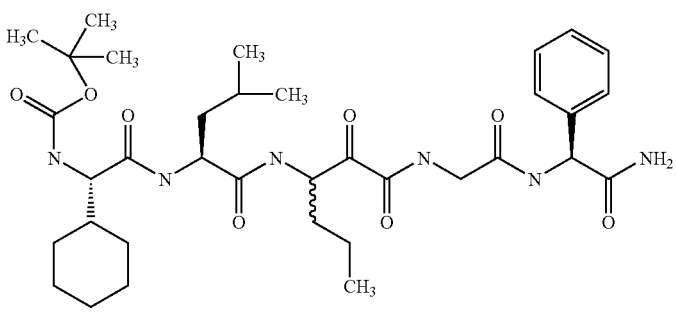 | C35 H54 N6 O8 | 687.4 |
| 6 | 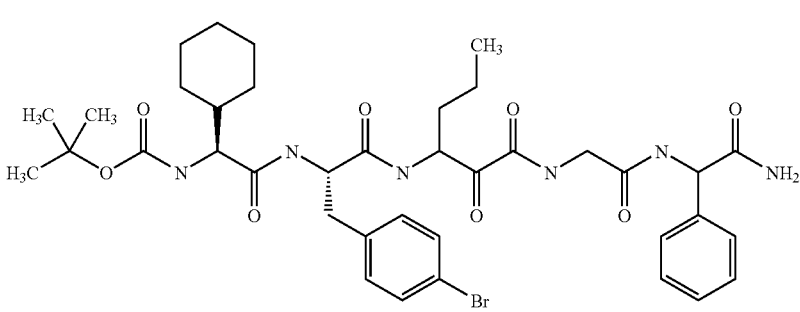 | C38 H51 Br N6 O8 | 720.4 |

TABLE 2-continued

| Compound From Example # | STRUCTURE | FORMULA | LRMS (FAB) M + H |
|---|---|---|---|
| 7 | 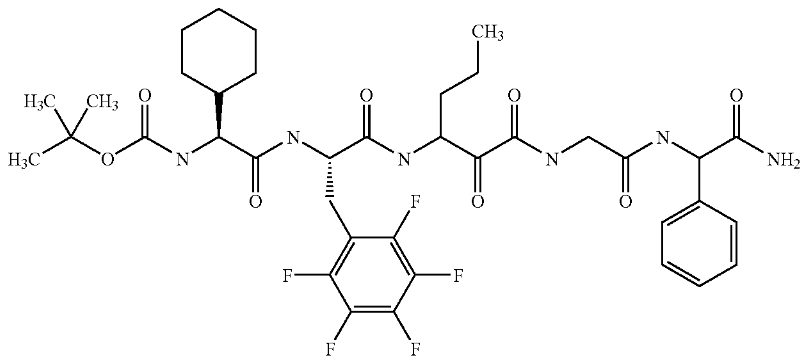 | C38 H47 F5 N6 O8 | 811.3 |
| 8 | 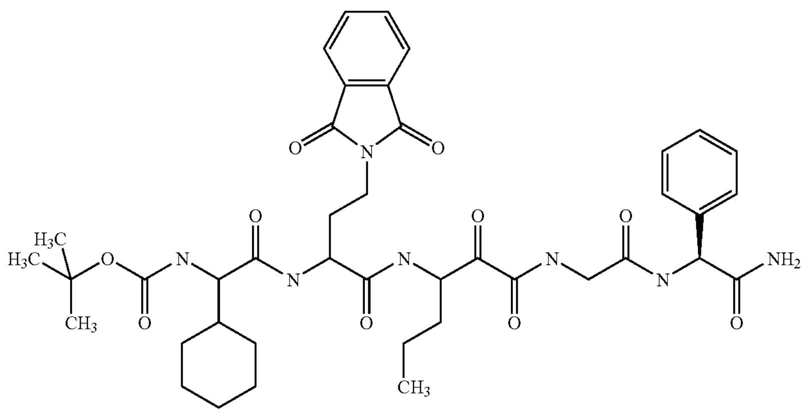 | C41 H53 N7 O10 | 804.4 |
| 9 | 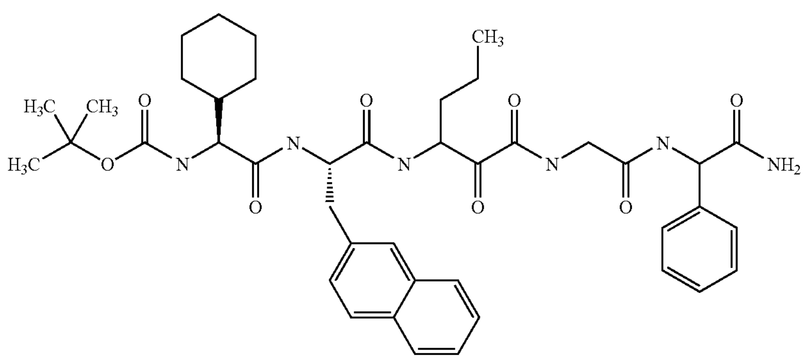 | C42 H54 N6 O8 | 771.4 |
| 10 | 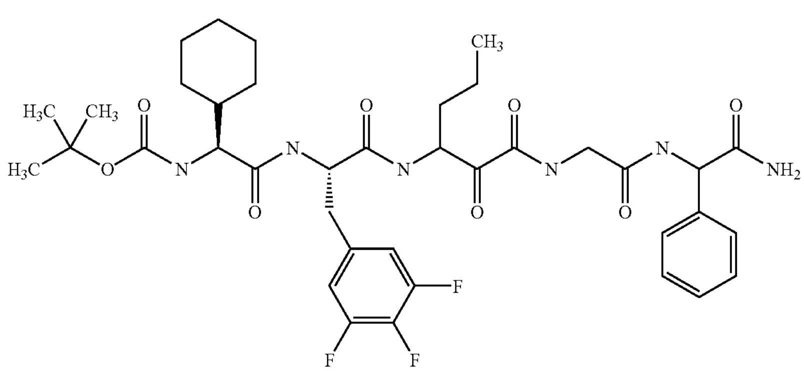 | C38 H49 F3 N6 O8 | 775.4 |

TABLE 2-continued

| Compound From Example # STRUCTURE | FORMULA | LRMS (FAB) M + H |
|---|---|---|
| 11 | C35 H35 N5 O9 | 688.4 |
| 12 | C39 H51 F3 N6 O8 | 789.4 |
| 13 | C42 H57 N5 O9 | 776.4 |
| 14 | C34 H49 F3 N6 O8 | 727.4 |

TABLE 2-continued
| Compound From Example # | STRUCTURE | FORMULA | LRMS (FAB) M + H |
|---|---|---|---|
| 15 | 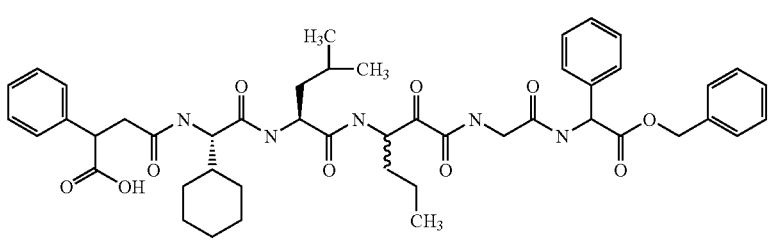 | C47 H59 N5 O10 | 854.4 |
| 16 | 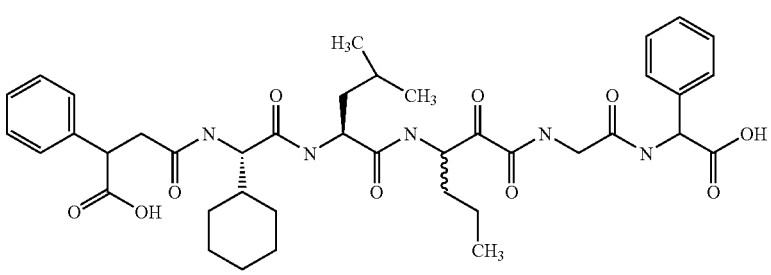 | C40 H35 N5 O10 | 764.4 |
| 17 | 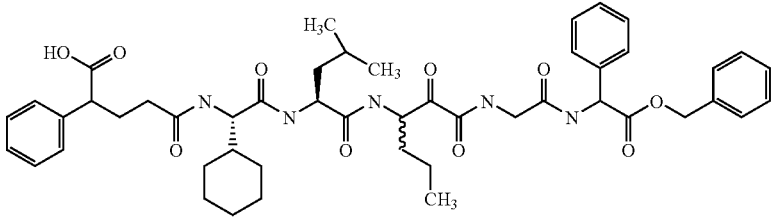 | C48 H61 N5 O10 | 868.4 |
| 18 | 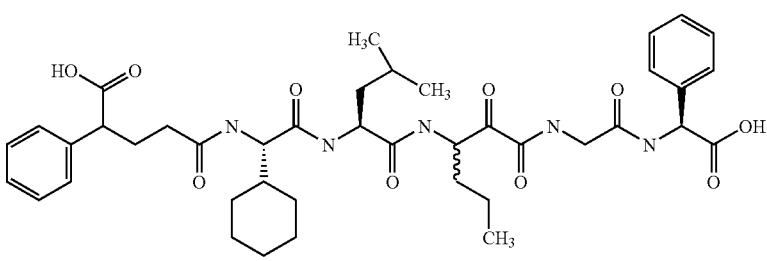 | C41 H55 N5 O10 | 778.4 |
| 19 | 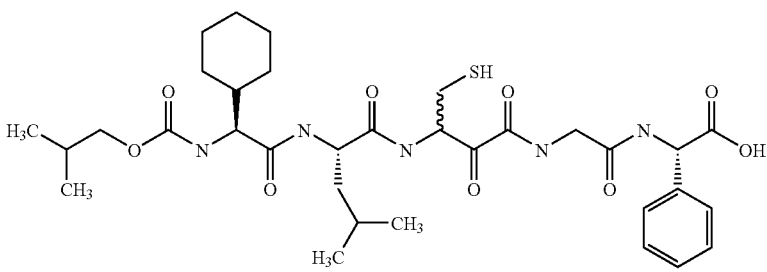 | C33 H49 N5 O9 S | 692.3 |

TABLE 2-continued
| Compound From Example # | STRUCTURE | FORMULA | LRMS (FAB) M + H |
|---|---|---|---|
| 20 | 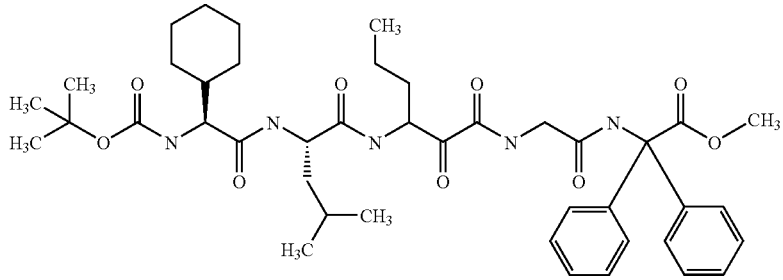 | C42 H59 N5 O9 | 778.4 |
| 21 | 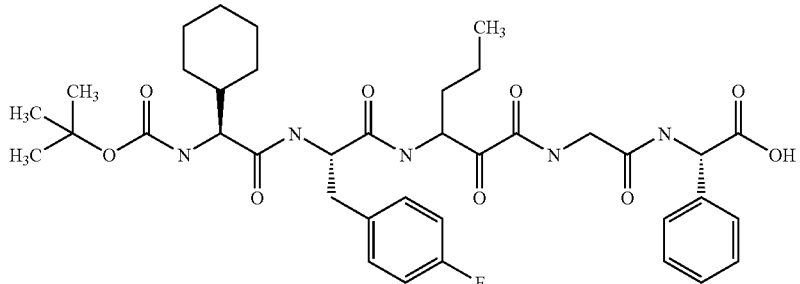 | C38 H50 F N5 O9 | 740.4 |
| 22 | 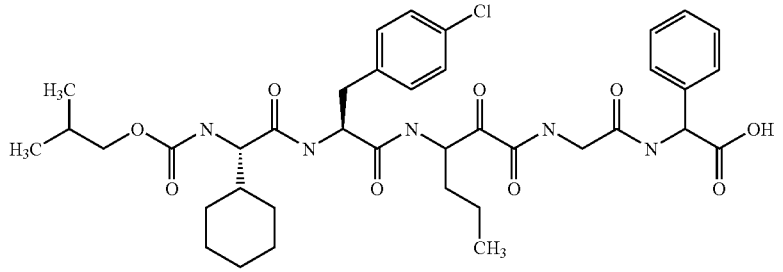 | C38 H50 Cl N5 O9 | 756.3 |
| 23 | 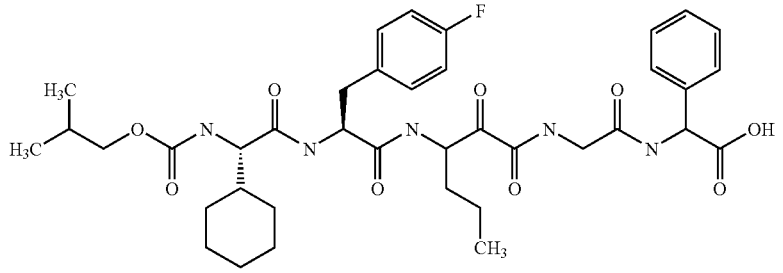 | C38 H50 F N5 O9 | 740.4 |

TABLE 2-continued
| Compound From Example # STRUCTURE | FORMULA | LRMS (FAB) M + H |
|---|---|---|
| 24 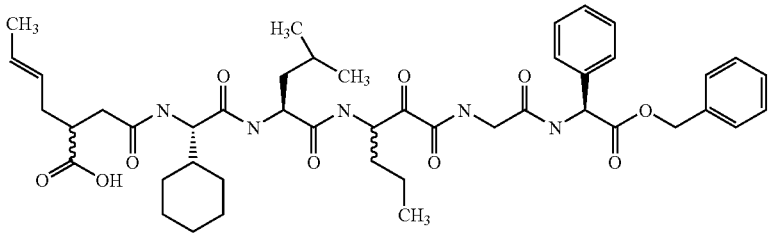 | C45 H61 N5 O10 | 832.4 |
| 25 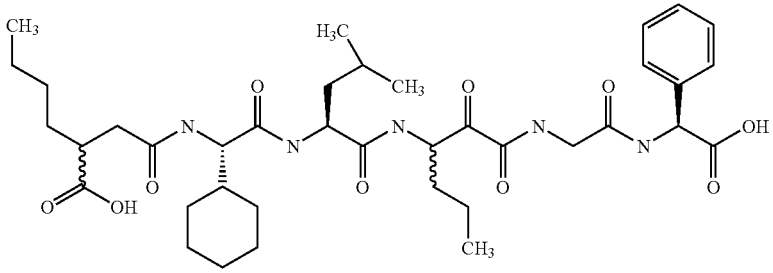 | C38 H57 N5 O10 | 744.4 |
| 26 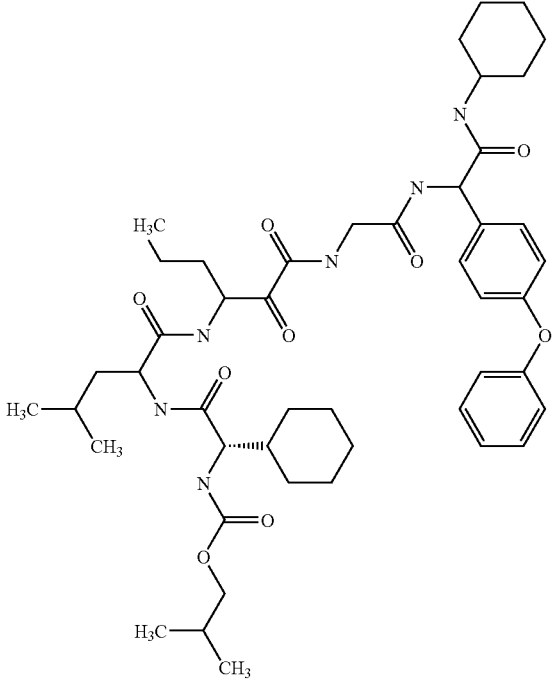 | C47 H68 N6 O9 | 861.5 |

TABLE 2-continued
| Compound From Example # STRUCTURE | FORMULA | LRMS (FAB) M + H |
|---|---|---|
| 27 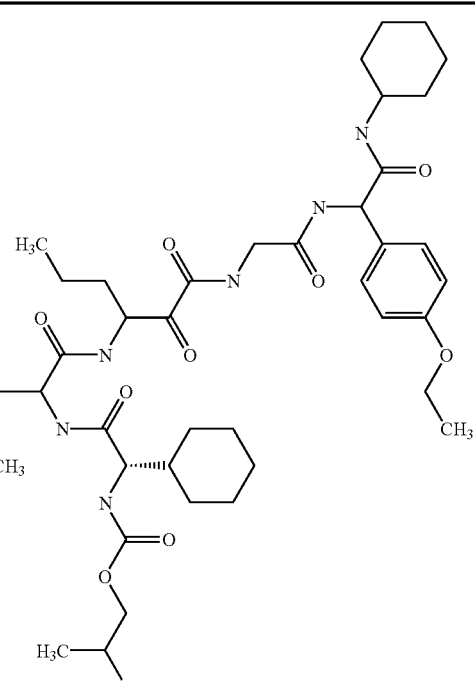 | C43 H68 N6 O9 | 813.5 |
| 28 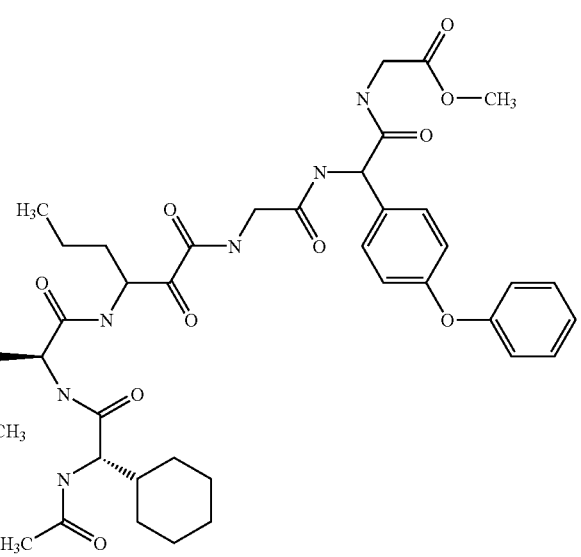 | C41 H56 N6 O10 | 793.4 |
| 29 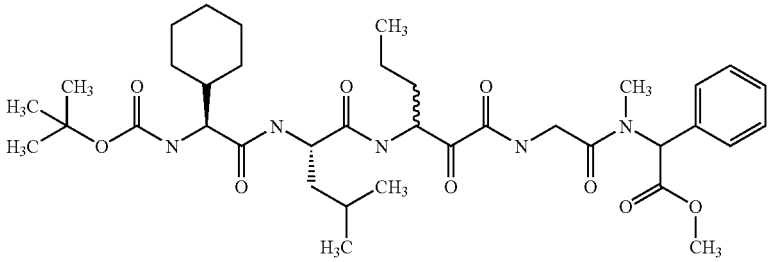 | C37 H57 N5 O9 | 716.4 |

TABLE 2-continued
| Compound From Example # | STRUCTURE | FORMULA | LRMS (FAB) M + H |
|---|---|---|---|
| 30 | 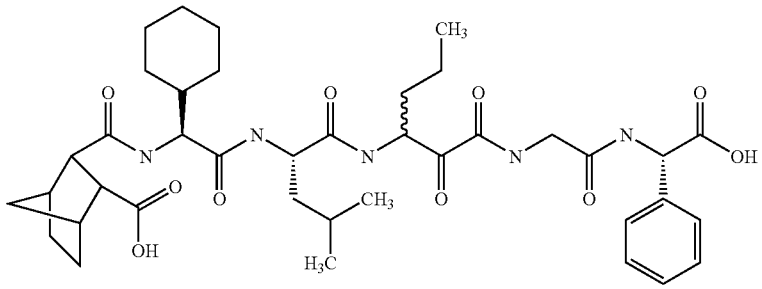 | C39 H55 N5 O10 | 754.4 |
| 31 | 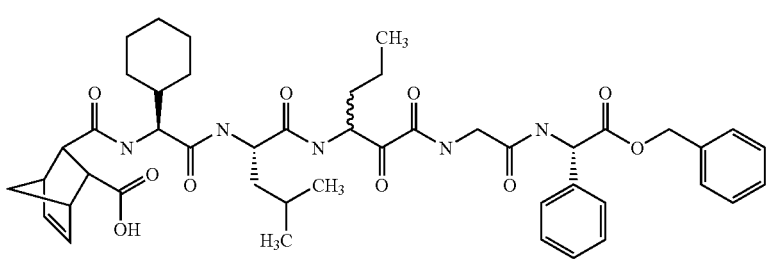 | C46 H59 N5 O10 | 842.4 |
| 32 | 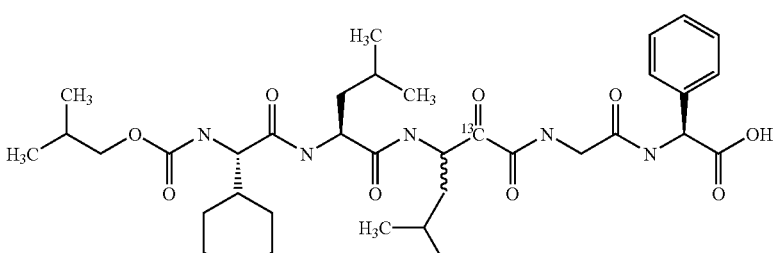 | C36 H55 N5 O9 | 702.4 |
| 33 | 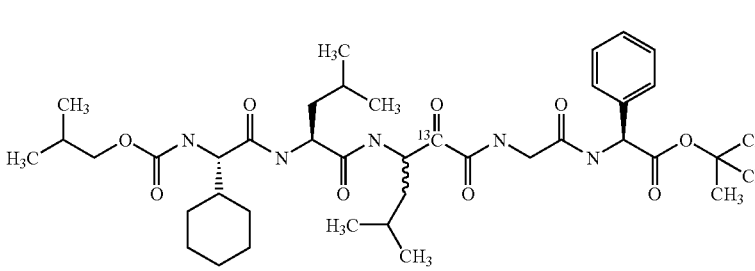 | C40 H63 N5 O9 | 758.5 |
| 34 | 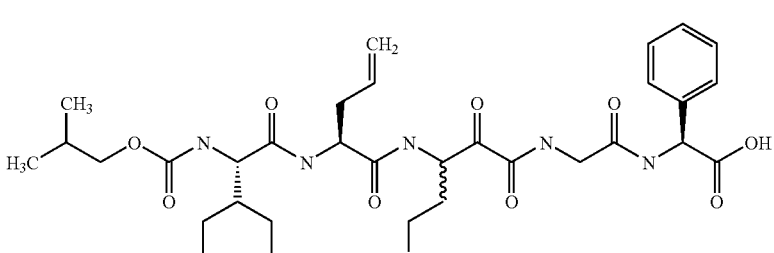 | C34 H49 N5 O9 | 672.4 |

TABLE 2-continued

| Compound From Example # STRUCTURE | FORMULA | LRMS (FAB) M + H |
|---|---|---|
| 35 | C38 H57 N5 O9 | 728.4 |
| 36 | C56 H71 N5 O9 | 990.5 |
| 37 | C44 H55 N5 O9 | 798.4 |
| 38 | C35 H49 N7 O9 | 712.4 |
| 39 | C40 H61 N5 O10 S2 | 836.4 |

TABLE 2-continued
| Compound From Example # | STRUCTURE | FORMULA | LRMS (FAB) M + H |
|---|---|---|---|
| 40 | 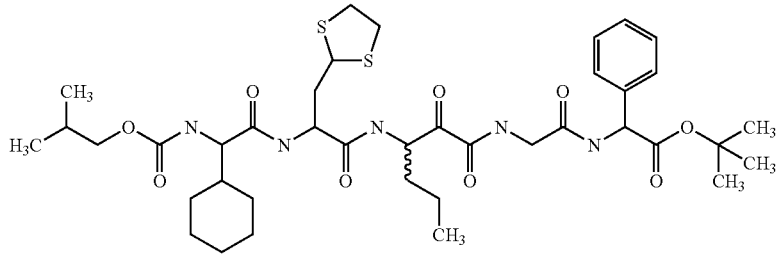 | C39 H59 N5 O9 S2 | 806.4 |
| 41 | 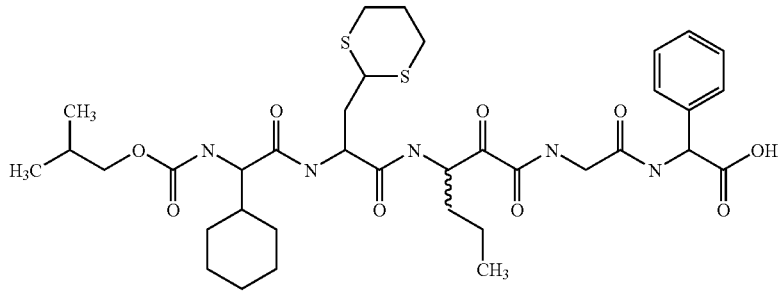 | C36 H53 N5 O9 S2 | 764.3 |
| 42 | 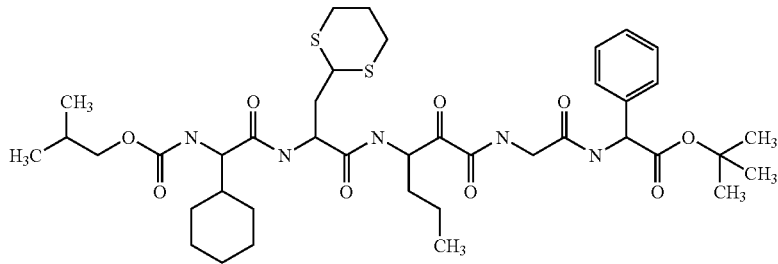 | C40 H61 N5 O9 S2 | 820.4 |
| 43 | 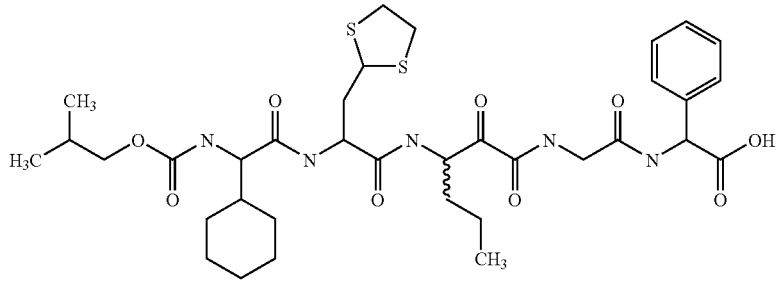 | C35 H51 N5 O9 S2 | 750.3 |
| 44 | 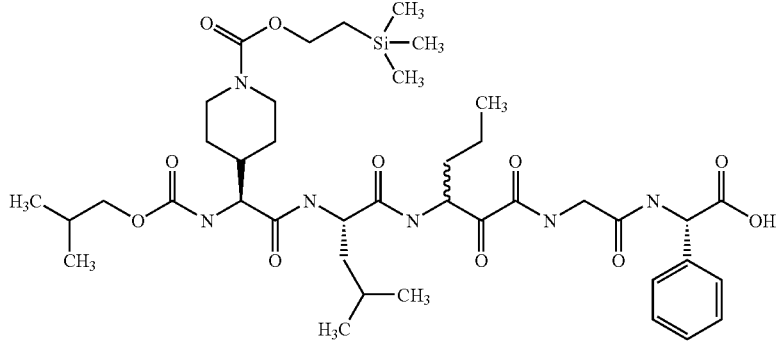 | C40 H64 N6 O11 Si | 805.5 |

TABLE 2-continued

| Compound From Example # | STRUCTURE | FORMULA | LRMS (FAB) M + H |
|---|---|---|---|
| 45 | 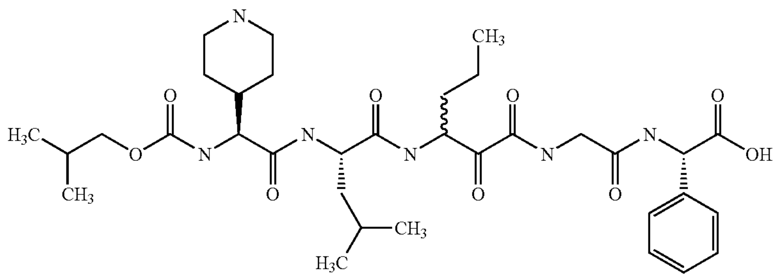 | C34 H52 N6 O9 | 689.4 |
| 47 | 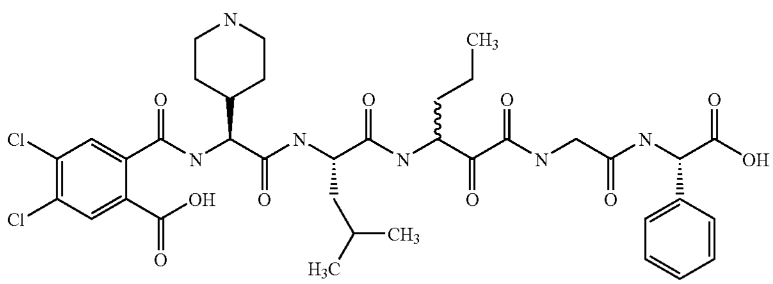 | C37 H46 Cl2 N6 O10 | 805.3 |
| 48 | 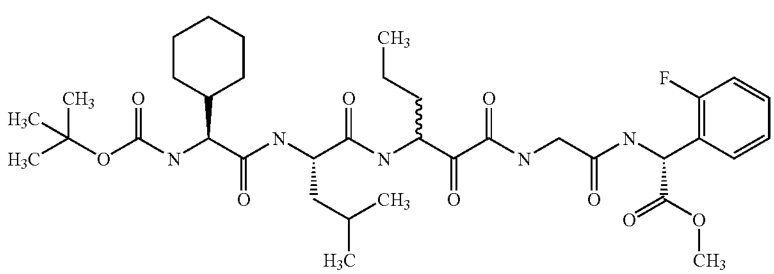 | C36 H54 F N5 O9 | 720.4 |
| 49 | 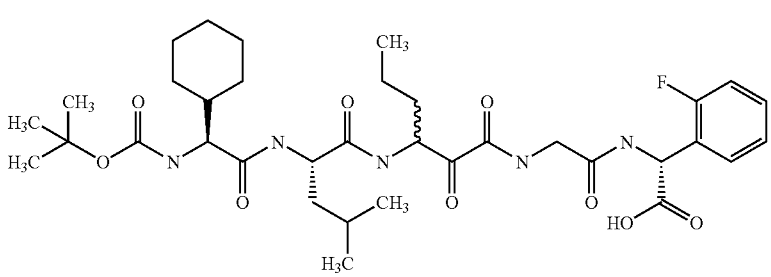 | C35 H52 F N5 O9 | 706.4 |

TABLE 2-continued

| Compound From Example # | STRUCTURE | FORMULA | LRMS (FAB) M + H |
|---|---|---|---|
| 50 | 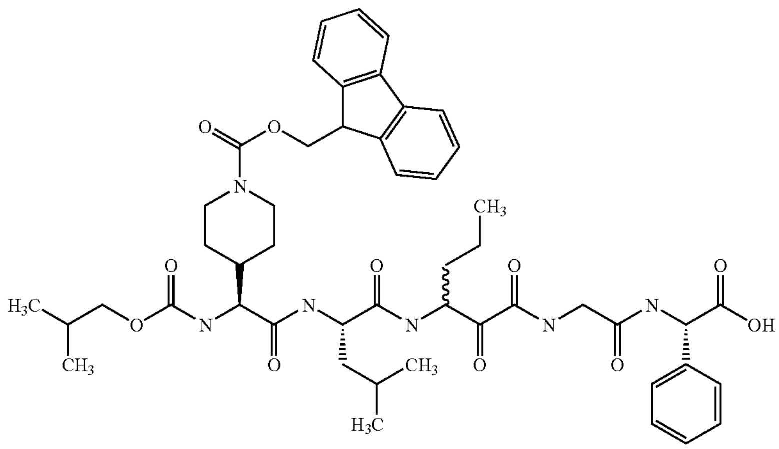 | C49 H62 N6 O11 | 911.5 |
| 51 | 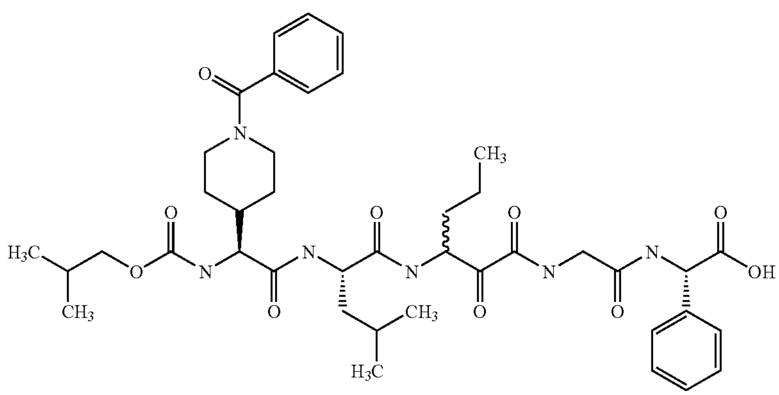 | C41 H56 N6 O10 | 793.4 |
| 52 | 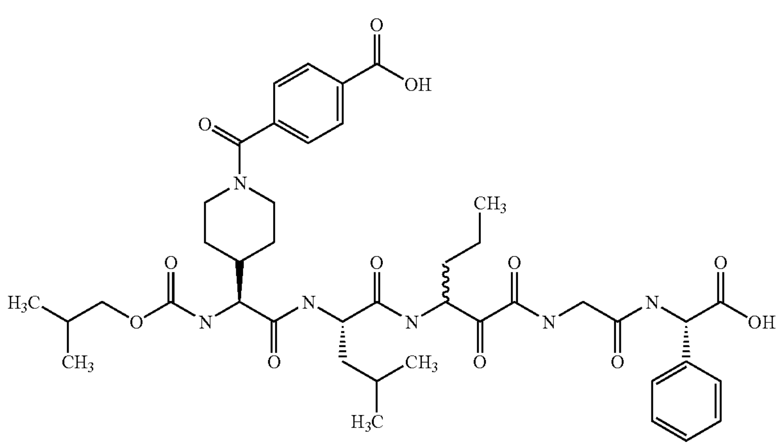 | C42 H56 N6 O12 | 837.4 |

TABLE 2-continued

| Compound From Example # | STRUCTURE | FORMULA | LRMS (FAB) M + H |
|---|---|---|---|
| 53 | 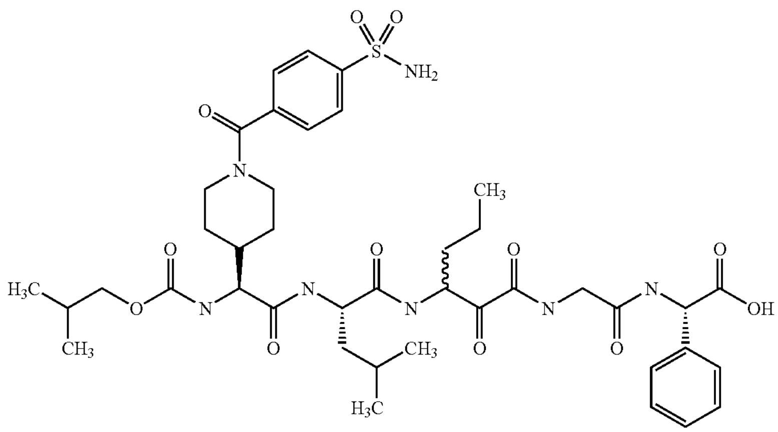 | C41 H57 N7 O12 S | 872.4 |
| 54 | 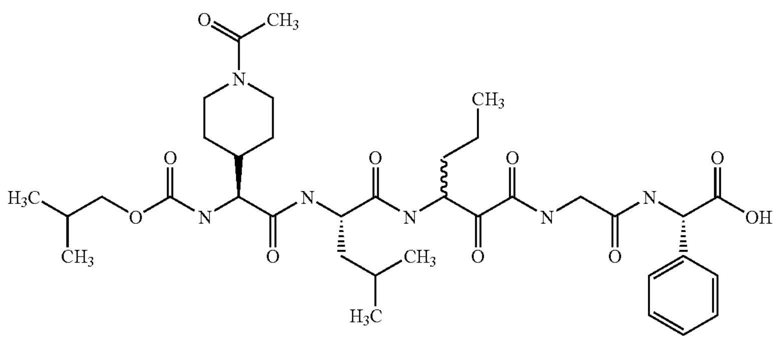 | C36 H54 N6 O10 | 731.4 |
| 55 | 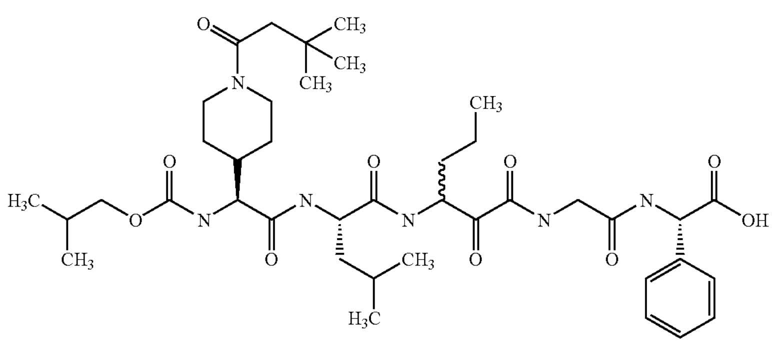 | C40 H62 N6 O10 | 787.5 |
| 56 | 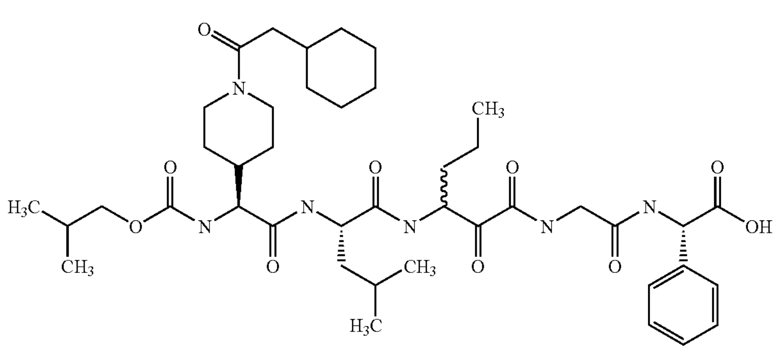 | C42 H64 N6 O10 | 813.5 |

TABLE 2-continued

| Compound From Example # STRUCTURE | FORMULA | LRMS (FAB) M + H |
|---|---|---|
| 57 | C40 H60 N6 O10 | 785.4 |
| 58 | C38 H57 N7 O11 | 788.4 |
| 59 | C41 H65 N7 O12 S | 880.4 |
| 60 | C40 H61 N5 O11 | 788.4 |

TABLE 2-continued
| Compound From Example # | STRUCTURE | FORMULA | LRMS (FAB) M + H |
|---|---|---|---|
| 61 | 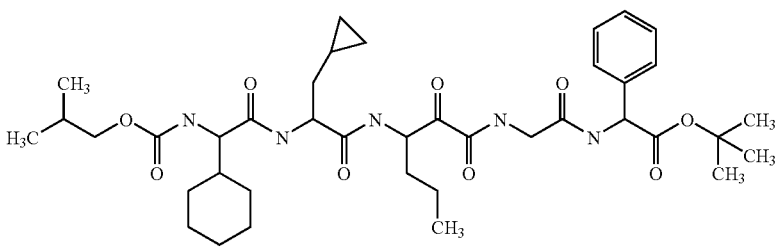 | C39 H59 N5 O9 | 742.4 |
| 62 | 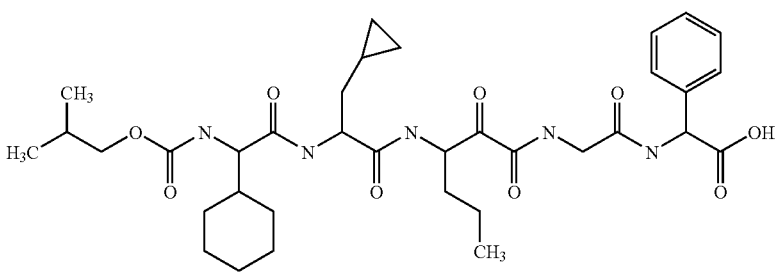 | C35 H51 N5 O9 | 686.4 |
| 63 | 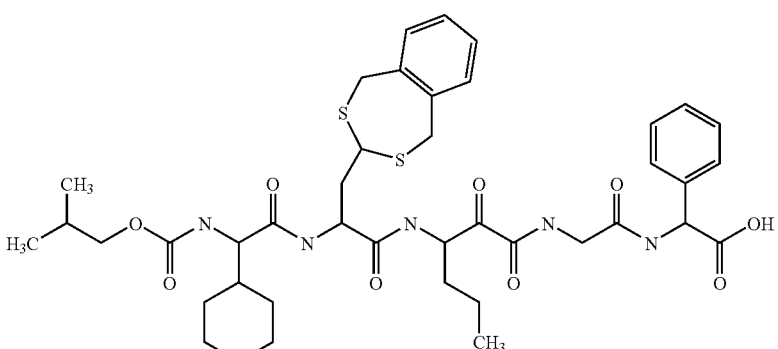 | C41 H55 N5 O9 S2 | 826.4 |
| 64 | 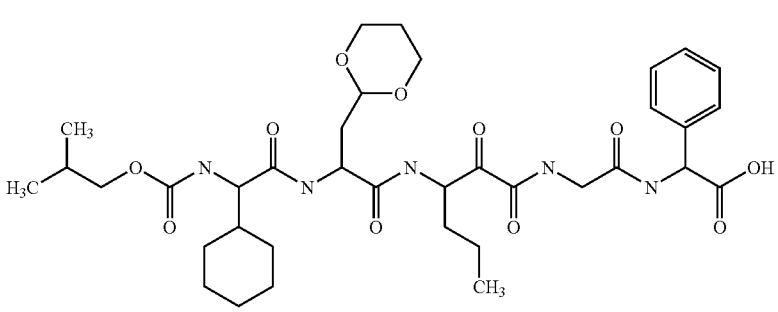 | C36 H53 N5 O11 | 732.4 |
| 65 | 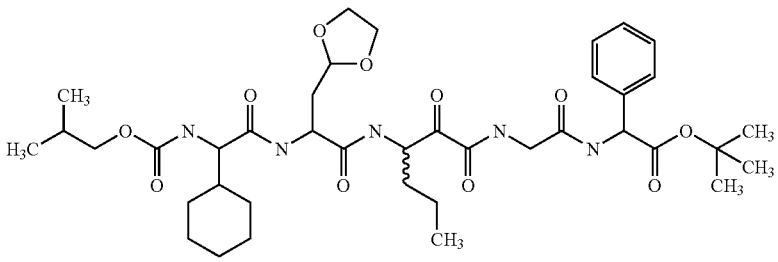 | C39 H59 N5 O11 | 774.4 |

TABLE 2-continued
| Compound From Example # | STRUCTURE | FORMULA | LRMS (FAB) M + H |
|---|---|---|---|
| 66 | 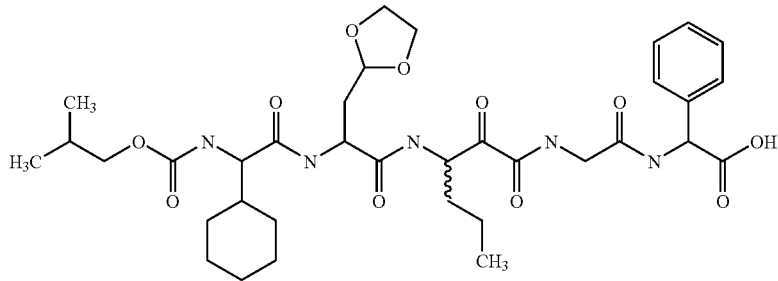 | C35 H51 N5 O11 | 718.4 |
| 67 | 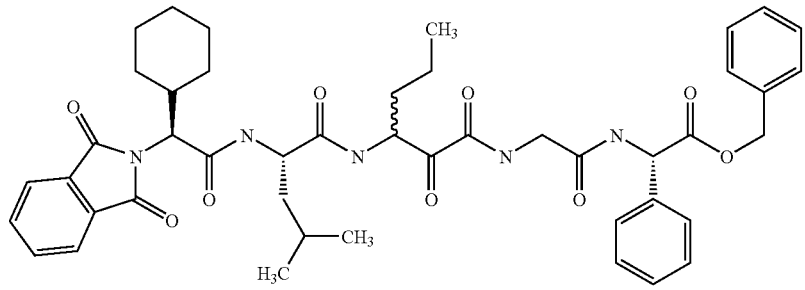 | C45 H53 N5 O9 | 808.4 |
| 68 | 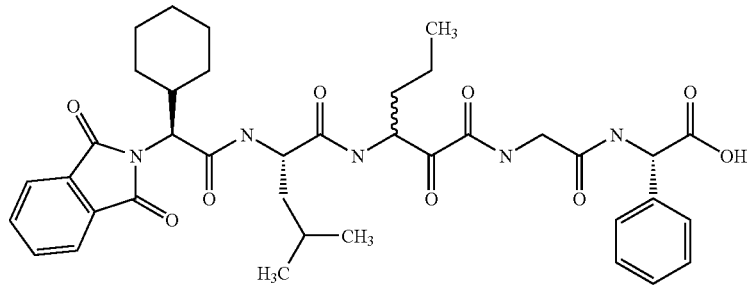 | C38 H47 N5 O9 | 718.3 |
| 69 | 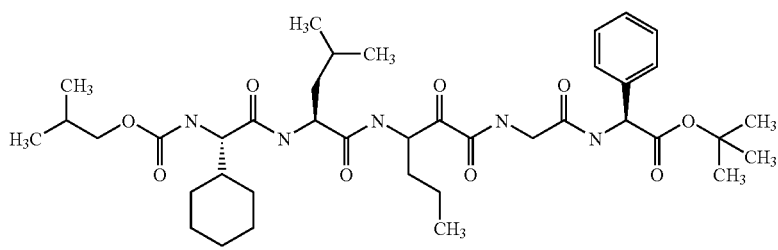 | C39 H61 N5 O9 | 744.5 |
| 70 | 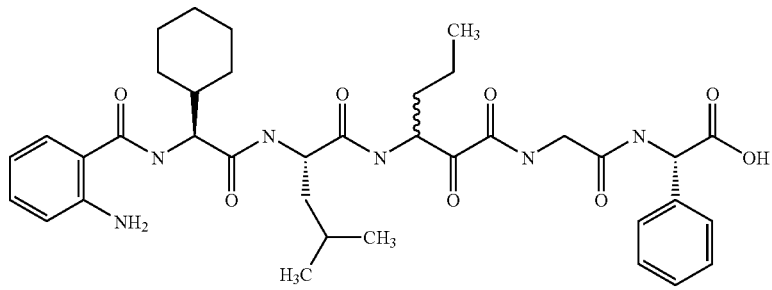 | C37 H50 N6 O8 | 707.4 |

TABLE 2-continued
| Compound From Example # | STRUCTURE | FORMULA | LRMS (FAB) M + H |
|---|---|---|---|
| 71 | 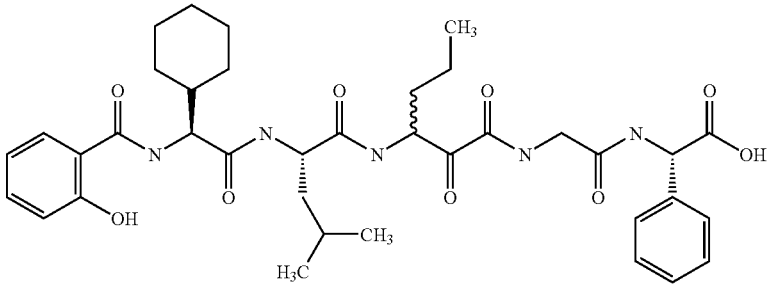 | C37 H49 N5 O9 | 708.4 |
| 72 | 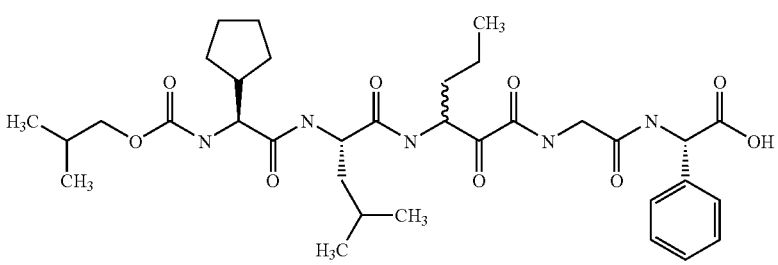 | C34 H51 N5 O9 | 674.4 |
| 73 | 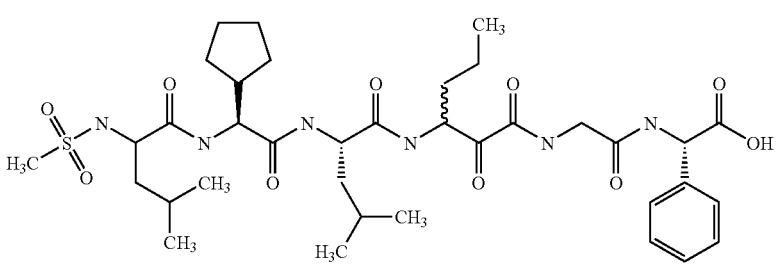 | C36 H56 N6 O10 | 765.4 |
| 74 | 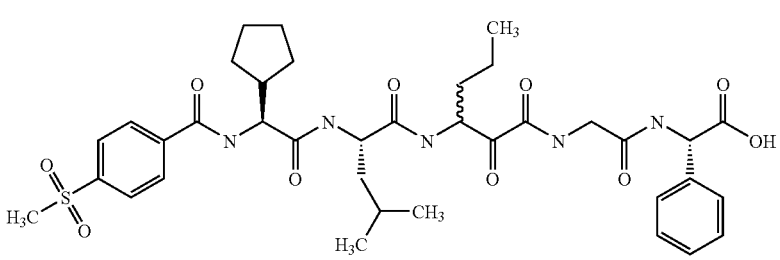 | C36 H48 N6 O10 S | 757.3 |
| 75 | 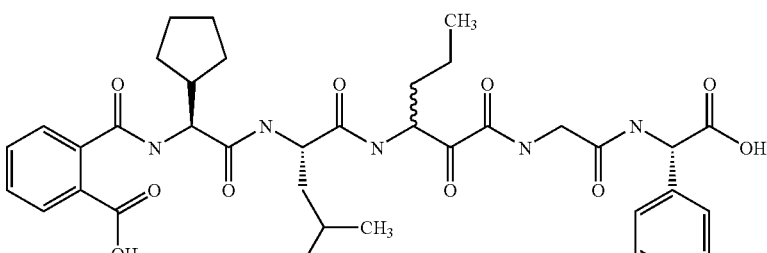 | C37 H47 N5 O10 | 722.3 |

TABLE 2-continued
| Compound From Example # | STRUCTURE | FORMULA | LRMS (FAB) M + H |
|---|---|---|---|
| 76 | 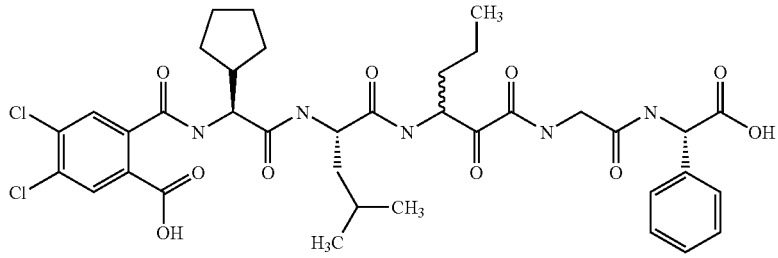 | C37 H45 Cl2 N5 O10 | 790.3 |
| 77 | 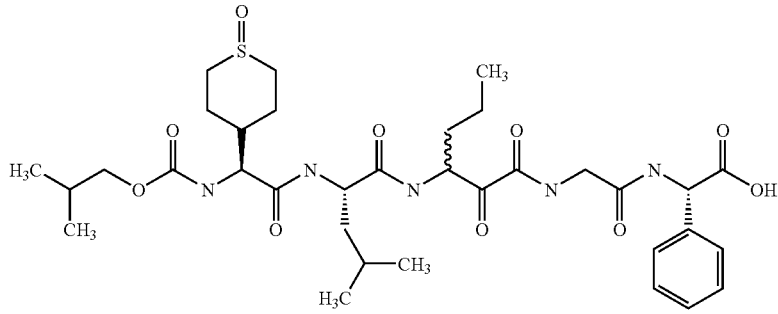 | C34 H51 N4 O10 S | 722.3 |
| 78 | 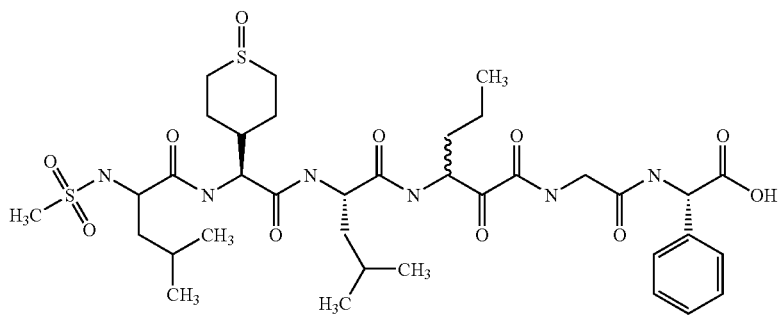 | C36 H56 N6 O11 S2 | 813.4 |
| 79 | 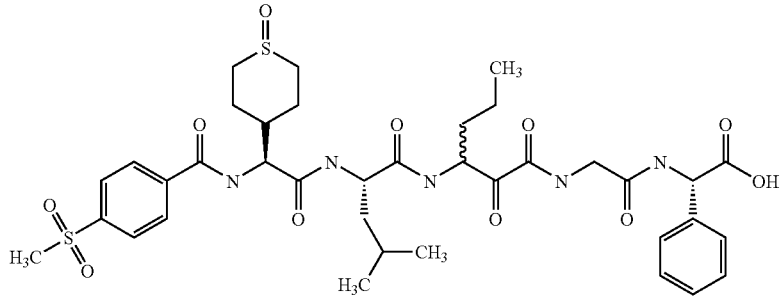 | C36 H48 N6 O11 S2 | 805.3 |

TABLE 2-continued

| Compound From Example # STRUCTURE | FORMULA | LRMS (FAB) M + H |
|---|---|---|
| 80 | C37 H47 N5 O11 S | 770.3 |
| 81 | C37 H45 Cl2 N5 O11 S | 838.2 |
| 82 | C39 H49 Cl2 N5 O10 | 818.3 |
| 83 | C37 H57 N5 O8 | 700.4 |
| 84 | C38 H60 N6 O10 S | 793.4 |

TABLE 2-continued
| Compound From Example # | STRUCTURE | FORMULA | LRMS (FAB) M + H |
|---|---|---|---|
| 85 | 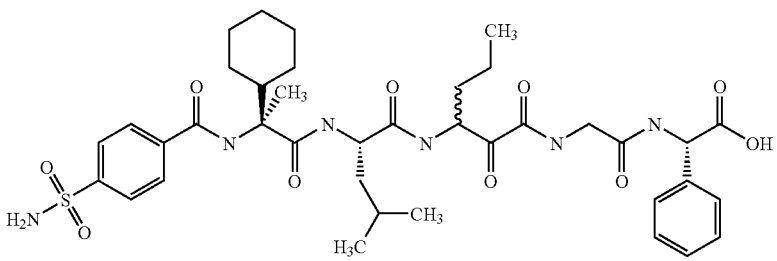 | C38 H52 N6 O10 S | 785.4 |
| 86 | 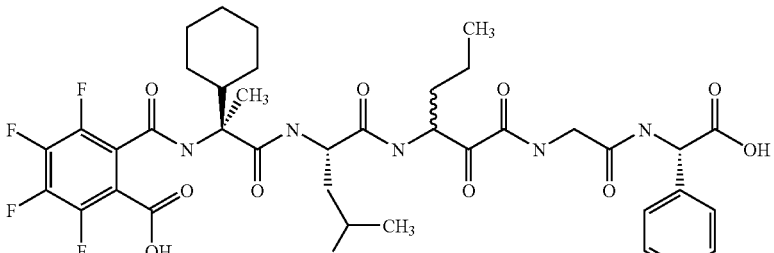 | C39 H47 F4 N5 O10 | 822.3 |
| 87 | 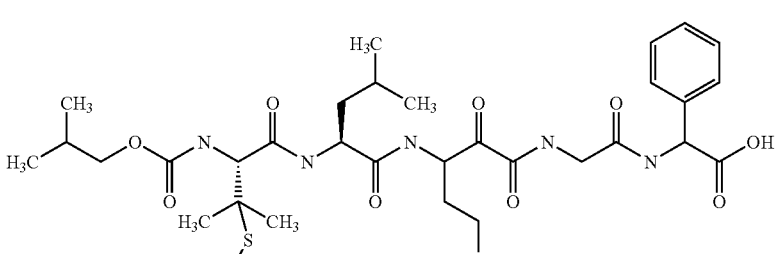 | C33 H51 N5 O9 S | 694.3 |
| 88 | 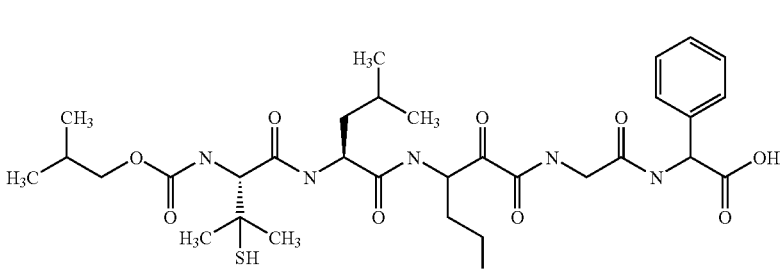 | C32 H49 N5 O9 S | 680.3 |
| 89 | 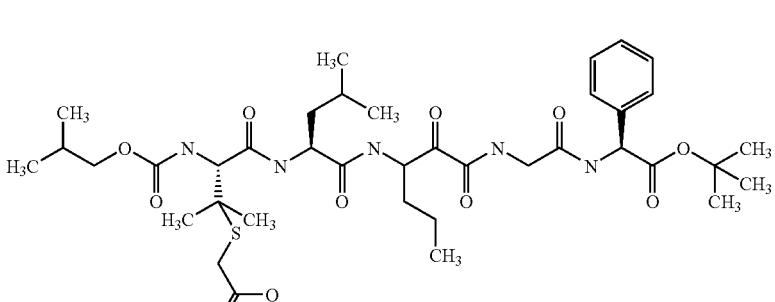 | C40 H63 N4 O11 S | 822.4 |

TABLE 2-continued

| Compound From Example # STRUCTURE | FORMULA | LRMS (FAB) M + H |
|---|---|---|
| 90 | C39 H55 N5 O9 S | 770.4 |
| 91 | C36 H55 N5 O11 S | 766.4 |
| 92 | C38 H57 N5 O10 | 744.4 |
| 93 | C34 H51 N5 O11 | 706.4 |
| 94 | C40 H59 N5 O9 | 754.4 |

TABLE 2-continued
| Compound From Example # STRUCTURE | FORMULA | LRMS (FAB) M + H |
|---|---|---|
| 95 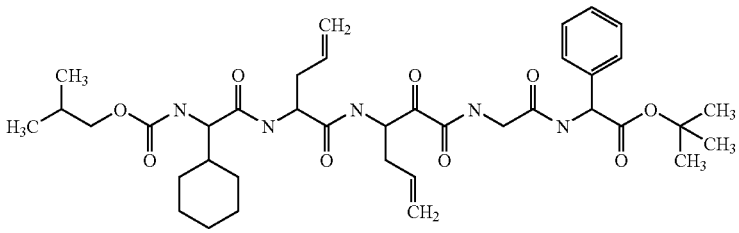 | C38 H55 N5 O9 | 726.4 |
| 96 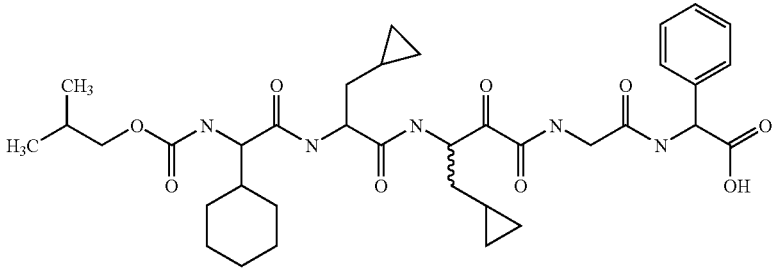 | C36 H51 N5 O9 | 698.4 |
| 97 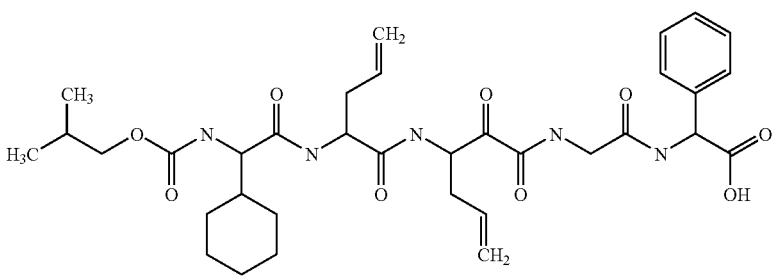 | C34 H47 N5 O9 | 670.3 |
| 98 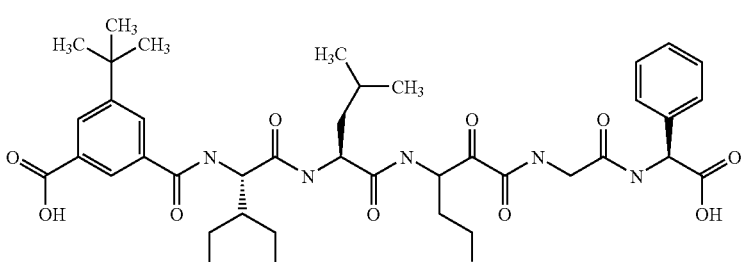 | C42 H57 N5 O10 | 792.4 |

TABLE 2-continued

| Compound From Example # | STRUCTURE | FORMULA | LRMS (FAB) M + H |
|---|---|---|---|
| 99 | (structure) | 2 C40 H61 N5 O10 | 772.4 |
|  | (structure) |  |  |
| 100 | (structure) | C37 H49 F N5 O8 | 710.4 |
| 101 | (structure) | C36 H49 N5 O8 S | 712.3 |
| 102 | (structure) | C40 H54 Cl N5 O8 | 768.4 |

TABLE 2-continued
| Compound From Example # | STRUCTURE | FORMULA | LRMS (FAB) M + H |
|---|---|---|---|
| 103 | 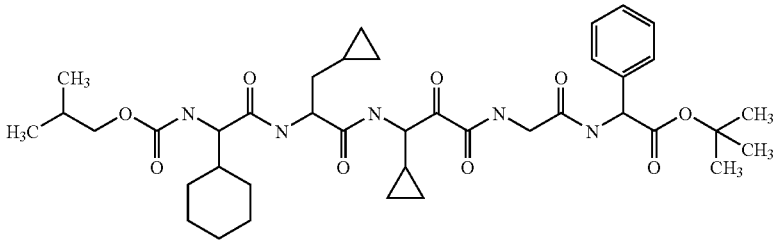 | C39 H57 N5 O9 | 740.4 |
| 104 | 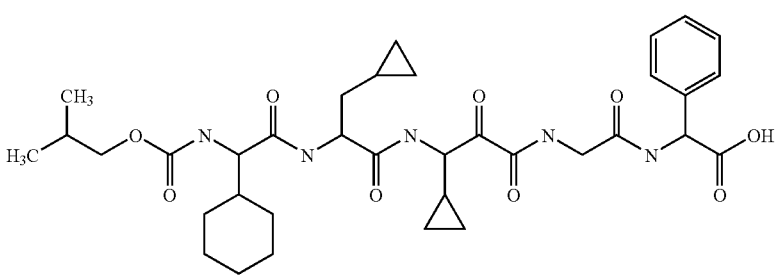 | C35 H49 N5 O9 | 684.4 |
| 105 | 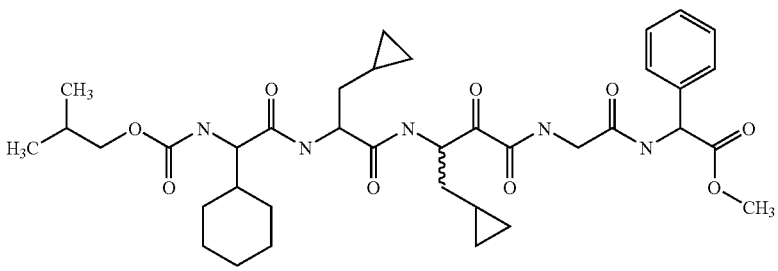 | C37 H53 N5 O9 | 712.4 |
| 106 | 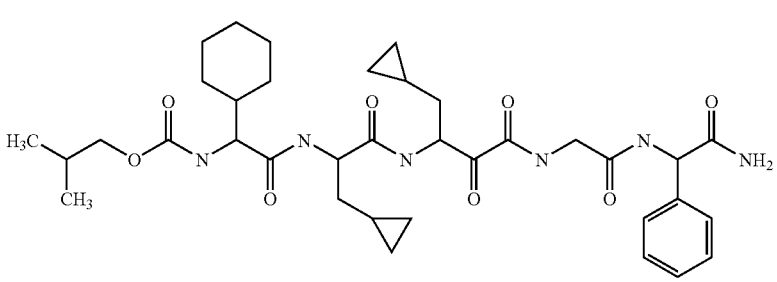 | C36 H52 N6 O8 | 697.4 |
| 107 | 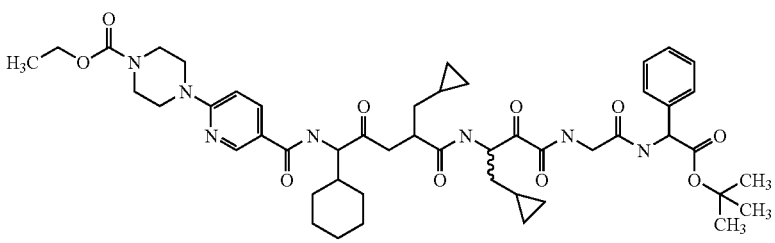 | C48 H66 N8 O10 | 915.5 |

TABLE 2-continued
| Compound From Example # | STRUCTURE | FORMULA | LRMS (FAB) M + H |
|---|---|---|---|
| 108 | 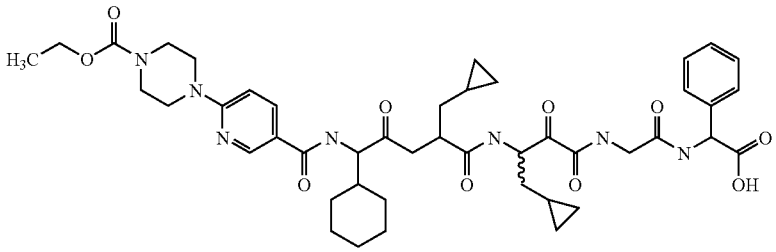 | C44 H58 N8 O10 | 859.4 |
| 109 | 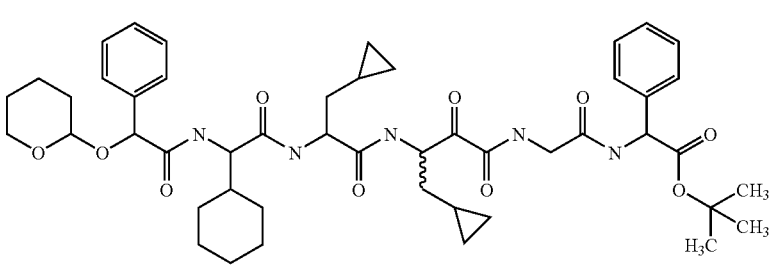 | C48 H65 N5 O10 | 872.5 |
| 110 | 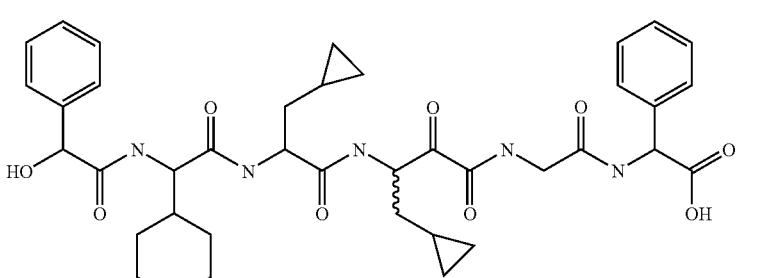 | C39 H49 N5 O9 | 732.4 |
| 111 | 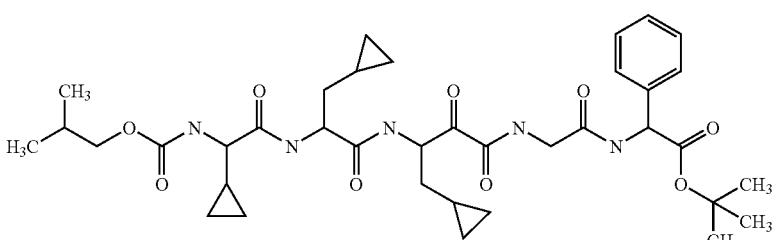 | C37 H53 N5 O9 | 712.4 |
| 112 | 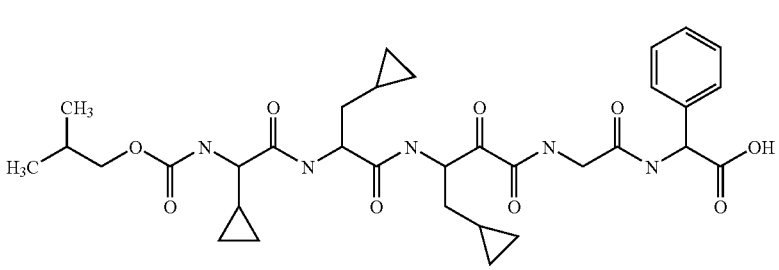 | C33 H45 N5 O9 | 656.3 |

TABLE 2-continued
| Compound From Example # STRUCTURE | FORMULA | LRMS (FAB) M + H |
|---|---|---|
| 113 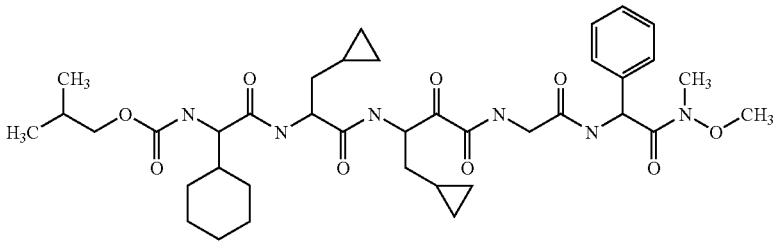 | C38 H56 N6 O9 | 741.4 |
| 114 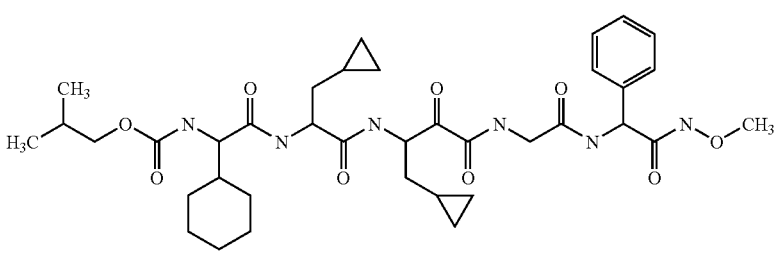 | C37 H54 N6 O9 | 727.4 |
| 115 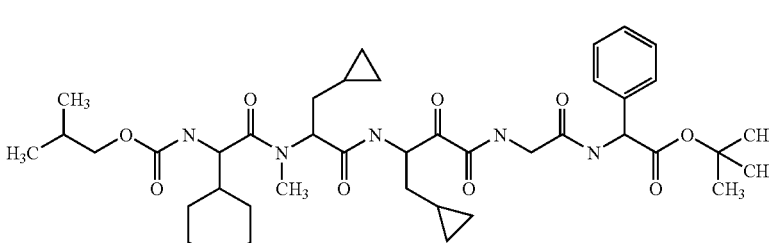 | C41 H61 N5 O9 | 768.5 |
| 116 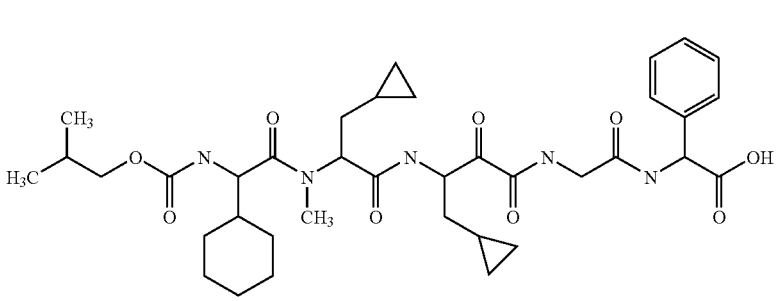 | C37 H53 N5 O9 | 712.4 |
| 117 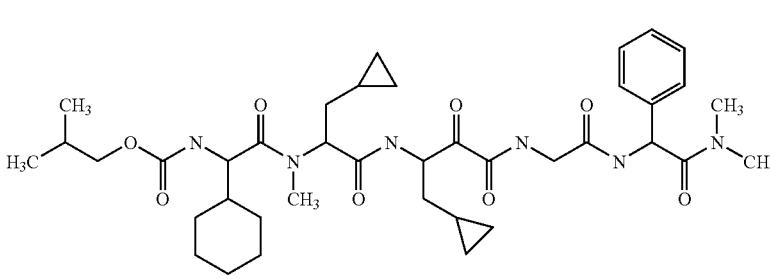 | C39 H58 N9 O8 | 739.4 |

TABLE 2-continued

| Compound From Example # STRUCTURE | FORMULA | LRMS (FAB) M + H |
|---|---|---|
| 118 | C40 H60 N6 O8 | 753.5 |
| 119 | C39 H58 N6 O9 | 755.4 |
| 120 | C38 H56 N6 O8 | 725.4 |
| 121 | C38 H57 N5 O9 | 728.4 |
| 122 | C34 H49 N5 O9 | 672.4 |
| 123 | C40 H55 N5 O9 | 750.4 |

TABLE 2-continued
| Compound From Example # | STRUCTURE | FORMULA | LRMS (FAB) M + H |
|---|---|---|---|
| 124 | 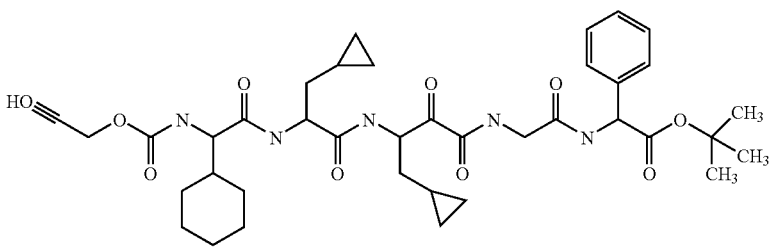 | C39 H53 N5 O9 | 736.4 |
| 125 | 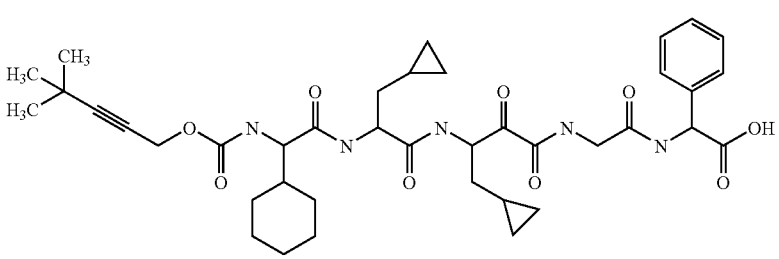 | C39 H53 N5 O9 | 736.4 |
| 126 | 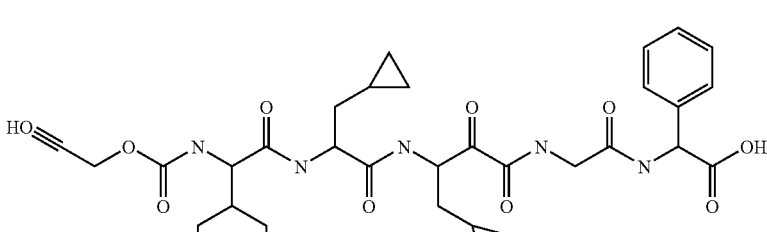 | C35 H45 N5 O9 | 680.3 |
| 127 | 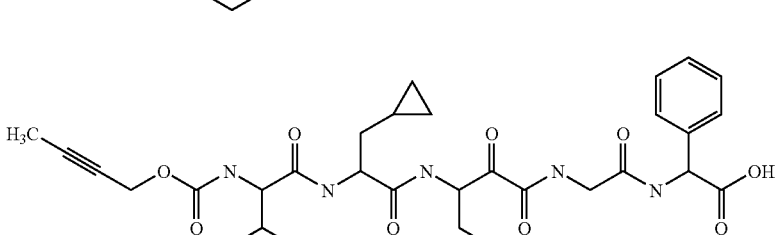 | C36 H47 N5 O9 | 694.3 |
| 128 | 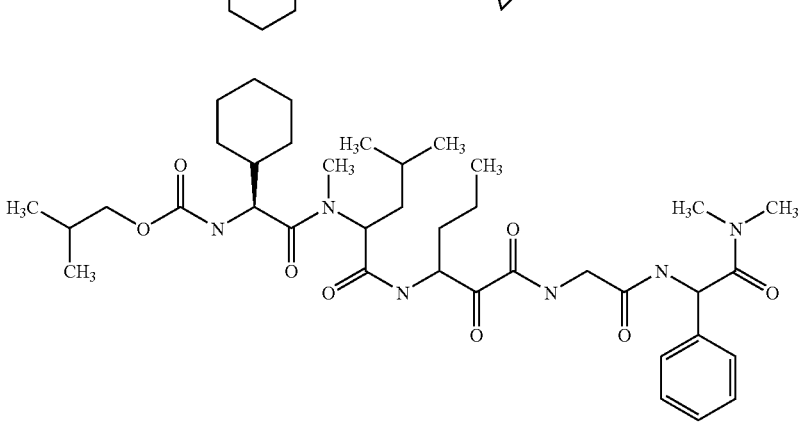 | C38 H60 N6 O8 | 729.5 |

TABLE 2-continued
| Compound From Example # | STRUCTURE | FORMULA | LRMS (FAB) M + H |
|---|---|---|---|
| 129 | 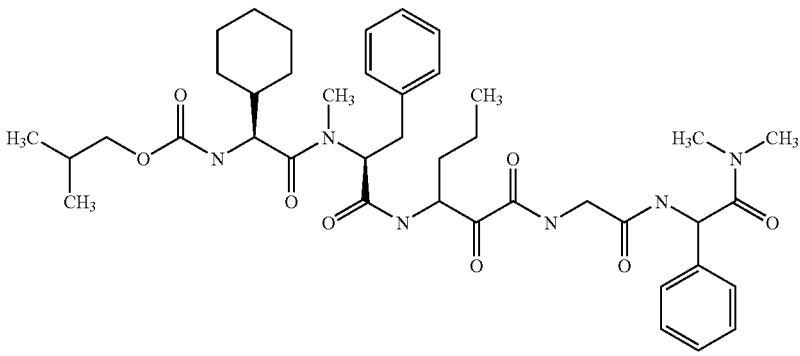 | C41 H58 N6 O8 | 763.4 |
| 130 | 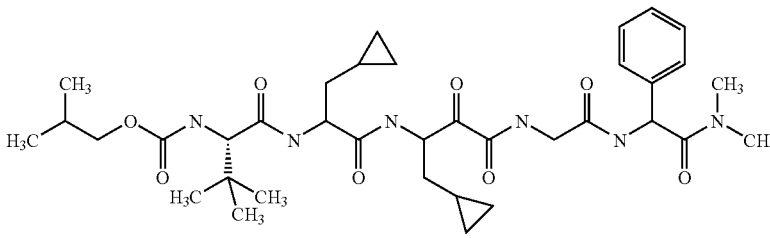 | C36 H54 N6 O8 | 699.4 |
| 131 | 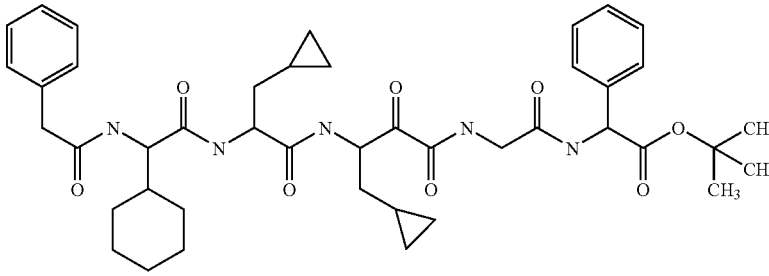 | C43 H57 N5 O8 | 772.4 |
| 132 | 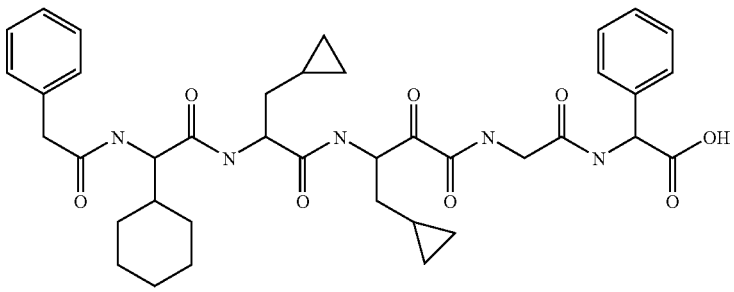 | C39 H49 N5 O8 | 716.4 |
| 133 | 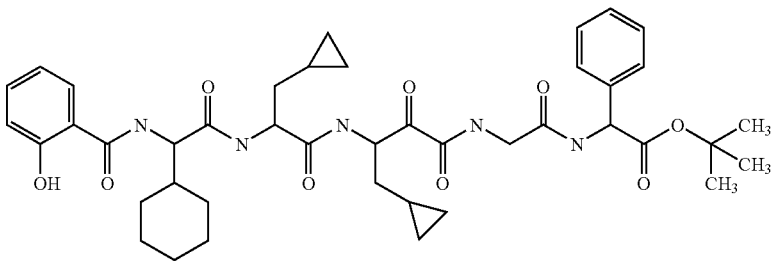 | C42 H55 N5 O9 | 774.4 |

TABLE 3
| STRUCTURE | Ki* CLASS |
|---|---|
| 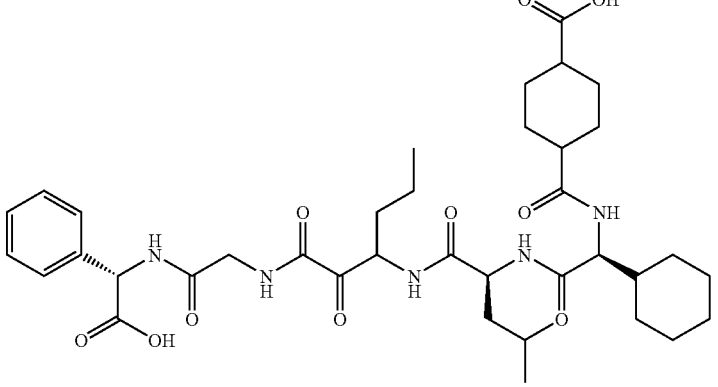 | B |
| 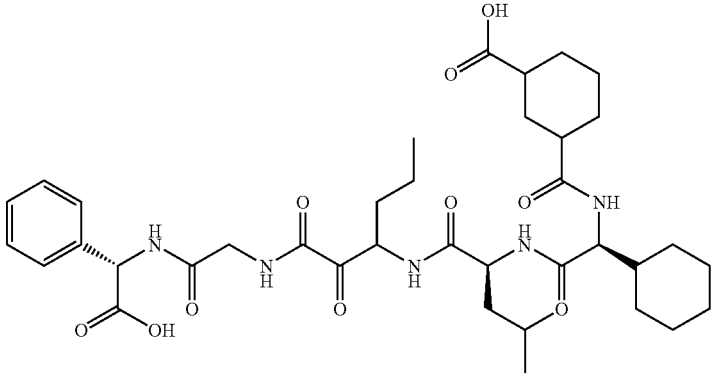 | B |
| 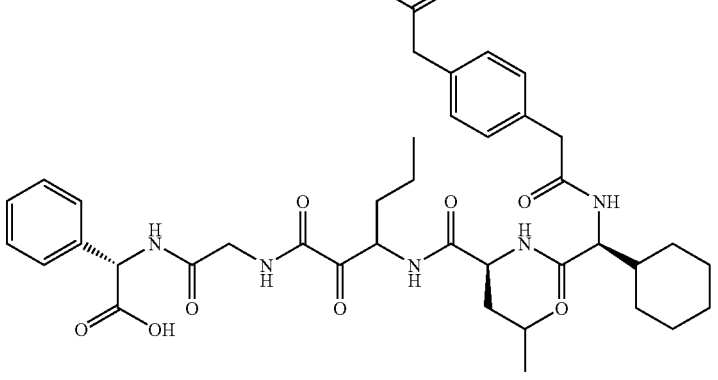 | B |
| 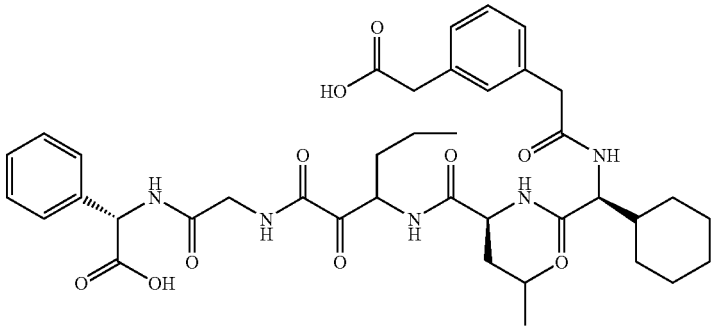 | B |

TABLE 3-continued

| STRUCTURE | Ki* CLASS |
|---|---|
| | B |
| | B |
| | B |
| | B |

TABLE 3-continued
| STRUCTURE | Ki* CLASS |
|---|---|
| 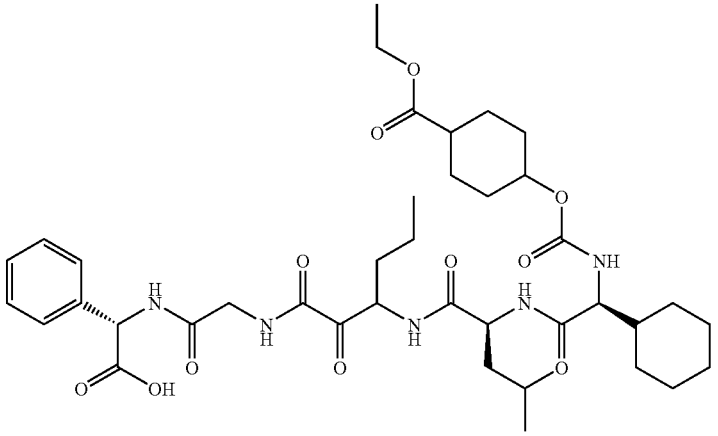 | B |
| 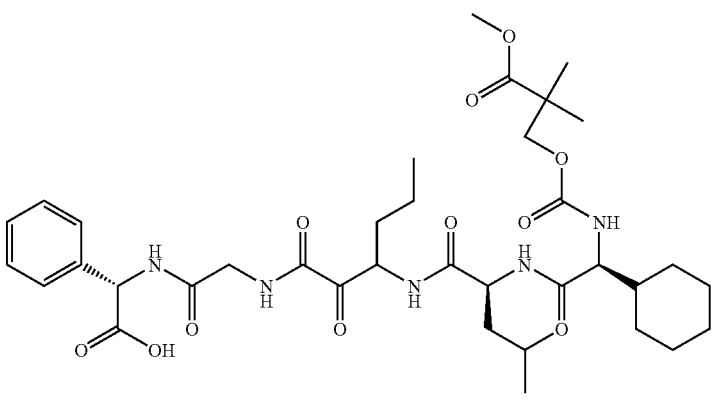 | B |
| 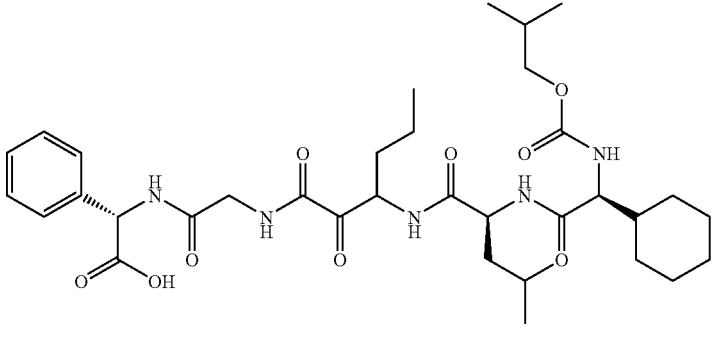 | B |
| 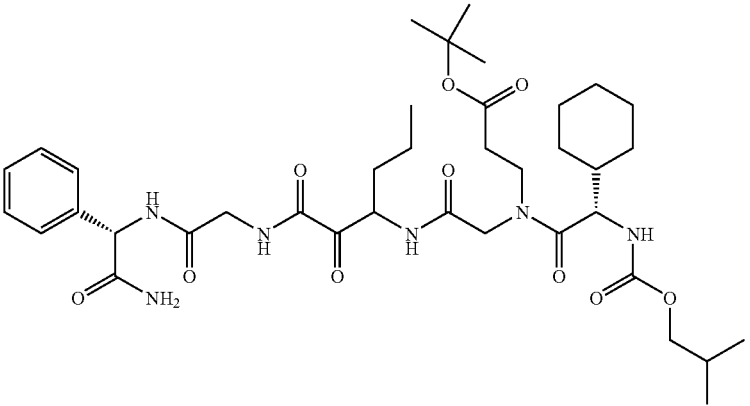 | C |

TABLE 3-continued

| STRUCTURE | Ki* CLASS |
|---|---|
| 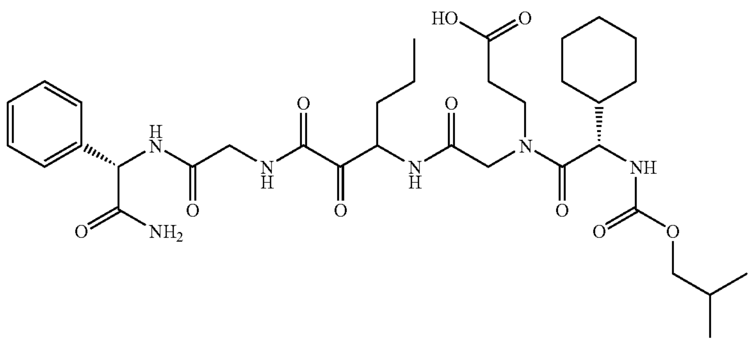 | C |
| 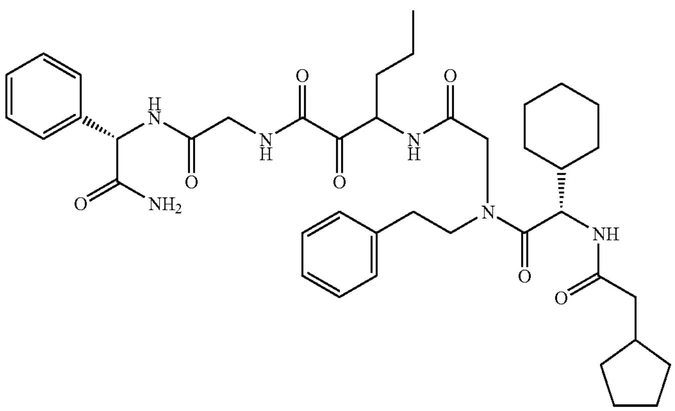 | B |

TABLE 4

| STRUCTURE | NAME | Ki* Range |
|---|---|---|
| 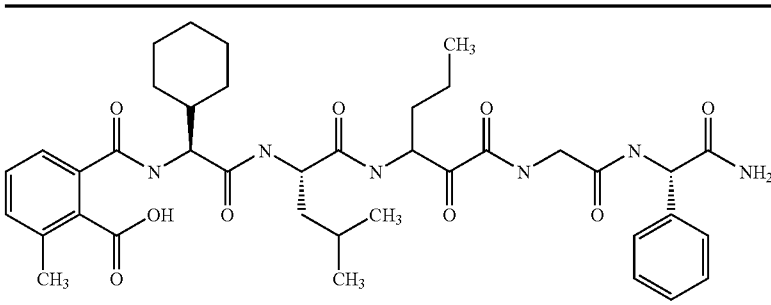 | (2-CO2,3-Me)PhCO-G(Chx)-L-nV-(CO)-G-G(Ph)-Am | a |
| 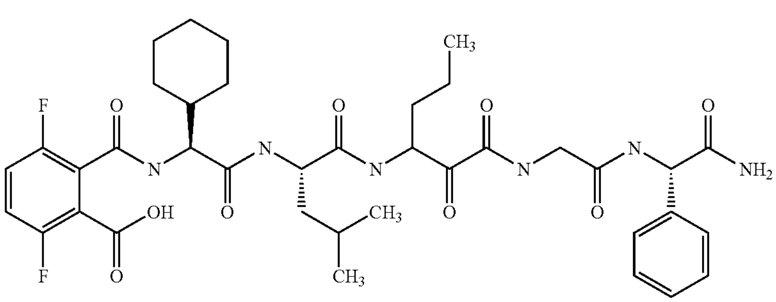 | (2,5-diF,6-CO2)PhCO-G(Chx)L-nV-(CO)-G-G(Ph)-Am | a |

TABLE 4-continued

| STRUCTURE | NAME | Ki* Range |
|---|---|---|
| 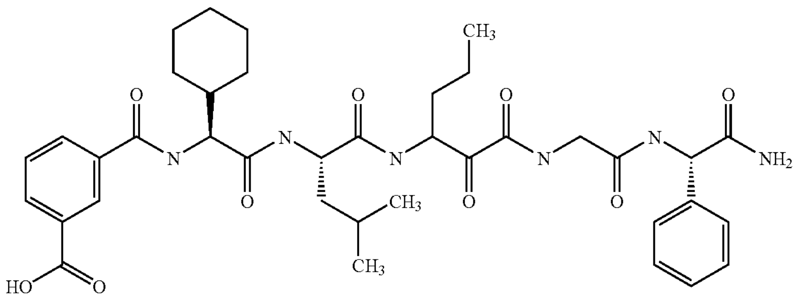 | (2-CO2)BnCO-G(Chx)-L-nV-(CO)-G-G(Ph)-Am | c |
| 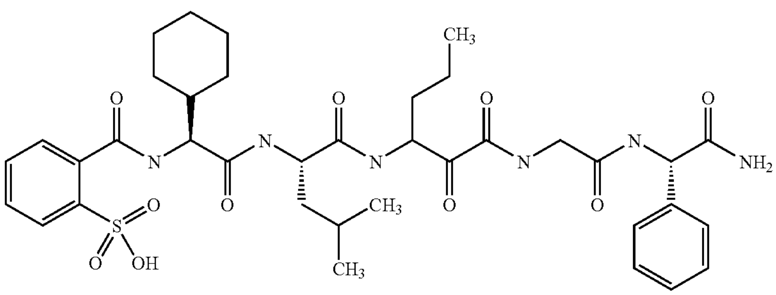 | (2-SO3)PhCO-G(Chx)-L-nV-(CO)-G-G(Ph)-Am | b |
| 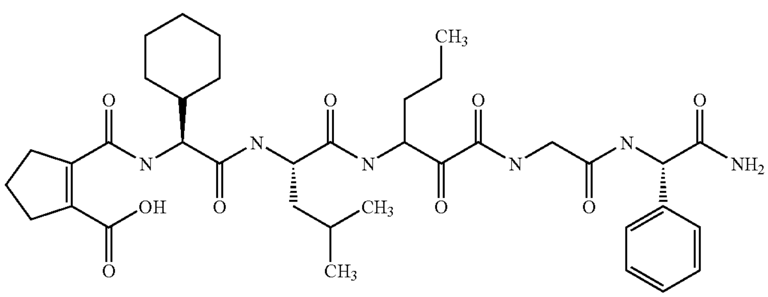 | (2-CO2)cyclopentenoyl-G(Chx)-L-nV-(CO)-G-G(Ph)-Am | c |
| 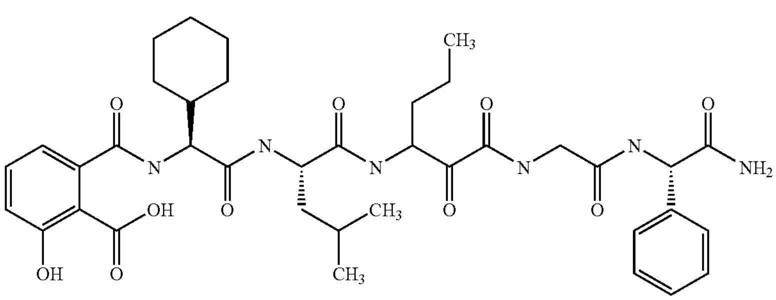 | (2-CO2,3-OH)PhCO-G(Chx)-L-nV-(CO)-G-G(Ph)-Am | a |
| 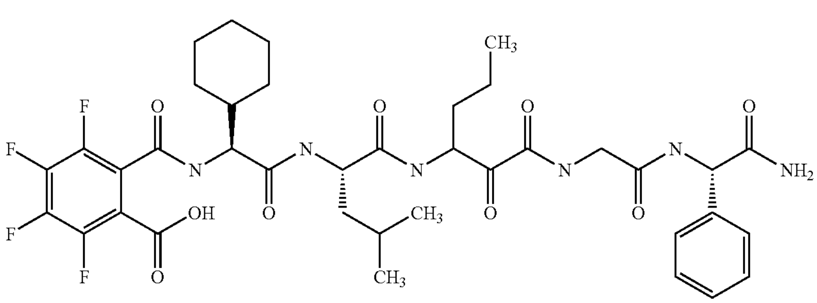 | (2,3,4,5-tetraF,6-CO2)PhCO-G(Chx)L-nV-(CO)-G-G(Ph)-Am | a |

TABLE 4-continued

| STRUCTURE | NAME | Ki* Range |
|---|---|---|
| | (2CO2)PhCO-G(Chx)-C((O2)Et)-nV-(CO)-G-G(Ph)-Am | b |
| | (2CO2)PhCO-G(Chx)-C((O2)Et)-nV-(CO)-G-G(Ph)-Am | b |
| 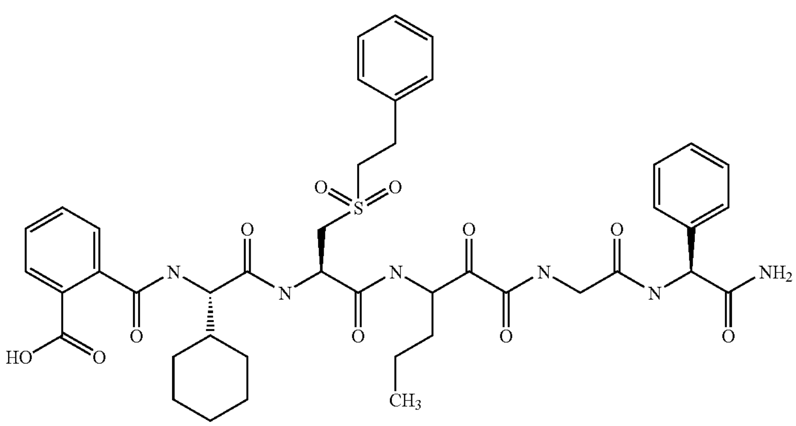 | (2CO2)PhCO-G(Chx)-C((O2)EtPh)-nV-(CO)-G-G(Ph)-Am | b |
| 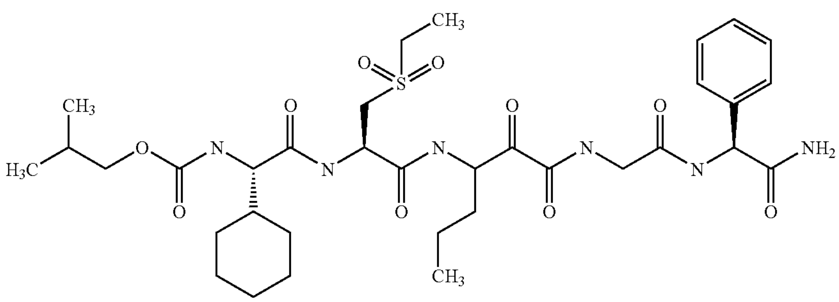 | iBoc-G(Chx)-C((O2)Et)-nV-(CO)-G-G(Ph)-Am | b |

TABLE 4-continued
| STRUCTURE | NAME | Ki* Range |
|---|---|---|
| 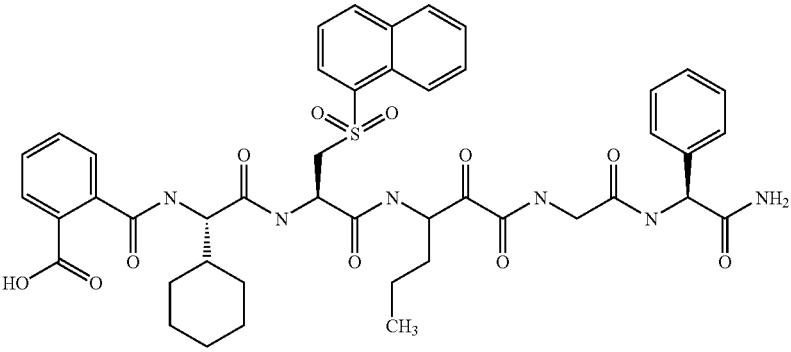 | (2CO2)PhCO-G(Chx)-C((O2)-1Np)-nV-(CO)-G-G(Ph)-Am | b |
| 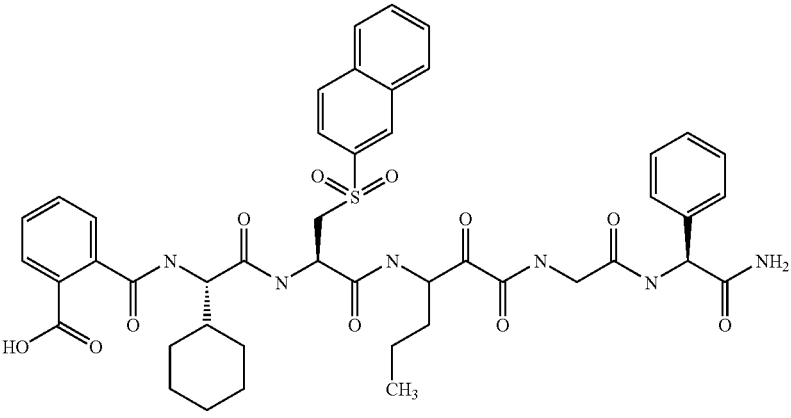 | (2CO2)PhCO-G(Chx)-C((O2)-2Np)-nV-(CO)-G-G(Ph)-Am | b |
| 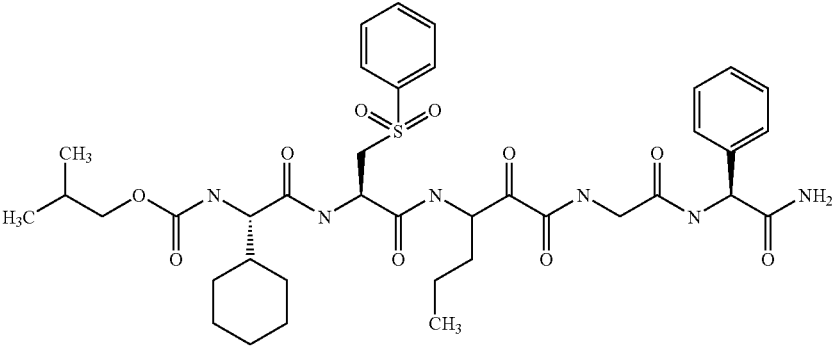 | iBoc-G(Chx)-C((O2)Ph)-nV-(CO)-G-G(Ph)-Am | b |
| 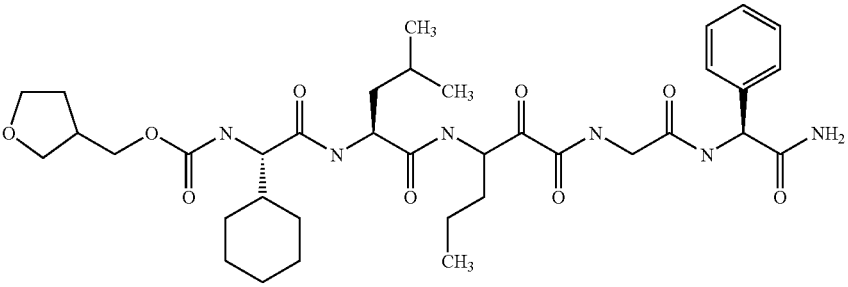 | ((3-tetrahydrofuran)-CH2O)CO-G(Chx)-L-nV-(CO)-G-G(Ph)-Am | b |

TABLE 4-continued

| STRUCTURE | NAME | Ki* Range |
|---|---|---|
| 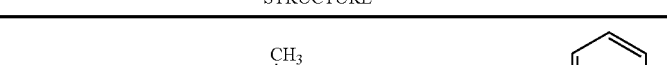 | 7-Me-3-iPr-Oct-4-ene-(CO)-L-nV-(CO)-G-G(Ph)-OH | c |

What is claimed is:

1. A compound, including enantiomers, stereoisomers, rotamers and tautomers of said compound, and pharmaceutically acceptable salts or solvates of said compound, said compound having the general structure shown in Formula I:

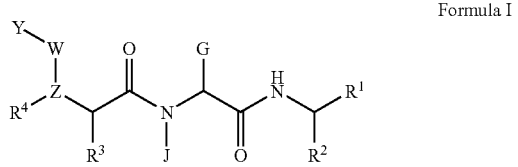

Formula I wherein:

G, J and Y may be the same or different and are independently selected from the group consisting of the moieties: H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe additionally optionally substituted with $X^{11}$ or $X^{12}$;

$X^{11}$ is selected from the group consisting of alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$ wherein $R^5$ is $COR^7$ wherein $R^7$ is $NHR^{10}$, wherein $R^{10}$ is selected from the group consisting of —CH($R^{1'}$)CONHCH($R^{2'}$)COO $R^{11}$, CH($R^{1'}$)CONHCH($R^{2'}$)CONR$^{12}$R$^{13}$, CH($R^{1'}$)CONHCH($R^{2'}$)R', CH($R^{1'}$)CONHCH($R^{2'}$)CONHCH($R^{3'}$)COOR$^{11}$, CH($R^{1'}$)CONHCH($R^{2'}$)CONHCH($R^{3'}$)CONR$^{12}$R$^{13}$, CH($R^{1'}$)CONHCH($R^{2'}$)CONHCH($R^{3'}$)CONHCH($R^{4'}$)COOR$^{11}$, CH($R^{1'}$)CONHCH($R^{2'}$)CONHCH($R^{3'}$)CONHCH($R^{4'}$)CONR$^{12}$R$^{13}$, CH($R^{1'}$)CONHCH($R^{2'}$)CONHCH($R^{3'}$)CONHCH($R^{4'}$)CONHCH($R^{5'}$)COOR$^{11}$, and CH($R^{1'}$)CONHCH($R^{2'}$)CONHCH($R^{3'}$)CONHCH($R^{4'}$)CONHCH($R^{5'}$)CONR$^{12}$R$^{13}$, wherein $R^{1'}$, $R^{2'}$, $R^{3'}$, $R^{4'}$, $R^{5'}$, $R^{11}$, $R^{12}$ and $R^{13}$ may be the same or different and are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W maybe present or absent, and if W is present, W is selected from C=O, C=S, or $SO_2$; and R', $R^2$, $R^3$ and $R^4$ are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino other than for $R^2$, amido, ester, carboxylic acid, carbamate, urea, ketone, aldehyde, cyano, nitro; oxygen, nitrogen, sulfur, or phosphorus atoms (with said oxygen, nitrogen, sulfur, or phosphorus atoms numbering zero to six); (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonylurea, hydrazide, and hydroxamate; with the proviso that $R^2$ is not arylalkyl or cyclohexylalkyl.

2. The compound of claim 1 wherein $R^1$ is $COR^5$, and $R^5$ is $CONHR^{10}$.

3. The compound of claim 2, wherein $R^1$ is $COCONHR^{10}$, and $R^{10}$ is selected from the group consisting of H, CH($R^{1'}$) COOR$^{11}$, CH($R^{1'}$) CONR$^{12}$R$^{13}$, CH($R^{1'}$)CONHCH($R^{2'}$)COOR$^{11}$, CH($R^{1'}$)CONHCH($R^{2'}$) CONR$^{12}$R$^{13}$, and CH($R^{1'}$) CONHCH($R^{2'}$)(R').

4. The compound of claim 3, wherein $R^{10}$ is CH($R^{1'}$) CONHCH($R^{2'}$)COOR$^{11}$, CH($R^{1'}$)CONHCH($R^{2'}$) CONR$^{12}$R$^{13}$, or CH($R^{1'}$)CONHCH($R^{2'}$)(R'), wherein $R^{1'}$ is H or alkyl, heteroalkyl and $R^{2'}$ is phenyl, substituted phenyl, hetero atom-substituted phenyl, thiophenyl, cycloalkyl, piperidyl and pyridyl.

5. The compound of claim 4, wherein $R^{1'}$ is H.

6. The compound of claim 5, wherein
R$^{11}$ is H or tert-butyl;
R' is hydroxymethyl; and
R$^{2'}$ is selected from the group consisting of:

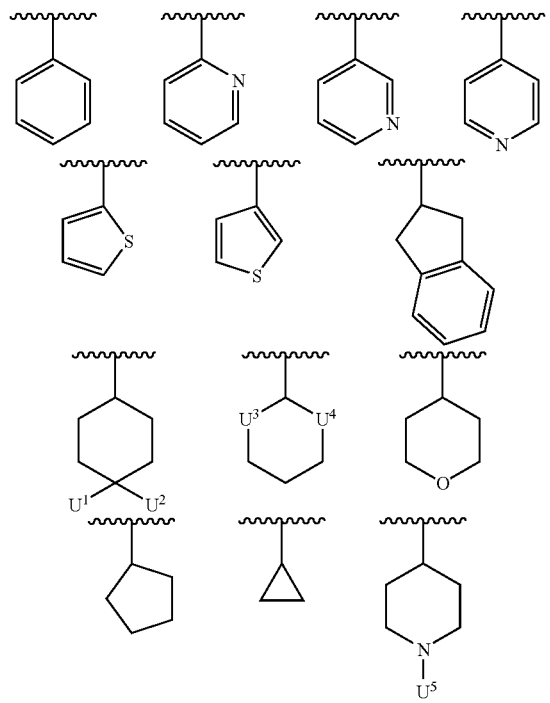

wherein:
U$^1$ and U$^2$ maybe same or different and are independently selected from the group consisting of H, F, CH$_2$COOH, CH$_2$COOMe, CH$_2$CONH$_2$, CH$_2$CONHMe, CH$_2$CONMe$_2$, azido, amino, hydroxyl, substituted amino, substituted hydroxyl;
U$^3$ and U$^4$ maybe same or different and are O or S;
U$^5$ is selected from the moieties consisting of alkylsulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl and heteroarylaminocarbonyl or combinations thereof; and
NR$^{12}$R$^{13}$ is selected from the group consisting of:

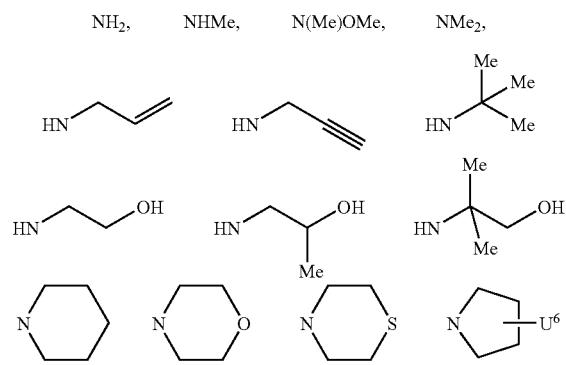

wherein U$^6$ is H, OH, or CH$_2$OH.

7. The compound of claim 2, wherein R$^2$ is selected from the group consisting of the following moieties:

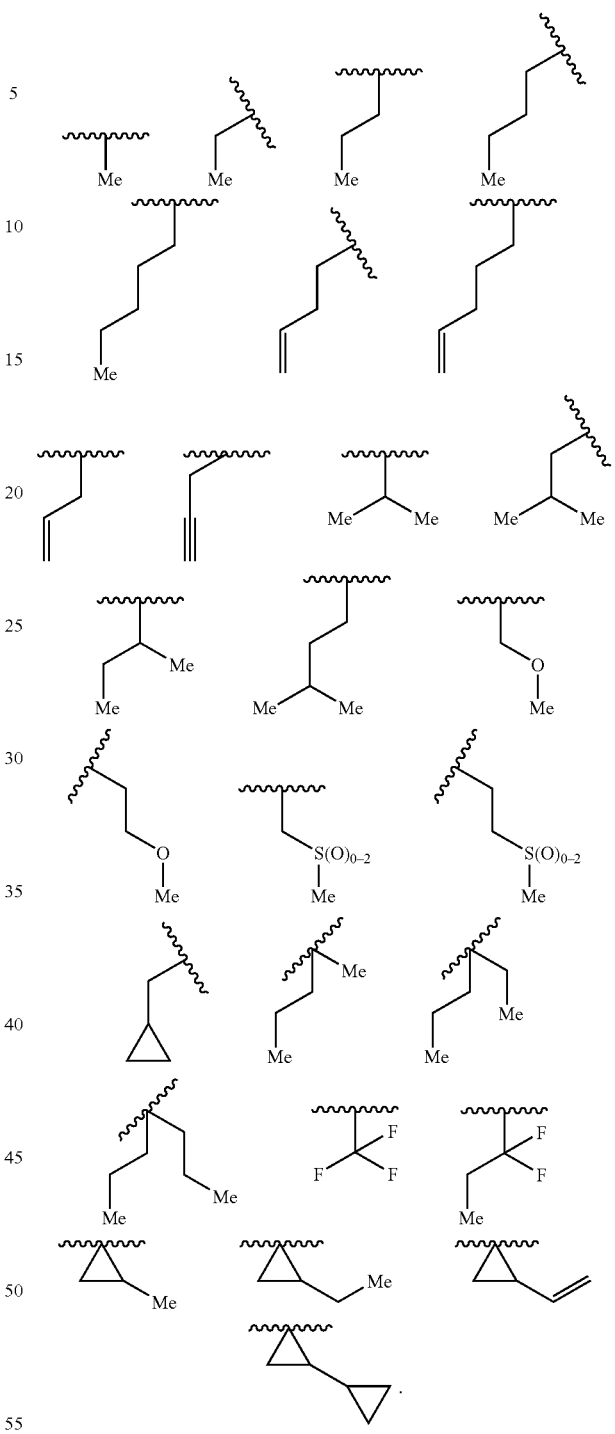

8. The compound of claim 7, wherein R$^3$ is selected from the group consisting of:

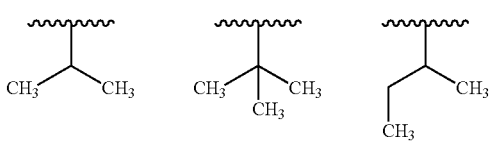

-continued
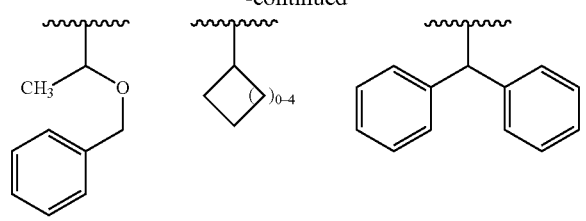
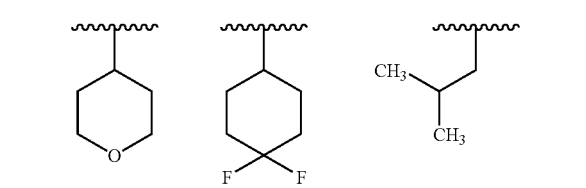
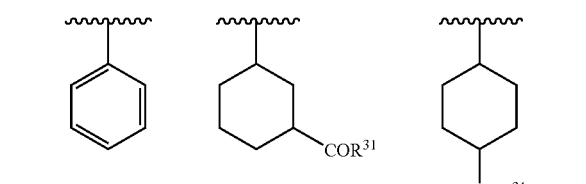
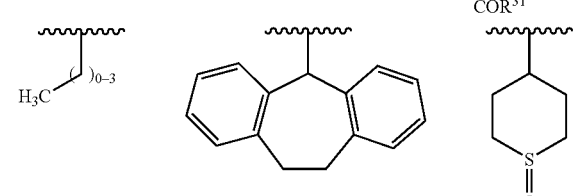
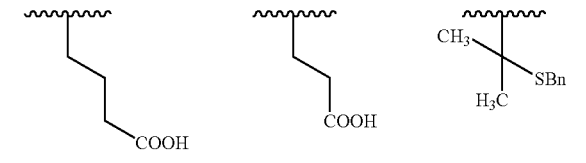
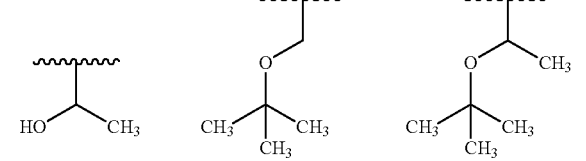
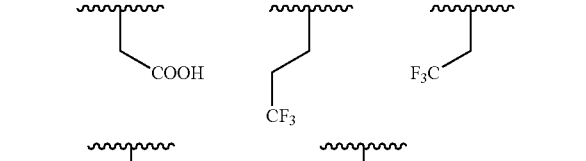
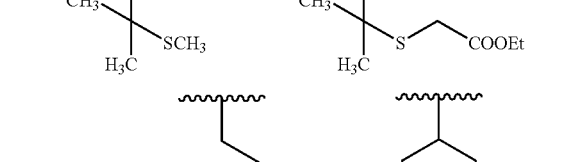
and
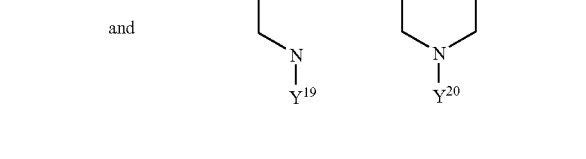
wherein $R^{31}$=OH or O—alkyl;
$Y^{19}$ is selected from the following moieties:
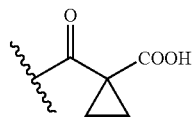 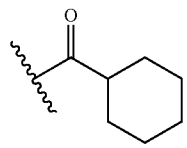
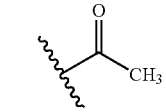 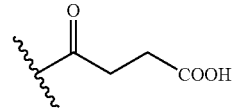
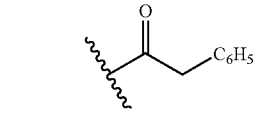 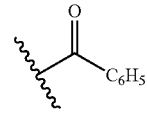
and $Y^{20}$ is selected from the following moieties:
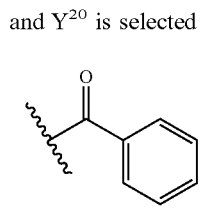 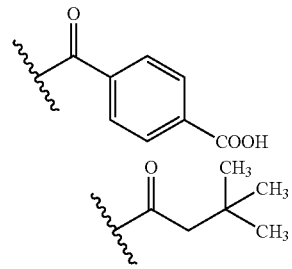
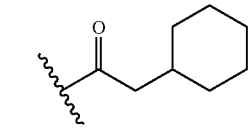 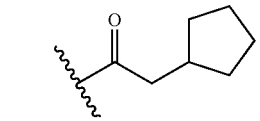
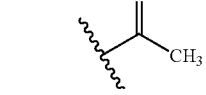 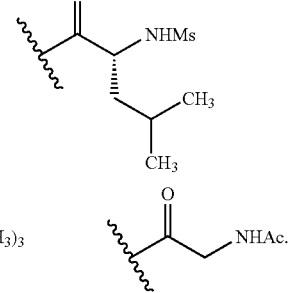
9. The compound of claim 8, wherein $R^3$ is selected from the following structures:
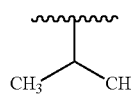 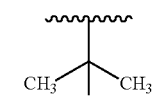 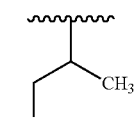
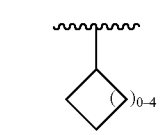 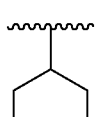 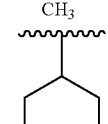

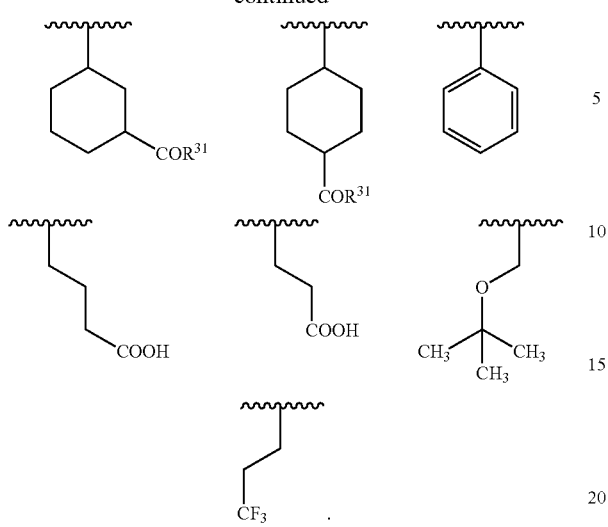
10. The compound of claim 9, wherein Z=N and $R^4$=H.
11. A compound of claim 10, wherein W is C=O, or $SO_2$.
12. A compound of claim 11, wherein Y is selected from the following moieties:
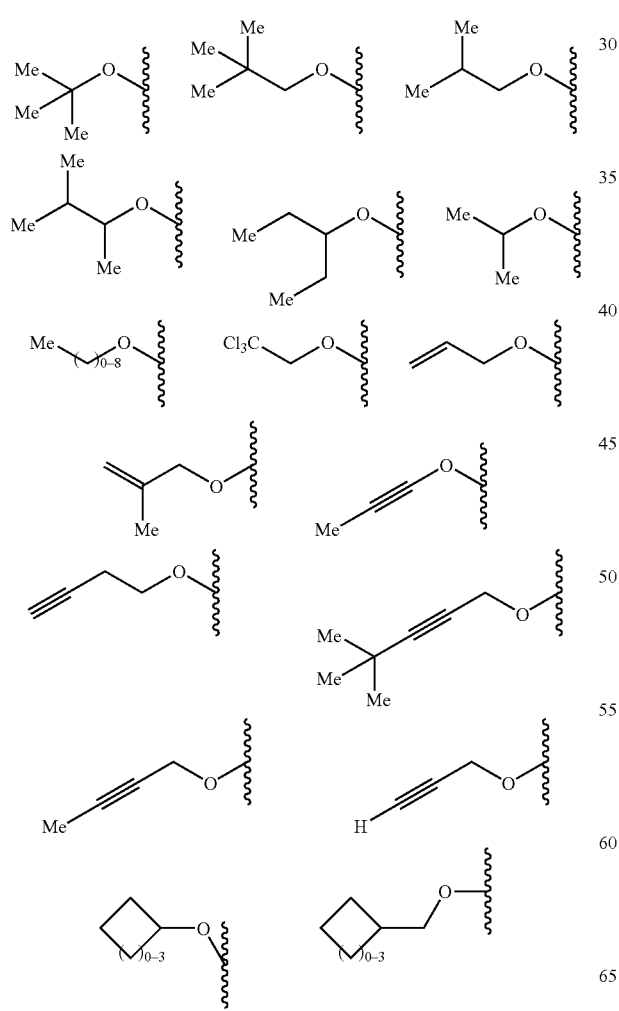
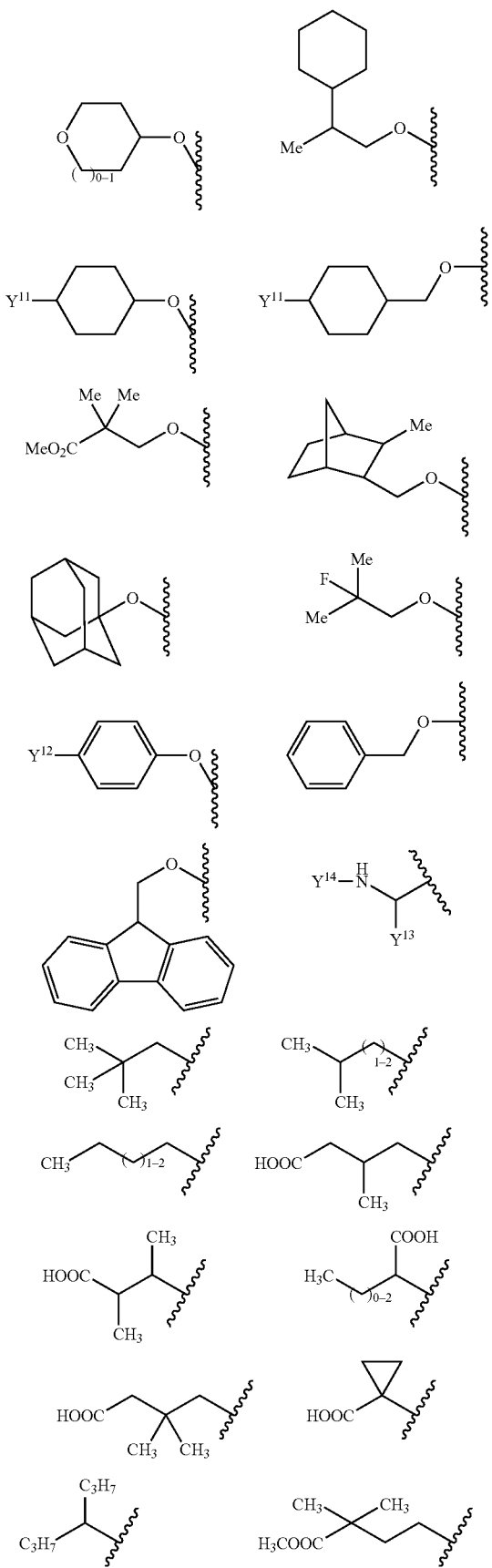

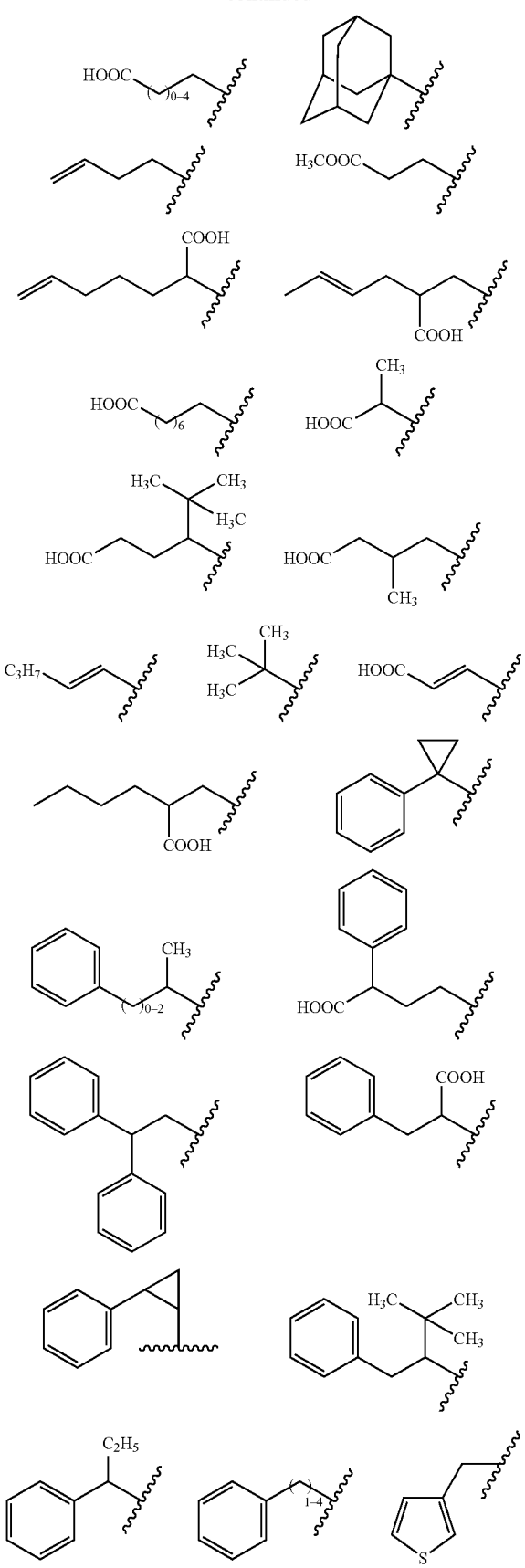
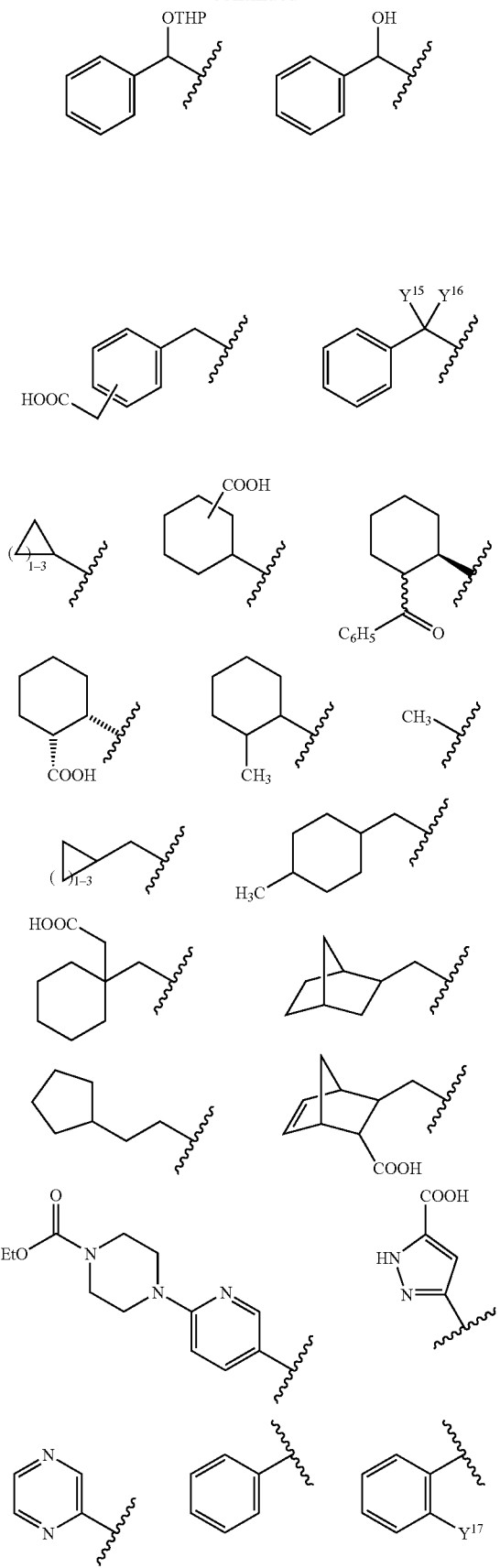

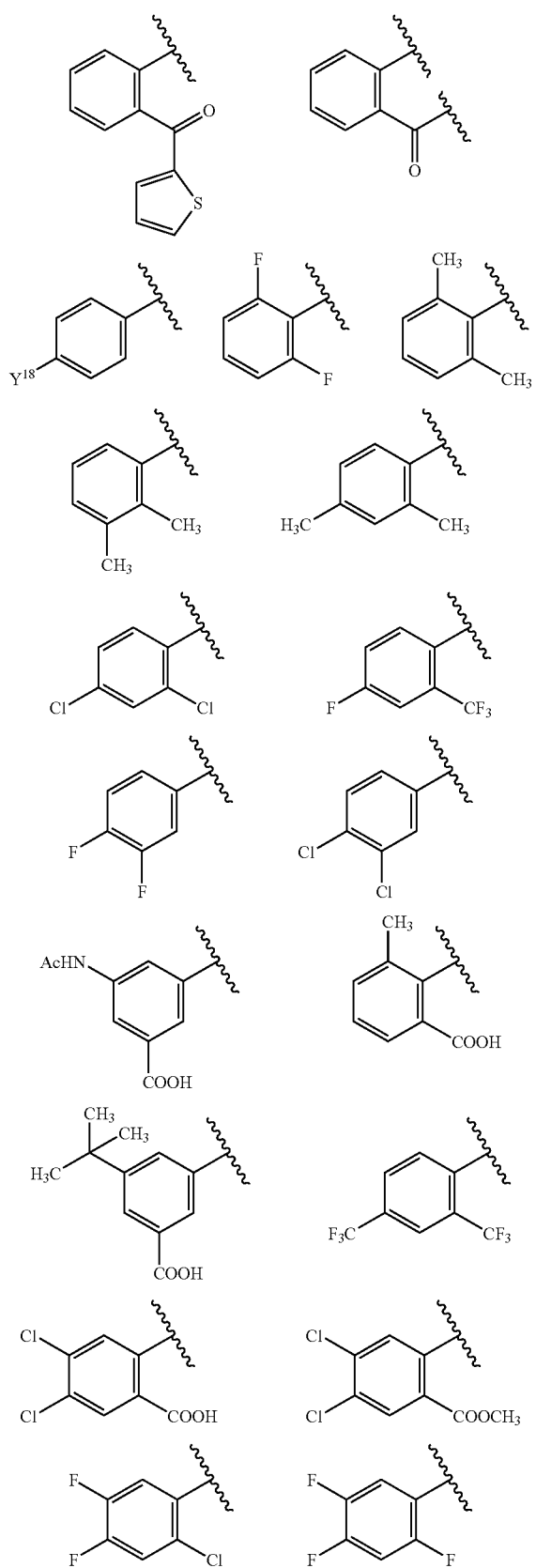
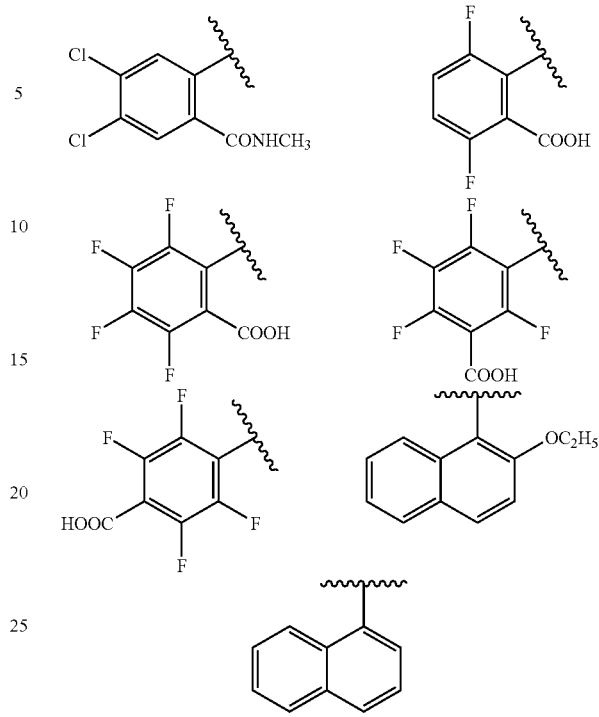
wherein:
Y[11] is selected from H, COOH, COOEt, Ome, Ph, Oph, NHMe, NHAc, NHPh, CH(Me)$_2$, 1-triazolyl, 1-imidazolyl, and NHCH$_2$COOH;
Y[12] is selected from H, COOH, COOMe, Ome, F, Cl, or Br;
Y[13] is selected from the following moieties:
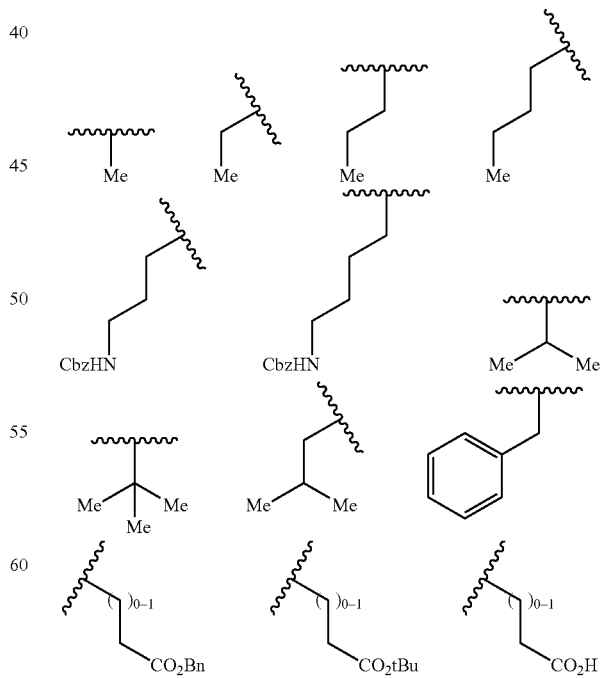

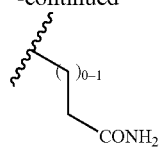

$Y^{14}$ is selected from $MeSO_2$, Ac, Boc, $^tBoc$, Cbz, or Alloc;

$Y^{15}$ and $Y^{16}$ may be the same or different and are independently selected from alkyl, aryl or herereoalkyl, or heteroaryl;

$Y^{17}$ is $CF_3$, $NO_2$, $CONH_2$, OH, $COOCH_3$, $OCH_3$, $OC_6H_5$, $C_6H_5$, $COC_6H_5$, $NH_2$, or COOH; and $Y^{18}$ is $COOCH_3$, $NO_2$, $N(CH_3)_2$, F, $OCH_3$, $CH_2COOH$, COOH, $SO_2NH_2$, or $NHCOCH_3$.

13. A compound of claim 12, wherein Y is selected from the group consisting of:

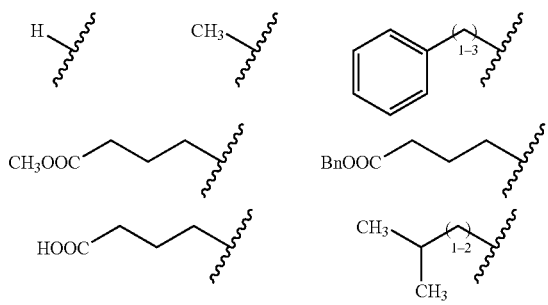

wherein:

$Y^{17}=CF_3$, $NO_2$, $CONH_2$, OH, $NH_2$, or COOH;
$Y^{18}=F$, COOH.

14. The compound of claim 13, wherein J is selected from the group consisting of:

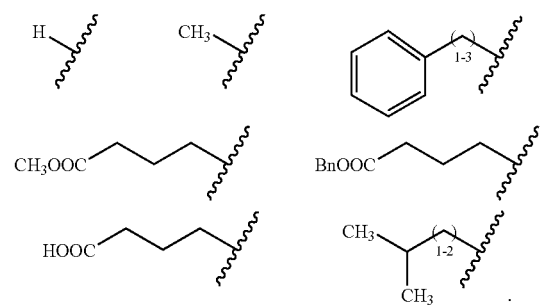

15. The compound of claim 14 where in J is H, $CH_3$ or Bn.

16. The compound of claim 15 wherein G is selected from moieties:

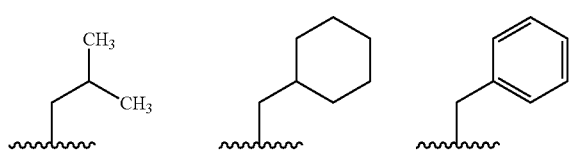

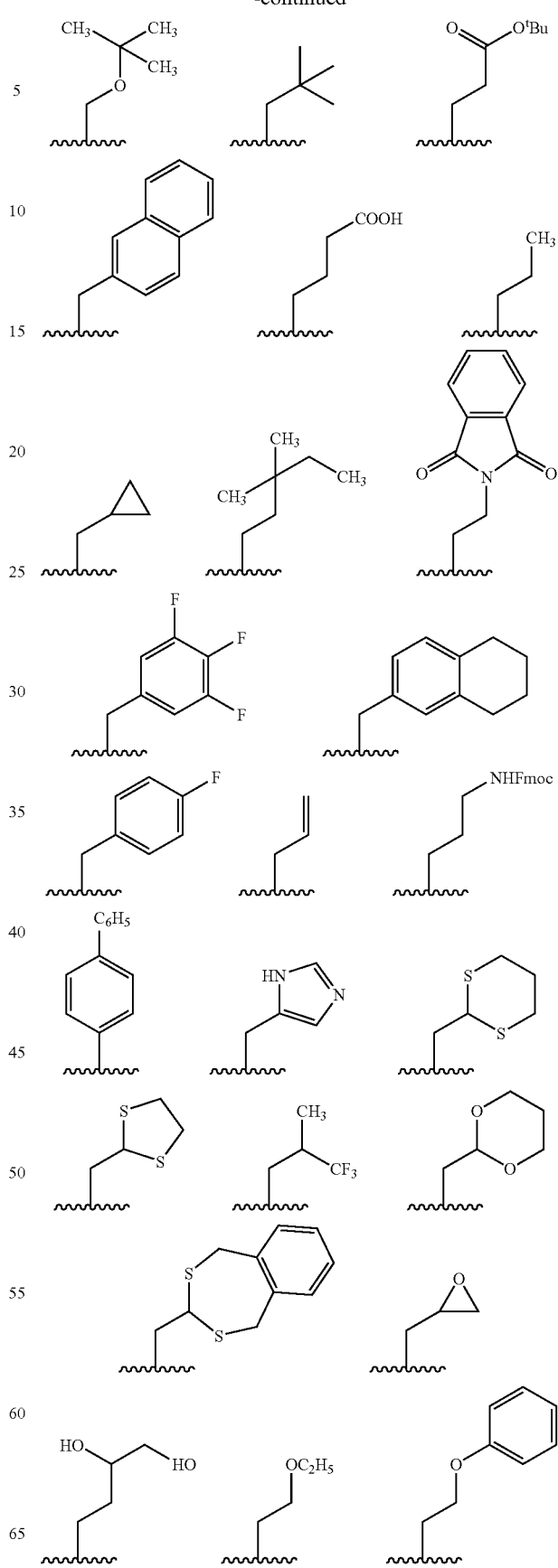

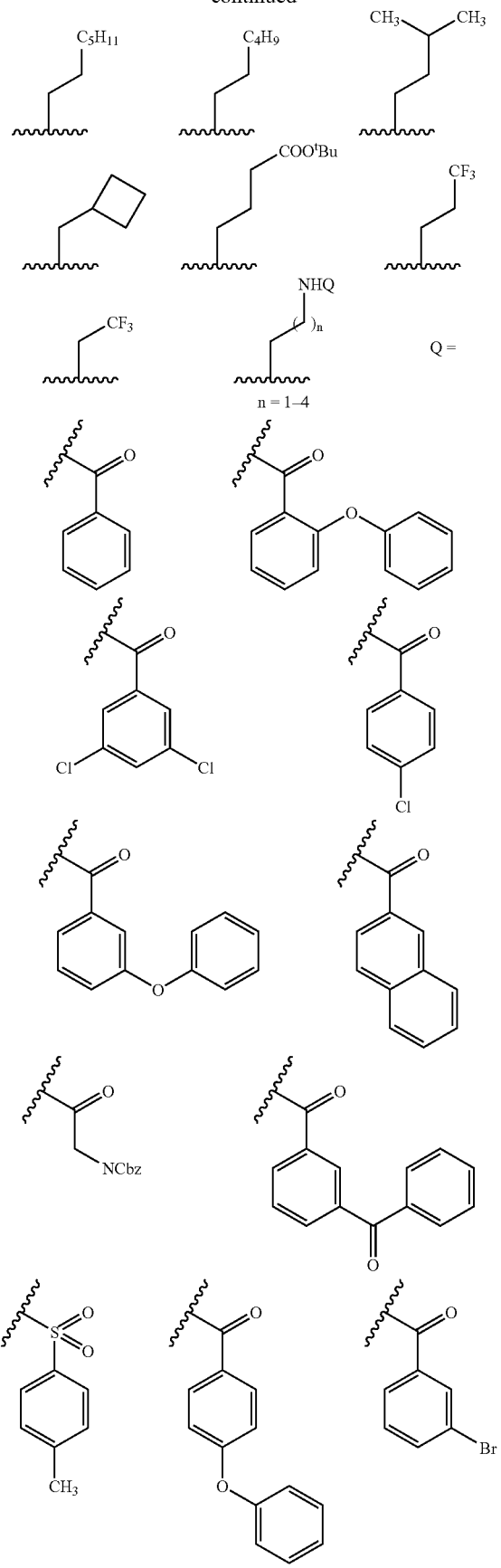

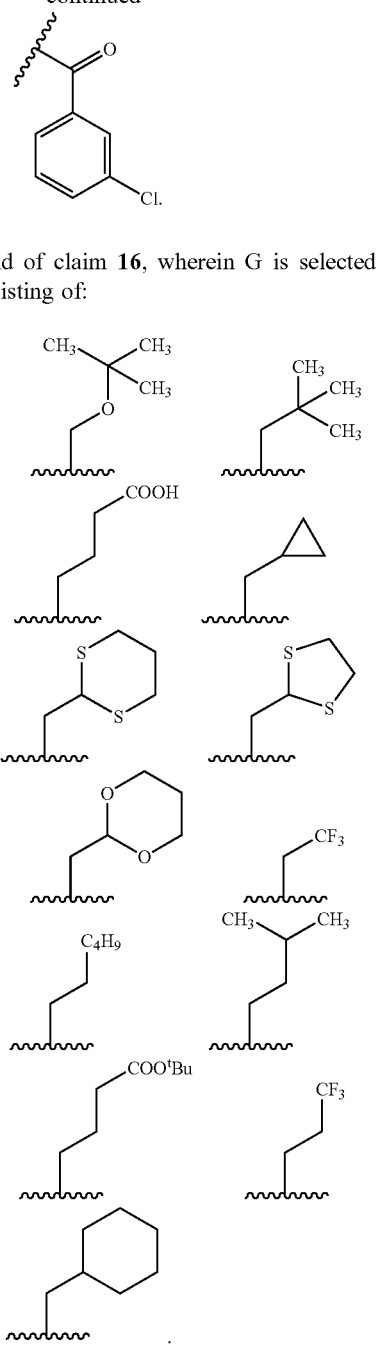

17. The compound of claim 16, wherein G is selected from the group consisting of:

18. A pharmaceutical composition comprising as an active ingredient a compound of claim 1.

19. The pharmaceutical composition of claim 18 suitable for use in treating disorders associated with Hepatitis C virus.

20. The pharmaceutical composition of claim 18 additionally comprising a pharmaceutically acceptable carrier.

21. A compound exhibiting hepatitis C virus (HCV) protease inhibitory activity, including enantiomers, stereoisomers, rotamers and tautomers of said compound, and pharmaceutically acceptable salts or solvates of said compound, said compound being selected from the group of compounds with structures listed below:

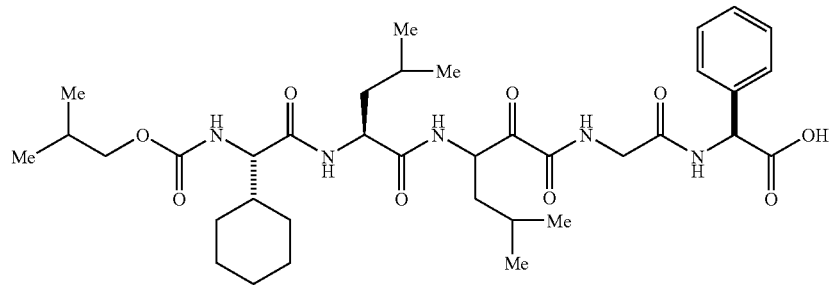
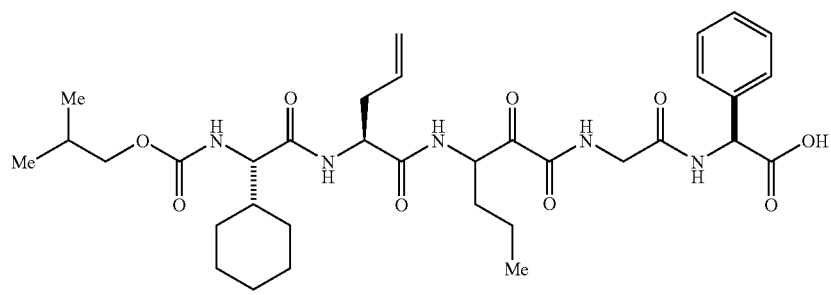
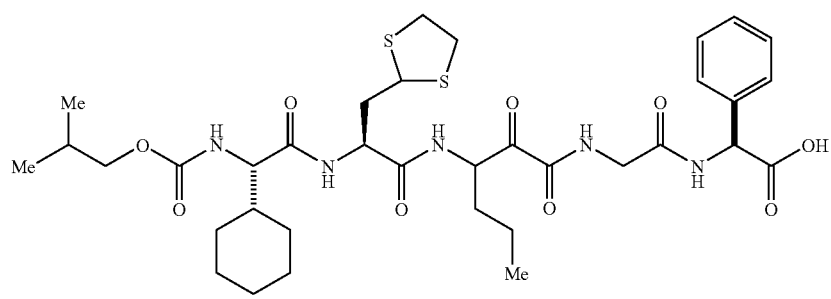
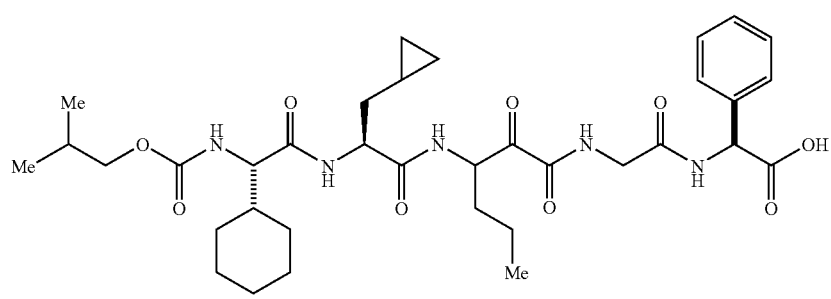
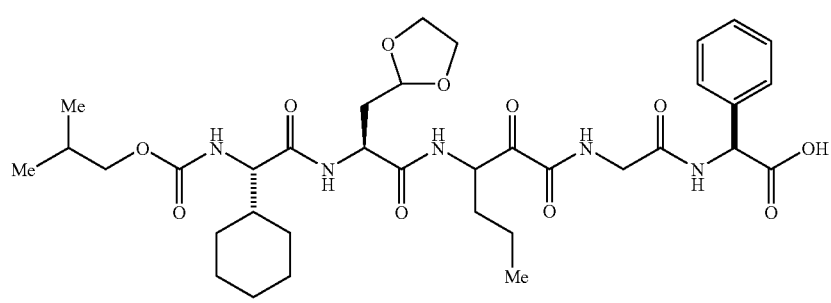

-continued
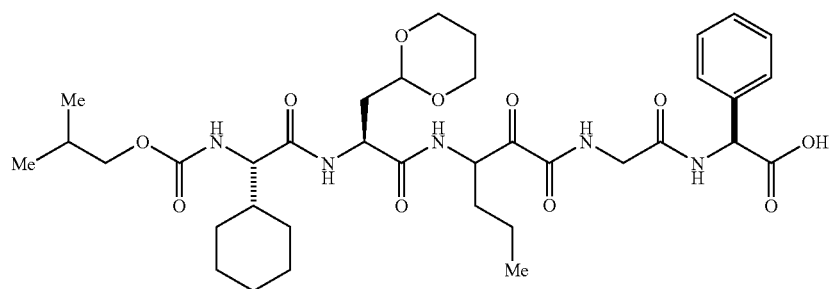
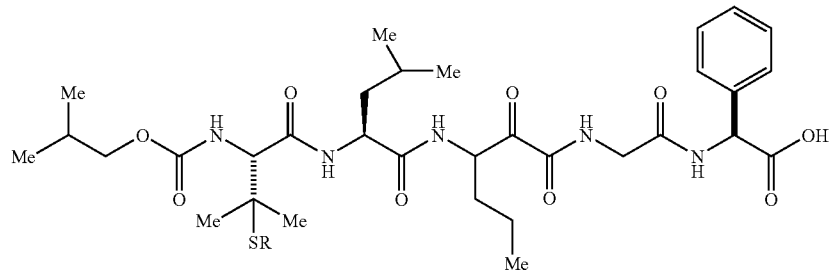
R = Me
R = Benzyl
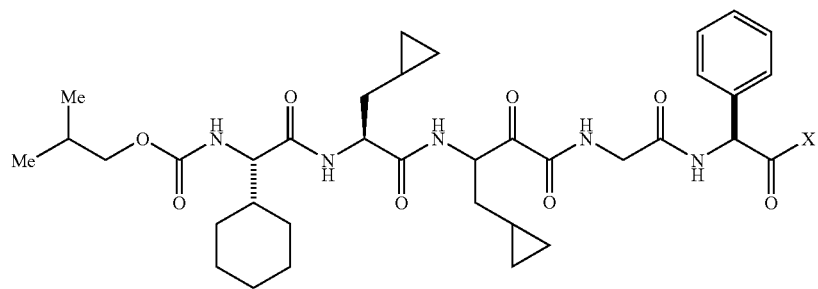
X = O<sup>t</sup>Bu
X = OH
X = NH<sub>2</sub>
X = NMeOMe
X = NMe<sub>2</sub>
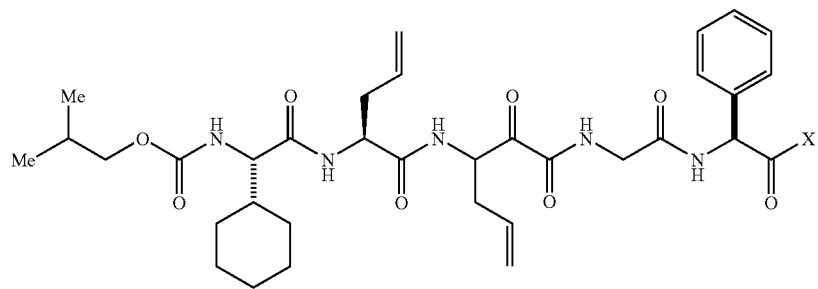
X = O<sup>t</sup>Bu
X = OH
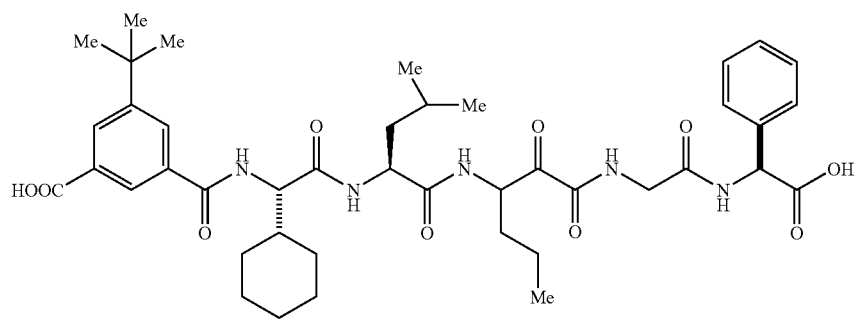

-continued
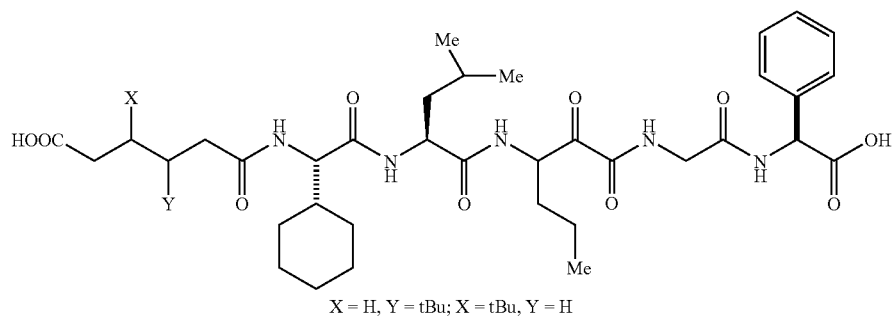
X = H, Y = tBu; X = tBu, Y = H
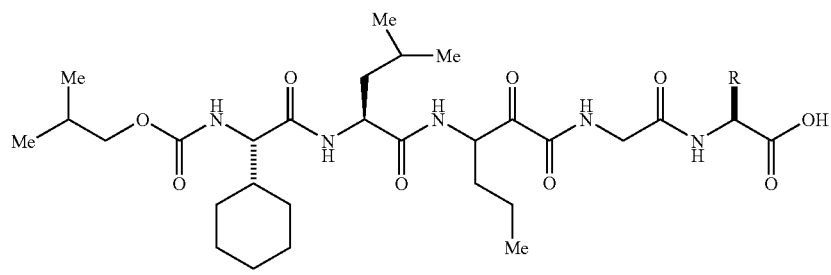
R = Propargyl; R = Allyl
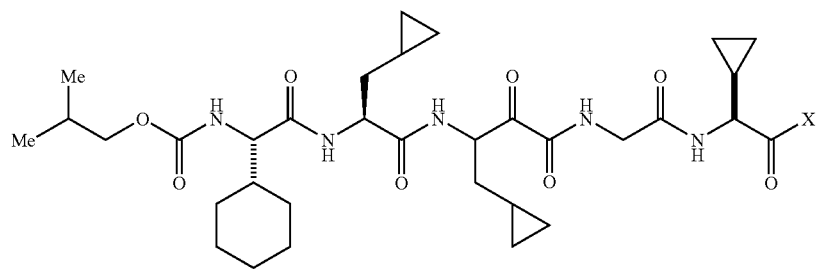
X = OtBu; X = OH
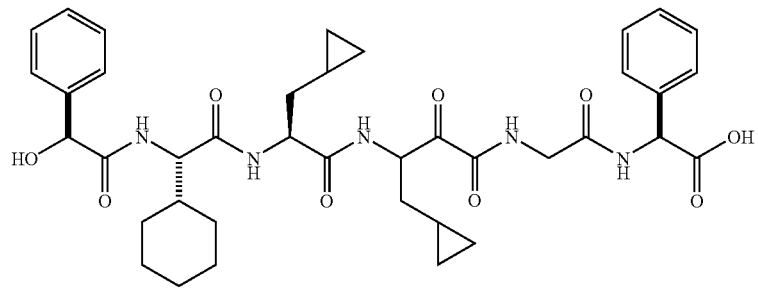
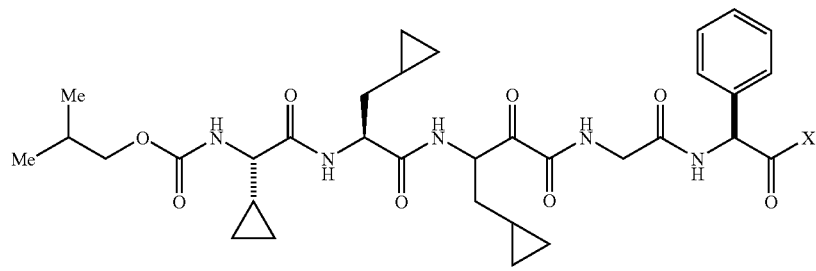
X = O^tbutyl
X = OH -continued
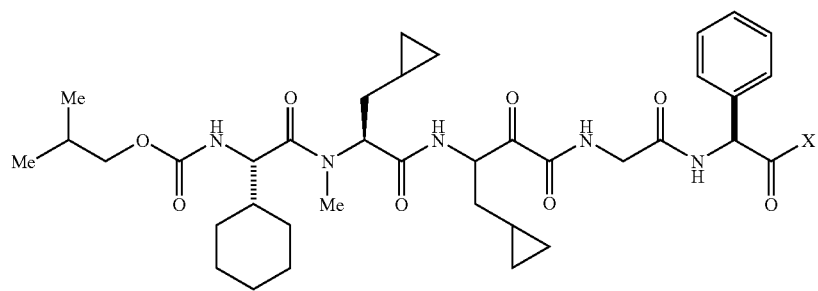
X = O^tButyl
X = OH
X = NMe_2
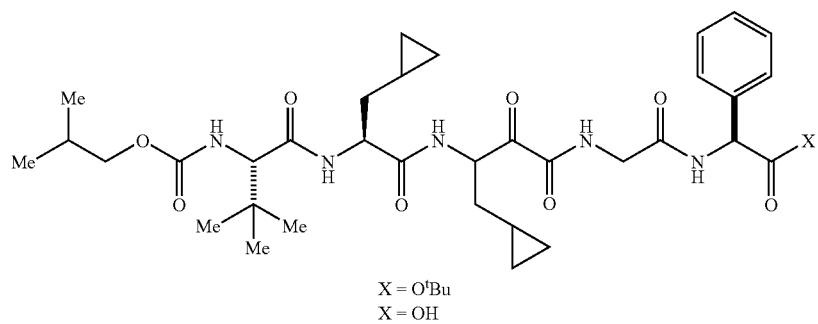
X = O^tBu
X = OH
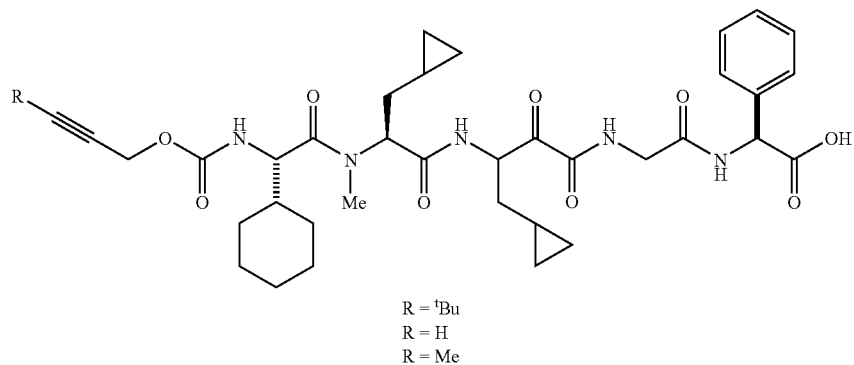
R = ^tBu
R = H
R = Me
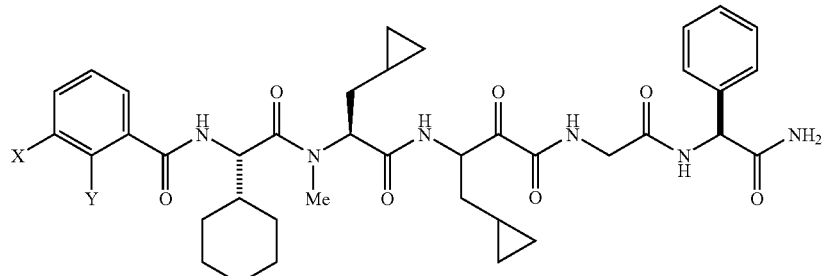
X = H, Y = COOH
X = COOH, Y = H
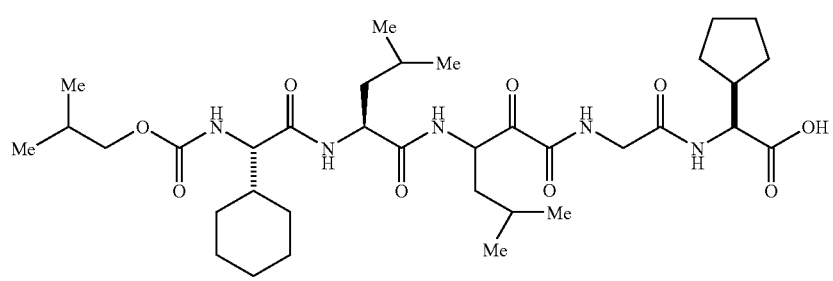

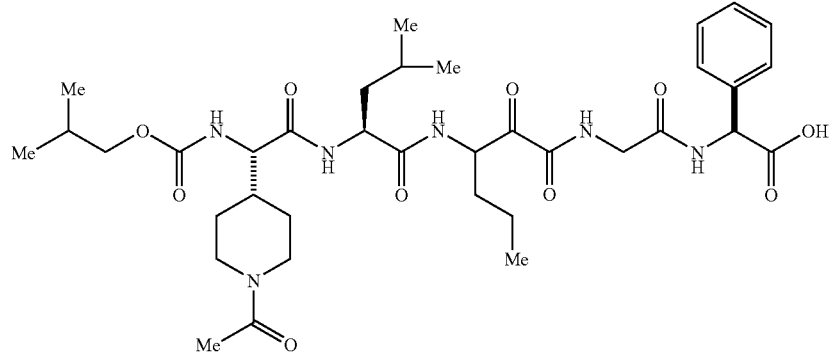

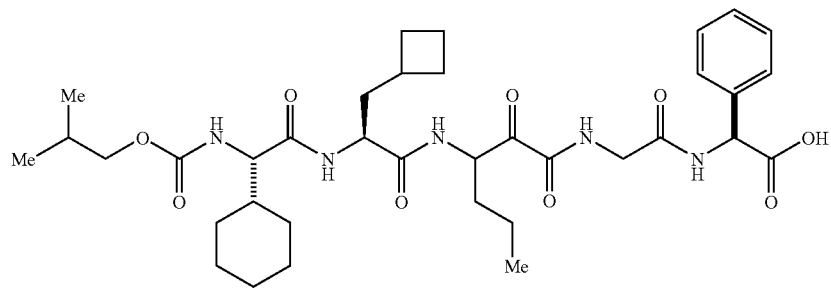

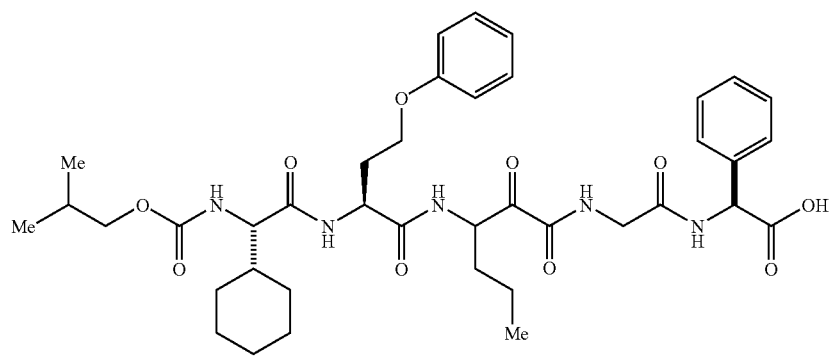

22. A pharmaceutical composition for treating disorders associated with the hepatitis C virus (HCV) protease, said composition comprising therapeutically effective amount of one or more compounds in claim 21 and a pharmaceutically acceptable carrier.

23. The pharmaceutical composition of claim 22, additionally containing an antiviral agent.

24. The pharmaceutical composition of claim 22 or claim 23, further containing an interferon.

25. The pharmaceutical composition of claim 24, wherein said antiviral agent is ribavirin and said interferon is α-interferon.

26. A compound selected from the group consisting of:

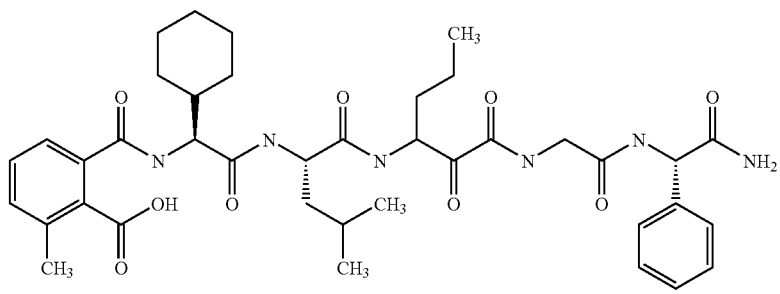

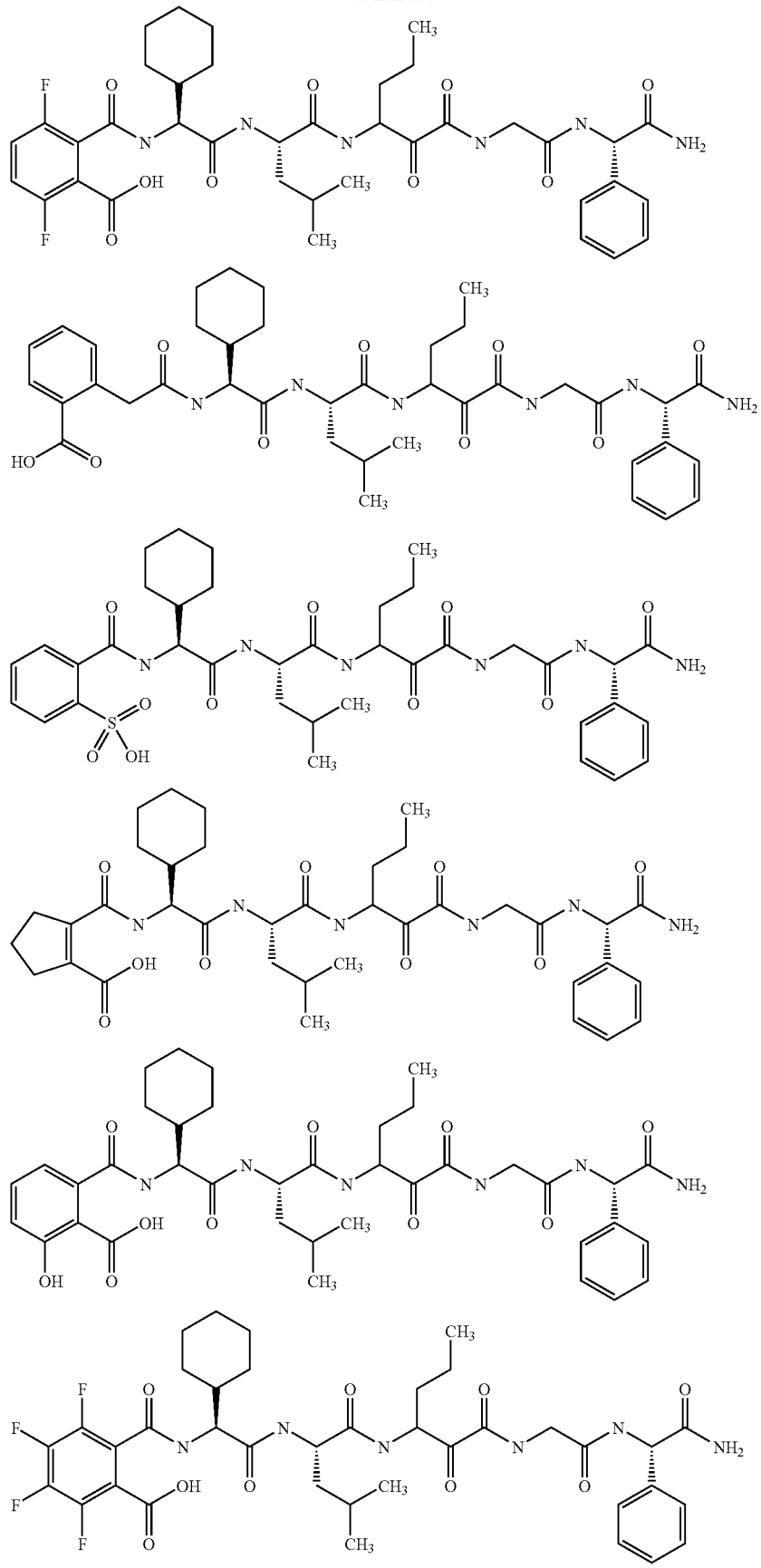

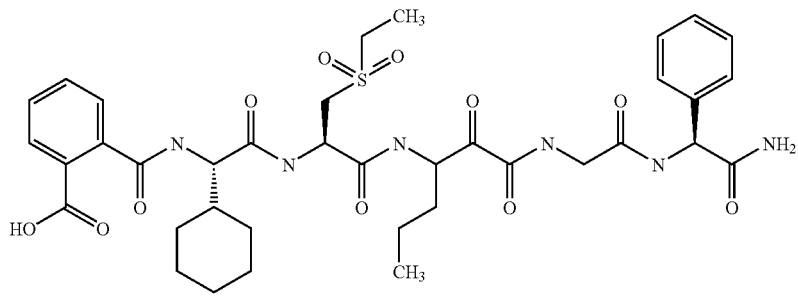
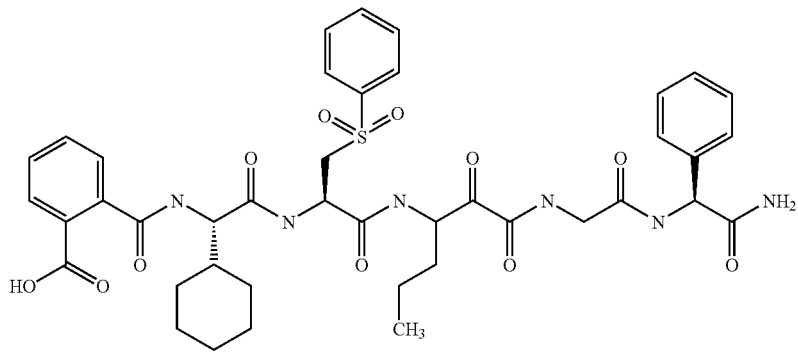
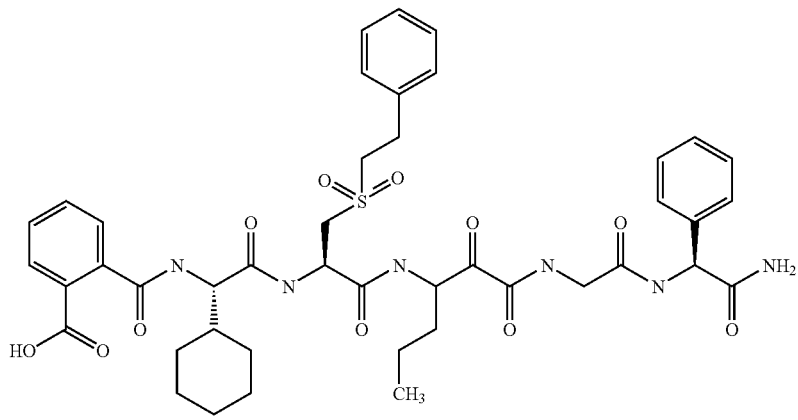
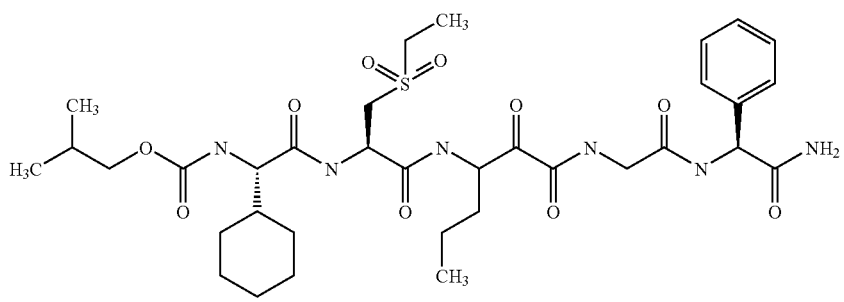
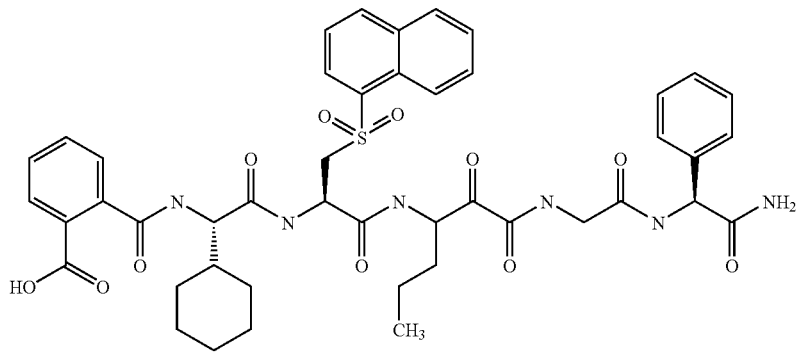

-continued

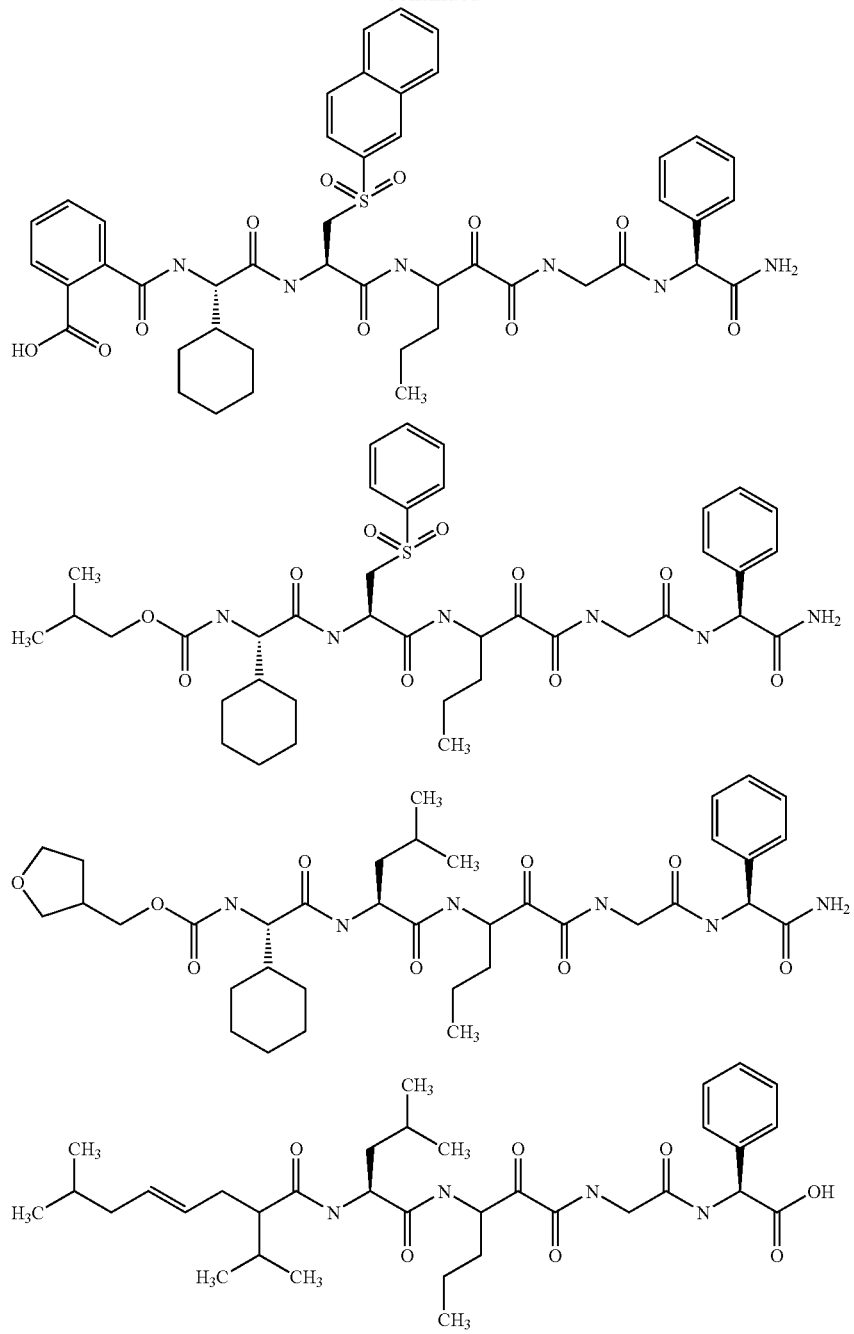

or an enantiomer, sterioisomer, rotamer or tautomer thereof, or a pharmaceutically acceptable salt or solvate thereof, wherein the compound exhibits hepatitis C virus (HCV) inhibitory activity.

27. A pharmaceutical composition, comprising one or more compounds of claim 26.

28. The compound of claim 7, wherein $R^3$ is cyclohexyl.

29. The compound of claim 11, wherein Y is selected from the group consisting of 2-carboxy-3-hydroxyphenyl, 3-tetrahydrofurylmethoxy, and 2-sulfophenyl.

30. The compound of claim 15, wherein G is selected from the group consisting of ethylsulfonylmethyl, phenylsulfonylmethyl, 2-phenylethylsulfonylmethyl and 1-naphthylsulfonylmethyl.

* * * * *

UNITED STATES PATENT AND TRADEMARK OFFICE
CERTIFICATE OF CORRECTION

PATENT NO. : 7,169,760 B2 Page 1 of 1
APPLICATION NO. : 09/909012
DATED : January 30, 2007
INVENTOR(S) : Anil K. Saksena et al.

It is certified that error appears in the above-identified patent and that said Letters Patent is hereby corrected as shown below:

On the Cover Page, right hand side column, Item 74 under "Attorney, Agent, or Firm":

Please correct "Larner" to --Lerner--

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,169,760 B2  Page 1 of 1
APPLICATION NO. : 09/909012
DATED : January 30, 2007
INVENTOR(S) : Anil K. Saksena et al.

It is certified that error appears in the above-identified patent and that said Letters Patent is hereby corrected as shown below:

In the Claims:

Claim 1, col. 206, line 28:    Please correct:

"$R', R^2, R^3$ and $R^4$"   to   "$R, R', R^2, R^3$ and $R^4$"

Claim 1, col. 206, line 55:    Please correct:

"$CONHR^{10}$"   to   "$CONR^9R^{10}$"

Claim 1, col. 206, lines 56-57:    Please correct:

"$COCONHR^{10}$, and $R^{10}$ is"

to

"$COCONR^9R^{10}$, is $R^9$ is H, $R^{10}$ is"

Signed and Sealed this

First Day of September, 2009

David J. Kappos
*Director of the United States Patent and Trademark Office*